United States Patent
Sloey et al.

(10) Patent No.: US 12,404,344 B2
(45) Date of Patent: Sep. 2, 2025

(54) LOW-VISCOSITY, HIGH CONCENTRATION EVOLOCUMAB FORMULATIONS AND METHODS OF MAKING THE SAME

(71) Applicant: AMGEN INC., Thousand Oaks, CA (US)

(72) Inventors: Christopher James Sloey, Newbury Park, CA (US); Sekhar Kanapuram, Thousand Oaks, CA (US); Huanchun Cui, Aesch (CH); Chio Mui Chan, Hillsboro, OR (US); Elaheh Binabaji, Los Angeles, CA (US)

(73) Assignee: AMGEN INC., Thousand Oaks, CA (US)

( * ) Notice: Subject to any disclaimer, the term of this patent is extended or adjusted under 35 U.S.C. 154(b) by 403 days.

(21) Appl. No.: 17/893,515

(22) Filed: Aug. 23, 2022

(65) Prior Publication Data

US 2023/0226177 A1    Jul. 20, 2023

Related U.S. Application Data

(62) Division of application No. 15/902,775, filed on Feb. 22, 2018, now Pat. No. 11,464,857.

(60) Provisional application No. 62/462,266, filed on Feb. 22, 2017.

(51) Int. Cl.

| | | |
|---|---|---|
| C07K 16/40 | (2006.01) | |
| A61K 39/395 | (2006.01) | |
| A61K 47/18 | (2017.01) | |
| C07K 1/34 | (2006.01) | |
| C07K 16/06 | (2006.01) | |
| A61K 9/00 | (2006.01) | |
| C07K 1/16 | (2006.01) | |
| C07K 1/36 | (2006.01) | |
| C07K 16/22 | (2006.01) | |

(52) U.S. Cl.
CPC ............. *C07K 16/40* (2013.01); *C07K 1/34* (2013.01); *C07K 16/065* (2013.01); *A61K 9/0019* (2013.01); *A61K 39/3955* (2013.01); *A61K 39/39591* (2013.01); *A61K 47/183* (2013.01); *C07K 1/16* (2013.01); *C07K 1/36* (2013.01); *C07K 16/22* (2013.01); *C07K 2317/565* (2013.01); *C07K 2317/76* (2013.01); *C07K 2317/90* (2013.01)

(58) Field of Classification Search
CPC ........ C07K 16/40; C07K 1/34; C07K 16/065; A61K 39/3955

See application file for complete search history.

(56) References Cited

U.S. PATENT DOCUMENTS

| | | |
|---|---|---|
| 6,767,892 B1 | 7/2004 | Shirley et al. |
| 7,153,507 B2 | 12/2006 | van de Winkel et al. |
| 7,592,429 B2 | 9/2009 | Paszty et al. |
| 7,648,702 B2 | 1/2010 | Gombotz et al. |
| 7,906,625 B2 | 3/2011 | Shen et al. |
| 7,982,016 B2 | 7/2011 | Comeau et al. |
| 8,030,467 B2 | 10/2011 | Seth et al. |
| 8,062,640 B2 | 11/2011 | Sleeman et al. |
| 8,080,243 B2 | 12/2011 | Liang et al. |
| 8,101,182 B2 | 1/2012 | Dong et al. |
| 8,232,372 B2 | 7/2012 | Presta et al. |
| 8,545,849 B2 | 10/2013 | Borras et al. |
| 8,715,663 B2 | 5/2014 | Paszty et al. |
| 8,961,964 B2 | 2/2015 | Liu et al. |
| 11,464,857 B2 | 10/2022 | Sloey et al. |
| 2004/0197324 A1 | 10/2004 | Liu et al. |
| 2005/0037084 A1 | 2/2005 | Nomura et al. |
| 2005/0176109 A1 | 8/2005 | Yumioka et al. |
| 2009/0186022 A1 | 7/2009 | Bardroff et al. |
| 2009/0291076 A1 | 11/2009 | Morichika et al. |
| 2012/0270782 A1 | 10/2012 | Gopinath et al. |
| 2013/0171128 A1 | 7/2013 | Huang et al. |
| 2014/0206845 A1 | 7/2014 | Kameoka et al. |
| 2014/0370003 A1 | 12/2014 | Winter |
| 2015/0004174 A1 | 1/2015 | Wasserman et al. |
| 2017/0333559 A1 | 11/2017 | Sloey et al. |
| 2018/0237501 A1 | 8/2018 | Sloey et al. |

FOREIGN PATENT DOCUMENTS

| | | |
|---|---|---|
| EP | 0804163 B1 | 11/2003 |
| EP | 1977763 A1 | 10/2008 |
| EP | 2080504 A2 | 7/2009 |
| JP | 2011-067202 A | 4/2011 |
| WO | 1990/000397 A1 | 1/1990 |
| WO | 1999/024063 A1 | 5/1999 |
| WO | 2000/024782 A2 | 5/2000 |
| WO | 2002/038170 A2 | 5/2002 |

(Continued)

OTHER PUBLICATIONS

Office Action in Chinese Patent Application No. 202210048275.7 dated Oct. 18, 2024 with English translation.
Office Action in U.S. Appl. No. 18/383,121 dated Jan. 3, 2025.
Examination report No. 1 in Australian Patent Application No. 2021200990 dated Feb. 28, 2022.
Office Action in Brazilian Patent Application No. 1120190173935 dated Jul. 9, 2024 with machine translation.
Office Action in Chinese Patent Application No. 201880025966.7 dated Sep. 15, 2022 with English translation.
Office Action in Argentinian Patent Application No. P20180100397 dated Sep. 19, 2024 with machine translation.

(Continued)

*Primary Examiner* — Zachary C Howard
(74) *Attorney, Agent, or Firm* — Julie J. Hong

(57) ABSTRACT

Provided herein are formulations of PCSK9-binding polypeptides, such as those comprising evolocumab, that comprise N-acetyl arginine and have reduced viscosities when compared to formulations lacking N-acetyl arginine. Provided herein are also methods of formulating such compositions that are advantageous in that they conserve certain components. Such formulations comprising PCSK9-binding polypeptides can be administered to patients to treat and/or prevent PCSK9-related diseases, conditions, and disorders.

12 Claims, 36 Drawing Sheets

Specification includes a Sequence Listing.

(56) References Cited

FOREIGN PATENT DOCUMENTS

| | | |
|---|---|---|
| WO | 2004/055164 A2 | 7/2004 |
| WO | 2004/066957 A2 | 8/2004 |
| WO | 2007/074880 A1 | 7/2007 |
| WO | 2009/026558 A1 | 2/2009 |
| WO | 2009/073569 A2 | 6/2009 |
| WO | 2011/095543 A1 | 8/2011 |
| WO | 2011/104381 A2 | 9/2011 |
| WO | 2011/139718 A1 | 11/2011 |
| WO | 2013/166448 A1 | 11/2013 |
| WO | 2013/186230 A1 | 12/2013 |
| WO | 2012/154999 A1 | 11/2015 |
| WO | 2015/173782 A1 | 11/2015 |
| WO | 2016/065181 A1 | 4/2016 |
| WO | 2016/087569 A1 | 6/2016 |
| WO | 2018/064307 A2 | 4/2018 |
| WO | 2018/067987 A1 | 4/2018 |

OTHER PUBLICATIONS

Office Action in Uruguayan Patent Application No. 37611 dated Sep. 10, 2024 with English translation.
Office Action in Canadian Patent Application No. 3,053,394 dated Aug. 2, 2023.
Office Action in Korean Patent Application No. 10-2019-7026969 dated Aug. 28, 2023 with English translation.
Examination report No. 1 in Australian Patent Application No. 2018224095 dated Feb. 16, 2024.
Office Action in Chilean Patent Application No. 201902362 dated Nov. 7, 2023 with English translation.
Office Action in Chinese Patent Application No. 201880025966.7 dated Jan. 16, 2024 with English translation.
Office Action in Eurasian Patent Application No. 202191513 dated Aug. 31, 2023 with English translation.
Office Action in Indian Application No. 201917034377 dated Jan. 17, 2024.
Office Action in Korean Patent Application No. 10-2019-7026969 dated Jan. 30, 2024 with English translation.
Arakawa et al., "Suppression of Protein Interactions by Arginine: A Proposed Mechanism of the Arginine Effects," *Biophys. Chem.* 127(1):1-8 (2007).
Chaudhri et al., "The Role of Amino Acid Sequence in the Self-Association of Therapeutic Monoclonal Antibodies: Insights from Coarse-Grained Modeling," *J. Phys. Chem. B* (2013), 117(5):1269-1279.
Cheng et al., "Linking the Solution Viscosity of an IgG2 Monoclonal Antibody to its Structure as a Function of pH and Temperature," *J. Pharm Sci.* 102:4291-4304 (2013).
Chennamsetty et al., "Design of Therapeutic Proteins with Enhanced Stability," *Proceedings of the National Academy of Sciences of the United States of America* (2009), 106:11937-11942.
Communication in EP Patent Application No. 18710193.6 dated Nov. 12, 2019.
Communication in EP Patent Application No. 18710193.6 dated Apr. 3, 2023.
Connolly et al., "Weak Interactions Govern the Viscosity of Concentrated Antibody Solutions: High-Throughput Analysis Using the Diffusion Interaction Parameter," *Biophys. J.* (2012), 103:69-78.
Ferrara et al., "Recombinant renewable polyclonal antibodies," 2015, mAbs, vol. 7, Issue 1: pp. 32-42, Taylor & Francis Group, LLC.
Guo et al., "Structure-Activity Relationship for Hydrophobic Salts as Viscosity-Lowering Excipients for Concentrated Solutions of Monoclonal Antibodies," *Pharm Res* (2012), 29(11):3102-3109.
Hamada et al., "Effect of Additives on Protein Aggregation," *Curr. Pharm. Biotechnol.* (2009) 10(4):400-407.
Inoue et al., "Arginine and Lysine Reduce the High Viscosity of Serum Albumin Solutions for Pharmaceutical Injection," *Journal of Bioscience and Bioengineering* 117(5):539-543 (2014).
Ishibashi et al., "Is Arginine a Protein-Denaturant?," *Protein Expr. Purif* 42(1):1-6 (2005).
Joshi et al. "Aggregation of Monoclonal Antibody Products: Formation and Removal," *BioPharm International* 26(3) : 1-7 (2013).
Jouyban et al., "Review of Pharmaceutical Applications of N-Methyl-2-Pyrrolidone," *J. Pharm. Pharmaceut.* Sci. (2010), 13(4):524-535.
Kamerzell et al., "Polar Solvents Decrease the Viscosity of High Concentration IgG1 Solutions through Hydrophobic Solvation and Interaction: Formulation and Biocompatibility Considerations," *J. Pharm Sci* (2013), 102(4):1182-1193.
Ketchem et al., "Mitigation of monoclonal antibody viscosity by modification of protein surface charge," *Ninth Annual PEGS Summit*, Apr. 29-May 3, 2013, Boston, MA (2013).
Li et al., "Concentration Dependent Viscosity of Monoclonal Antibody Solutions: Explaining Experimental Behavior in Terms of Molecular Properties," *Pharm. Res. 31* (2014), 3161-3178.
Neergaard et al., "Viscosity of High Concentration Protein Formulations of Monoclonal Antibodies of The IgGI And IgG4 Subclass— Prediction Of Viscosity Through Protein-Protein Interaction Measurements," *Eur. J. Pharm Sci.* (2013), 49(3):400-410.
Nichols et al., "Rational Design of Viscosity Reducing Mutants of a Monoclonal Antibody: Hydrophobic Versus Electrostatic Inter-Molecular Interactions," *mAbs* (2015), 7(1):212-230.
Notice of Allowance and Fees Due dated May 18, 2022 in U.S. Appl. No. 15/902,775.
Office Action in Brazilian Patent Application No. 1120170081253 dated Feb. 7, 2023 with machine translation.
Office Action in Brazilian Patent Application No. 1120170081253 dated May 16, 2023 with machine translation.
Office Action dated Mar. 31, 2020 in Chinese Application No. 201580057461.5 (with English Translation).
Office Action in Eurasian Patent Application No. 201991951 dated Dec. 21, 2022 with English translation.
Office Action in Israeli Patent Application No. 287947 dated Feb. 16, 2023.
Office Action in Japanese Patent Application No. 2018-023742 dated Oct. 4, 2022 with English translation.
Office Action in Japanese Patent Application No. 2021-170676 dated Dec. 13, 2022 with English translation.
Office Action in Korean Patent Application No. 10-2019-7026969 dated Feb. 9, 2023 with English translation.
Office Action in Mexican Patent Application No. MX/a/2019/009952 dated May 24, 2023 with English translation.
Office Action dated Dec. 26, 2019 in U.S. Appl. No. 15/902,775.
Office Action dated Jul. 31, 2020 in U.S. Appl. No. 15/902,775.
Office Action dated Dec. 20, 2021 in U.S. Appl. No. 15/902,775.
Rudikoff et al., "Single Amino Acid Substitution Altering Antigen-Binding Specificity", Proc. Natl. Acad. Sci. U S A., vol. 79, pp. 1979-1983 (1982).
Sharma et al., "In silico Selection of Therapeutic Antibodies for Development: Viscosity, Clearance, and Chemical Stability," *Proc. Natl. Acad. Sci. U. S. A 111* (2014), 18601-18606.
Singh et al., "Dipole-Dipole Interaction in Antibody Solutions: Correlation with Viscosity Behavior at High Concentration," *Pharm Res* (2014), 31(9):2549-2558.
Tsumoto et al., "Review: Why is Arginine Effective in Suppressing Aggregation?" *Protein & Peptide Letters* (2005) 12:613-619.
Wang et al., "Viscosity-Lowering Effect of Amino Acids and Salts on Highly Concentrated Solutions of Two IgGI Monoclonal Antibodies," *Mol. Pharmaceutics* 12(12):4478-4487 (2015).
Yadav et al., "Specific Interactions in High Concentration Antibody Solutions Resulting in High Viscosity," *J. Pharm. Sci.* 99(3):1152-1168 (2010).
Yadav et al., "Viscosity Behavior of High-Concentration Monoclonal Antibody Solutions: Correlation with Interaction Parameter and Electroviscous Effects," *J. Pharm Sci.* 101(3):998-1011 (2012).
Office Action in Brazilian Patent Application No. 1120170081253 dated Oct. 25, 2022 with machine translation.
Office Action in Japanese Patent Application No. 2018-023742 dated Jun. 6, 2023 with English translation.
Office Action in Japanese Patent Application No. 2021-170676 dated Jun. 6, 2023 with English translation.
Notice of Allowance and Fees Due in U.S. Appl. No. 15/521,057 dated Mar. 17, 2022.

(56) References Cited

OTHER PUBLICATIONS

Notice of Allowance and Fees Due in U.S. Appl. No. 15/521,057 dated Nov. 22, 2022.
Notice of Allowance and Fees Due in U.S. Appl. No. 15/521,057 dated Oct. 2, 2023.
Office Action in U.S. Appl. No. 15/521,057 dated Aug. 31, 2018.
Office Action in U.S. Appl. No. 15/521,057 dated Apr. 2, 2019.
Office Action in U.S. Appl. No. 15/521,057 dated Mar. 13, 2020.
Office Action in U.S. Appl. No. 15/521,057 dated Oct. 23, 2020.
Office Action in U.S. Appl. No. 15/521,057 dated Nov. 30, 2021.
Office Action in Chinese Patent Application No. 201880025966.7 dated Aug. 16, 2023 with English translation.
Office Action in Chinese Patent Application No. 202210048275.7 dated Jul. 29, 2023 with English translation.
Arakawa et al., "Recombinant Production of Native Proteins from *Escherichia coli*", Rational Design of Stable Protein Formulations, Theory and Practice, edited by Carpenter and Manning, Springer (2002), 27-60.
Baynes et al., Rational Design of Solution Additives for the Prevention of Protein Aggregation, *Biophysical Journal* (2004), 87:1631-1639.
Baynes et al., Role of Arginine in the Stabilization of Proteins Against Aggregation, *Biochemistry* (2005), 44:4919-4925.
Binabaji, Elaheh, Ultrafiltration of Highly Concentrated Monoclonal Antibody Solutions, The Pennsylvania State University, The Graduate School, College of Engineering, Thesis (2015) 1-190.
Binabaji et al., Intermolecular Interactions and the Viscosity of Highly Concentrated Monoclonal Antibody Solutions, Pharm. Res. (2015) 32:3102-3109.
Binabaji et al., Theoretical Analysis of the Ultrafiltration Behavior of Highly Concentrated Protein Solutions, Journal of Membrane Science 494 (2015) 216-223.
Binabaji et al., Ultrafiltration of Highly Concentrated Antibody Solutions: Experiments and Modeling for the Effects of Module and Buffer Conditions, *Biotechnol. Prog.* (2016), 32(3): 692-701.
Carpenter and Manning, Rational Design of Stable Protein Formulations, Theory and Practice, *Pharm. Biotech.* (2002), 13:1-222.
Communication dated Jan. 3, 2020 in EP Application No. 15790759.3.
Cunningham et al., Structural and biophysical studies of PCSK9 and its mutants linked to familial hypercholesterolemia, *Nat Struct Mol Biol* (2007), 14(5), 413-419.
Das et al., Inhibition of Protein Aggregation: Supramolecular Assemblies of Arginine Hold the Key, *A. PLoS ONE* (2007), w:e1176.
Examination report No. 1 dated Dec. 11, 2019 in AU Application No. 2015335743.
Examination report No. 2 dated Dec. 3, 2020 in AU Application No. 2015335743.
First Office Action dated Apr. 23, 2019 in Japanese Patent Application No. 2017-522169 (with English translation).
First Office Action dated Dec. 21, 2021 in Japanese Application No. 2018-023742.
First Office Action dated Nov. 4, 2020 in Japanese Patent Application No. 2019- 191701 (with English translation).
First Office Action dated Jan. 8, 2021 in Mexican Application No. MX/a/2017/005243 (with English translation).
Horton et al., "Molecular biology of PCSK9: its role LDL metabolism", Trends Biochem Sci., vol. 32 (2), pp. 71-77 (2007).
Inoue et al., Specific Decrease in Solution Viscosity of Antibodies by Arginine for Therapeutic Formulations, *Molecular pharmaceutics* (2014), 11:1889-1896.
International Search Report dated Dec. 16, 2015 in PCT Application No. PCT/US2015/056972.
International Search Report dated May 9, 2018 in PCT Application No. PCT/US2018/019189.
Jezek et al., "Viscosity of concentrated therapeutic protein compositions," Advanced Drug Delivery Reviews 63 (2011) pp. 1107-1117.
Lutz et al., High Concentration Biotherapeutic Formulation and Ultrafiltration: Part 1 Pressure Limits, *Biotechnol. Prog.* (2016), 00(00):1-12.
Notice of Preliminary Rejection dated Jul. 26, 2022 for Korean Patent Application 10-2017-7011706 with English translation.
Office Action dated Nov. 29, 2021 in Canadian Application No. 2,964,78.6.
Office Action dated Jun. 1, 2022 in Chilean patent application 201700984 with English translation.
Office Action dated Feb. 19, 2021in CL Application No. 201902190 (with English translation).
Office Action dated Oct. 22, 2020 in Chilean Application No. 201902362.
Office Action and Search Report in Chilean Patent Application No. 201902362 dated Oct. 29, 2021 with summary English translation.
Office Action dated Apr. 15, 2021 in Chinese Application No. 201580057461.5 (with English translation).
Official Action dated Dec. 18, 2017 in Eurasia Application No. 201790787 (with English translation).
Office Action dated Mar. 22, 2021 in EA Application No. 201991951.
Office Action dated Nov. 18, 2019 in Indian Application No. 201717014850.
Office Action dated May 6, 2020 in Israel Application No. 251726 (with English translation).
Second Office Action dated Jun. 15, 2021 in Mexican Application No. MX/a/2017/005243 (with English translation).
Piper et al., "The crystal structure of PCSK9: a regulator of plasma LDL-cholesterol", Structure, vol. 15 (5), pp. 545-552 (2007).
Rishi et al., Role of Non-Compatible Osmolytes in the Stabilization of Proteins During Heat Stress, Biochem. J. (1998), 329:137-143.
Schneider et al., "Arginine and the Hofmeister Series: The Role of Ion-Ion Interactions in Protein Aggregation Suppression," *J. Phys. Chem B*. (2011), 115(2):7447-7458.
Schneider et al., "Effects of Solute-Solute Interactions on Protein Stability Studied Using Various Counterions and Dendrimers," PloS ONE (2011), 6:e27665.
Seidah et al., "The Secretory Proprotein Convertase Neural Apoptosis-Regulated Convertase 1 (NARC-1): Liver Regeneration and Neuronal Differentiation," PNAS, vol. 100 (3), pp. 928-933 (Feb. 4, 2003).
Seidah et al., "The proprotein convertases are potential 2011 targets in the treatment of dyslipidemia," *J Mol Med* (Berl)(2007), 85(7), 685-696.
Shukla et al., "Complex Interactions between Molecular Ions in Solution and Their Effect on Protein Stability," *J. Am. Chem. Soc.* (2011), 133:18713-18718.
Shulka et al., "Interaction of Arginine with Proteins and the Mechanism by which it Inhibits Aggregation," *The Journal of Physical Chemistry. B* (2010), 114:13426-13438.
Shulka et al., "Molecular Level Insight into Intra-Solvent Interaction Effects on Protein Stability and Aggregation," *Advanced Drug Delivery Reviews* (2011), 63:1074-1085.
Srivastava et al., "Viscosity Reduction and Stability Enhancement of Monoclonal Antibody Formulations Using Derivatives of Amino Acids," *Journal of Pharmaceutical Sciences*, (2022) pp. 1-9, in press, corrected proof DOI: 10.1016/j.xphs.2022.05.011.
Tsumoto et al., "Role of Arginine in Protein Refolding, Solubilization, and Purification," *Biotechnol. Prog.* (2004), 20:1301-08.
Voynov et al., "Predictive Tools for Stabilization of Therapeutic Proteins." *mAbs* (2009), 1:580-582.
Written Opinion dated Dec. 16, 2015 in PCT Application No. PCT/US2015/056972.
Written Opinion dated May 9, 2018 in PCT Application No. PCT/US2018/019189.
Written Opinion dated Jul. 14, 2020 in SG Application No. 11201703152R.
Written Opinion dated Jan. 29, 2021 in SG Application No. 11201907505T.
Yadav et al., "The Influence of Charge Distribution on Self-Association and Viscosity Behavior of Monoclonal Antibody Solutions," *Mol. Pharm* (2012), 9(4):791-802.
International Preliminary Report on Patentability in PCT Application No. PCT/US2015/056972 dated May 4, 2017.

(56) References Cited

OTHER PUBLICATIONS

International Preliminary Report on Patentability in PCT Application No. PCT/US2018/019189 dated Sep. 6, 2019.
Office Action in Chinese Patent Application No. 202210048275.7 dated Jun. 8, 2024 with English translation.
Office Action in Korean Patent Application No. 10-2024-7014122 dated Aug. 30, 2024 with English translation.
Office Action in Mexican Patent Application No. MX/a/2021/015789 dated Jul. 10, 2024 with English translation.
Office Action in Uruguayan Patent Application No. 37611 dated May 10, 2024 with English translation.
Written Opinion in Singaporean Application No. 11201907505T dated Sep. 2, 2022.
Written Opinion in Singaporean Application No. 11201907505T dated May 30, 2024.

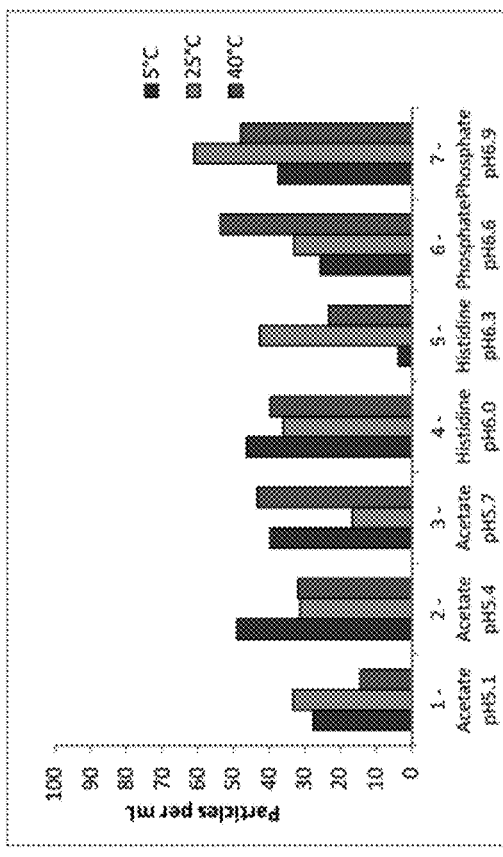
FIGURE 21A
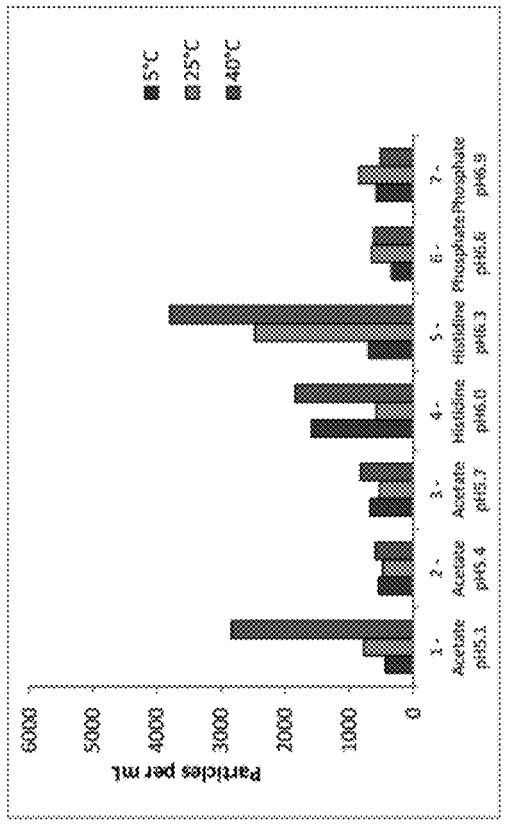
FIGURE 21B
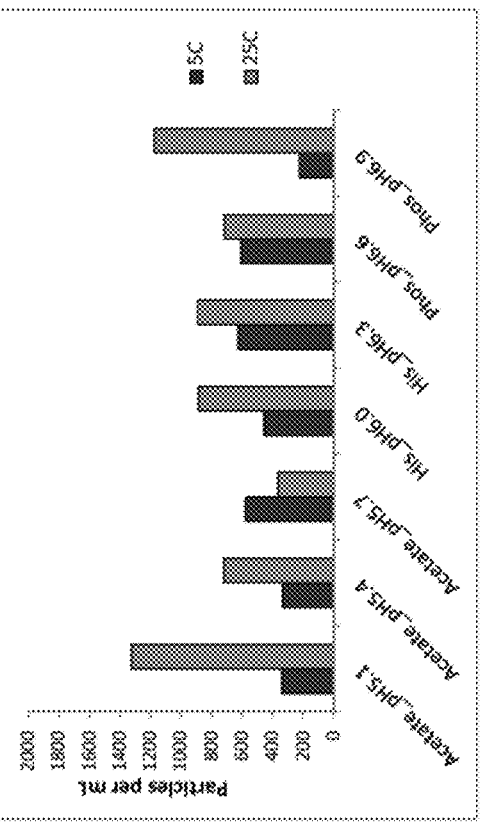
FIGURE 21C
FIGURE 21D

Evolocumab NAR DS pH5.2 SE-HPLC

Evolocumab NAR DS pH5.2 CE - HPLC

Evolocumab NAR DS pH5.4 SE-HPLC

Evolocumab NAR DS pH5.4 CE - HPLC

Evolocumab NAR DS pH5.6 SE-HPLC

Evolocumab NAR DS pH5.6 CE - HPLC

SEQUENCE LISTING

```
Sequence total quantity: 17
SEQ ID NO: 1            moltype = AA  length = 441
FEATURE                 Location/Qualifiers
source                  1..441
                        mol_type = protein
                        organism = Homo sapiens
SEQUENCE: 1
EVQLVQSGAE VKKPGASVKV SCKASGYTLT SYGISWVRQA PGQGLEWMGW VSFYNGNTNY  60
AQKLQGRGTM TTDPSTSTAY MELRSLRSDD TAVYYCARGY GMDVWGQGTT VTVSSASTKG 120
PSVFPLAPCS RSTSESTAAL GCLVKDYFPE PVTVSWNSGA LTSGVHTFPA VLQSSGLYSL 180
SSVVTVPSSN FGTQTYTCNV DHKPSNTKVD KTVERKCCVE CPPCPAPPVA GPSVFLFPPK 240
PKDTLMISRT PEVTCVVVDV SHEDPEVQFN WYVDGVEVHN AKTKPREEQF NSTFRVVSVL 300
TVVHQDWLNG KEYKCKVSNK GLPAPIEKTI SKTKGQPREP QVYTLPPSRE EMTKNQVSLT 360
CLVKGFYPSD IAVEWESNGQ PENNYKTTPP MLDSDGSFFL YSKLTVDKSR WQQGNVFSCS 420
VMHEALHNHY TQKSLSLSPG K                                          441

SEQ ID NO: 2            moltype = AA  length = 215
FEATURE                 Location/Qualifiers
source                  1..215
                        mol_type = protein
                        organism = Homo sapiens
SEQUENCE: 2
ESALTQPASV SGSPGQSITI SCTGTSSDVG GYNSVSWYQQ HPGKAPKLMI YEVSNRPSGV  60
SNRFSGSKSG NTASLTISGL QAEDEADYYC NSYTSTSMVF GGGTKLTVLG QPKAAPSVTL 120
FPPSSEELQA NKATLVCLIS DFYPGAVTVA WKADSSPVKA GVETTTPSKQ SNNKYAASSY 180
LSLTPEQWKS HRSYSCQVTH EGSTVEKTVA PTECS                           215

SEQ ID NO: 3            moltype = AA  length = 692
FEATURE                 Location/Qualifiers
source                  1..692
                        mol_type = protein
                        organism = Homo sapiens
SEQUENCE: 3
MGTVSSRRSW WPLPLLLLLL LLLGPAGARA QEDEDGDYEE LVLALRSEED GLAEAPEHGT  60
TATFHRCAKD PWRLPGTYVV VLKEETHLSQ SERTARRLQA QAARRGYLTK ILHVFHGLLP 120
GFLVKMSGDL LELALKLPHV DYIEEDSSVF AQSIPWNLER ITPPRYRADE YQPPDGGSLV 180
EVYLLDTSIQ SDHREIEGRV MVTDFENVPE EDGTRFHRQA SKCDSHGTHL AGVVSGRDAG 240
VAKGASMRSL RVLNCQGKGT VSGTLIGLEF IRKSQLVQPV GPLVVLLPLA GGYSRVLNAA 300
CQRLARAGVV LVTAAGNFRD DACLYSPASA PEVITVGATN AQDQPVTLGT LGTNFGRCVD 360
LFAPGEDIIG ASSDCSTCFV SQSGTSQAAA HVAGIAAMML SAEPELTLAE LRQRLIHFSA 420
KDVINEAWFP EDQRVLTPNL VAALPPSTHG AGWQLFCRTV WSAHSGPTRM ATAIARCAPD 480
EELLSCSSFS RSGKRRGERM EAQGGKLVCR AHNAFGGEGV YAIARCCLLP QANCSVHTAP 540
PAEASMGTRV HCHQQGHVLT GCSSHWEVED LGTHKPPVLR PRGQPNQCVG HREASIHASC 600
CHAPGLECKV KEHGIPAPQG QVTVACEEGW TLTGCSALPG TSHVLGAYAV DNTCVVRSRD 660
VSTTGSTSEE AVTAVAICCR SRHLAQASQE LQ                              692

SEQ ID NO: 4            moltype = AA  length = 14
FEATURE                 Location/Qualifiers
source                  1..14
                        mol_type = protein
                        organism = Homo sapiens
SEQUENCE: 4
TGTSSDVGGY NSVS                                                   14

SEQ ID NO: 5            moltype = AA  length = 7
FEATURE                 Location/Qualifiers
source                  1..7
                        mol_type = protein
                        organism = Homo sapiens
SEQUENCE: 5
EVSNRPS                                                            7

SEQ ID NO: 6            moltype = AA  length = 9
FEATURE                 Location/Qualifiers
source                  1..9
                        mol_type = protein
                        organism = Homo sapiens
SEQUENCE: 6
NSYTSTSMV                                                          9
```

-continued

```
SEQ ID NO: 7              moltype = AA   length = 10
FEATURE                   Location/Qualifiers
source                    1..10
                          mol_type = protein
                          organism = Homo sapiens
SEQUENCE: 7
GYTLTSYGIS                                                              10

SEQ ID NO: 8              moltype = AA   length = 16
FEATURE                   Location/Qualifiers
source                    1..16
                          mol_type = protein
                          organism = Homo sapiens
SEQUENCE: 8
WVSFYNGNTN YAQKLQ                                                       16

SEQ ID NO: 9              moltype = AA   length = 6
FEATURE                   Location/Qualifiers
source                    1..6
                          mol_type = protein
                          organism = Homo sapiens
SEQUENCE: 9
GYGMDV                                                                   6

SEQ ID NO: 10             moltype = DNA  length = 345
FEATURE                   Location/Qualifiers
source                    1..345
                          mol_type = other DNA
                          organism = Homo sapiens
SEQUENCE: 10
caggttcagc tggtgcagtc tggagctgag gtgaagaagc ctggggcctc agtgaaggtc        60
tcctgcaagg cttctggtta cacccttaacc agctatggta tcagctgggt gcgacaggcc     120
cctggacaag ggcttgagtg gatgggatgg tcagttttt ataatggtaa cacaaactat       180
gcacagaagc tccagggcag aggcaccatg accacagacc catccacgag cacagcctac     240
atggagctga ggagcctgag atctgacgac acggccgtgt attactgtgc gagaggctac     300
ggtatgacgc tctggggcca agggaccacg gtcaccgtct cctct                      345

SEQ ID NO: 11             moltype = DNA  length = 327
FEATURE                   Location/Qualifiers
source                    1..327
                          mol_type = other DNA
                          organism = Homo sapiens
SEQUENCE: 11
cagtctgccc tgactcagcc tgcctccgtg tctgggtctc ctggacagtc gatcaccatc        60
tcctgcactg gaaccagcag tgacgttggt ggttataact ctgtctcctg gtaccaacag     120
cacccaggca aagcccccaa actcatgatt tatgaggtca gtaatcggcc ctcaggggtt     180
tctaatcgct tctctggctc caagtctggc aacacggcct ccctgaccat ctctgggctc     240
caggctgagg acgaggctga ttattactgc aattcatata caagcaccag catggtattc     300
ggcggaggga ccaagctgac cgtccta                                          327

SEQ ID NO: 12             moltype = DNA  length = 1380
FEATURE                   Location/Qualifiers
source                    1..1380
                          mol_type = other DNA
                          organism = Homo sapiens
SEQUENCE: 12
atggactgga cctggaggat ccttttcttg gtggcagcag ccacaggtgt ccactccgag        60
gttcagctgg tgcagtctgg agctgaggtg aagaagcctg gggcctcagt gaaggtctcc     120
tgcaaggctt ctggttacac cttaaccagc tatggtatca gctgggtgcg acaggcccct     180
ggacaagggc ttgagtggat gggatgggtc agttttttata atggtaacac aaactatgca     240
cagaagctcc agggcagagg caccatgacc acagacccat ccacgagcac agcctacatg     300
gagctgagga gcctgagatc tgacgacacg gccgtgtatt actgtgcgag aggctacggt     360
atggacgtct ggggccaagg gaccacggtc accgtctcca gcaagggccca              420
tcggtcttcc ccctggcgcc ctgctccagg agcacctccg agagcacagc ggccctgggc     480
tgcctggtca aggactactt ccccgaaccg gtgacggtgt cgtggaactc aggcgctctg     540
accagcggcg tgcacacctt cccagctgtc ctacagtcct caggactcta ctccctcagc     600
agcgtggtga ccgtgccctc cagcaacttc ggcacccaga cctacacctg caacgtagat     660
cacaagccca gcaacaccaa ggtggacaag acagttgagc gcaaatgttg tgtcgagtgc     720
ccaccgtgcc cagcaccacc tgtggcagga ccgtcagtct tcctcttccc cccaaaaccc     780
aaggacaccc tcatgatctc ccggacccct gaggtcacgt gcgtggtggt ggacgtgagc     840
cacgaagacc ccgaggtcca gttcaactgg tacgtggacg gcgtggaggt gcataatgcc     900
aagacaaagc cacgggagga gcagttcaac agcacgttcc gtgtggtcag cgtcctcacc     960
gttgtgcacc aggactggct gaacggcaag gagtacaagt gcaaggtctc caacaaaggc    1020
ctcccagccc ccatcgagaa aaccatctcc aaaaccaaag gcagccccg agaaccacag    1080
gtgtacaccc tgcccccatc ccgggaggag atgaccaaga accaggtcag cctgacctgc    1140
ctggtcaaag gcttctaccc cagcgacatc gccgtggagt gggagagcaa tgggcagccg    1200
gagaacaact acaagaccac acctcccatg ctggactccg acggctcctt cttcctctac    1260
agcaagctca ccgtggacaa gagcaggtgg cagcagggga acgtctttc atgctccgtg    1320
```

```
atgcatgagg ctctgcacaa ccactacacg cagaagagcc tctccctgtc tccgggtaaa   1380

SEQ ID NO: 13           moltype = DNA  length = 711
FEATURE                 Location/Qualifiers
source                  1..711
                        mol_type = other DNA
                        organism = Homo sapiens
SEQUENCE: 13
atggacatga gggtgcccgc tcagctcctg gggctcctgc tgctgtggct gagaggtgcc    60
agatgtgagt ctgccctgac tcagcctgcc tccgtgtctg ggtctcctgg acagtcgatc   120
accatctcct gcactggaac cagcagtgac gttggtggtt ataactctgt ctcctggtac   180
caacagcacc caggcaaagc ccccaaactc atgatttatg aggtcagtaa tcggccctca   240
gggggtttcta atcgcttctc tggctccaag tctggcaaca cggcctccct gaccatctct   300
gggctccagg ctgaggacga ggctgattat tactgcaatt catatacaag caccagcatg   360
gtattcggcg gagggaccaa gctgaccgtc ctaggtcagc ccaaggctgc ccctcggtc    420
actctgttcc cgccctcctc tgaggagctt caagccaaca aggccacact ggtgtgtctc   480
ataagtgact tctacccggg agccgtgaca gtggcctgga aggcagatag cagccccgtc   540
aaggcgggag tggagaccac cacacccctcc aaacaaagca acaacaagta cgcggccagc   600
agctatctga gcctgacgcc tgagcagtgg aagtcccaca gaagctacag ctgccaggtc   660
acgcatgaag ggagcaccgt ggagaagaca gtggccccta cagaatgttc a            711

SEQ ID NO: 14           moltype = AA  length = 115
FEATURE                 Location/Qualifiers
source                  1..115
                        mol_type = protein
                        organism = Homo sapiens
SEQUENCE: 14
QVQLVQSGAE VKKPGASVKV SCKASGYTLT SYGISWVRQA PGQGLEWMGW VSFYNGNTNY    60
AQKLQGRGTM TTDPSTSTAY MELRSLRSDD TAVYYCARGY GMDVWGQGTT VTVSS        115

SEQ ID NO: 15           moltype = AA  length = 109
FEATURE                 Location/Qualifiers
source                  1..109
                        mol_type = protein
                        organism = Homo sapiens
SEQUENCE: 15
QSALTQPASV SGSPGQSITI SCTGTSSDVG GYNSVSWYQQ HPGKAPKLMI YEVSNRPSGV    60
SNRFSGSKSG NTASLTISGL QAEDEADYYC NSYTSTSMVF GGGTKLTVL               109

SEQ ID NO: 16           moltype = AA  length = 115
FEATURE                 Location/Qualifiers
source                  1..115
                        mol_type = protein
                        organism = Homo sapiens
SEQUENCE: 16
QVQLVQSGAE VKKPGASVKV SCKASGYTLT SYGISWVRQA PGQGLEWMGW VSFYNGNTNY    60
AQKLQGRGTM TTDPSTSTAY MELRSLRSDD TAVYYCARGY GMDVWGQGTT VTVSS        115

SEQ ID NO: 17           moltype = AA  length = 109
FEATURE                 Location/Qualifiers
source                  1..109
                        mol_type = protein
                        organism = Homo sapiens
SEQUENCE: 17
QSALTQPASV SGSPGQSITI SCTGTSSDVG GYNSVSWYQQ HPGKAPKLMI YEVSNRPSGV    60
SNRFSGSKSG NTASLTISGL QAEDEADYYC NSYTSTSMVF GGGTKLTVL               109
```

LOW-VISCOSITY, HIGH CONCENTRATION EVOLOCUMAB FORMULATIONS AND METHODS OF MAKING THE SAME

RELATED APPLICATIONS

This application claims the benefit of U.S. Provisional Patent Application No. 62/462,266 filed Feb. 22, 2017, which is incorporated in its entirety by reference herein.

SEQUENCE LISTING

The present application is being filed with a sequence listing in electronic format. The sequence listing provided as a file titled, "A-2112-WO-PCT_sequence_listing_ST25.txt," created Jan. 31, 2018, and is 21 KB in size. The information in the electronic format of the sequence listing is incorporated herein by reference in its entirety.

FIELD

The presented subject matter relates to the field of pharmaceutical compositions of evolocumab and other PCSK9-binding polypeptides and methods of reducing viscosity of such compositions. Specifically, the presented subject matter relates to pharmaceutical compositions of evolocumab and other PCSK9-binding polypeptides comprising N-acetyl arginine, and the use of N-acetyl arginine to decrease viscosity of high-concentration evolocumab and other PCSK9-binding polypeptides formulations. Furthermore, the disclosed subject matter presents methods related to making such pharmaceutical compositions.

BACKGROUND

Therapeutic antibodies are formulated in solution for administration, such as parenteral injection. For products that are administered subcutaneously in self administration, formulations requiring delivery volumes greater than 1-2 milliliters are poorly tolerated. To solve this issue, antibodies can be formulated at high concentrations (e.g., such as 70 mg/mL to 210 mg/mL or greater), thus reducing the size of the dose.

Some highly concentrated antibody formulations can be challenging to manufacture and administer, however. For example, in the formulation of evolocumab (REPATHA®), a monoclonal antibody that binds PCSK9, concentrations of evolocumab above about 70 mg/mL have increased viscosity. However, effective doses of evolocumab are 210 mg Q2W or 420 mg Q4W. High viscosity formulations are not only difficult to handle during manufacturing, including at the bulk and filling stages, but they are also difficult to draw into a syringe and inject, making administration to the patient difficult and unpleasant.

To reduce viscosity of antibody formulations, unmodified arginine, glycine, serine, or proline amino acids have been added to antibody compositions. For example, antibody formulations containing 80 mg/mL of antibody and 75 mg/mL to about 125 mg/mL of arginine can be lyophilized and reconstituted to 120-200 mg/mL; the final arginine concentrations can be 431 mM to 718 mM (Morichika & Kameoka, 2007). While arginine reduced the viscosity of the formulations when compared to controls (Morichika & Kameoka, 2007). Furthermore, the effect of arginine was not sufficient to reduce evolocumab viscosity to desired levels.

There is a need in the art to reduce the viscosity of evolocumab- and other PCSK9-binding polypeptides-containing formulations with compounds that are more efficient than arginine.

SUMMARY

In a first aspect, provided herein is a pharmaceutical composition comprising
a. a PCSK9-binding polypeptide that selected from the group consisting of:
  i. a monoclonal antibody comprising a heavy chain polypeptide having an amino acid sequence of SEQ ID NO:1 and a light chain polypeptide having an amino acid sequence of SEQ ID NO:2 (evolocumab), or an antigen-binding fragment thereof;
  ii. a monoclonal antibody that competes with evolocumab for binding to PCSK9;
  iii. a monoclonal antibody, comprising:
    1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
    2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
  iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;
  v. a monoclonal antibody that binds to PCSK9 at an epitope on PCSK9 that overlaps with an epitope that is bound by an antibody that comprises:
    1. a heavy chain variable region of the amino acid sequence in SEQ ID NO:1; and
    2. a light chain variable region of the amino acid sequence in SEQ ID NO:2, and
    3. wherein the epitope of the monoclonal antibody further overlaps with a site to which an EGF-A domain of LDLR;
and
b. N-acetyl arginine,
wherein the pharmaceutical composition has a viscosity of at least less than about 80 cP. In such first aspect, the PCSK9-binding polypeptide can be a monoclonal antibody that comprises a heavy chain polypeptide comprising the following complementarity determining regions (CDRs):
a. heavy chain CDR1, CDR2, and CDR3 having an amino acid sequence of SEQ ID NOs:7, 8, and 9, respectively; and
b. light chain CDR1, CDR2, and CDR3 having an amino acid sequence of SEQ ID NOs:4, 5, and 6, respectively. Furthermore, in this first aspect, the pharmaceutical composition can have a viscosity of at least less than about 50 cP. The pharmaceutical composition can have an osmolality of about 250 to about 400 mOsm/kg, such as about 300 mOsm/kg, or is isotonic to a human blood cell. The concentration of the PCSK9-binding polypeptide can be from about 140 mg/mL to about 260 mg/mL, such as 210 mg/mL. The N-acetyl arginine can be present at a concentration from about 25 mM to about 230 mM, such as 140 mM to about 170 mM, or 140 mM. The pharmaceutical composition of this aspect can further comprise a buffer, such as a buffer selected from the group consisting of acetate, glutamate, histidine, and phosphate buffers, or a combination thereof. The buffer can be present at a concentration from about 5 mM to about 30 mM. In some cases, the buffer is sodium acetate and is present at a concentration of about 10 mM. The pH of such pharmaceutical compositions can be from about 4.8 to about 6.9, such as a pH of about 5.4. The pharmaceutical compositions of this aspect can further comprise a surfactant, such as a surfactant selected from the group consisting of polyoxyethylenesorbitan monooleate (polysorbate 80 or polysorbate 20), polyoxyethylene-polyoxypropylene block copolymer (Poloxamers such as Pluronic® F-68 and other Pluronics®), Sorbitan alkyl esters (Spans®) Polyethylene glycol octylphenyl ethers (Triton X-100), Polyethylene glycol alkyl ethers (Brij), Polypropylene glycol alkyl ethers, Glucoside alkyl ethers, and D-α-tocopherol polyethylene glycol succinate (vitamin E TPGS). The surfactant can be present at a concentration of about 0.0001% (w/v) to about 1% (w/v). In some pharmaceutical compositions of this aspect, the surfactant is polyoxyethylenesorbitan monooleate (polysorbate 80) and is present at a concentration of about 0.01% (w/v). Furthermore, the pharmaceutical compositions of this aspect can further comprise proline, which can be present at a concentration of about 50 mM to about 150 mM, such as 90 to 120 mM, or about 120 mM. In some cases, the pharmaceutical composition of this first aspect can further comprise an arginine salt, which can be present at a concentration of about 25 mM to about 150 mM, such as about 50 mM to about 100 mM. The arginine salt can be, for example, arginine-HCl, arginine acetate, or arginine glutamate. In some cases, the arginine salt is arginine HCl and is present at a concentration of about 50 mM. The PCSK9-binding polypeptide can be stable for at least about two years or even five years or more when stored at about −30° C. or colder in the pharmaceutical compositions of this first aspect. At 5° C., the PCSK9-binding polypeptide can be stable for at least about six months to about 24 months or more in such pharmaceutical compositions. At 25° C., the PCSK9-binding polypeptide can be stable for at least about one month or longer, three months or longer, or even six months or longer. At 40° C., the PCSK9-binding polypeptide can be stable for at least one month or longer. The pharmaceutical compositions of this first aspect can comprise high molecular weight aggregates or oligomers of PCSK9-binding polypeptides at less than about 3%, such as 2.5% or less, of the total PCSK9-binding polypeptide concentration.

In a second aspect, disclosed herein is a pharmaceutical composition comprising
a. a PCSK9-binding polypeptide that selected from the group consisting of:
i. a monoclonal antibody comprising a heavy chain polypeptide having an amino acid sequence of SEQ ID NO:1 and a light chain polypeptide having an amino acid sequence of SEQ ID NO:2 (evolocumab), or an antigen-binding fragment thereof;
ii. a monoclonal antibody that competes with evolocumab for binding to PCSK9;
iii. a monoclonal antibody, comprising:
1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;
v. a monoclonal antibody that binds to PCSK9 at an epitope on PCSK9 that overlaps with an epitope that is bound by an antibody that comprises:
1. a heavy chain variable region of the amino acid sequence in SEQ ID NO:1; and
2. a light chain variable region of the amino acid sequence in SEQ ID NO:2, and
3. wherein the epitope of the monoclonal antibody further overlaps with a site to which an EGF-A domain of LDLR;

and
b. N-acetyl arginine;
c. an arginine salt;
d. a buffer; and
e. a surfactant
wherein the pharmaceutical composition has a viscosity of at least less than about 80 cP.

In this second aspect, the PCSK9-binding polypeptide is a monoclonal antibody that comprises a heavy chain polypeptide comprising the following complementarity determining regions (CDRs):
a. heavy chain CDR1, CDR2, and CDR3 having an amino acid sequence of SEQ ID NOs:7, 8, and 9, respectively; and
b. light chain CDR1, CDR2, and CDR3 having an amino acid sequence of SEQ ID NOs:4, 5, and 6, respectively.

The pharmaceutical compositions of this second aspect can have a viscosity of at least less than about 50 cP. The pharmaceutical composition can have an osmolality of about 250 to about 400 mOsm/kg, such as about 300 mOsm/kg, or is isotonic to a human blood cell. The concentration of the PCSK9-binding polypeptide can be from about 140 mg/mL to about 260 mg/mL, such as 210 mg/mL. The N-acetyl arginine can be present at a concentration from about 25 mM to about 230 mM, such as 140 mM to about 170 mM, or 140 mM. The pharmaceutical composition of this aspect can further comprise a buffer, such as a buffer selected from the group consisting of acetate, glutamate, histidine, and phosphate buffers, or a combination thereof. The buffer can be present at a concentration from about 5 mM to about 30 mM. In some cases, the buffer is sodium acetate and is present at a concentration of about 10 mM. The pH of such pharmaceutical compositions can be from about 4.8 to about 6.9, such as a pH of about 5.4. The pharmaceutical compositions of this aspect can further comprise a surfactant, such as a surfactant selected from the group consisting of polyoxyethylenesorbitan monooleate (polysorbate 80 or polysorbate 20), polyoxyethylene-polyoxypropylene block copolymer (Poloxamers such as Pluronic® F-68 and other Pluronics®), Sorbitan alkyl esters (Spans®) Polyethylene glycol octylphenyl ethers (Triton X-100), Polyethylene glycol alkyl ethers (Brij), Polypropylene glycol alkyl ethers, Glucoside alkyl ethers, and D-α-tocopherol polyethylene glycol succinate (vitamin E TPGS). The surfactant can be present at a concentration of about 0.0001% (w/v) to about 1% (w/v). In some pharmaceutical compositions of this aspect, the surfactant is polyoxyethylenesorbitan monooleate (polysorbate 80) and is present at a concentration of about 0.01% (w/v). Furthermore, the pharmaceutical compositions of this aspect can further comprise proline; the proline can be present at a concentration of about 50 mM to about 150 mM, such as 90 to 120 mM, or about 120 mM. In some cases, the pharmaceutical composition of this second aspect can further comprise an arginine salt, which can be present at a concentration of about 25 mM to about 150 mM, such as about 50 mM to about 100 mM. The arginine salt can be, for example, arginine-HCl, arginine acetate, or arginine glutamate. In some cases, the arginine salt is arginine HCl and is present at a concentration of about 50 mM. The PCSK9-binding polypeptide can be stable for at least about two years or even five years or more when stored at about −30° C. or colder in the pharmaceutical compositions of this second aspect. At 5° C., the PCSK9-binding polypeptide can be stable for at least about six months to about 24 months or more in such pharmaceutical compositions. At 25° C., the PCSK9-binding polypeptide can be stable for at least about one month or longer, three months or longer, or even six months or longer. At 40° C., the PCSK9-binding polypeptide can be stable for at least one month or longer. The pharmaceutical compositions of this second aspect can comprise high molecular weight aggregates or oligomers of PCSK9-binding polypeptides at less than about 3%, such as 2.5% or less, of the total PCSK9-binding polypeptide concentration.

In a third aspect, disclosed herein is a pharmaceutical composition comprising
  a. a PCSK9-binding polypeptide that at a concentration of about 195-225 mg/mL selected from the group consisting of:
    i. a monoclonal antibody comprising a heavy chain polypeptide having an amino acid sequence of SEQ ID NO:1 and a light chain polypeptide having an amino acid sequence of SEQ ID NO:2 (evolocumab), or an antigen-binding fragment thereof;
    ii. a monoclonal antibody that competes with evolocumab for binding to PCSK9;
    iii. a monoclonal antibody, comprising:
      1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
      2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
    iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;
    v. a monoclonal antibody that binds to PCSK9 at an epitope on PCSK9 that overlaps with an epitope that is bound by an antibody that comprises:
      1. a heavy chain variable region of the amino acid sequence in SEQ ID NO:1; and
      2. a light chain variable region of the amino acid sequence in SEQ ID NO:2, and
      3. wherein the epitope of the monoclonal antibody further overlaps with a site to which an EGF-A domain of LDLR;
  b. N-acetyl arginine present at a concentration of about 140 mM;
  c. arginine HCl present at a concentration of about 50 mM;
  d. polyoxyethylenesorbitan monooleate (polysorbate 80) at a concentration of from about 0.005% (w/v) to about 0.015% (w/v); and
  e. sodium acetate at a concentration of about 10 mM.

In this third aspect, the pharmaceutical composition can have a pH of about 5.1 to about 5.7, such as a pH of about 5.4. The pharmaceutical composition can have a viscosity of at least less than about 50 cP.

In a fourth aspect, disclosed herein is a pharmaceutical composition comprising
  a. a PCSK9-binding polypeptide that at a concentration of about 195-225 mg/mL selected from the group consisting of:
    i. a monoclonal antibody comprising a heavy chain polypeptide having an amino acid sequence of SEQ ID NO:1 and a light chain polypeptide having an amino acid sequence of SEQ ID NO:2 (evolocumab), or an antigen-binding fragment thereof;
    ii. a monoclonal antibody that competes with evolocumab for binding to PCSK9;
    iii. a monoclonal antibody, comprising:
      1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
      2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
    iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;

v. a monoclonal antibody that binds to PCSK9 at an epitope on PCSK9 that overlaps with an epitope that is bound by an antibody that comprises:
1. a heavy chain variable region of the amino acid sequence in SEQ ID NO:1; and
2. a light chain variable region of the amino acid sequence in SEQ ID NO:2, and
b. wherein the epitope of the monoclonal antibody further overlaps with a site to which an EGF-A domain of LDLR;
c. N-acetyl arginine present at a concentration of about 140 mM;
d. arginine HCl present at a concentration of about 63 mM;
e. polyoxyethylenesorbitan monooleate (polysorbate 80) at a concentration of about 0.005% (w/v) to about 0.015%; and
f. sodium acetate at a concentration of about 10 mM.

In this fourth aspect, the pharmaceutical composition can have a pH of about 5.1 to about 5.7, such as a pH of about 5.4. The pharmaceutical composition can have a viscosity of at least less than about 80 cP.

In a fifth aspect, disclosed herein is a pharmaceutical composition comprising
a. a PCSK9-binding polypeptide that at a concentration of about 195-225 mg/mL selected from the group consisting of:
  i. a monoclonal antibody comprising a heavy chain polypeptide having an amino acid sequence of SEQ ID NO:1 and a light chain polypeptide having an amino acid sequence of SEQ ID NO:2 (evolocumab), or an antigen-binding fragment thereof;
  ii. a monoclonal antibody that competes with evolocumab for binding to PCSK9;
  iii. a monoclonal antibody, comprising:
    1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
    2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
  iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;
  v. a monoclonal antibody that binds to PCSK9 at an epitope on PCSK9 that overlaps with an epitope that is bound by an antibody that comprises:
    1. a heavy chain variable region of the amino acid sequence in SEQ ID NO:1; and
    2. a light chain variable region of the amino acid sequence in SEQ ID NO:2, and
    3. wherein the epitope of the monoclonal antibody further overlaps with a site to which an EGF-A domain of LDLR;
b. N-acetyl arginine present at a concentration of about 155 mM;
c. arginine HCl present at a concentration of about 70 mM;
d. polyoxyethylenesorbitan monooleate (polysorbate 80) at a concentration of about 0.005% (w/v) to about 0.015% (w/v); and
e. sodium acetate at a concentration of about 10 mM.

In this fifth aspect, the pharmaceutical composition can have a pH of about 5.1 to about 5.7, such as a pH of about 5.4. The pharmaceutical composition can have a viscosity of at least less than about 45 cP.

In a sixth aspect, disclosed herein is a pharmaceutical composition comprising
a. a PCSK9-binding polypeptide that at a concentration of about 195-225 mg/mL selected from the group consisting of:
  i. a monoclonal antibody comprising a heavy chain polypeptide having an amino acid sequence of SEQ ID NO:1 and a light chain polypeptide having an amino acid sequence of SEQ ID NO:2 (evolocumab), or an antigen-binding fragment thereof;
  ii. a monoclonal antibody that competes with evolocumab for binding to PCSK9;
  iii. a monoclonal antibody, comprising:
    1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
    2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
  iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;
  v. a monoclonal antibody that binds to PCSK9 at an epitope on PCSK9 that overlaps with an epitope that is bound by an antibody that comprises:
    1. a heavy chain variable region of the amino acid sequence in SEQ ID NO:1; and
    2. a light chain variable region of the amino acid sequence in SEQ ID NO:2, and
    3. wherein the epitope of the monoclonal antibody further overlaps with a site to which an EGF-A domain of LDLR;
b. N-acetyl arginine present at a concentration of about 170 mM;
c. arginine HCl present at a concentration of about 63 mM;
d. polyoxyethylenesorbitan monooleate (polysorbate 80) at a concentration of about 0.005% (w/v) to about 0.015%; and
e. sodium acetate at a concentration of about 10 mM.

In this sixth aspect, the pharmaceutical composition can have a pH of about 5.1 to about 5.7, such as a pH of about 5.4. The pharmaceutical composition can have a viscosity of at least less than about 60 cP.

In a seventh aspect, disclosed herein is a pharmaceutical composition comprising
- a. a PCSK9-binding polypeptide that at a concentration of about 195-225 mg/mL selected from the group consisting of:
  - i. a monoclonal antibody comprising a heavy chain polypeptide having an amino acid sequence of SEQ ID NO:1 and a light chain polypeptide having an amino acid sequence of SEQ ID NO:2 (evolocumab), or an antigen-binding fragment thereof;
  - ii. a monoclonal antibody that competes with evolocumab for binding to PCSK9;
  - iii. a monoclonal antibody, comprising:
    1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
    2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
  - iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;
  - v. a monoclonal antibody that binds to PCSK9 at an epitope on PCSK9 that overlaps with an epitope that is bound by an antibody that comprises:
    1. a heavy chain variable region of the amino acid sequence in SEQ ID NO:1; and
    2. a light chain variable region of the amino acid sequence in SEQ ID NO:2, and
    3. wherein the epitope of the monoclonal antibody further overlaps with a site to which an EGF-A domain of LDLR;
- b. N-acetyl arginine present at a concentration of about 155 mM;
- c. proline present at a concentration of about 120 mM;
- d. polyoxyethylenesorbitan monooleate (polysorbate 80) at a concentration of about 0.005% (w/v) to about 0.015% (w/v); and
- e. sodium acetate at a concentration of about 10 mM.

In this seventh aspect, the pharmaceutical composition can have a pH of about 5.1 to about 5.7, such as a pH of about 5.4. The pharmaceutical composition can have a viscosity of at least less than about 60 cP.

In these third through seventh aspects, the PCSK9-binding polypeptide can be stable for at least about two years or even five years or more when stored at about −30° C. or colder in the pharmaceutical compositions of these aspects. At 5° C., the PCSK9-binding polypeptide can be stable for at least about six months to about 24 months or more in such pharmaceutical compositions. At 25° C., the PCSK9-binding polypeptide can be stable for at least about one month or longer, three months or longer, or even six months or longer. At 40° C., the PCSK9-binding polypeptide can be stable for at least one month or longer. The pharmaceutical compositions of these aspects can comprise high molecular weight aggregates or oligomers of PCSK9-binding polypeptides at less than about 3%, such as 2.5% or less, of the total PCSK9-binding polypeptide concentration.

In any of the preceding aspects, the pharmaceutical composition can be a liquid.

In an eighth aspect, disclosed herein is a method of treating a subject in need thereof, comprising administering the pharmaceutical composition of any of the preceding seven aspects.

In a ninth aspect, disclosed herein is a kit comprising a pharmaceutical composition of any of the first through seventh aspects and a delivery device. The delivery device can be selected from the group consisting of a syringe, an injector pen, a body injector, and an autoinjector. The kit can further comprise instructions for administering the pharmaceutical composition using the delivery device.

In a tenth aspect, disclosed herein is a method of preparing a PCSK9-binding polypeptide pharmaceutical composition comprising at least 140 mg/mL of PCSK9-binding polypeptide, comprising adding to a pharmaceutical composition comprising the PCSK9-binding polypeptide an effective amount of N-acetyl arginine, such that the viscosity of the pharmaceutical composition is reduced when compared to the pharmaceutical composition lacking the N-acetyl arginine, and wherein the PCSK9-binding polypeptide is selected from the group consisting of:
- a. a monoclonal antibody comprising a heavy chain polypeptide having an amino acid sequence of SEQ ID NO:1 and a light chain polypeptide having an amino acid sequence of SEQ ID NO:2 (evolocumab), or an antigen-binding fragment thereof;
- b. a monoclonal antibody that competes with evolocumab for binding to PCSK9;
- c. a monoclonal antibody, comprising:
  - i. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
  - ii. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
- d. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238; and
- e. a monoclonal antibody that binds to PCSK9 at an epitope on PCSK9 that overlaps with an epitope that is bound by an antibody that comprises:
  - i. a heavy chain variable region of the amino acid sequence in SEQ ID NO:1; and
  - ii. a light chain variable region of the amino acid sequence in SEQ ID NO:2, and
  - iii. wherein the epitope of the monoclonal antibody further overlaps with a site to which an EGF-A domain of LDLR.

In this tenth aspect, the viscosity of the pharmaceutical composition is less than about 80 cP, or less than about 50 cP. The pharmaceutical composition of method of this aspect can have an osmolality of about 250 to about 400 mOsm/kg, such as about 300 mOsm/kg, or is isotonic to a human blood cell. The concentration of the PCSK9-binding polypeptide can be from about 140 mg/mL to about 260 mg/mL, such as 210 mg/mL. The N-acetyl arginine can be present at a concentration from about 25 mM to about 230 mM, such as 140 mM to about 170 mM, or 140 mM. The pharmaceutical composition of this aspect can further comprise a buffer, such as a buffer selected from the group consisting of acetate, glutamate, histidine, and phosphate buffers, or a combination thereof. The buffer can be present at a concentration from about 5 mM to about 30 mM. In some cases, the buffer is sodium acetate and is present at a concentration of about 10 mM. The pH of such pharmaceutical compositions can be from about 4.8 to about 6.9, such as a pH of about 5.4. The pharmaceutical compositions of this aspect can further comprise a surfactant, such as a surfactant selected from the group consisting of polyoxyethylenesorbitan monooleate (polysorbate 80 or polysorbate 20), polyoxyethylene-polyoxypropylene block copolymer (Poloxamers such as Pluronic® F-68 and other Pluronics®), Sorbitan alkyl esters (Spans®) Polyethylene glycol octylphenyl ethers (Triton X-100), Polyethylene glycol alkyl ethers (Brij), Polypropylene glycol alkyl ethers, Glucoside alkyl ethers, and D-α-tocopherol polyethylene glycol succinate (vitamin E TPGS). The surfactant can be present at a concentration of about 0.0001% (w/v) to about 1% (w/v). In some pharmaceutical compositions of this aspect, the surfactant is polyoxyethylenesorbitan monooleate (polysorbate 80) and is present at a concentration of about 0.01% (w/v). Furthermore, the pharmaceutical compositions of this aspect can further comprise proline; the proline can be present at a concentration of about 50 mM to about 150 mM, such as 90 to 120 mM, or about 120 mM. In some cases, the pharmaceutical composition of this tenth aspect can further comprise an arginine salt, which can be present at a concentration of about 25 mM to about 150 mM, such as about 50 mM to about 100 mM. The arginine salt can be, for example, arginine-HCl, arginine acetate, or arginine glutamate. In some cases, the arginine salt is arginine HCl and is present at a concentration of about 50 mM. The PCSK9-binding polypeptide can be stable for at least about two years or even five years or more when stored at about −30° C. or colder in the pharmaceutical compositions of this tenth aspect. At 5° C., the PCSK9-binding polypeptide can be stable for at least about six months to about 24 months or more in such pharmaceutical compositions. At 25° C., the PCSK9-binding polypeptide can be stable for at least about one month or longer, three months or longer, or even six months or longer. At 40° C., the PCSK9-binding polypeptide can be stable for at least one month or longer. The pharmaceutical compositions of this tenth aspect can comprise high molecular weight aggregates or oligomers of PCSK9-binding polypeptides at less than about 3%, such as 2.5% or less, of the total PCSK9-binding polypeptide concentration.

In an eleventh aspect, disclosed herein is a method of formulating a therapeutic polypeptide, comprising
  a. a first concentration step, wherein the polypeptide in a first solution is concentrated;
  b. a first solution exchange step, wherein the concentrated polypeptide in the first solution is exchanged into a second solution comprising N-acetyl arginine using diafiltration;
  c. a second concentration step, wherein the polypeptide in the second solution is concentrated;
  d. a second solution exchange step, wherein the polypeptide in the concentrated second solution is exchanged into a third solution comprising N-acetyl arginine using diafiltration; and
  e. a third concentration step, wherein the polypeptide in the third solution is concentrated;
  wherein the therapeutic polypeptide comprises a PCSK9-binding polypeptide that blocks binding of PCSK9 to LDLR and is selected from the group consisting of:
    i. a monoclonal antibody comprising a heavy chain having an amino acid sequence of SEQ ID NO:1 and a light chain having an amino acid sequence of SEQ ID NO:2 (evolocumab), or an antigen-binding fragment thereof;
    ii. a monoclonal antibody that competes with evolocumab for binding to PCSK9;
    iii. a monoclonal antibody, comprising:
      1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
      2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
    iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, D238, K243, S373, D374, S376, T377, F379, I154, T1897, H193, E195, I196, M201, V202, C223, T228, S235, G236, A239, G244, M247, I369, S372, C375, C378, R237, D238;
    v. a monoclonal antibody that binds to PCSK9 at an epitope on PCSK9 that overlaps with an epitope that is bound by an antibody that comprises:
      1. a heavy chain variable region of the amino acid sequence in SEQ ID NO:1; and
      2. a light chain variable region of the amino acid sequence in SEQ ID NO:2, and
      3. wherein the epitope of the monoclonal antibody further overlaps with a site to which an EGFa domain of LDLR.

In the methods of this eleventh aspect, the PCSK9-binding polypeptide that blocks binding of PCSK9 to LDLR can be a monoclonal antibody that comprises a heavy chain polypeptide comprising the following complementarity determining regions (CDRs):
  a. heavy chain CDR1, CDR2, and CDR3 having an amino acid sequence of SEQ ID NOs: 7, 8, and 9, respectively; and
  b. light chain CDR1, CDR2, and CDR3 having an amino acid sequence of SEQ ID NOs: 4, 5, and 6, respectively.

Furthermore, in this eleventh aspect, before the third concentration step, the temperature of the solution comprising the polypeptide can be increased from about 25° C. to about 37° C. Also, the first solution exchange step can be accomplished using at least three diavolumes of the second solution. In some sub-aspects of this eleventh aspect, the second solution exchange step is accomplished using at least four diavolumes of the third solution. In other sub-aspects, the initial concentration of the therapeutic protein is about 11 mg/mL or less. Additionally, the therapeutic polypeptide concentration can be increased from about 3- to about 7-fold, such as, for example, where the increased concentration of the polypeptide is from about 35 mg/mL to about 70 mg/mL. In some sub-aspects, in the second concentration step, the therapeutic polypeptide concentration is increased from about 2- to 4-fold from the first concentration step, such as to about 140 mg/mL, for example. In the third concentration step, the therapeutic polypeptide concentration can be increased from about 1.5- to about 2-fold from the second concentration step, such as to about 260 mg/mL. The therapeutic polypeptide can therefore have a final concentration that is at least about 19-20-fold more concentrated than the initial concentration of the therapeutic polypeptide, such as about 210 mg/mL. The concentration steps can comprise fed-batch ultrafiltration; furthermore, the second solution and the third solution can be identical. For example, the second or third solution comprising N-acetyl arginine can comprise an arginine salt and a buffer, wherein, for example, the N-acetyl arginine is present at a concentration of about 25 mM to about 230 mM; the arginine salt is Arg HCl, Arg acetate, or Arg glutamate and is present at a concentration of about 25 mM to about 150 mM; and the buffer is a sodium acetate buffer at a concentration of about 5 mM to about 30 mM. In other sub-aspects, the N-acetyl arginine is present at a concentration of about 140 to about 170 mM; the Arg HCl, Arg acetate, or Arg glutamate is present at a concentration of about 63 to about 70 mM and the sodium acetate buffer is present at a concentration of about 10 mM. In yet other sub-aspects, the N-acetyl arginine is present at a concentration of about 140 mM, the Arg HCl, Arg acetate, or Arg glutamate is present at a concentration of about 63 mM, the sodium acetate buffer is present at a concentration of about 10 mM. In further sub-aspects, the N-acetyl arginine is present at a concentration of about 155 mM, the Arg HCl, Arg acetate, or Arg glutamate is present at a concentration of about 70 mM, the sodium acetate buffer is present at a concentration of about 10 mM. In yet other sub-aspects, the N-acetyl arginine is present at a concentration of about 170 mM, the Arg HCl, Arg acetate, or Arg glutamate is present at a concentration of about 63 mM, the sodium acetate buffer is present at a concentration of about 10 mM. Furthermore, the compositions can further comprise proline, wherein the proline is present at a concentration of about 50 mM to about 150 mM. The second or third solution can have a pH from about 4.8 to about 6.9, such as 5.4. In the first and second solution exchange steps, a diafiltration membrane can be used having at least one characteristic selected from the group consisting of:

a. mesh openings that are greater than about 350 µm but less than or equal to about 500 µm;
b. an open area that is greater than about 32% but less than or equal to about 36% of the membrane area;
c. a mesh count of less than about 16.2 n/cm but greater than or equal to about 12.2 n/cm;
d. a wire diameter that is greater than about 270 am but less than or equal to about 340 µm;
e. a basis weight that is greater than about 160 g/m² but less than or equal to 180 g/m²;
f. a thickness greater than about 515 am but less than or equal to about 610 µm;
g. a membrane load of greater than about 1138.1 g/m² but less than or equal to about 1919.3 g/m²; and
h. a maximum feed pressure of about 60 psi.

Furthermore, surfactant can be added to the third solution after being concentrated, such as a surfactant selected from the group consisting of polyoxyethylenesorbitan monooleate (polysorbate 80 or polysorbate 20), polyoxyethylene-polyoxypropylene block copolymer (Poloxamers such as Pluronic® F-68 and other Pluronics®), Sorbitan alkyl esters (Spans®) Polyethylene glycol octylphenyl ethers (Triton X-100), Polyethylene glycol alkyl ethers (Brij), Polypropylene glycol alkyl ethers, Glucoside alkyl ethers, and D-α-tocopherol polyethylene glycol succinate (vitamin E TPGS). The surfactant can be present at a concentration of about 0.0001% (w/v) to about 1% (w/v). In some pharmaceutical compositions of this aspect, the surfactant is polyoxyethylenesorbitan monooleate (polysorbate 80) and is present at a concentration of about 0.01% (w/v).

In a twelfth aspect, disclosed herein is a method of formulating a therapeutic polypeptide, comprising
a. a first concentration step, wherein the polypeptide in a first solution is concentrated using fed-batch ultrafiltration;
b. a first solution exchange step, wherein the concentrated polypeptide in the first solution is exchanged into a second solution comprising N-acetyl arginine, arginine salt, and a buffer, using diafiltration and three diavolumes of the second solution;
c. a second concentration step, wherein the polypeptide in the second solution is concentrated using fed-batch ultrafiltration;
d. a second solution exchange step, wherein the polypeptide in the concentrated second solution is exchanged into third solution comprising N-acetyl arginine, arginine salt, and a buffer using diafiltration and four diavolumes of the third solution;
e. the temperature of the solution comprising the polypeptide is increased from about 25° C. to about 37° C. after the second solution exchange step; and
f. a third concentration step, wherein the polypeptide is further concentrated using fed-batch ultrafiltration concentration;

wherein in the first and second solution exchange steps, a diafiltration membrane is used having at least one characteristic selected from the group consisting of:

a. mesh openings that are greater than about 350 µm but less than or equal to about 500 µm;
b. an open area that is greater than about 32% but less than or equal to about 36% of the membrane area;
c. a mesh count of less than about 16.2 n/cm but greater than or equal to about 12.2 n/cm;
d. a wire diameter that is greater than about 270 µm but less than or equal to about 340 µm;
e. a basis weight that is greater than about 160 g/m² but less than or equal to 180 g/m²;
f. a thickness greater than about 515 am but less than or equal to about 610 µm;
g. a membrane load of greater than about 1138.1 g/m² but less than or equal to about 1919.3 g/m²; and
h. a maximum feed pressure of about 60 psi;

and
wherein the therapeutic polypeptide comprises a PCSK9-binding polypeptide that blocks binding of PCSK9 to LDLR and is selected from the group consisting of:
  i. a monoclonal antibody comprising a heavy chain having an amino acid sequence of SEQ ID NO:1 and a light chain having an amino acid sequence of SEQ ID NO:2 (evolocumab), or an antigen-binding fragment thereof;
  ii. a monoclonal antibody that competes with evolocumab for binding to PCSK9;
  iii. a monoclonal antibody, comprising:
    1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and 2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;

iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, D238, K243, S373, D374, S376, T377, F379, I154, T1897, H193, E195, I196, M201, V202, C223, T228, S235, G236, A239, G244, M247, I369, S372, C375, C378, R237, D238;

v. a monoclonal antibody that binds to PCSK9 at an epitope on PCSK9 that overlaps with an epitope that is bound by an antibody that comprises:
  1. a heavy chain variable region of the amino acid sequence in SEQ ID NO:1; and
  2. a light chain variable region of the amino acid sequence in SEQ ID NO:2, and
  3. wherein the epitope of the monoclonal antibody further overlaps with a site to which an EGFa domain of LDLR.

Furthermore, in this twelfth aspect, the first solution exchange step can be accomplished using at least three diavolumes of the second solution. In some sub-aspects of this twelfth aspect, the second solution exchange step is accomplished using at least four diavolumes of the third solution. In other sub-aspects, the initial concentration of the therapeutic protein is about 11 mg/mL or less. Additionally, the therapeutic polypeptide concentration can be increased from about 3- to about 7-fold, such as, for example, where the increased concentration of the polypeptide is from about 35 mg/mL to about 70 mg/mL. In some sub-aspects, in the second concentration step, the therapeutic polypeptide concentration is increased from about 2- to 4-fold from the first concentration step, such as to about 140 mg/mL, for example. In the third concentration step, the therapeutic polypeptide concentration can be increased from about 1.5- to about 2-fold from the second concentration step, such as to about 260 mg/mL. The therapeutic polypeptide can therefore have a final concentration that is at least about 19-20-fold more concentrated than the initial concentration of the therapeutic polypeptide, such as about 210 mg/mL. The concentration steps can comprise fed-batch ultrafiltration; furthermore, the second solution and the third solution can be identical. The N-acetyl arginine present at a concentration of about 25 mM to about 230 mM; the arginine salt can be Arg HCl, Arg acetate, or Arg glutamate, wherein the Arg HCl, Arg acetate, or Arg glutamate is present at a concentration of about 25 mM to about 150 mM; and the buffer is a sodium acetate buffer at a concentration of about 5 mM to about 30 mM. In other sub-aspects, the N-acetyl arginine is present at a concentration of about 140 to about 170 mM; the Arg HCl, Arg acetate, or Arg glutamate is present at a concentration of about 63 to about 70 mM and the sodium acetate buffer is present at a concentration of about 10 mM. In yet other sub-aspects, the N-acetyl arginine is present at a concentration of about 140 mM, the Arg HCl, Arg acetate, or Arg glutamate is present at a concentration of about 63 mM, the sodium acetate buffer is present at a concentration of about 10 mM. In further sub-aspects, the N-acetyl arginine is present at a concentration of about 155 mM, the Arg HCl, Arg acetate, or Arg glutamate is present at a concentration of about 70 mM, the sodium acetate buffer is present at a concentration of about 10 mM. In yet other sub-aspects, the N-acetyl arginine is present at a concentration of about 170 mM, the Arg HCl, Arg acetate, or Arg glutamate is present at a concentration of about 63 mM, the sodium acetate buffer is present at a concentration of about 10 mM. Furthermore, the compositions can further comprise proline, wherein the proline is present at a concentration of about 50 mM to about 150 mM. The second or third solution can have a pH from about 4.8 to about 6.9, such as 5.4. Furthermore, surfactant can added to the third solution after being concentrated, such as a surfactant selected from the group consisting of polyoxyethylenesorbitan monooleate (polysorbate 80 or polysorbate 20), polyoxyethylene-polyoxypropylene block copolymer (Poloxamers such as Pluronic® F-68 and other Pluronics®), Sorbitan alkyl esters (Spans®) Polyethylene glycol octylphenyl ethers (Triton X-100), Polyethylene glycol alkyl ethers (Brij), Polypropylene glycol alkyl ethers, Glucoside alkyl ethers, and D-α-tocopherol polyethylene glycol succinate (vitamin E TPGS). The surfactant can be present at a concentration of about 0.0001% (w/v) to about 1% (w/v). In some pharmaceutical compositions of this aspect, the surfactant is polyoxyethylenesorbitan monooleate (polysorbate 80) and is present at a concentration of about 0.01% (w/v).

In a thirteenth aspect, disclosed herein is a method of formulating a therapeutic polypeptide, comprising
  a. a first concentration step, wherein the polypeptide in a first solution is concentrated using fed-batch ultrafiltration;
  b. a first solution exchange step, wherein the concentrated polypeptide in the first solution is exchanged into a second using diafiltration and three diavolumes of the second solution;
  c. a second concentration step, wherein the polypeptide in the second solution is concentrated using fed-batch ultrafiltration;
  d. a second solution exchange step, wherein the polypeptide in the concentrated second solution is exchanged into third solution using diafiltration and four diavolumes of the third solution;
  e. the temperature of the solution comprising the polypeptide is increased from about 25° C. to about 37° C. after the second solution exchange step; and
  f. a third concentration step, wherein the polypeptide is further concentrated using fed-batch ultrafiltration concentration;
  g. alternatively, a step adding polyoxyethylenesorbitan monooleate (polysorbate 80) at a concentration of about 0.01% (w/v) to the resulting solution of the third concentration step,
  wherein the second and third solutions comprise a solution selected from the group consisting of a solution comprising about 140 mM N-acetyl arginine, about 50 mM Arg HCl, and about 10 mM sodium acetate, the solution having a pH of about 5.2; a solution comprising about 155 mM N-acetyl arginine, about 70 mM Arg HCl, and about 10 mM sodium acetate, the solution having a pH of about 5.4; and a solution comprising about 170 mM N-acetyl arginine, about 10 mM sodium acetate, the solution having a pH of about 5.6;
  wherein in the first and second solution exchange steps, a diafiltration membrane is used having at least one characteristic selected from the group consisting of:

a. mesh openings that are greater than about 350 μm but less than or equal to about 500 μm;
b. an open area that is greater than about 32% but less than or equal to about 36% of the membrane area;
c. a mesh count of less than about 16.2 n/cm but greater than or equal to about 12.2 n/cm;
d. a wire diameter that is greater than about 270 am but less than or equal to about 340 μm;
e. a basis weight that is greater than about 160 g/m² but less than or equal to 180 g/m²;
f. a thickness greater than about 515 am but less than or equal to about 610 μm;
g. a membrane load of greater than about 1138.1 g/m² but less than or equal to about 1919.3 g/m²; and
h. a maximum feed pressure of about 60 psi;

and
wherein the therapeutic polypeptide comprises a PCSK9-binding polypeptide that blocks binding of PCSK9 to LDLR and is selected from the group consisting of:
  i. a monoclonal antibody comprising a heavy chain having an amino acid sequence of SEQ ID NO:1 and a light chain having an amino acid sequence of SEQ ID NO:2 (evolocumab), or an antigen-binding fragment thereof;
  ii. a monoclonal antibody that competes with evolocumab for binding to PCSK9;
  iii. a monoclonal antibody, comprising:
    1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
    2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
  iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, D238, K243, S373, D374, S376, T377, F379, I154, T1897, H193, E195, I196, M201, V202, C223, T228, S235, G236, A239, G244, M247, I369, S372, C375, C378, R237, D238;
  v. a monoclonal antibody that binds to PCSK9 at an epitope on PCSK9 that overlaps with an epitope that is bound by an antibody that comprises:
    1. a heavy chain variable region of the amino acid sequence in SEQ ID NO:1; and
    2. a light chain variable region of the amino acid sequence in SEQ ID NO:2, and
    3. wherein the epitope of the monoclonal antibody further overlaps with a site to which an EGFa domain of LDLR.

BRIEF DESCRIPTION OF THE DRAWINGS

(FIG. 6A); 25° C. (FIG. 6B)). The tested evolocumab N-acetyl arginine formulations at 210 mg/mL are compared to an evolocumab proline formulation control at 140 mg/mL. Key to formulations: [acetate (mM)]/[N-acetyl arginine (mM)]/[arginine HCl (mM)].

(FIG. 13A), 25° C. (FIG. 13B), and 40° C. (FIG. 13C). In addition to 10 mM of each listed buffer, samples all contain 165 mM N-acetyl arginine, 75 mM arginine HCl, and 0.01% polysorbate-80.

FIG. 16A shows percent main peak for samples held at 5° C. over time, while FIG. 16B shows the same type of data for samples held at 25° C. and FIG. 16C shows the same type of data for samples held at 40° C. In addition to 10 mM of each listed buffer, samples all contain 165 mM N-acetyl arginine, 75 mM arginine HCl, and 0.01% polysorbate-80.

FIGS. 21A-21B show graphs of sub-visible particles as determined by light obscuration liquid borne particle counting (equal to or greater than 10 μM, FIG. 21A; or equal to or greater than 25 μM, FIG. 21B) per milliliter of various evolocumab formulations differing by pH and buffer held at 5° C., 25° C., and 40° C. for two months. FIGS. 21C-21D show graphs of sub-visible particles (greater than or equal to 10 μM, FIG. 21C; greater than or equal to 25 μM, FIG. 21D) of evolocumab formulations differing by pH and buffer held at 5° C. or 25° C. for six months. In addition to 10 mM of each listed buffer, samples all contain 165 mM N-acetyl arginine, 75 mM arginine HCl, and 0.01% polysorbate-80.

(FIG. 25A), 25° C. (FIG. 25B), and 40° C. (FIG. 25C). Key to formulations: [acetate (mM)]/[N-acetyl arginine (mM)]/[arginine HCl (mM)].

(FIG. 26A), 25° C. (FIG. 26B), and 40° C. (FIG. 26C). Key to formulations: [acetate (mM)]/[N-acetyl arginine (mM)]/[arginine HCl (mM)].

(FIG. 35A), 25° C. (FIG. 35B), and 40° C. (FIG. 35C).

(FIG. 36A (% acidic), FIG. 36B (% basic)), 25° C. (FIG. 36C (% acidic), FIG. 36D (% basic)), and 40° C. (FIG. 36E (% acidic), FIG. 36F (% basic)).

(FIG. 37A (% main peak), FIG. 37B (% LMW species)) and 40° C. (FIG. 37C (% main peak), FIG. 37D (% LMW species)).

FIG. 38A: HIAC-≥10 μm-4° C.; FIG. 38B: HIAC-≥25 μm-4° C.; FIG. 38C: HIAC-≥10 μm-40° C.; and HIAC-≥25 μm-40° C.

DETAILED DESCRIPTION

Figure 1:
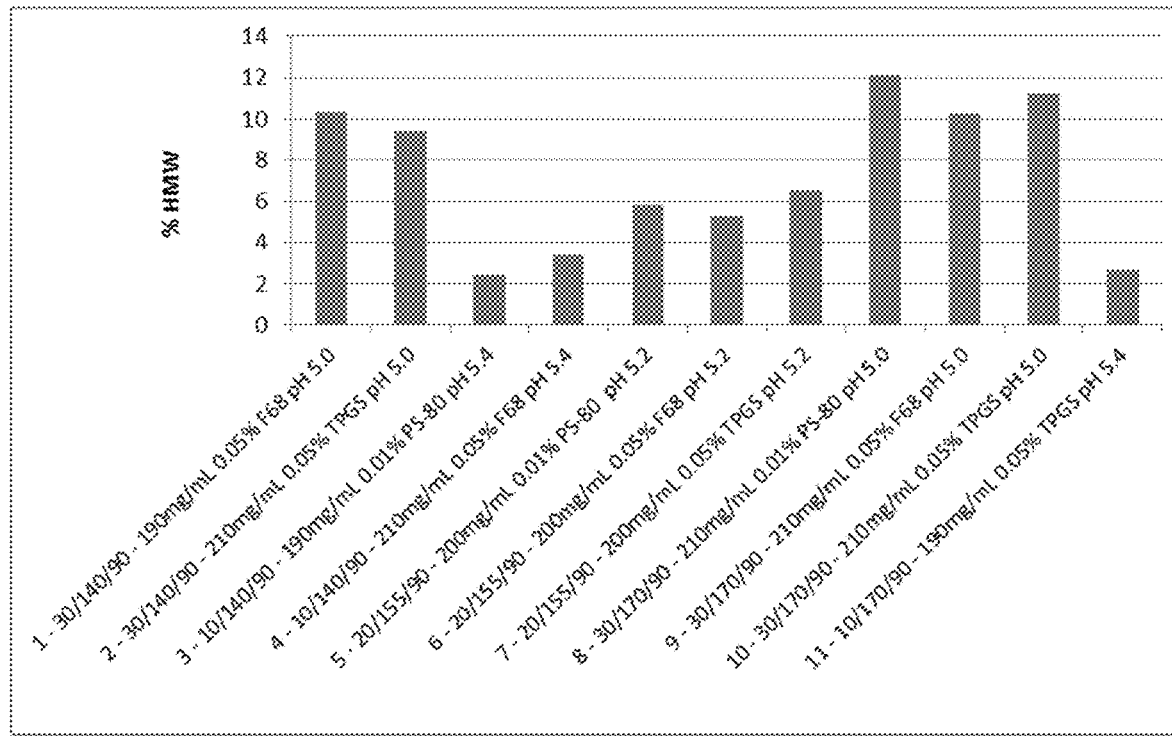
FIG. 1 shows a graph of the data from size-exclusion chromatography-high pressure liquid chromatography (SE-HPLC) of evolocumab samples at high concentrations in various formulations containing N-acetyl arginine following 1 month incubation at 40° C. Key to formulations indicated on x-axis: [acetate (mM)]/[N-acetyl arginine (mM)]/[proline (mM)]. Y-axis indicates percentage of sample that is high molecular weight (HMW) species (aggregates and oligomers of evolocumab).

The inventors have surprisingly discovered that a derivative of arginine, N-acetyl arginine (NAR), efficiently reduces the viscosity of pharmaceutical compositions comprising high concentrations (greater than 100 mg/mL, such as 140 mg/mL and greater) of evolocumab more so than unacetylated arginine. Pharmaceutical compositions having a viscosity of 50 cP or less are amenable to manufacturing and patient administration without significant complications, while higher viscosity preparations are difficult to handle (such as when syringes are filled), and to administer. While unmodified arginine is known to reduce viscosity of high protein concentration formulations, arginine glutamate only reduced the viscosity of a comparable proline-containing evolocumab (210 mg/mL) formulation by 50 cP (from 159 cP to 109 cP), substantially higher than a target of 50 cP or less. Furthermore, arginine monohydrochloride (Arg HCl) addition alone did not achieve this goal, reducing viscosity from 159 cP of the proline-containing formulation to 70 cP. However, NAR achieved a surprising effect of further reducing the viscosity to 58 cP—a reduction of over 101 cP relative to a proline formulation, and when combined with Arg HCl (to increase the solubility of NAR and achieve an isotonic formulation), a viscosity of under 50 cP was achieved; in fact, the goal was exceeded by 7 cP, the formulation having a viscosity of 43 cP. See FIG. 2. Since NAR solubility is limited to less than 230 mM, another excipient is necessary to achieve an isotonic formulation for subcutaneous administration. The unexpected discovery that the chloride salt of arginine is more effective at reducing viscosity of evolocumab than other arginine salts such as glutamate was critical to minimizing formulation viscosity.

Another unexpected discovery was the pH dependent evolocumab stability and viscosity effects seen in the presence of NAR and arginine HCl. A significant increase in the rate of evolocumab aggregation was seen at pH less than 5.0 at elevated temperatures. Also, a pH dependent decrease in viscosity was observed as pH increased from pH 5.1 to 6.9.

The inventors further discovered that a two-step ultrafiltration/diafiltration (UF/DF) process can prepare such NAR-containing, high evolocumab concentration pharmaceutical formulations with a significant savings in NAR material compared to traditional one-step traditional processes. Such methods allow for significant cost savings, as NAR is about ten-fold more expensive than Arg HCl.

Definitions

Both the foregoing general description and the following detailed description are exemplary and explanatory only and are not restrictive. The use of the singular includes the plural unless specifically stated otherwise. The use of "or" means "and/or" unless stated otherwise. The use of the term "including", as well as other forms, such as "includes" and "included", is not limiting. Terms such as "element" or "component" encompass both elements and components comprising one unit and elements and components that comprise more than one subunit unless specifically stated otherwise. The use of the term "portion" can include part of a moiety or the entire moiety. When a numerical range is mentioned, e.g., 1-5, all intervening values are explicitly included, such as 1, 2, 3, 4, and 5, as well as fractions thereof, such as 1.5, 2.2, 3.4, and 4.1.

"About" or "~" mean, when modifying a quantity (e.g., "about" 3 mM), that variation around the modified quantity can occur. These variations can occur by a variety of means, such as typical measuring and handling procedures, inadvertent errors, ingredient purity, and the like.

"N-acetyl arginine" (NAR) means the molecule of formula 1.

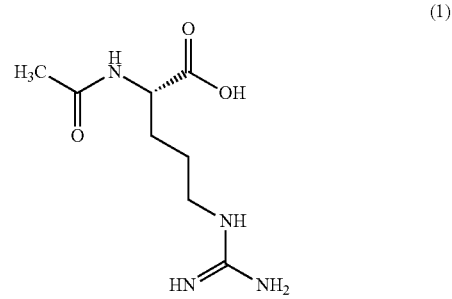

(1)

"Additive" means, in the context of a pharmaceutical composition, a substance not naturally part of a material (e.g., drug substance) but deliberately added to fulfill some specific purpose (e.g., preservation, viscosity reduction, stabilization).

"Analog" refers to an amino acid sequence that has insertions, deletions or substitutions relative to the parent sequence, while still substantially maintaining the biological activity of the parent sequence, as determined using biological assays. Analogs include polypeptides with modified glycosylation, polypeptides without glycosylation. Formulations can also include derivatives of naturally occurring or analog polypeptides which have been chemically modified, for example, to attach water soluble polymers (e.g., PEGylated), radionuclides, or other diagnostic or targeting or therapeutic moieties.

"Antibody" refers to an intact immunoglobulin of any isotype, and includes, for instance, chimeric, humanized, human, and bispecific antibodies. An intact antibody will generally comprise at least two full-length heavy chains and two full-length light chains. Antibody sequences can be derived solely from a single species, or can be "chimeric," that is, different portions of the antibody can be derived from two different species. "Antibody" also includes antibodies comprising two substantially full-length heavy chains and two substantially full-length light chains provided the antibodies retain the same or similar binding and/or function as the antibody comprised of two full length light and heavy chains. For example, antibodies having 1, 2, 3, 4, or 5 amino acid residue substitutions, insertions or deletions at the N-terminus and/or C-terminus of the heavy and/or light chains are included in the definition provided that the antibodies retain the same or similar binding and/or function as the antibodies comprising two full length heavy chains and two full length light chains. Antibodies include, for example, monoclonal antibodies, polyclonal antibodies, chimeric antibodies, humanized antibodies, human antibodies, bispecific antibodies, and synthetic antibodies.

Typical antibody structural units comprise a tetramer. Each such tetramer typically is composed of two identical pairs of polypeptide chains, each pair having one full-length "light" (about 25 kDa) and one full-length "heavy" chain (about 50-70 kDa). The amino-terminal portion of each chain typically includes a variable region of about 100 to 110 or more amino acids that typically is responsible for antigen recognition. The carboxy-terminal portion of each chain typically defines a constant region that can be responsible for effector function. Light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG antibodies have several subclasses, including IgG1, IgG2, IgG3, and IgG4. IgM has subclasses including IgM1 and IgM2. IgA is similarly subdivided into subclasses including IgA1 and IgA2. Within full-length light and heavy chains, typically, the variable and constant regions are joined by a "J" region of about 12 or more amino acids, with the heavy chain also including a "D" region of about ten more amino acids. The variable regions of each light/heavy chain pair typically form the antigen binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat (Kabat, Wu, Perry, Gottesman, & Foeller, 1991; Kabat, Wu, Reid-Miller, Perry, & Gottesman, 1987) or Chothia (Chothia & Lesk, 1987; Chothia et al., 1989).

Instead of a full length antibody, a "fragment" or "antigen binding fragment" of an antibody can be used. An "antibody fragment" refers to the Fab, Fab', F(ab')2, and Fv fragments that contain at least one CDR of an immunoglobulin that is sufficient to confer specific antigen binding to the target protein, such as PCSK9.

An antibody heavy chain can bind to an antigen in the absence of an antibody light chain. An antibody light chain can bind to an antigen in the absence of an antibody heavy chain. An antibody binding region can bind to an antigen in the absence of an antibody light chain. An antibody binding region can bind to an antigen in the absence of an antibody heavy chain. An individual variable region can specifically bind to an antigen in the absence of other variable regions.

The CDR regions in the heavy chain are typically referred to as H1, H2, and H3 and are numbered sequentially in the direction from the amino terminus to the carboxy terminus. The CDR regions in the light chain are referred to as L1, L2, and L3 and are numbered sequentially in the direction from the amino terminus to the carboxy terminus.

The term "light chain" includes a full-length light chain and fragments thereof having sufficient variable region sequence to confer binding specificity. A full-length light chain includes a variable region domain, VL, and a constant region domain, CL. The variable region domain of the light chain is at the amino-terminus of the polypeptide. Light chains include kappa chains and lambda chains.

The term "heavy chain" includes a full-length heavy chain and fragments thereof having sufficient variable region sequence to confer binding specificity. A full-length heavy chain includes a variable region domain, VH, and three constant region domains, CH1, CH2, and CH3. The VH domain is at the amino-terminus of the polypeptide, and the CH domains are at the carboxyl-terminus, with the CH3 being closest to the carboxy-terminus of the polypeptide. Heavy chains can be of any isotype, including IgG (including IgG1, IgG2, IgG3 and IgG4 subtypes), IgA (including IgA1 and IgA2 subtypes), IgM and IgE.

Each individual immunoglobulin chain is typically composed of several "immunoglobulin domains," each consisting of roughly 90 to 110 amino acids and having a characteristic folding pattern. These domains are the basic units of antibody polypeptides. In humans, the IgA and IgD isotypes contain four heavy chains and four light chains; the IgG and IgE isotypes contain two heavy chains and two light chains; and the IgM isotype contains five heavy chains and five light chains. The heavy chain C region typically comprises one or more domains that can be responsible for effector function. The number of heavy chain constant region domains depend on the isotype. IgG heavy chains, for example, contain three C region domains known as CH1, CH2 and CH3. In certain cases, an anti-PCSK9 antibody is an IgG1 or IgG2 or IgG4 subtype.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. The variable region of an antibody typically determines specificity of a particular antibody for its target.

"Antigen" means a molecule or a portion of a molecule capable of being bound by a selective binding agent, such as a PCSK9-binding polypeptide (including, e.g., an antibody or binding fragment thereof). In some cases, the antigen is capable of being used in an animal to produce antibodies capable of binding to that antigen. An antigen can possess one or more epitopes that are capable of interacting with different PCSK9-binding polypeptides.

"Arginine salt" means a salt of arginine. Examples include arginine monohydrochloride (Arg HCl), arginine acetate (Arg acetate) and arginine glutamate (Arg glutamate).

"Buffer" means any pharmaceutically acceptable buffer, including acetate, glutamate, histidine, and phosphate buffers, and salts thereof.

"Compete" when used in the context of antibodies that compete for the same epitope means competition between antibodies as determined by an assay in which the antibodies being tested prevents or inhibits (e.g., reduces) specific binding of a reference antibody (e.g., a ligand, or a reference antibody) to a common antigen (e.g., PCSK9 or a fragment thereof). Numerous types of competitive binding assays can be used to determine if one antibody competes with another, for example: solid phase direct or indirect immunoassays using a variety or art-accepted reagents and labels. Competitive inhibition is measured by determining the amount of label bound to the solid surface or cells in the presence of the test antibody. Usually the test antibody is present in excess. Antibodies identified by competition assay include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit (e.g., reduce) specific binding of a reference antibody to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more.

"Diafiltration," "DF," and like terms mean using an ultrafiltration membrane (i.e., a semi-permeable membrane that can discriminate between molecules having different shapes and sizes) to remove, replace, or lower the concentration of salts or solvents from solutions or mixtures containing, for example, polypeptides or other biomolecules.

"Diavolume (DV)" means, in the context of filtration, the volume of diafiltration buffer introduced into the unit operation compared to the retentate volume.

"Epitope" includes any determinant capable of being bound by a PCSK9-binding polypeptide, such as an antibody. An epitope is a region of an antigen that is bound by a PCSK9-binding polypeptide that targets that antigen, and when the antigen is a protein, includes specific amino acids that directly contact the PCSK9-binding polypeptide. Epitope determinants can include chemically active surface groupings of molecules such as amino acids, sugar side chains, phosphoryl groups and sulfonyl groups and can have specific three dimensional structural characteristics and specific charge characteristics. Generally, antibodies specific for a particular target antigen preferentially recognize an epitope on the target antigen in a complex mixture of proteins or other macromolecules.

"Excipient" means more or less an inert substance added in a prescription as a diluent or vehicle or to give form or consistency when the remedy is given in pill form; e.g., simple syrup, vegetable gums, aromatic powder, honey, and various elixirs.

"Feed Cross-flow" means the feed flow rate (L/hour) divided by membrane area ($m^2$).

"Flux (LMH)" means, in the context of filtration, liters per hour per square meter of membrane area ($L/h/m^2$).

"High molecular weight species" or "HMW species" means, in the context of a pharmaceutical formulation containing a therapeutic polypeptide, therapeutic proteins that are larger than the original therapeutic polypeptide, as determined by art-accepted assays. HMW species include oligomers of therapeutic polypeptides and aggregates of therapeutic polypeptides.

"Holdup Volume (HUV)" means, in the context of filtration, the line volume of the TFF system, including that of the cartridge.

"Identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or algorithm. These techniques are well-known in the art.

In calculating percent identity, the sequences being compared are typically aligned to maximize the largest match between the sequences.

Certain alignment schemes for aligning two amino acid sequences can result in matching only a short region of the two sequences, and this small aligned region may have very high sequence identity even though there is no significant relationship between the two full-length sequences. Accordingly, the selected alignment method can be adjusted if so desired to result in an alignment that spans a desired number of contiguous amino acids (e.g., 50 amino acids) of the target polypeptide.

Stereoisomers (e.g., D-amino acids) of the twenty conventional amino acids, unnatural amino acids such as α-, α-disubstituted amino acids, N-alkyl amino acids, lactic acid, and other unconventional amino acids can also be suitable components for PCSK9-binding polypeptides. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline).

Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties.

In making changes to the antigen binding protein or the PCSK9 protein, the hydropathic index of amino acids can be considered. Each amino acid has been assigned a hydropathic index on the basis of its hydrophobicity and charge characteristics. The importance of the hydropathic amino acid index in conferring interactive biological function on a protein is understood in the art. Certain amino acids can be substituted for other amino acids having a similar hydropathic index or score and still retain a similar biological activity.

The substitution of like amino acids can be made effectively on the basis of hydrophilicity. One can also identify epitopes from primary amino acid sequences on the basis of hydrophilicity. These regions are also referred to as "epitopic core regions."

"Low molecular weight species" or "LMW species" means, in the context of a pharmaceutical formulation containing a therapeutic polypeptide, polypeptides that are smaller than the original therapeutic polypeptide, as determined by art-accepted assays. LMW species include fragments of the therapeutic polypeptide.

"Neutralizing antibody" or an "antibody that neutralizes a target" as used in "anti-PCSK9 neutralizing antibody" refers to an antibody that binds to a target and prevents or reduces the biological activity of that target. This can be done, for example, by directly blocking a binding site on the target or by binding to the target and altering the target's ability to bind through indirect means, such as structural or energetic alterations in the target. In assessing the binding and/or specificity of an antibody or immunologically functional fragment thereof, an antibody or fragment can substantially inhibit binding of a target to its binding partner when an excess of antibody reduces the quantity of binding partner bound to the ligand by at least about 1-20%, 20-30%, 30-40%, 40-50%, 50-60%, 60-70%, 70-80%, 80-85%, 85-90%, 90-95%, 95-97%, 97-98%, 98-99% or more (as measured in an in vitro competitive binding assay). In the case of PCSK9 antibodies, such a neutralizing molecule can diminish the ability of PCSK9 to bind the LDLR. In some cases, the neutralizing ability is characterized or described via a competition assay. In some cases, the neutralizing ability is described in terms of an IC50 or EC50 value. In some cases, the antibodies neutralize by binding to PCSK9 and preventing PCSK9 from binding to LDLR, or reducing the ability of PCSK9 to bind to LDLR. In some cases, the antibodies neutralize by binding to PCSK9, while still allowing PCSK9 to bind to LDLR, preventing or reducing the PCSK9 mediated degradation of LDLR. Thus, in some instances, a neutralizing antibody can still permit PCSK9/LDLR binding, but prevents or reduces subsequent PCSK9 involved degradation of LDLR. Neutralizing results in the lowering LDL-C (and/or other lipids, such as ApoB, Lp(a), etc.). PCSK9-binding polypeptides beyond antibodies, including variants of such PCSK-binding polypeptides, can have these same activities.

"PCSK9-binding polypeptide" means a polypeptide that binds proprotein convertase subtilisin/kexin type 9 (PCSK9) protein. In some cases, the PCSK9-binding polypeptide blocks binding of PCSK9 to low-density lipid receptors (LDLRs). Such blocking PCSK9-binding polypeptides can be monoclonal antibodies (mAbs) and can be one of the following:

a. a mAb comprising a heavy chain polypeptide having an amino acid sequence of SEQ ID NO:1 and a light chain polypeptide having an amino acid sequence of SEQ ID NO:2 (evolocumab), or an antigen-binding fragment thereof;

b. a mAb that competes with evolocumab for binding to PCSK9;

c. a mAb, comprising:
  i. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
  ii. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;

d. a mAb that binds to at least one of the following residues of PCSK9, the PCSK9 comprising an amino acid sequence of SEQ ID NO:3: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;

e. a mAb that binds to PCSK9 at an epitope on PCSK9 that overlaps with an epitope that is bound by an antibody that comprises:
  i. a heavy chain variable region of the amino acid sequence in SEQ ID NO:1; and
  ii. a light chain variable region of the amino acid sequence in SEQ ID NO:2, and
  iii. wherein the epitope of the mAb further overlaps with a site to which an epidermal growth factor-like repeat A (EGF-A) domain of LDLR; or f. a mAb the comprises a heavy chain polypeptide comprising the following complementarity determining regions (CDRs):
  i. heavy chain CDR1, CDR2, and CDR3 having an amino acid sequence of SEQ ID NOs:7, 8, and 9, respectively; and
  ii. light chain CDR1, CDR2, and CDR3 having an amino acid sequence of SEQ ID NOs:4, 5, and 6, respectively.

The indicated amino acid sequences are presented in Table 1, which also presents the heavy chain variable region and light chain variable region of evolocumab. Evolocumab heavy chain and light chain full-length nucleotide sequences are given in Table 2, as are the nucleotide sequences for the evolocumab HCVR and LCVR.

TABLE 1

PCSK9 and PCSK9-binding polypeptide sequences

```
Evolocumab HC sequence (USAN; SEQ ID NO: 1)
EVQLVQSGAE  VKKPGASVKV  SCKASGYTLT  SYGISWVRQA  PGQGLEWMGW  VSFYNGNTNY     60
AQKLQGRGTM  TTDPSTSTAY  MELRSLRSDD  TAVYYCARGY  GMDVWGQGTT  VTVSSASTKG    120
PSVFPLAPCS  RSTSESTAAL  GCLVKDYFPE  PVTVSWNSGA  LTSGVHTFPA  VLQSSGLYSL    180
SSVVTVPSSN  FGTQTYTCNV  DHKPSNTKVD  KTVERKCCVE  CPPCPAPPVA  GPSVFLFPPK    240
PKDTLMISRT  PEVTCVVVDV  SHEDPEVQFN  WYVDGVEVHN  AKTKPREEQF  NSTFRVVSVL    300
TVVHQDWLNG  KEYKCKVSNK  GLPAPIEKTI  SKTKGQPREP  QVYTLPPSRE  EMTKNQVSLT    360
CLVKGFYPSD  IAVEWESNGQ  PENNYKTTPP  MLDSDGSFFL  YSKLTVDKSR  WQQGNVFSCS    420
VMHEALHNHY  TQKSLSLSPG  K                                                 441

Evolocumab LC sequence (USAN; SEQ ID NO: 2)
ESALTQPASV  SGSPGQSITI  SCTGTSSDVG  GYNSVSWYQQ  HPGKAPKLMI  YEVSNRPSGV     60
SNRFSGSKSG  NTASLTISGL  QAEDEADYYC  NSYTSTSMVF  GGGTKLTVLG  QPKAAPSVTL    120
FPPSSEELQA  NKATLVCLIS  DFYPGAVTVA  WKADSSPVKA  GVETTTPSKQ  SNNKYAASSY    180
LSLTPEQWKS  HRSYSCQVTH  EGSTVEKTVA  PTECS                                 215

PCSK9 preproprotein (human; SEQ ID NO: 3)
MGTVSSRRSW  WPLPLLLLLL  LLLGPAGARA  QEDEDGDYEE  LVLALRSEED  GLAEAPEHGT     60
TATFHRCAKD  PWRLPGTYVV  VLKEETHLSQ  SERTARRLQA  QAARRGYLTK  ILHVFHGLLP    120
GFLVKMSGDL  LELALKLPHV  DYIEEDSSVF  AQSIPWNLER  ITPPRYRADE  YQPPDGGSLV    180
EVYLLDTSIQ  SDHREIEGRV  MVTDFENVPE  EDGTRFHRQA  SKCDSHGTHL  AGVVSGRDAG    240
VAKGASMRSL  RVLNCQGKGT  VSGTLIGLEF  IRKSQLVQPV  GPLVVLLPLA  GGYSRVLNAA    300
CQRLARAGVV  LVTAAGNFRD  DACLYSPASA  PEVITVGATN  AQDQPVTLGT  LGTNFGRCVD    360
LFAPGEDIIG  ASSDCSTCFV  SQSGTSQAAA  HVAGIAAMML  SAEPELTLAE  LRQRLIHFSA    420
KDVINEAWFP  EDQRVLTPNL  VAALPPSTHG  AGWQLFCRTV  WSAHSGPTRM  ATAIARCAPD    480
EELLSCSSFS  RSGKRRGERM  EAQGGKLVCR  AHNAFGGEGV  YAIARCCLLP  QANCSVHTAP    540
PAEASMGTRV  HCHQQGHVLT  GCSSHWEVED  LGTHKPPVLR  PRGQPNQCVG  HREASIHASC    600
CHAPGLECKV  KEHGIPAPQG  QVTVACEEGW  TLTGCSALPG  TSHVLGAYAV  DNTCVVRSRD    660
VSTTGSTSEE  AVTAVAICCR  SRHLAQASQE  LQ                                    692

Evolocumab HCVR sequence (SEQ ID NO: 14)
QVQLVQSGAE  VKKPGASVKV  SCKASGYTLT  SYGISWVRQA  PGQGLEWMGW  VSFYNGNTNY     60
AQKLQGRGTM  TTDPSTSTAY  MELRSLRSDD  TAVYYCARGY  GMDVWGQGTT  VTVSS         115
```

TABLE 1-continued

PCSK9 and PCSK9-binding polypeptide sequences

Evolocumab LCVR sequence (SEQ ID NO: 15)
QSALTQPASV SGSPGQSITI SCTGTSSDVG GYNSVSWYQQ HPGKAPKLMI YEVSNRPSGV    60
SNRFSGSKSG NTASLTISGL QAEDEADYYC NSYTSTSMVF GGGTKLTVL              109

LC CDR1 (SEQ ID NO: 4)
TGTSSDVGGY NSVS                                                     14

LC CDR2 (SEQ ID NO: 5)
EVSNRPS                                                              7

LC CDR3 (SEQ ID NO: 6)
NSYTSTSMV                                                            9

HC CDR1 (SEQ ID NO: 7)
GYTLTSYGIS                                                          10

HC CDR2 (SEQ ID NO: 8)
WVSFYNGNTN YAQKLQ                                                   16

HC CDR3 (SEQ ID NO: 9)
GYGMDV                                                               6

TABLE 2

Evolocumab polynucleotide sequences

Evolocumab HC sequence (SEQ ID NO: 12)(Note that nucleotides 1 to 57
encode the native signal peptide)
atggactgga cctggaggat ccttttcttg gtggcagcag ccacaggtgt ccactccgag     60
gttcagctgg tgcagtctgg agctgaggtg aagaagcctg ggcctcagt gaaggtctcc    120
tgcaaggctt ctggttacac cttaaccagc tatggtatca gctgggtgcg acaggccct    180
ggacaagggc ttgagtggat gggatgggtc agttttata atggtaacac aaactatgca   240
cagaagctcc agggcagagg caccatgacc acagacccat ccacgagcac agcctacatg   300
gagctgagga gcctgagatc tgacgacacg gccgtgtatt actgtgcgag aggctacggt   360
atggacgtct ggggccaagg gaccacggtc accgtctcct ctgcctccac caagggccca   420
tcggtcttcc ccctggcgcc ctgctccagg agcacctccg agagcacagc ggccctgggc   480
tgcctggtca aggactactt ccccgaaccg gtgacggtgt cgtggaactc aggcgctctg   540
accagcggcg tgcacacctt cccagctgtc ctacagtcct caggactcta ctccctcagc   600
agcgtggtga ccgtgccctc cagcaacttc ggcacccaga cctacacctg caacgtagat   660
cacaagccca gcaacaccaa ggtggacaag acagttgagc gcaaatgttg tgtcgagtgc   720
ccaccgtgcc cagcaccacc tgtggcagga ccgtcagtct tcctcttccc cccaaaaccc   780
aaggacaccc tcatgatctc ccggacccct gaggtcacgt gcgtggtggt ggacgtgagc   840
cacgaagacc ccgaggtcca gttcaactgg tacgtggacg gcgtggaggt gcataatgcc   900
aagacaaagc cacgggagga gcagttcaac agcacgttcc gtgtggtcag cgtcctcacc   960
gttgtgcacc aggactggct gaacggcaag gagtacaagt gcaaggtctc caacaaaggc  1020
ctcccagccc ccatcgagaa aaccatctcc aaaaccaaag ggcagccccg agaaccacag  1080
gtgtacaccc tgcccccatc ccgggaggag atgaccaaga accaggtcag cctgacctgc  1140
ctggtcaaag gcttctaccc cagcgacatc gccgtggagt gggagagcaa tgggcagccg  1200
gagaacaact acaagaccac acctcccatg ctggactccg acggctcctt cttcctctac  1260
agcaagctca ccgtggacaa gagcaggtgg cagcagggga acgtcttctc atgctccgtg  1320
atgcatgagg ctctgcacaa ccactacacg cagaagagcc tctccctgtc tccgggtaaa  1380

Evolocumab LC sequence (SEQ ID NO: 13)
atggacatga gggtgcccgc tcagctcctg gggctcctgc tgctgtggct gagaggtgcc    60
agatgtgagt ctgccctgac tcagcctgcc tccgtgtctg ggtctcctgg acagtcgatc   120
accatctcct gcactggaac cagcagtgac gttggtggtt ataactctgt ctcctggtac   180
caacagcacc caggcaaagc ccccaaactc atgatttatg aggtcagtaa tcggccctca   240
gggggtttcta atcgcttctc tggctccaag tctggcaaca cggcctcctg accatctct   300
gggctccagg ctgaggacga ggctgattat tactgcaatt catatacaag caccagcatg   360
gtattcggcg agggaccaa gctgaccgtc taggtcagc ccaaggctgc ccctcggtc   420
actctgttcc cgccctcctc tgaggagctt caagccaaca aggccacact ggtgtgtctc   480
ataagtgact tctacccggg agccgtgaca gtggcctgga aggcagatag cagccccgtc   540
aaggcgggag tggagaccac cacaccctcc aaacaaagca acaacaagta cgcggccagc   600
agctatctga gcctgacgcc tgagcagtgg aagtcccaca gaagctacag ctgccaggtc   660
acgcatgaag ggagcaccgt ggagaagaca gtggccccta cagaatgttc a            711

Evolocumab HCVR sequence (SEQ ID NO: 10)
caggttcagc tggtgcagtc tggagctgag gtgaagaagc ctgggcctc agtgaaggtc     60
tcctgcaagg cttctggtta caccttaacc agctatggta tcagctgggt gcgacaggcc   120
cctggacaag ggcttgagtg gatgggatgg gtcagttttt ataatggtaa cacaaactat   180
gcacagaagc tccagggcag aggcaccatg accacagacc catccacgag cacagcctac   240
atggagctga ggagcctgag atctgacgac acggccgtgt attactgtgc gagaggctac   300
ggtatggacg tctggggcca agggaccacg gtcaccgtct cctct                   345

TABLE 2-continued

Evolocumab polynucleotide sequences

Evolocumab LCVR sequence (SEQ ID NO: 11)
```
cagtctgccc tgactcagcc tgcctccgtg tctgggtctc ctggacagtc gatcaccatc    60
tcctgcactg gaaccagcag tgacgttggt ggttataact ctgtctcctg gtaccaacag   120
cacccaggca aagcccccaa actcatgatt tatgaggtca gtaatcggcc ctcaggggtt   180
tctaatcgct tctctggctc caagtctggc aacacggcct ccctgaccat ctctgggctc   240
caggctgagg acgaggctga ttattactgc aattcatata caagcaccag catggtattc   300
ggcggaggga ccaagctgac cgtccta                                       327
```

Evolocumab is CAS Registry Number 1256937-27-5.

A variant of evolocumab which does not affect its PCSK9-binding and inhibitory properties is shown in Table 3.

TABLE 3

Evolocumab variant HCVR and LCR sequences

Variant evolocumab HCVR sequence (SEQ ID NO: 16)
```
QVQLVQSGAE VKKPGASVKV SCKASGYTLT SYGISWVRQA PGQGLEWMGW VSFYNGNTNY    60
AQKLQGRGTM TTDPSTSTAY MELRSLRSDD TAVYYCARGY GMDVWGQGTT VTVSS        115
```

Variant evolocumab LC sequence (SEQ ID NO: 17)
```
QSALTQPASV SGSPGQSITI SCTGTSSDVG GYNSVSWYQQ HPGKAPKLMI YEVSNRPSGV    60
SNRFSGSKSG NTASLTISGL QAEDEADYYC NSYTSTSMVF GGGTKLTVL               109
```

"Pharmaceutical composition" or "pharmaceutical formulation" and the like means a composition, usually sterile, of a pharmaceutically active drug, such as a biologically active protein (e.g., a PCSK9-binding polypeptide), that is suitable for administration, such as parenteral administration (including intravenous, intramuscular, subcutaneous, aerosolized, intrapulmonary, intranasal or intrathecal) to a subject in need thereof and includes only pharmaceutically acceptable excipients, diluents, and other additives deemed safe by the Federal Drug Administration or other foreign national authorities. Pharmaceutical formulations include liquid, e.g., aqueous, solutions that can be directly administered, and lyophilized powders which can be reconstituted into solutions by adding a diluent before administration.

"Polypeptide" or "protein" means a macromolecule having the amino acid sequence of a native protein, that is, a protein produced by a naturally-occurring and non-recombinant cell; or is produced by a genetically-engineered or recombinant cell, and comprises molecules having the amino acid sequence of the native protein, or molecules having deletions from, additions to, and/or substitutions of one or more amino acids of the native sequence. The term also embraces amino acid polymers in which one or more amino acids are chemical analogs of a corresponding naturally-occurring amino acid and polymers. "Polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. Fragments can be about five to 500 amino acids long. For example, fragments can be at least 5, 6, 8, 10, 14, 20, 50, 70, 100, 110, 150, 200, 250, 300, 350, 400, or 450 amino acids long. Useful polypeptide fragments include immunologically functional fragments of antibodies, including binding domains. In the case of a PCSK9-binding antibody, useful fragments include but are not limited to a CDR region, a variable domain of a heavy and/or light chain, a portion of an antibody chain or just its variable region including two CDRs.

To "prevent" (such as the onset of symptoms, a disease, or disorder) does not require the elimination of the possibility of an event. Rather, it denotes that the likelihood of the occurrence of the event has been reduced in the presence of a compound or method. Preventing in a therapeutic sense includes prophylactic treatments and applications in which one reduces the risk that a subject will develop a disorder or other risk factor.

"Stable pharmaceutical formulation," "stable formulation" or "a pharmaceutical formulation is stable" refers to a pharmaceutical formulation of PCSK9-binding polypeptides that exhibit limited increased aggregation and/or reduced loss of biological activity of not more than 5% when stored at about −30° C. (or colder) to about 5° C. to about 40° C. for at least 1 month, or 2 months, or three months, or 6 months, or 1 year, or 2 years, or 5 years, or longer when compared to a control formulation sample. Formulation stability can be determined by a person of skill in the art using any number of standard assays, including size-exclusion HPLC (SEC-HPLC), cation-exchange HPLC (CEX-HPLC), Subvisible Particle Detection by Light Obscuration ("HIAC") and/or visual inspection. Typically, the warmer the storage temperature, the shorter the shelf life of the formulation.

Techniques for assessing degradation vary depending upon the identity of the protein in the pharmaceutical formulation. Exemplary techniques include size-exclusion chromatography (SEC)-HPLC to detect, e.g., aggregation, reverse phase (RP)-HPLC to detect, e.g. protein fragmentation, ion exchange-HPLC to detect, e.g., changes in the charge of the protein, mass spectrometry, fluorescence spectroscopy, circular dichroism (CD) spectroscopy, Fourier transform infrared spectroscopy (FT-IR), and Raman spectroscopy to detect protein conformational changes. All of these techniques can be used singly or in combination to assess the degradation of the protein in the pharmaceutical formulation and determine the shelf life of that formulation. Pharmaceutical formulations disclosed herein typically exhibit not more than about 2% to about 3% increases in degradation (e.g., fragmentation, aggregation or unfolding) over two years when stored at 2-8° C.

"Subject" or "patient" are used interchangeably and include human and non-human animal subjects, as well as those with formally diagnosed disorders, those without formally recognized disorders, those receiving medical attention, and those at risk of developing disorders.

"Surfactant" means surface-active agents, including substances commonly referred to as wetting agents, surface tension depressants, detergents, dispersing agents, emulsifiers, and quaternary ammonium antiseptics. Surfactants are further discussed below.

"Tangential flow filtration," or "TFF" means a process where a solution is passed tangentially across an ultrafiltration membrane (i.e., a semi-permeable membrane that can discriminate between molecules of different size and shape) where lower molecular weight salts and/or solutes are passed through under pressure.

"Therapeutically effective amount" refers to the amount of a PCSK9 antigen binding polypeptide determined to produce a therapeutic response in a subject. Such therapeutically effective amounts are readily ascertained by one of ordinary skill in the art.

"Trans Membrane Pressure (TMP)" means, in the context of filtration, the average differential pressure from the feed to the filtrate side of the membrane and can be expressed by Equation (1):

$$TMP = \frac{\text{Feed Pressure} + \text{RetentatePressure}}{2} - \text{PermeatePressure} \quad (\text{Eq}(1))$$

To "treat" and provide "treatment" includes providing therapeutic treatments. Treatment does not require the complete curing of a disorder and encompasses instances in which one reduces symptoms or underlying risk factors.

"Ultrafiltration," "ultrafiltering", "UF," and similar terms mean using a semi-permeable membrane that discriminates between molecules of different shapes and sizes to separate molecules from different molecules, or to concentrate similar, or substantially the same, molecules.

A "variant" of a PCSK9-binding means an amino acid sequence wherein one or more amino acid residues are inserted into, deleted from and/or substituted into the amino acid sequence relative to another polypeptide sequence. Variants include fusion proteins.

"Viscosity" means a fluid's resistance to flow, and can be measured in units of centipoise (cP) or milliPascal·second (mPa·s), where 1 cP=1 mPa·s, at a given shear rate. Viscosity can be measured by using a viscometer, e.g., Brookfield Engineering (Middleboro, MA) Dial Reading Viscometer, or a rheometer, such as a m-VROC™ rheometer or TA Instruments (New Castle, DE) AESR-G2 cone and plate rheometer. Viscosity can be measured using any other methods and in any other units known in the art (e.g. absolute, kinematic or dynamic viscosity). Regardless of the method used to determine viscosity, the percent reduction in viscosity in excipient formulations versus control formulations will remain approximately the same at a given shear rate.

Components of the Compositions and Methods
PCSK9-Binding Polypeptides

The description of PCSK9-binding polypeptides, including evolocumab, have been well described (Chan et al., 2012).

Proprotein convertase subtilisin kexin type 9 (PCSK9) is a serine protease involved in regulating the levels of the low density lipoprotein receptor (LDLR) protein (Horton, Cohen, & Hobbs, 2007; Seidah & Prat, 2007). PCSK9 is a prohormone-proprotein convertase in the subtilisin (S8) family of serine proteases (Seidah et al., 2003). An exemplary human PCSK9 amino acid sequence is shown as SEQ ID NO:3 in Table 1, which is the pre-protein form (unprocessed) of PCSK9. PCSK9 proteins can also include fragments of the full length PCSK9 protein. The structure of the PCSK9 protein has been solved (Cunningham et al., 2007; Piper et al., 2007). PCSK9 includes a signal sequence, an N-terminal prodomain, a subtilisin-like catalytic domain, and a C-terminal domain.

PCSK9-binding polypeptides are polypeptides that comprise one or more complementary determining regions (CDRs). In some PCSK9-binding polypeptides, the CDRs are embedded into a framework region, which orients the CDR(s) such that the proper PCSK9 binding properties of the CDR(s) is achieved. PCSK9-binding polypeptides can interfere with, block, reduce or modulate the interaction between PCSK9 and LDLR. Such PCSK9-binding polypeptides are denoted as "neutralizing." Binding between PCSK9 and LDLR can still occur, even though the PCSK9-binding polypeptide is neutralizing and bound to PCSK9. For example, the PCSK9-binding polypeptide prevents or reduces the adverse influence of PCSK9 on LDLR without blocking the LDLR binding site on PCSK9. Thus, the PCSK9-binding polypeptide can modulate or alter PCSK9's ability to degrade LDLR, without preventing binding between PCSK9 and LDLR. Such PCSK9-binding polypeptides can be described as "non-competitively neutralizing." The neutralizing PCSK9-binding polypeptide can bind to PCSK9 in a location or manner that prevents PCSK9 from binding to LDLR. Such PCSK9-binding polypeptides can be described as "competitively neutralizing." PCSK9 neutralizers can result in a greater amount of free LDLR being present in a subject, resulting in more LDLR binding to LDL, and thereby reducing the amount of LDL in the subject. In turn, this results in a reduction in the amount of serum cholesterol present in a subject.

Some PCSK9-binding polypeptides can inhibit PCSK9-mediated activity (including binding). PCSK9-binding polypeptides can also inhibit interactions between PCSK9 and LDLR and other physiological effects mediated by PCSK9. PCSK9-binding polypeptides can be human, such as fully human antibodies to PCSK9.

Some PCSK9-binding polypeptides can bind to the catalytic domain of PCSK9. PCSK9-binding polypeptides can also bind the mature form of PCSK9. In other cases, PCSK9-binding polypeptides can bind the prodomain of PCSK9. The PCSK9-binding polypeptides, in some cases, can selectively bind to the mature form of PCSK9. In some cases, PCSK9-binding proteins bind to the catalytic domain such that PCSK9 cannot bind or bind as efficiently to LDLR. Some PCSK9-binding polypeptides do not bind to the C-terminus of the catalytic domain. In other cases, the PCSK9-binding polypeptide does not bind to the N-terminus of the catalytic domain. In other cases, the PCSK9-binding polypeptide does not bind to the N- or C-terminus of the PCSK9 protein. In some cases, the PCSK9-binding polypeptide binds to any one of the epitopes bound by anti-PCSK9 antibodies. In some cases, this can be determined by competition assays between a candidate antibody and a reference antibody, such as evolocumab. In some cases, the PCSK9-binding polypeptides bind to a specific conformational state of PCSK9 so as to prevent PCSK9 from interacting with LDLR. In some cases, the PCSK9-binding polypeptide binds to the V domain of PCSK9. In some cases, the PCSK9-binding polypeptide binds to the V domain of PCSK9 and prevents (or reduces) PCSK9 from binding to LDLR. In some cases, the PCSK9-binding polypeptide binds to the V domain of PCSK9, and while it does not prevent (or reduce) the binding of PCSK9 to LDLR, the PCSK9-binding polypeptide prevents or reduces the adverse activities mediated through PCSK9 on LDLR.

In some cases, the PCSK9-binding polypeptides comprise one or more CDRs (e.g., 1, 2, 3, 4, 5, or 6 CDRs). In some cases, the PCSK9-binding polypeptide comprises (a) a polypeptide structure and (b) one or more CDRs that are inserted into and/or joined to the polypeptide structure. The polypeptide structure can take a variety of different forms. For example, it can be, or comprise, the framework of a naturally occurring antibody, or fragment or variant thereof, or can be synthetic.

The polypeptide structure of PCSK9-binding polypeptides can be an antibody or is derived from an antibody, including monoclonal antibodies, bispecific antibodies, minibodies, domain antibodies, synthetic antibodies (antibody mimetics), chimeric antibodies, humanized antibodies, antibody fusions (sometimes referred to as "antibody conjugates"), and portions or fragments of each, respectively. In some instances, the PCSK9-binding polypeptide is a fragment of an antibody (e.g., a Fab, a Fab', a F(ab')$_2$, or a scFv).

Certain PCSK9-binding polypeptides specifically or selectively bind to human PCSK9. In some cases, the PCSK9-binding polypeptide specifically or selectively binds to human PCSK9 protein having or consisting of residues 153-692 of SEQ ID NO:3. In some cases, the PCSK9-binding polypeptide specifically binds to at least a fragment of the PCSK9 protein and/or a full length PCSK9 protein, with or without a signal sequence.

In some instances, the antibodies include at least one variable heavy chain and one variable light chain. In other instances, the antibodies contain two identical light chains and two identical heavy chains. As an example, an antibody or PCSK9-binding polypeptide can include a heavy chain and a light chain, two heavy chains, or two light chains. In some cases, the PCSK9-binding polypeptide comprises (or consists) of 1, 2, and/or 3 heavy and/or light CDRs from at least one of the sequences (SEQ ID NOs:4-9) listed in Table 1. In some cases, all six CDRs (CDR1-3 from the light (CDRL1, CDRL2, CDRL3) and CDR1-3 from the heavy (CDRH1, CDRH2, and CDRH3)) are part of the PCSK9-binding polypeptide. In some cases, 1, 2, 3, 4, 5, or more CDRs are included in the PCSK9-binding polypeptide. In some cases, one heavy and one light CDR from the CDRs in the sequences in Table 1 is included in the PCSK9-binding polypeptide. In some cases, additional sections are included in the PCSK9-binding polypeptide.

The PCSK9-binding polypeptide can be encoded by a nucleic acid sequence, as shown in Table 2 for evolocumab.

In some cases, the PCSK9-binding polypeptide binds to (but does not block) variants of PCSK9 that are at least 50, 50-60, 60-70, 70-80, 80-90, 90-95, 95-99 percent identical, or greater percent identity to the PCSK9 of SEQ ID NO:3. In some cases, the PCSK9-binding polypeptide binds to (but does not block) such variants. In some cases, the PCSK9-binding polypeptide binds to and prevents such variants of PCSK9 from interacting with LDLR. In some cases, the PCSK9-binding polypeptide binds to and prevents variants of PCSK9 from interacting with LDLR. In some cases, the variant of PCSK9 is a human variant, such as variants at position 474, E620G, and/or E670G. In some cases, the amino acid at position 474 is valine.

Humanized PCSK9-Binding Polypeptides (e.g., Antibodies)

A PCSK9-binding polypeptide can comprise a humanized antibody and/or part thereof.

A humanized antibody is substantially non-immunogenic in humans and has substantially the same affinity for a target as an antibody from another species from which the humanized antibody is derived.

Antibody modification can be designed to achieve increased binding affinity for a target and/or to reduce immunogenicity of the antibody in a recipient. In certain cases, humanized antibodies are modified to eliminate glycosylation sites in order to increase affinity of the antibody for its cognate antigen. Techniques such as "reshaping," "hyperchimerization," or "veneering/resurfacing" can be used to produce humanized antibodies. Such techniques typically reduce antibody immunogenicity by reducing the number of foreign residues, but do not prevent anti-idiotypic and anti-allotypic responses following repeated administration of the antibodies. Other methods of reducing immunogenicity are known in the art.

The CDRs of the light and heavy chain variable regions of an antibody to PCSK9 can be grafted to framework regions (FRs) from the same, or another, species. The CDRs of the light and heavy chain variable regions can be grafted to consensus human FRs. In some cases, the FRs of an antibody to PCSK9 heavy chain or light chain can be replaced with the FRs from a different heavy chain or light chain. The grafted variable regions from an antibody can be used with a constant region that is different from the constant region of an antibody to PCSK9. The grafted variable regions can be part of a single chain Fv antibody.

PCSK9-Binding Polypeptide Variants

Other antibodies that are useful are variants of the PCSK9-binding polypeptides listed above formed by combination or subparts of the variable heavy and variable light chains shown in Table 1 and comprise variable light and/or variable heavy chains that each have at least 50%, 50-60%, 60-70%, 70-80%, 80-85%, 85-90%, 90-95%, 95-97%, 97-99%, or above 99% identity to the amino acid sequences of the sequences in Table 1 (either the entire sequence or a subpart of the sequence, e.g., one or more CDR). In some instances, such antibodies include at least one heavy chain and one light chain, whereas in other instances the variant forms contain two identical light chains and two identical heavy chains (or subparts thereof).

In certain cases, an PCSK9-binding polypeptide comprises a heavy chain comprising a variable region comprising an amino acid sequence at least 90%, at least 95%, or at least 99% identical to an amino acid sequence of SEQ ID NO:1.

In some cases, the PCSK9-binding polypeptide comprises a sequence that is at least 90%, 90-95%, and/or 95-99% identical to one or more CDRs from the CDRs in at least one of sequences of SEQ ID NOs:4-9. In some cases, 1, 2, 3, 4, 5, or 6 CDRs (each being at least 90%, 90-95%, and/or 95-99% identical to the above sequences) is present.

In certain cases, an PCSK9-binding polypeptide comprises a light chain comprising a variable region comprising an amino acid sequence at least 90%, at least 95%, or at least 99% identical to an amino acid sequence of SEQ ID NO:11 or 15.

In other cases, an PCSK9-binding polypeptide comprises a heavy chain comprising a variable region comprising an amino acid sequence at least 90%, at least 95%, or at least 99% identical to an amino acid sequence of SEQ ID NO:10 or 14.

A skilled artisan is able to determine suitable variants of PCSK9-binding polypeptides using well-known techniques. In certain cases, one skilled in the art can identify suitable areas of the molecule that can be changed without destroying activity by targeting regions not believed to be important for activity. In certain cases, one can identify residues and portions of the molecules that are conserved among similar polypeptides. In certain cases, even areas that can be important for biological activity or for structure can be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art can opt for chemically similar amino acid substitutions for such predicted important amino acid residues.

One skilled in the art can also analyze the three-dimensional structure and amino acid sequence in relation to that structure in similar PCSK9-binding polypeptides. In view of such information, one skilled in the art can predict the alignment of amino acid residues of an antibody with respect to its three-dimensional structure. In certain cases, one skilled in the art can choose not to make radical changes to amino acid residues predicted to be on the surface of the protein, since such residues can be involved in important interactions with other molecules. Moreover, one skilled in the art can generate test variants containing a single amino acid substitution at each desired amino acid residue. The variants can then be screened using activity assays known in the art. Such variants can be used to gather information about suitable variants. For example, if one observed that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

In certain cases, PCSK9-binding polypeptide variants include glycosylation variants wherein the number and/or type of glycosylation site has been altered compared to the amino acid sequences of a parent polypeptide. In certain cases, protein variants comprise a greater or a lesser number of N-linked glycosylation sites than the native protein. Additional preferred antibody variants include cysteine variants wherein one or more cysteine residues are deleted from or substituted for another amino acid (e.g., serine) as compared to the parent amino acid sequence. Cysteine variants can be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Competing PCSK9-Binding Polypeptides

PCSK9-binding polypeptides that compete with evolocumab or functional fragments binding to an epitope bound by evolocumab for specific binding to PCSK9 can be used. Such PCSK9-binding polypeptides can also bind to the same epitope PCSK9-binding polypeptides or an overlapping epitope. PCSK9-binding polypeptides and fragments that compete with or bind to the same epitope as evolocumab show similar functional properties. Thus, as a specific example, the PCSK9-binding polypeptides that are provided include those that compete with an antibody or PCSK9-binding polypeptide having all six of the CDRs of evolocumab (SEQ ID NOs:4-9) or two light chains and two heavy chains of SEQ ID NOs:2 and 1, respectively).

Exemplary Epitopes

Epitopes of SEQ ID NO:3 (human PCSK9 polypeptide) to which anti-PCSK9 antibodies bind are provided. In the case of evolocumab (and the evolocumab variant, having HCVR of SEQ ID NO:14 and a LCVR of SEQ ID NO:15), they are S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238.

Preparation of PCSK9-Binding Polypeptides (e.g., Antibodies)

Certain strategies can be used to manipulate the inherent properties of an antibody, such as the affinity of an antibody for its target. Such strategies include the use of site-specific or random mutagenesis of the polynucleotide molecule encoding an antibody to generate an antibody variant. In certain cases, such generation is followed by screening for antibody variants that exhibit the desired change, e.g. increased or decreased affinity.

The amino acid residues targeted in mutagenic strategies can be those in the CDRs or the FRs.

In certain cases, smaller and more effectively screened libraries of antibody variants are produced by restricting random or site-directed mutagenesis to hyper-mutation sites in the CDRs, which are sites that correspond to areas prone to mutation during the somatic affinity maturation process.

Antibodies can be expressed in cell lines. Sequences (such as polynucleotides encoding the polypeptides of SEQ ID NOs:1 and 2, such as the polynucleotides of SEQ ID NOs:12 and 13) encoding particular antibodies can be used to transform a suitable mammalian host cell. Transformation can be by any known method for introducing polynucleotides into a host cell. The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines.

In certain cases, antibodies are produced by the 21B12 hybridoma cell line (Jackson et al., 2009). In certain cases, PCSK9-binding polypeptides bind to PCSK9 with a dissociation constant ($K_D$) of less than approximately 1 nM, e.g., 1000 pM to 100 pM, 100 pM to 10 pM, 10 pM to 1 pM, and/or 1 pM to 0.1 pM or less.

PCSK9-binding polypeptides can comprise an immunoglobulin molecule of at least one of the IgG1, IgG2, IgG3, IgG4, Ig E, IgA, IgD, and IgM isotype. In certain cases, PCSK9-binding polypeptides comprise a human kappa light chain and/or a human heavy chain. In certain cases, the heavy chain is of the IgG1, IgG2, IgG3, IgG4, IgE, IgA, IgD, or IgM isotype. In certain cases, PCSK9-binding polypeptides have been cloned for expression in mammalian cells. In certain cases, PCSK9-binding polypeptides comprise a constant region other than any of the constant regions of the IgG1, IgG2, IgG3, IgG4, IgE, IgA, IgD, and IgM isotype.

In certain cases, PCSK9-binding polypeptides comprise a human lambda light chain and a human IgG2 heavy chain. In certain cases, PCSK9-binding polypeptides comprise a human lambda light chain and a human IgG4 heavy chain. In certain cases, PCSK9-binding polypeptides comprise a human lambda light chain and a human IgG1, IgG3, IgE, IgA, IgD or IgM heavy chain. In other embodiments, PCSK9-binding polypeptides comprise a human kappa light chain and a human IgG2 heavy chain. In certain cases, PCSK9-binding polypeptides comprise a human kappa light chain and a human IgG4 heavy chain. In certain cases, PCSK9-binding polypeptides comprise a human kappa light chain and a human IgG1, IgG3, IgE, IgA, IgD or IgM heavy chain. In certain cases, PCSK9-binding polypeptides comprise variable regions of antibodies ligated to a constant region that is neither the constant region for the IgG2 isotype, nor the constant region for the IgG4 isotype. In certain cases, PCSK9-binding polypeptides have been cloned for expression in mammalian cells.

In the case of evolocumab, the antibody is an IgG2-lambda human monoclonal antibody; gamma 2 heavy chain-disulfide with lambda light chain tetrakisdisulfide. Evolocumab is glycosylated at Asn-291 and Asn-291" and has disulfide bridges between residues 22'-90', 22"-90", 22'-96', 22"-96", 129-214', 129"-214", 137'-196', 137"-196", 142-198, 142"-198", 217-217', 218-218', 221-221", 224-224", 255-315, 255"-315", 361-419, and 361"-419".

In certain cases, conservative modifications to the heavy and light chains of evolocumab or to those of an antibody having HCVR and LCVR of SEQ ID NOs:14 and 15 can produce antibodies to PCSK9 having functional and chemical characteristics similar to those of the antibodies from the hybridoma line 21B12. In contrast, substantial modifications in the functional or chemical characteristics of antibodies to PCSK9 can be accomplished by selecting substitutions in the amino acid sequence of the heavy and light chains that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a conservative amino acid substitution can involve a substitution of a native amino acid residue with a nonnative residue such that there is little or no effect on the polarity or charge of the amino acid residue at that position.

PCSK9-binding polypeptides often comprise one or more polypeptides. Any of a variety of expression vector/host systems can be used to express polynucleotide molecules encoding polypeptides comprising one or more PCSK9-binding polypeptide components or the PCSK9-binding polypeptide itself. Such systems include microorganisms, such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV, tobacco mosaic virus, TMV) or transformed with bacterial expression vectors (e.g., Ti or pBR322 plasmid); or animal cell systems.

A polypeptide comprising one or more PCSK9-binding polypeptide components or the PCSK9-binding polypeptide itself can be purified from the various expression systems; such techniques are well-known to those of skill in the art.

Pharmaceutical Formulation Components

In some embodiments, the pharmaceutical formulation comprising a PCSK9-binding polypeptide comprises more than one different PCSK9-binding polypeptide. In certain embodiments, pharmaceutical formulations comprise more than one PCSK9-binding polypeptide wherein the antigen binding proteins to PCSK9 bind more than one epitope. In some embodiments, the various antigen binding proteins will not compete with one another for binding to PCSK9. In some embodiments, the pharmaceutical formulation comprises evolocumab.

A PCSK9-binding polypeptide can be linked to a half-life extending vehicle. Such vehicles include polyethylene glycol (PEG), glycogen (e.g., glycosylation of the PCSK9-binding polypeptide), and dextran.

Acceptable formulation components preferably are nontoxic to recipients at the dosages and concentrations used. Pharmaceutical formulations can comprise agents for modifying, maintaining or preserving, for example, the pH, osmolarity, viscosity, clarity, color, isotonicity, odor, sterility, stability, rate of dissolution or release, adsorption or penetration of the composition.

For example, suitable formulation materials include amino acids (such as proline, arginine, lysine, methionine, taurine, glycine, glutamine, or asparagine); antimicrobials; antioxidants (such as ascorbic acid, sodium sulfite or sodium hydrogen-sulfite); buffers (such as borate, bicarbonate, sodium phosphate, sodium acetate ("NaOAC"), Tris-HCl, Tris buffer, citrates, phosphate buffer, phosphate-buffered saline (i.e., PBS buffer) or other organic acids); bulking agents (such as mannitol or glycine); chelating agents (such as ethylenediamine tetra acetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, sucrose, fructose, lactose, mannose, trehelose, or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants.

In one aspect, the pharmaceutical formulation comprises high concentrations of PCSK9-binding polypeptide. In certain embodiments, the PCSK9-binding polypeptide concentration ranges from about 70 mg/mL to about 260 mg/mL, e.g., about 70 mg/mL, about 80 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, about 200 mg/mL, about 210 mg/mL, about 220 mg/mL, about 230 mg/mL, about 240 mg/mL, about 250 mg/mL, or about 260 mg/mL. In some embodiments, the concentration of evolocumab ranges from about 140 mg/mL to about 210 mg/mL, e.g., about 140 mg/mL, about 150 mg/mL, about 160 mg/mL, about 170 mg/mL, about 180 mg/mL, about 190 mg/mL, about 200 mg/mL, about 210 mg/mL, about 220 mg/mL, about 230 mg/mL, about 240 mg/mL, about 250 mg/mL, or about 260 mg/mL.

In another aspect, the pharmaceutical formulation comprises at least one buffering agent such as, for example, sodium acetate, phosphates, phosphate buffered saline ("PBS"), histidine, and/or Tris buffer of about pH 7.0-8.5. The buffer serves to maintain a physiologically suitable pH. In addition, the buffer can enhance isotonicity and chemical stability of the pharmaceutical formulation. In certain embodiments, the buffering agent ranges from about 5 mM to about 100 mM, e.g., about 5 mM, about 10 mM, about 15 mM, about 20 mM, about 30 mM, about 40 mM, about 50 mM, about 60 mM, about 70 mM, about 80 mM, about 90 mM, or about 100 nM buffering agent. In certain embodiments, the buffering agent is NaOAC. In certain embodiments, the buffering agent is NaOAC and is present at a concentration of about 10 mM. In other embodiments, the buffer is sodium glutamate. In certain embodiments, the buffering agent is sodium glutamate and is present at a concentration of about 10 mM. In yet other embodiments, the buffering agent is a phosphate buffer. In certain embodiments, the phosphate buffer is present at a concentration of about 10 mM. In yet further embodiments, the buffering agent is histidine. In some of these embodiments, the histidine buffer is present at a concentration of about 10 mM. Useful pH values of the pharmaceutical formulation include from about 4 to about 7, or from about 4.8 to about 6.9, or from about 5.0 to about 5.5, or about 5, or about 5.4.

In certain embodiments, the pharmaceutical formulation is isotonic with an osmolality ranging from between about 250 to about 400 mOsm/kg, e.g., about 250 mOsm/kg, about 260 mOsm/kg, about 270 mOsm/kg, about 280 mOsm/kg, about 290 mOsm/kg, about 300 mOsm/kg, about 310 mOsm/kg, about 320 mOsm/kg, about 330 mOsm/kg, about 340 mOsm/kg, about 350 mOsm/kg, about 360 mOsm/kg, about 370 mOsm/kg, about 380 mOsm/kg, about 390 mOsm/kg, or about 400 mOsm/kg.

Osmolality is the measure of the ratio of solutes to volume fluid. In other words, it is the number of molecules and ions (or molecules) per kilogram of a solution. In certain embodiments, the osmolality is 300 mOsm/kg. Osmolality may be measured by an osmometer, such as Advanced Instruments 2020 Multi-sample Osmometer, Norwood, MA. The Advanced Instruments 2020 Multi-sample Osmometer measures osmolality by using the Freezing Point Depression method. The higher the osmolytes in a solution, the temperature in which it will freeze drops. Osmolality may also be measured using any other methods and in any other units known in the art such as linear extrapolation. In other embodiments, the pharmaceutical formulation is isotonic to a human blood cell, such as a red blood cell.

In still another aspect, the pharmaceutical formulation comprises at least one surfactant polyoxyethylenesorbitan monooleate (polysorbate 80 or polysorbate 20), polyoxyethylene-polyoxypropylene block copolymer (Poloxamers such as Pluronic® F-68 and other Pluronics®), Sorbitan alkyl esters (Spans®) Polyethylene glycol octylphenyl ethers (Triton X-100), Polyethylene glycol alkyl ethers (Brij), Polypropylene glycol alkyl ethers, Glucoside alkyl ethers, and D-α-tocopherol polyethylene glycol succinate (vitamin E TPGS). In certain embodiments, the pharmaceutical formulation comprises a surfactant at a concentration that ranges from about 0.0001% to about 10% weight per volume (w/v) of the formulation, e.g., about 0.0001%, about 0.005%, about 0.006%, about 0.007%, about 0.008%, about 0.009%, about 0.01%, about 0.05%, about 0.1%, about 0.5%, about 1%, about 5%, or about 10% surfactant (w/v) of the formulation. In certain embodiments, the pharmaceutical formulation comprises polysorbate 80 at a concentration that ranges from about 0.0001% to about 1% w/v of the formulation. In certain embodiments, the pharmaceutical formulation comprises polysorbate 80 at a concentration at about 0.01% w/v of the formulation. In other embodiments, the formulation comprises Pluronic® F-68 at a concentration that ranges from about 0.0001% to about 1% w/v of the formulation. In certain embodiments, the pharmaceutical formulation comprises Pluronic® F-68 at a concentration at about 0.01% w/v of the formulation. In still other embodiments, the formulation comprises vitamin E TPGS at a concentration that ranges from about 0.0001% to about 1% w/v of the formulation. In certain embodiments, the pharmaceutical formulation comprises vitamin E TPGS at a concentration at about 0.01% w/v of the formulation.

The pharmaceutical formulation can comprise at least one stabilizing agent, such as a polyhydroxy hydrocarbon (including sorbitol, mannitol, glycerol and dulcitol) and/or a disaccharide (including sucrose, lactose, maltose and trehalose) and/or an amino acid (beyond those formulations including an arginine salt, such as arginine monohydrochloride, and an acetyl derivative of arginine, such as N-acetyl arginine and can include, for example, proline, lysine, methionine, and taurine) and or benzyl alcohol; the total of said polyhydroxy hydrocarbon and/or disaccharide and/or amino acid and/or benzyl alcohol being about 0.5% to about 10% w/v of the formulation. The pharmaceutical formulation can comprise proline, for example, at about 10 mM to about 200 mM, such as from about 50 mM to about 150 mM, such as from about 90 mM to about 120 mM, such as about 120 mM.

In one aspect, the pharmaceutical formulation has a viscosity level of less than about 80 centipoise (cP) as measured at room temperature (i.e., 25° C.). In certain embodiments, the pharmaceutical formulation has a viscosity level of less than about 70 cP, about 60 cP, about 50 cP, about 40 cP, about 30 cP, about 25 cP, about 20 cP, about 18 cP, about 15 cP, about 12 cP, about 10 cP; about 8 cP, about 6 cP, about 4 cP; about 2 cP; or about 1 cP.

In one aspect, the pharmaceutical formulation is stable as measured by at least one stability assay, such as an assay that examines the biophysical or biochemical characteristics of the PCSK9-binding polypeptide over time. Pharmaceutical formulation stability can be measured using SEC-HPLC. SEC-HPLC separates proteins based on differences in their hydrodynamic volumes. Molecules with larger hydrodynamic proteins volumes elute earlier than molecules with smaller volumes. In the case of SEC-HPLC, a stable pharmaceutical formulation exhibits no more than about a 5% increase in HMW species as compared to a control sample, such as, for example no more than about a 4%, no more than about a 3%, no more than about a 2%, no more than about a 1%, no more than about a 0.5% increase in HMW species as compared to a control sample.

Alternatively, or in addition, stability can be measured using cation-exchange HPLC (CEX-HPLC). CEX-HPLC separates proteins based on differences in their surface charge. At a set pH, charged isoforms of an anti-PCSK9 ABP are separated on a cation-exchange column and eluted using a salt gradient. The eluent is monitored by ultraviolet light (UV) absorbance. The charged isoform distribution is evaluated by determining the peak area of each isoform as a percent of the total peak area. In the case of CEX-HPLC, a stable pharmaceutical formulation exhibits no more than about a 5% decrease in the main isoform peak as compared to a control sample, such as, for example, no more than about a 3% to about a 5% decrease in the main isoform peak as compared to a control sample; no more than about a 4% decrease, no more than about a 3% decrease, no more than about a 2% decrease, no more than about a 1% decrease, no more than about a 0.5% decrease in the main isoform peak as compared to a control sample.

Also alternatively, or in addition, formulation stability can be measured using Subvisible Particle Detection by Light Obscuration (HIAC). An electronic, liquid-borne particle-counting system (HIAC/Royco 9703 (Hach Company; Loveland, CO) or equivalent) containing a light-obscuration sensor (HIAC/Royco HRLD-150 or equivalent) with a liquid sampler quantifies the number of particles and their size range in a given test sample. When particles in a liquid pass between the light source and the detector they diminish or "obscure" the beam of light that falls on the detector. When the concentration of particles lies within the normal range of the sensor, these particles are detected one-by-one. The passage of each particle through the detection zone reduces the incident light on the photo-detector and the voltage output of the photo-detector is momentarily reduced. The changes in the voltage register as electrical pulses that are converted by the instrument into the number of particles present. The method is non-specific and measures particles regardless of their origin. Particle sizes monitored are generally 10 µm, and 25 µm. In the case of HIAC, a stable pharmaceutical formulation exhibits no more than 6000 10 am particles per container (or unit), as compared to a control sample, such as, for example no more than 5000, no more than 4000, no more than 3000, no more than 2000, no more than 1000, 10 µm particles per container (or unit) as compared to a control sample. In other cases, a stable pharmaceutical formulation exhibits no more than 600 25 µm particles per container (or unit) as compared to a control sample, such as, for example, no more than 500, no more than 400, no more than 300, no more than 200, no more than 100, no more than 50 25 µm particles per container (or unit) as compared to a control sample.

Pharmaceutical formulation stability can also be assessed using visual assessment. Visual assessment is a qualitative method used to describe the visible physical characteristics of a sample. The sample is viewed against a black and/or white background of an inspection booth, depending on the characteristic being evaluated (e.g., color, clarity, presence of particles or foreign matter). Samples are also viewed against an opalescent reference standard and color reference standards. In the case of visual assessment, a stable pharmaceutical formulation exhibits no significant change in color, clarity, presence of particles or foreign matter as compared to a control sample.

Exemplary Pharmaceutical Formulations

Shown in Table 4 are exemplary pharmaceutical formulations of PCSK9-binding polypeptides. In some of the formulations, ranges are given, and in the sub-examples (e.g., 1.1), a specific example is given.

TABLE 4

Exemplary pharmaceutical formulations of PCSK9-binding polypeptides

| Example | PCSK9-binding polypeptide | Buffer | Excipients | Surfactant | Final pH | Viscosity @1000/s (cP) | Osmolality |
|---|---|---|---|---|---|---|---|
| 1 | 195-227 mg/ml | 10 mM NaOAc | 140 mM NAR 63 mM Arg HCl | 0.01% (w/v) polysorbate 80 | 5.2 | ~80 | ~270 mOsm/kg |
| 1.1 | 227 mg/mL | 10 mM NaOAc | 140 mM NAR 63 mM Arg HCl | 0.01% (w/v) polysorbate 80 | 5.2 | 77.4 | 269 |
| 2 | 195-227 mg/ml | 10 mM NaOAc | 155 mM NAR 70 mM Arg HCl | 0.01% (w/v) polysorbate 80 | 5.4 | ~50 | ~300 |
| 2.1 | 218 mg/ml | 10 mM NaOAc | 170 mM NAR 63 mM Arg HCl | 0.01% (w/v) polysorbate 80 | 5.6 | 49.6 cP | 302 |
| 3 | 195-227 mg/ml | 10 mM NaOAc | 170 mM NAR 63 mM Arg HCl | 0.01% (w/v) polysorbate 80 | 5.6 | ~50 cP | ~300 mOsm/kg |
| 3.1 | 222 mg/ml | 10 mM NaOAc | 170 mM NAR 63 mM Arg HCl | 0.01% (w/v) polysorbate 80 | 5.6 | 52.3 cP | 296 mOsm/kg |
| 4 | 195-227 mg/ml | 10 mM NaOAc | 140 mM NAR 50 mM Arg HCl | 0.005%-0.015% polysorbate 80 | 5.1-5.7 | | |
| 4.1 | 210 mg/mL | 10 mM NaOAc | 140 mM NAR 50 mM Arg HCl | 0.01% (w/v) polysorbate 80 | 5.4 | ~40 cP | |
| 5 | 188-190 mg/ml | 10 mM NaOAc | 155 mM NAR 120 mM proline | 0.01% (w/v) polysorbate 80 | 5.4 | 290 | ~23 |
| 5.1 | 190 mg/ml | 10 mM NaOAc | 155 mM NAR 120 mM proline | 0.01% (w/v) polysorbate 80 | 5.4 | 290 | 22.8 |
| 6 | 200-201 mg/mL | 10 mM NaOAc | 155 mM NAR | 0.01% (w/v) polysorbate 80 | 5.4 | 295 | ~35 |
| 6.1 | 200 mg/ml | 10 mM NaOAc | 155 mM NAR 120 mM proline | 0.01% (w/v) polysorbate 80 | 5.4 | 295 | 34.5 |
| 7 | 210-214 mg/mL | 10 mM NaOAc | 155 mM NAR 120 mM proline | 0.01% (w/v) polysorbate 80 | 5.4 | 298 | ~50 |
| 7.1 | 210 mg/mL | 10 mM NaOAc | 155 mM NAR 120 mM proline | 0.01% (w/v) polysorbate 80 | 5.4 | 298 | 51.4 |

*expected variability in concentration measurements, formulation process and viscosity measurements were observed Therapeutic Applications PCSK9-binding polypeptides such as evolocumab can be used in a variety of therapeutic applications. For example, PCSK9-binding polypeptides are useful for treating conditions associated with PCSK9, such as cholesterol related disorders (serum cholesterol related disorders) such as hypercholesterolemia. PCSK9-binding polypeptides can be useful in treating consequences, symptoms, and/or the pathology associated with PCSK9 activity.

Disorders that relate to, involve, or can be influenced by elevated levels of molecules, or groups of molecules, including cholesterol (including serum cholesterol), LDL, LDLR, PCSK9, VLDL-C, apoprotein B ("ApoB"), lipoprotein A ("Lp(a)"), triglycerides, HDL-C, non-HDL-C, and total cholesterol levels can be addressed by methods that use the evolocumab pharmaceutical compositions disclosed herein to treat and/or prevent and/or reduce the risk of such disorders in a subject. The disclosed evolocumab compositions can be used to modulate the levels of these molecules or groups of molecules, such as reducing the amount of these molecules or groups of molecules. For example, the disclosed evolocumab compositions can be used in methods to decrease the amount of these molecules or groups of these molecules from an abnormally high level or from even a normal level, that is, the amount of cholesterol (including serum cholesterol), LDL, LDLR, PCSK9, VLDL-C, ApoB, Lp(a), triglycerides, HDL-C, non-HDL-C, and total cholesterol levels can be reduced.

A "cholesterol related disorder" (which includes "serum cholesterol related disorders") includes any one or more of the following: familial hypercholesterolemia, non-familial hypercholesterolemia, hyperlipidemia, heart disease, metabolic syndrome, diabetes, coronary heart disease, stroke, cardiovascular diseases, Alzheimer's disease and generally dyslipidemias, which can be manifested, for example, by an elevated total serum cholesterol, elevated LDL, elevated triglycerides, elevated VLDL, and/or low HDL. Some non-limiting examples of primary and secondary dyslipidemias include metabolic syndrome, diabetes mellitus, familial combined hyperlipidemia, familial hypertriglyceridemia, familial hypercholesterolemias, including heterozygous hypercholesterolemia, homozygous hypercholesterolemia, familial defective apop lipoprotein B-100; polygenic hypercholesterolemia; remnant removal disease, hepatic lipase deficiency; dyslipidemia secondary to any of the following: dietary indiscretion, hypothyroidism, drugs including estrogen and progestin therapy, beta-blockers, and thiazide diuretics; nephrotic syndrome, chronic renal failure, Cushing's syndrome, primary biliary cirrhosis, glycogen storage diseases, hepatoma, cholestasis, acromegaly, insulinoma, isolated growth hormone deficiency, and alcohol-induced hypertriglyceridemia. The disclosed evolocumab compositions can also be used to treat and/or prevent and/or reduce the risk of atherosclerotic diseases, such as cardiovascular death, non-cardiovascular or all-cause death, coronary heart disease, coronary artery disease, peripheral arterial disease, stroke (ischemic and hemorrhagic), angina pectoris, or cerebrovascular disease and acute coronary syndrome, myocardial infarction and unstable angina. The disclosed evolocumab compositions can also be useful in reducing the risk of fatal and nonfatal heart attacks, fatal and non-fatal strokes, certain types of heart surgery, hospitalization for heart failure, chest pain in patients with heart disease, and/or cardiovascular events because of established heart disease such as prior heart attack, prior heart surgery, and/or chest pain with evidence of clogged arteries and/or transplant-related vascular disease. In some cases, the disclosed evolocumab compositions can be used in methods of preventing or reducing the cardiovascular risk due to elevated CRP or hsCRP. In some embodiments, the ABP and methods can be used to reduce the risk of recurrent cardiovascular events.

Diseases or disorders that are generally addressable (either treatable or preventable) through the use of statins can also benefit from the application of the disclosed evolocumab compositions. Furthermore, disorders or diseases that can benefit from the prevention of cholesterol synthesis or increased LDLR expression can also be treated using the disclosed evolocumab compositions. In addition, the use of the disclosed evolocumab compositions can be especially useful in the treatment of diabetes. Not only is diabetes a risk factor for coronary heart disease, but insulin increases the expression of PCSK9. That is, people with diabetes have elevated plasma lipid levels (which can be related to high PCSK9 levels) and can benefit from lowering those levels.

Where a PCSK9-binding polypeptide is used for therapeutic applications, a PCSK9-binding polypeptide can inhibit, interfere with, or modulate one or more biological activities of PCSK9. For example, a PCSK9-binding polypeptide can bind specifically to human PCSK9 and/or substantially inhibit binding of human PCSK9 to LDLR by at least about 20%-40%, 40-60%, 60-80%, 80-85%, or more (for example, by measuring binding in an in vitro competitive binding assay). In some cases, the PCSK9-binding polypeptide has a $K_d$ of less (binding more tightly) than $10^{-7}$, $10^{-8}$, $10^{-9}$, $10^{-10}$, $10^{-11}$, $10^{-12}$, $10^{-13}$ M. In some cases, the PCSK9-binding polypeptide has an IC50 for blocking the binding of LDLR to PCSK9 of less than 1 µM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM.

Pharmaceutical formulations can be administered in combination therapy, i.e., combined with other agents. The combination therapy can comprise a PCSK9-binding polypeptide in combination with at least one anti-cholesterol agent. Agents include in vitro synthetically prepared chemical formulations, antibodies, antigen binding regions, and combinations and conjugates thereof. In certain embodiments, an agent can act as an agonist, antagonist, allosteric modulator, or toxin. In certain embodiments, an agent can act to inhibit or stimulate its target (e.g., receptor or enzyme activation or inhibition), and thereby promote increased expression of LDLR or decrease serum cholesterol levels.

A PCSK9-binding polypeptide can be administered prior to, concurrent with, and subsequent to treatment with a cholesterol-lowering (serum and/or total cholesterol) agent. For example, a PCSK9-binding polypeptide can be administered prophylactically to prevent or mitigate the onset of hypercholesterolemia, heart disease, diabetes, and/or any cholesterol related disorder. Furthermore, a PCSK9-binding polypeptide can be administered for the treatment of an existing hypercholesterolemia condition. In some cases, administration of a PCSK9-binding polypeptide can delay the onset of the disorder and/or symptoms associated with the disorder. In some cases, the PCSK9-binding polypeptide is provided to a subject lacking any symptoms of any one of the cholesterol related disorders or a subset thereof.

A PCSK9-binding polypeptide can be used with particular therapeutic agents to treat various cholesterol related disorders, such as hypercholesterolemia. In view of the condition and the desired level of treatment, two, three, or more agents can be administered. Such agents can be provided together by inclusion in the same formulation. Alternatively, such agents can be formulated separately and, if desired, provided together by inclusion in a treatment kit. In another example, such agents can be provided separately.

Dosage and Dosing Regimens

The amount of a PCSK9-binding polypeptide, such as a mAb, such as evolocumab, administered to a patient is a therapeutically effective amount. A typical dosage of a PCSK9-binding protein can range from about 0.1 µg/kg to up to about 100 mg/kg or more. In certain cases, the dosage can range from 0.1 µg/kg up to about 100 mg/kg; or 1 µg/kg up to about 100 mg/kg; or 5 µg/kg up to about 100 mg/kg; or 1 mg/kg to about 50 mg/kg; or 2 mg/kg to about 20 mg/kg; or 2 mg/kg to about 10 mg/kg of PCSK9-binding polypeptide.

The amount (or dose) of PCSK9-binding polypeptide can range from at least about 10 mg to at about 1400 mg; or about 14 mg to about 1200 mg; or about 14 mg to about 1000 mg; or about 14 mg to about 800 mg; or about 14 mg to about 700 mg; or about 14 mg to about 480 mg; or about 20 mg up to about 480 mg; or about 70 mg up to about 480 mg; or about 80 mg to about 480 mg; or about 90 mg to about 480 mg; or about 100 mg to about 480 mg, or about 105 mg to about 480 mg; or about 110 mg to about 480 mg; or about 115 mg to about 480 mg; or about 120 mg to about 480 mg; or about 125 mg to about 480 mg; or about 130 mg to about 480 mg; or about 135 mg to about 480 mg; or about 140 mg to about 480 mg; or about 145 mg to about 480 mg; or about 150 mg to about 480 mg; or about 160 mg to about 480 mg; or about 170 mg to about 480 mg; or about 180 mg to about 480 mg or about 190 mg to about 480 mg or about 200 mg to about 480 mg; or about 210 mg to about 480 mg; or about 220 mg to about 480 mg; or about 230 mg to about 480 mg; or about 240 mg to about 480 mg; or about 250 mg to about 480 mg; or about 260 mg to about 480 mg; or about 270 mg to about 480 mg; or about 280 mg to about 480 mg; or about 290 mg to about 480 mg; or about 300 mg to about 480 mg; or about 310 mg to about 480 mg; or about 320 mg to about 480 mg; or about 330 mg to about 480 mg; or about 340 mg to about 480 mg; or about 350 mg to about 480 mg; or about 360 mg to about 480 mg; or about 370 mg to about 480 mg; or about 380 mg to about 480 mg; or about 390 mg to about 480 mg; or about 400 mg to about 480 mg; or about 410 mg to about 480 mg; or about 420 mg to about 480 mg; or about 430 mg to about 480 mg; or about 440 mg to about 480 mg; or about 450 mg to about 480 mg; or about 460 mg to about 480 mg; or about 470 mg to about 480 mg of PCSK9-binding polypeptide.

The frequency of dosing will take into account the pharmacokinetic parameters of a PCSK9-binding polypeptide and/or any additional therapeutic agents in the formulation. A clinician can administer the formulation until a dosage is reached that achieves the desired effect. The formulation can be administered as a single dose, or as two, three, four or more doses (which may or may not contain the same amount of the PCSK9-binding polypeptide) over time, or as a continuous infusion via an implantation device or catheter. The formulation can also be delivered subcutaneously or intravenously with a needle and syringe. With respect to subcutaneous delivery, pen delivery devices, as well as body injector and autoinjector delivery devices, can deliver pharmaceutical formulations comprising PCSK9-binding polypeptides.

In certain cases, a dose of at least about 10 mg; or up to about 14 mg; or up to about 20 mg; or up to about 35 mg; or up to about 40 mg, or up to about 45 mg, or up to about 50 mg; or up to about 70 mg of an PCSK9-binding polypeptide is administered once a week (QW) to a patient in need thereof.

In other cases, a dose of at least about 70 mg, or up to about 100 mg; or up to about 105 mg, or up to about 110 mg; or up to about 115 mg, or up to about 120 mg; or up to about 140 mg; or up to about 160 mg; or up to about 200 mg; or up to about 250 mg; or up to 280 mg; or up to about 300 mg; or up to 350 mg; or up to about 400 mg; or up to about 420 mg of an PCSK9-binding polypeptide is administered once every other week, (or every two weeks; "Q2W:"), to a patient in need thereof.

In certain other cases, a dose of at least about 250 mg; or up to about 280 mg; or up to about 300 mg; or up to about 350 mg; or up to about 400 mg; or up to about 420 mg; or up to about 450 mg; or up to 480 mg of a an PCSK9-binding polypeptide is administered once every four weeks ("Q4W"), (or once a calendar month) to a patient in need thereof.

For example, evolocumab can be administered Q2W as 210 mg doses. Alternatively, evolocumab can be administered Q4W as 420 mg doses. Depending on the circumstances of the condition being treated, both these drug doses can be administered weekly.

In some cases, the serum LDL cholesterol level is reduced by at least about 15%, as compared to a pre-dose serum LDL cholesterol level. In some embodiments, the serum LDL cholesterol level is reduced by at least about 20%, or by at least about 25%, 30%, 35%, 40%, 45%, 50%, 55%, 60%, 65%, 70%, 75%, 80%, 85%, 90%, or even more.

Storage and Kits

Formulations comprising a PCSK9-binding polypeptide, with or without at least one additional therapeutic agents, can be prepared for storage by mixing the selected formulation having the desired degree of purity with optional formulation agents in the form of a lyophilized cake or an aqueous solution. Further, a formulation comprising a PCSK9-binding polypeptide, with or without at least one additional therapeutic agent, can be formulated as a lyophilisate using appropriate excipients.

Once the pharmaceutical formulation has been formulated, it can be stored in sterile vials as a solution, suspension, gel, emulsion, solid, or as a dehydrated or lyophilized powder. Such formulations can be stored either in a ready-to-use form or in a form (e.g., lyophilized) that is reconstituted prior to administration. In some cases, the PCSK9-binding polypeptide formulations can be stored in containers, such as suitable storage bags (e.g., as manufactured by Sartorius (Gottingen, DE)) or in polycarbonate carboys. Once the pharmaceutical formulation has been formulated, it can also be stored in pre-filled syringes (PFS; such as 2.25 mL PFS's) as a solution or suspension in a ready-to-use form, as well as in glass vials (such as 5 cc glass vials).

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

Ultrafiltration/Diafiltration of PCSK9-Binding Polypeptide Formulations Comprising N-Acetyl Arginine PCSK9-binding polypeptides can be formulated to about 210 g/L in the disclosed UF/DF processes. For example, in the disclosed methods, a first diafiltration (DF1) concentration of 70 g/L (or 35 g/L) is diafiltered three times and concentrated to 140 g/L. Then, a second diafiltration (DF2) concentration of 140 g/L is diafiltered four times and concentrated to a concentration of 260 g/L. The concentrated pool is then recovered from the system with formulation flush to a final concentration of 210 g/L.

In the disclosed methods, the first ultrafiltration (UF1) concentration of about 70 mg/mL and about 35 mg/mL are shown in the Examples to not have a significant effect on HWM (%) in final drug substance (DS). Furthermore, in the disclosed methods, only seven diavolumes of DF is necessary at the DF stage to ensure that diafiltration is completed.

The disclosed UF/DF process is summarized in Tables 5 and 6

TABLE 5

UF/DF general procedure and operating parameters

| Process Description | Condition |
|---|---|
| General | Membrane/Temperature/Membrane sizing |
| Equilibrium | NAR formulation buffers |
| (EQ)/DF buffer | Concentrate to a target DF conc. |
| Concentration 1 (UF1) | Transmembrane pressure (TMP) at 18 psi |
| | Feed cross-flow rate at 300 LMH (liters/m²/hr) |
| | 3 diavolumes |
| Diafiltration 1 (DF1) | TMP at 18 psi |
| | Feed cross-flow rate at 300 LMH |
| | Concentrate to a target DF concentration |
| Concentration 2 (UF2) | TMP at 18 psi |
| | Feed cross-flow rate at 300 LMH |
| | 4 diavolumes |
| Diafiltration 2 (DF2) | TMP at 18 psi |
| | Feed cross-flow rate at 300 LMH |
| | Concentrate to a target concentration |
| Concentration 3 (over-concentrated; OC) | TMP Initially at 18 psi; control value fully open |
| | Feed cross-flow rate at 60 LMH |
| | Operating temp. 37° C. |
| | 10 minute recirculation |
| Recirculation | Feed cross-flow rate at 60 LMH |
| | Permeate path closed (no TMP) |
| Recovery | Recover protein solution through low point or retentate port |
| | Chase with buffer through retentate port |
| Cleaning | ≥20 L/m² single-pass |
| | 30 min recirculation, 20 L/m² |
| Storage | ≥20 L/m² single-pass |

TABLE 6

UF/DF process operating parameters

| Step | Parameter | Unit of Measure | Target | Operating Range |
|---|---|---|---|---|
| Flush | Flush solution | | PW/water for injection (WFI) or DIW | n/a |
| | Feed flow | LMH | 300 | n/a |
| | Feed volume | L/m² | 20 | n/a |
| | Permeate volume | L/m² | >10 | n/a |
| | Operational control strategy | | Single pass filtrate open | n/a |
| | Integrity test solution | | PW/WFI or DIWW | n/a |
| Integrity Test | Diffusion flow | mL/min | 0.11 m² = 14 | n/a |
| | | | 0.57 m² = 60 | |
| | | | 1.14 m² = 117 | |
| | Test pressure | psig | 30 | n/a |
| | Test time | min | 10 | n/a |
| NWP | NWP solution | | PW/WFI or DIW | n/a |
| | NWP | LMH/psig | 8-14, >70% of new membrane NWP | n/a |
| Membrane Equilibration | Feed flow | LMH | 300 | n/a |
| | EQ solution | | NAR solution | n/a |
| | Feed volume | L/m² | 20 | n/a |
| | Permeate volume | L/m² | >10 | n/a |
| | TMP | psig | 20 | n/a |
| | Operational control strategy | | Single pass filtrate open | n/a |
| | Concentration target | g/L | 70 | n/a |
| Concentration 1 | Feed flow | LMH | ≤300 | n/a |
| | TMP | psig | 18 | n/a |
| | Operating temp. | ° C. | 20 | ±5.0 |
| | Diafiltration buffer | | NAR solution | n/a |
| | Number of diavolumes | number | 3 | n/a |
| Diafiltration 1 | Feed flow | LMH | ≤300 | n/a |
| | TMP | psig | 18 | ±5.0 |
| | Operating temp. | ° C. | 20 | ±5.0 |
| | Concentration target | g/L | 140 | n/a |
| Concentration 2 | Feed flow | LMH | ≤300 | n/a |
| | TMP | psig | 18 | ±5.0 |
| | Operating temp. | ° C. | 20 | ±5.0 |
| | Diafiltration buffer | | NAR solution | n/a |

TABLE 6-continued

UF/DF process operating parameters

| Step | | Parameter | Unit of Measure | Target | Operating Range |
|---|---|---|---|---|---|
| | | Number of diavolumes | number | 4 | n/a |
| Diafiltration 2 | | Feed flow | LMH | ≤300 | n/a |
| | | TMP | psig | 18 | n/a |
| | | Operating temp. | ° C. | 20 | n/a |
| | | Concentration target | g/L | 260 | n/a |
| Concentration 3 | | Feed flow | LMH | ≤60 | n/a |
| | | TMP | psig | Initially at 18. As TMP valve becomes fully open, TMP is no longer controlled | n/a |
| | | Operating temp. | ° C. | 37 | ±2.0 |
| Product Recovery | Low pressure recirculation | Flow mode | description | Total recycle filtrate closed | n/a |
| | | Flow rate | LMH | 60 | n/a |
| | | Recirculation time | minutes | 10 | n/a |
| | | concentration target | g/L | 240 | n/a |
| | Product Recovery | Recovery buffer | | NAR solution | n/a |
| | | Volume of flush through retentate | Skid hold-up | 1 | n/a |
| | | Retentate tank temperature after recovery | ° C. | 20 | ±2.0 |
| Membrane Cleaning | Initial flush | Flow mode | | Single pass filtrate open | n/a |
| | | Cleaning solution | | 0.5M NaOH | n/a |
| | | Feed volume | L/m² | 20 | n/a |
| | | Permeate volume | L/m² | >10 | n/a |
| | | Feed Flow | LMH | 300 | n/a |
| | | TMP | psig | 20 | n/a |
| | | Flow mode | | Total recycle filtrate open | n/a |
| | | Cleaning solution | | 0.5M NaOH | n/a |
| | Recirculation | Recirculation Time | minutes | 30 | n/a |
| | | Recirculation Volume | L/m² | 20 | n/a |
| | | Feed Flow | LMH | 300 | n/a |
| | | TMP | psig | 20 | n/a |
| Storage | | Flow mode | | Single pass filtrate open | |
| | | Storage solution | | 0.1M NaOH | |
| | | Feed volume | L/m² | 20 | |
| | | Permeate volume | L/m² | >10 | |
| | | Feed flow | LMH | 300 | |
| | | TMP | psig | 20 | |

Thus, disclosed herein is a method of formulating a PCSK9-binding polypeptide, such as a PCSK9-binding polypeptide that blocks binding of PCSK9 to LDLR, comprising
 a. a first concentration step, wherein the polypeptide in a first solution is concentrated;
 b. a first solution exchange step, wherein the concentrated polypeptide in the first solution is exchanged into a second solution comprising N-acetyl arginine using diafiltration;
 c. a second concentration step, wherein the polypeptide in the second solution is concentrated;
 d. a second solution exchange step, wherein the polypeptide in the concentrated second solution is exchanged into a third solution comprising N-acetyl arginine using diafiltration; and
 e. a third concentration step, wherein the polypeptide in the third solution is concentrated;

Before the third concentration step, the temperature of the solution comprising the polypeptide can be increased from about 25° C. to about 37° C., such as about 25, 26, 27, 28, 29, 30, 31, 32, 33, 34, 35, 36, and about 37° C. Also, the first solution exchange step can be accomplished using at least three diavolumes of the second solution; in some cases, additional diavolumes can be used, such as four, five, or six diavolumes. The second solution exchange step can be accomplished using at least four diavolumes of the third solution; however, additional diavolumes can be used, include five, six, or seven diavolumes. The initial concentration of the PCSK9-binding polypeptide can be about 11 mg/mL or less, such as less than 1 mg, or about 1, 2, 3, 4, 5, 6, 7, 8, 9, 10, or about 11 mg/mL. Additionally, the PCSK9-binding polypeptide concentration can be increased from about 3- to about 7-fold, such as about 3-, 4-, 5-, 6-, or about 7-fold. For example, the increased concentration of the polypeptide is from about 35 mg/mL to about 70 mg/mL or more, such as about 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or about 70 mg/mL or more. In the second concentration step, the PCSK9-binding polypeptide concentration is increased from about 2- to 4-fold from the first concentration step (such as from about 2-, 3-, or about 4-fold), such as to about 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 145, 150, 155, 160, 165, 170, 175, 180, 185, 190, 195, 200, 250, or about 300 mg/mL. In the third concentration step, the PCSK9-binding polypeptide concentration can be increased from about 1.5- to about 2-fold from the second concentration step, such as to about 140, 145, 150, 155, 160, 165, 170, 175, 180, 185, 190, 200, 250, or about 300 mg/mL, such as about 260 mg/mL. The PCSK9-binding polypeptide can therefore have a final concentration that is at least about 19-20-fold more concentrated than the initial concentration of the therapeutic polypeptide, such as about 210 mg/mL. The concentration steps can comprise fed-batch ultrafiltration; furthermore, the second solution and the third solution can be identical.

The second or third solution comprising N-acetyl arginine (e.g., "NAR solution") can comprise an arginine salt and a buffer, wherein, for example, the N-acetyl arginine is present at a concentration of about 25 mM to about 230 mM, such as about 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, or about 230 mM; the arginine salt is Arg HCl, Arg acetate, or Arg glutamate and is present at a concentration of about 25 mM to about 150 mM, such as about 25, 25, 30, 35, 40, 45, 50, 55, 60, 65, 70, 75, 80, 85, 90, 95, 100, 105, 110, 115, 120, 125, 130, 135, 140, 145, or about 150 mM; and the buffer is a sodium acetate buffer at a concentration of about 5 mM to about 30 mM, such as about 5, 10, 15, 20, 25, or about 30 mM. In other sub-aspects, the N-acetyl arginine is present at a concentration of about 140 to about 170 mM; the Arg HCl, Arg acetate, or Arg glutamate is present at a concentration of about 63 to about 70 mM (such as about 63, 64, 65, 66, 67, 68, 69, or about 70 mM) and the sodium acetate buffer is present at a concentration of about 10 mM. For example, the N-acetyl arginine can be present at a concentration of about 140 mM, the Arg HCl, Arg acetate, or Arg glutamate is present at a concentration of about 63 mM, the sodium acetate buffer is present at a concentration of about 10 mM. In further sub-aspects, the N-acetyl arginine is present at a concentration of about 155 mM, the Arg HCl, Arg acetate, or Arg glutamate is present at a concentration of about 70 mM, the sodium acetate buffer is present at a concentration of about 10 mM. In yet another example, the N-acetyl arginine is present at a concentration of about 170 mM, the Arg HCl, Arg acetate, or Arg glutamate is present at a concentration of about 63 mM, the sodium acetate buffer is present at a concentration of about 10 mM.

Furthermore, the compositions (including the NAR solutions) can further comprise proline, wherein the proline is present at a concentration of about 50 mM to about 150 mM, such as about 50, 55, 60, 65, 70, 75, 80, 85, 90, 95, 100, 105, 110, 115, 120, 125, 130, 135, 140, 145, or about 150 mM. The second or third solution can have a pH from about 4.8 to about 6.9, such as about 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, or about 6.9, such as 5.3, 5.4, or 5.5. In the first and second solution exchange steps, a diafiltration membrane can be used having at least one characteristic selected from the group consisting of:

a. mesh openings that are greater than about 350 μm but less than or equal to about 500 μm, such as about 350, 360, 370, 380, 390, 400, 410, 420, 430, 440, 450, 460, 470, 480, 490, or about 500 μm;

b. an open area that is greater than about 32% but less than or equal to about 36% (such as about 32, 33, 34, 35, or about 36%) of the membrane area;

c. a mesh count of less than about 16.2 n/cm but greater than or equal to about 12.2 n/cm, such as about 16.2, 16, 15.8, 15.6, 15.4, 15.2, 15, 14.8, 14.6, 14.4, 14.2, 14, 13.8, 13.6, 13.4, 13.2, 13, 12.8, 12.6, 12.4 or about 12.2 n/cm;

d. a wire diameter that is greater than about 270 μm but less than or equal to about 340 μm, such as about 270, 280, 290, 300, 310, 320, 330, or 340 μm;

e. a basis weight that is greater than about 160 g/m$^2$ but less than or equal to 180 g/m$^2$, such as about 160, 161, 162, 163, 164, 165, 166, 167, 168, 169, 170, 171, 172, 173, 174, 175, 176, 177, 178, 179, or 180 g/m$^2$;

f. a thickness greater than about 515 am but less than or equal to about 610 μm;

g. a membrane load of greater than about 1138.1 g/m$^2$ but less than or equal to about 1919.3 g/m$^2$; and h. a maximum feed pressure of about 60 psi.

Furthermore, surfactant can added to the third solution after being concentrated, such as polyoxyethylenesorbitan monooleate (polysorbate 80 or polysorbate 20), polyoxyethylene-polyoxypropylene block copolymer (Poloxamers such as Pluronic® F-68 and other Pluronics®), Sorbitan alkyl esters (Spans®) Polyethylene glycol octylphenyl ethers (Triton X-100), Polyethylene glycol alkyl ethers (Brij), Polypropylene glycol alkyl ethers, Glucoside alkyl ethers, and D-α-tocopherol polyethylene glycol succinate (vitamin E TPGS). In some cases, the surfactant is polyoxyethylene-polyoxypropylene block copolymer (Pluronic® F-68) or D-α-tocopherol polyethylene glycol succinate (vitamin E TPGS). The surfactant can range from a concentration from about 0.0001% to about 10% weight per volume ("w/v") of the formulation, e.g., about 0.0001%, about 0.005%, about 0.006%, about 0.007%, about 0.008%, about 0.009%, about 0.01%, about 0.05%, about 0.1%, about 0.5%, about 1%, about 5%, or about 10% surfactant (w/v) of the formulation. In certain embodiments, the pharmaceutical formulation comprises polysorbate 80 at a concentration that ranges from about 0.0001% to about 1% w/v of the formulation. In certain embodiments, the pharmaceutical formulation comprises polysorbate 80 at a concentration at about 0.01% w/v of the formulation. In other embodiments, the formulation comprises Pluronic® F-68 at a concentration that ranges from about 0.0001% to about 1% w/v of the formulation. In certain embodiments, the pharmaceutical formulation comprises Pluronic® F-68 at a concentration at about 0.01% w/v of the formulation. In still other embodiments, the formulation comprises vitamin E TPGS at a concentration that ranges from about 0.0001% to about 1% w/v of the formulation. In certain embodiments, the pharmaceutical formulation comprises vitamin E TPGS at a concentration at about 0.01% w/v of the formulation.

The following Examples section is given solely by way of example and are not set forth to limit the disclosure or claims in any way.

EXAMPLES

Viscosity measurements were made using a TA Instruments (New Castle, DE) AESR-G2 cone and plate rheometer unless otherwise noted.

Example 1—Design of Experiment (DOE) Study; Optimization of Evolocumab Formulations Containing N-Acetyl Arginine A Design of Experiment (DOE) study was initiated to optimize evolocumab formulations containing N-acetyl arginine. Eleven formulations were tested for viscosity, pre-filled syringe extrusion force, stability, pH, and osmolality. Data on the initial formulation parameters are shown in Table 7.

TABLE 8

Time zero data for 10 mM acetate, 155 mM N-acetyl arginine, 120 mM proline, 0.01% polysobate-80, pH 5.4 at 190-210 mg/mL evolocumab formulations

| Formulation | [evolocumab] | pH | Osmolality | Viscosity |
|---|---|---|---|---|
| 10/155/120—0.01% PS-80—190 mg/ml | 188 | 5.38 | 290 | 22. |
| 10/155/120—0.01% PS-80—200 mg/mL | 201 | 5.40 | 295 | 34.5 |
| 10/155/120—0.01% PS-80—210 mg/ml | 214 | 5.43 | 298 | 51.4 |

Example 2—DOE Study to Assess the Impact of Excipient Concentration, pH, and Buffer Examples 2-4 are directed to formulations that were optimized to reduce viscosity as much as possible while minimizing any impact to aggregation, deamidation, and other stability indicating factors.

N-acetyl arginine (NAR) was selected based on its superior effect in reducing viscosity in excipient screening studies (see for example, Example 1). The concentration of NAR was limited by its solubility at 2-8° C. A NAR concentration of 155 mM in diafiltration (DF) buffer was selected based on stability studies showing no crystallization of NAR at con-

TABLE 7

Evolocumab NAR design of experiment, time zero data

| # | pH target | Target [evolocumab] (mg/mL) | Target [NAR] | Surfactant | Target [Acetate] | pH | Osmolality | [evolocumab] (mg/mL) | viscosity @ 1000/s (cP) | E force 10 s extrusion time (N) | E force 12 s extrusion time (N) | E force 20 s extrusion time (N) |
|---|---|---|---|---|---|---|---|---|---|---|---|---|
| 1 | 5 | 190 | 140 | 0.05% F68 | 30 | 4.94 | 257 | 192 | 29.5 | 34 | 28 | 17 |
| 2 | 5 | 210 | 140 | 0.05% TPGS | 30 | 4.94 | 261 | 204 | 42.7 | 47 | 38 | 23 |
| 3 | 5.4 | 190 | 140 | 0.01% PS80 | 10 | 5.35 | 243 | 192 | 26.8 | 29 | 24 | 15 |
| 4 | 5.4 | 210 | 140 | 0.05% F68 | 10 | 5.36 | 254 | 207 | 49.0 | 51 | 41 | 25 |
| 5 | 5.2 | 200 | 155 | 0.01% PS 80 | 20 | 5.11 | 265 | 198 | 33.5 | 37 | 30 | 19 |
| 6 | 5.2 | 200 | 155 | 0.05% F68 | 20 | 5.10 | 261 | 197 | 34.6 | 38 | 31 | 19 |
| 7 | 5.2 | 200 | 155 | 0.05% TPGS | 20 | 5.10 | 266 | 201 | 32.3 | 38 | 31 | 19 |
| 8 | 5 | 210 | 170 | 0.01% PS 80 | 30 | 4.99 | 299 | 213 | 45.2 | 47 | 38 | 23 |
| 9 | 5 | 210 | 170 | 0.05% F68 | 30 | 5.01 | 290 | 213 | 46.7 | 48 | 39 | 24 |
| 10 | 5 | 210 | 170 | 0.05% TPGS | 30 | 4.98 | 292 | 214 | 49.4 | 49 | 40 | 25 |
| 11 | 5.4 | 190 | 170 | 0.05% TPGS | 10 | 5.34 | 286 | 189 | 24.3 | 29 | 24 | 15 |

Acetate concentration was minimized to reduce aggregation rate based one month 40° C. data shown in FIG. 1. Proline concentration was increased to 120 mM to make the formulation isotonic. N-acetyl arginine (155 mM) was selected to balance between viscosity reduction and the crystallization of N-acetyl arginine seen at 170 mM at 4° C. Data also indicated that varying surfactant between polysorbate-80 (TWEEN® 80; polyoxyethylenesorbitan monooleate), Pluronic® F-68 (polyoxyethylene-polyoxypropylene block copolymer), and Vitamin E TPGS (D-α-Tocopherol polyethylene glycol succinate) did not lead to a significant difference in viscosity or stability.

Based on these data, a formulation of 10 mM acetate, 155 mM N-acetyl arginine, 120 mM proline, 0.01% polysorbate-80, pH 5.4 was found to be suitable for a reduced viscosity formulation of evolocumab at high concentrations (e.g., 190-210 mg/mL). Data presented in Table 8 indicated that this formulation is isotonic and has a low viscosity.

centrations as high as 175 mM. Arginine HCl (70 Mm) was added to the DF buffer to achieve an isotonic drug product formulation with the lowest viscosity and to improve the solubility of NAR. The formulation pH of 5.4 was selected to minimize aggregation and deamidation of evolocumab. Buffer and surfactant (acetate/polysorbate-80) showed minimal effect on evolocumab formulation viscosity and stability.

Three main studies were performed to study the stability of evolocumab in NAR/arginine HCl formulations. They were:

1. A DOE study to assess the impact of excipient concentration, pH, and buffer (acetate vs. glutamate) (Example 2).
2. A broad pH study which was designed to assess the impact of pH (5.1-6.9) on viscosity/stability (Example 3).
3. A scale down study to assess the stability of top formulation candidates including the effects of drug product manufacturing unit operations (Example 4).

Results

Figure 2:
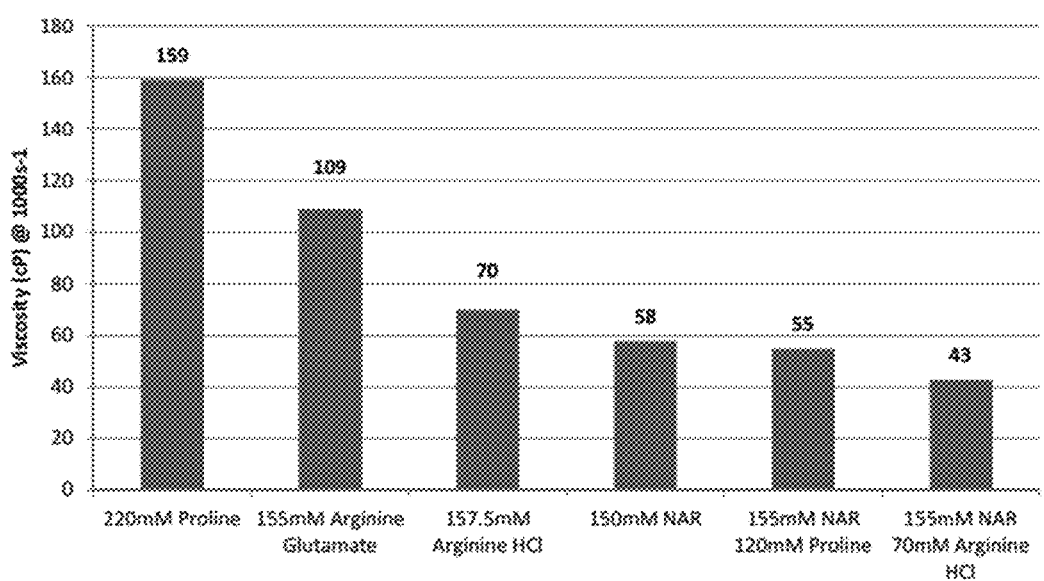
FIG. 2 shows a graph of a formulation viscosity comparison of evolocumab at 210 mg/mL-1000 sec$^{-1}$ shear rate at 25° C.

A viscosity target of ≤50 cP was established as a target. Formulation viscosity screening indicated that NAR was the most effective excipient to reduce viscosity. However, due to limited NAR solubility, a combination of NAR and arginine HCl was used to achieve an isotonic formulation and to meet the objective of a 210 mg/mL evolocumab formulation with a viscosity less than or equal to 50 cP. A summary of selected formulations that were evaluated during screening is shown in FIG. 2.

A DOE study was designed to assess the impact of NAR/arginine HCl concentration, pH, and buffer species on evolocumab stability and viscosity at 210 mg/mL. Formulation variables for each sample are shown in Table 9. The study design included NAR concentrations from 155-175 mM, arginine HCl concentrations from 50-100 mM, and pH from 4.8 to 5.4. The study also included a comparison between acetate and glutamate buffers at 10 mM. The study included a 140 mg/mL proline formulation control which was prepared and filled in PFS from the same lot of starting material as NAR/Arg HCl samples. Samples were sterile filtered using 0.2 μm PVDF filters and hand-filled in glass PFS at a fill volume of ~2.0 mL.

TABLE 9

DOE study design

| pH | NAR (mM) | Arg HCl (mM) | Buffer | PS-80 | Evolocumab (mg/mL) | Sample code |
|---|---|---|---|---|---|---|
| 4.8 | 155 | 50 | 10 mM Acetate | 0.01% | 210 | DOE 1-10/155/50 pH 4.8 |
| 5.4 | 155 | 50 | 10 mM Glutamate | 0.01% | 210 | DOE 2-10/155/50 pH 5.4 |
| 4.8 | 175 | 50 | 10 mM Glutamate | 0.01% | 210 | DOE 3-10/175/50 pH 4.8 |
| 5.4 | 175 | 50 | 10 mM Acetate | 0.01% | 210 | DOE 4-10/175/50 pH 5.4 |
| 5.1 | 165 | 75 | 10 mM Acetate | 0.01% | 210 | DOE 5-10/165/75 pH 5.1 |
| 5.1 | 165 | 75 | 10 mM Glutamate | 0.01% | 210 | DOE 6-10/165/75 pH 5.1 |
| 4.8 | 155 | 100 | 10 mM Glutamate | 0.01% | 210 | DOE 7-10/155/100 pH 4.8 |
| 5.4 | 155 | 100 | 10 mM Acetate | 0.01% | 210 | DOE 8-10/155/100 pH 5.4 |
| 4.8 | 175 | 100 | 10 mM Acetate | 0.01% | 210 | DOE 9-10/175/100 pH 4.8 |
| 5.4 | 175 | 100 | 10 mM Glutamate | 0.01% | 210 | DOE 10-10/175/100 pH 5.4 |
| 5.0 | 0 | 0 | 20 mM Acetate | 0.01% | 140 | 140 mg/ml Proline Control |

Data are tabulated for pH, concentration, osmolality, and viscosity in Table 10. pH values were observed to be close to targets for all samples. Osmolality in the study covered a range from 256-392 mOsm/kg. Viscosity appeared to show an inconsistent trend towards lower viscosity at higher pH.

TABLE 10 pH, concentration, osmolality, and viscosity data from DOE

| Sample | pH | Conc. | mOsm/kg | Viscosity (cP @ 1000 sec$^{-1}$, 25° C.) |
|---|---|---|---|---|
| 1—10/155/50 pH 4.8 | 4.83 | 209.0 | 256 | 45.3 |
| 2—10/155/50 pH 5.4 | 5.29 | 209.0 | 271 | 43.8 |
| 3—10/175/50 pH 4.8 | 4.81 | 210.6 | 301 | 46.6 |
| 4—10/175/50 pH 5.4 | 5.31 | 212.9 | 297 | 41.0 |
| 5—10/165/75 pH 5.1 | 5.07 | 211.9 | 326 | 48.2 |
| 6—10/165/75 pH 5.1 | 5.03 | 209.8 | 340 | 47.5 |
| 7—10/155/100 pH 4.8 | 4.80 | 208.5 | 369 | 44.9 |
| 8—10/155/100 pH 5.4 | 5.29 | 210.3 | 366 | 38.8 |
| 9—10/175/100 pH 4.8 | 4.84 | 208.7 | 376 | 43.9 |
| 10—10/175/100 pH 5.4 | 5.33 | 209.2 | 392 | 36.6 |

Figure 3A:
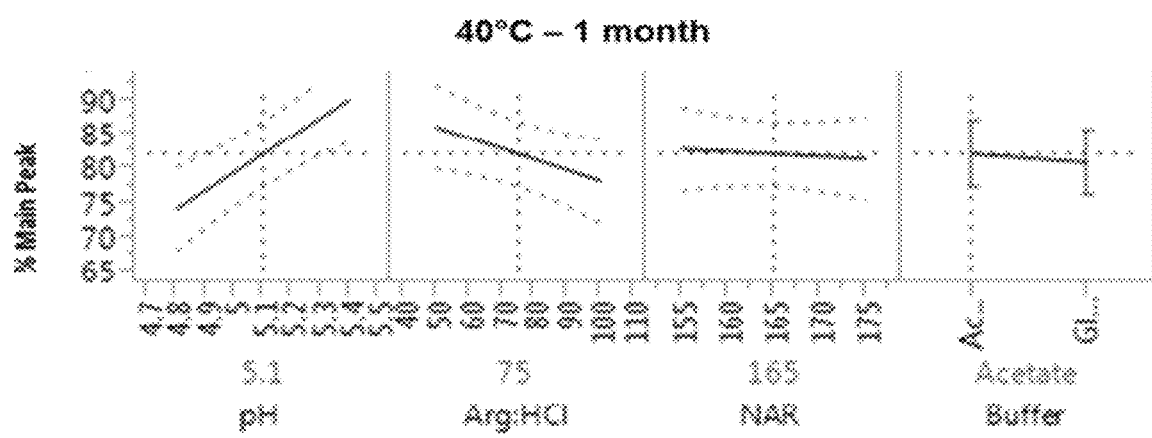
FIG. 3A shows graphs produced by JMP Prediction Profiler software of SE-HPLC data for evolocumab formulation held at 40° C. for one month.
Figure 3B:
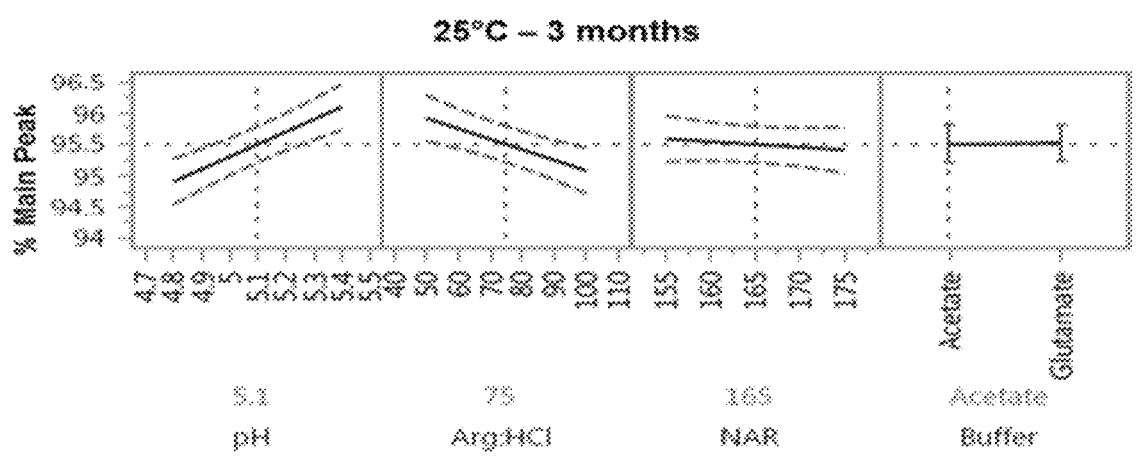
FIG. 3B shows similar data, except the samples were held at 25° C. for three months.
Figure 4:
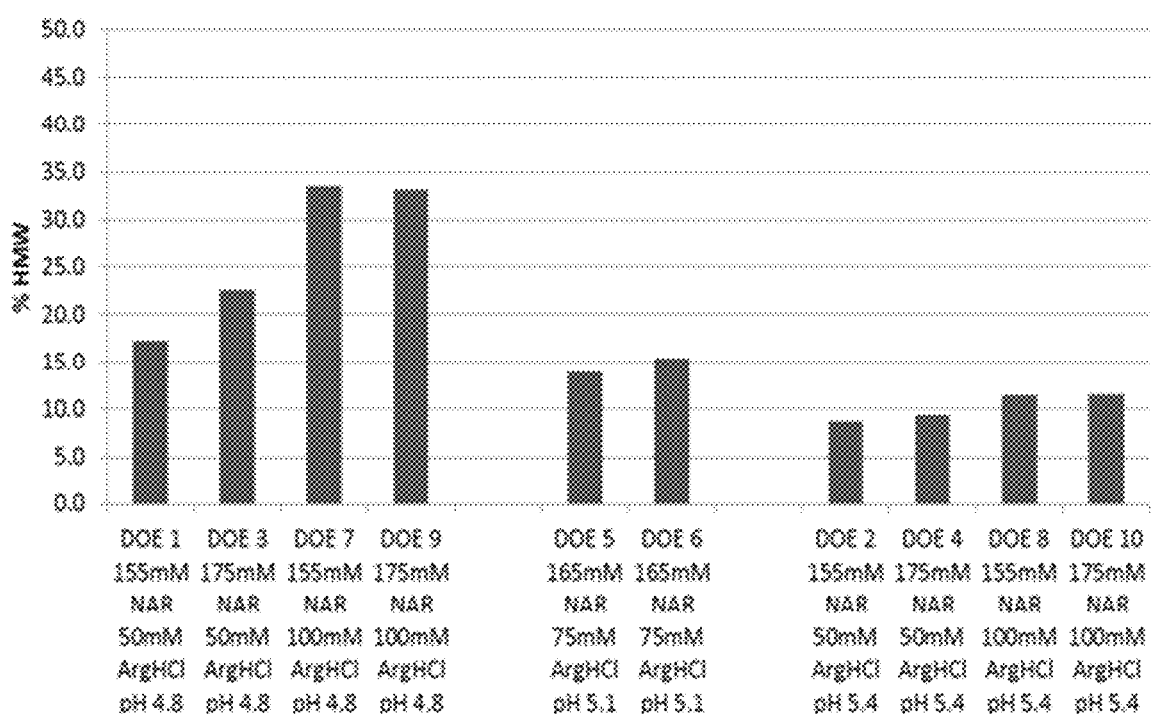
FIG. 4 shows a bar graph of the percent HMW species by SE-HPLC of 210 mg/mL evolocumab formulations held at 40° C. for one month. Formulations vary by concentrations of N-acetyl arginine and arginine HCl concentration at varying pH.

Analysis of size-exclusion high pressure liquid chromatography (SE-HPLC) data using JMP statistical analysis software (SAS; Cary, NC; FIGS. 3A and 3B) revealed significant effects of pH and arginine HCl concentration on loss of percent main peak at 40° C. for 1 month (FIG. 3A). Lower pH and higher arginine HCl concentration caused greater loss of main peak primarily due to an increase in aggregate peak and to a lesser extent, oligomer peak. Both peaks combined were categorized as high molecular weight (HMW) species. FIG. 4 shows the effects of pH and arginine HCl on percent of HMW species for the 1 month, 40° C. time point. There were significantly higher levels of percent of HMW species seen in pH 4.8 samples compared to pH 5.4 samples. Also, the effect of higher arginine HCl concentration leading to higher percent of HMW species was significantly more pronounced at pH 4.8 compared to pH 5.4.

Figure 5A:
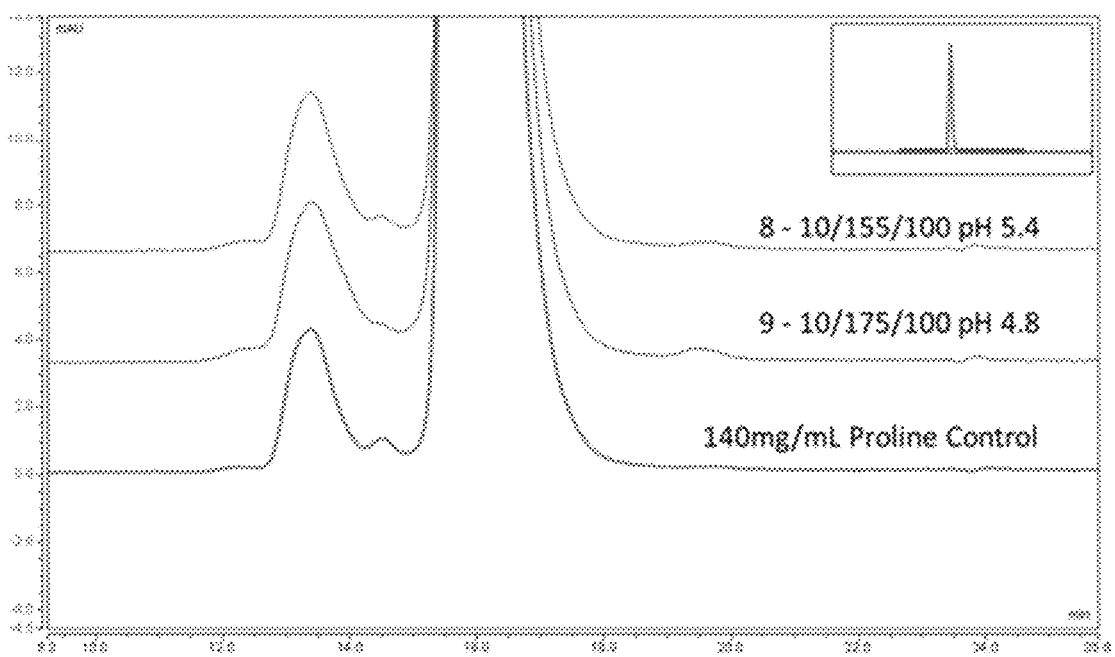
FIGS. 5A-5C show SE-HPLC chromatographs of selected pH 4.8 and pH 5.4 evolocumab samples held at the indicated temperatures and times (5° C. for six months (FIG. 5A); 25° C. for three months (FIG. 5B); and 40° C. for one month (FIG. 5C)) and compared to a evolocumab proline formulation control. Key to formulations: [acetate (mM)]/[N-acetyl arginine (mM)]/[arginine HCl (mM)].
Figure 5B:
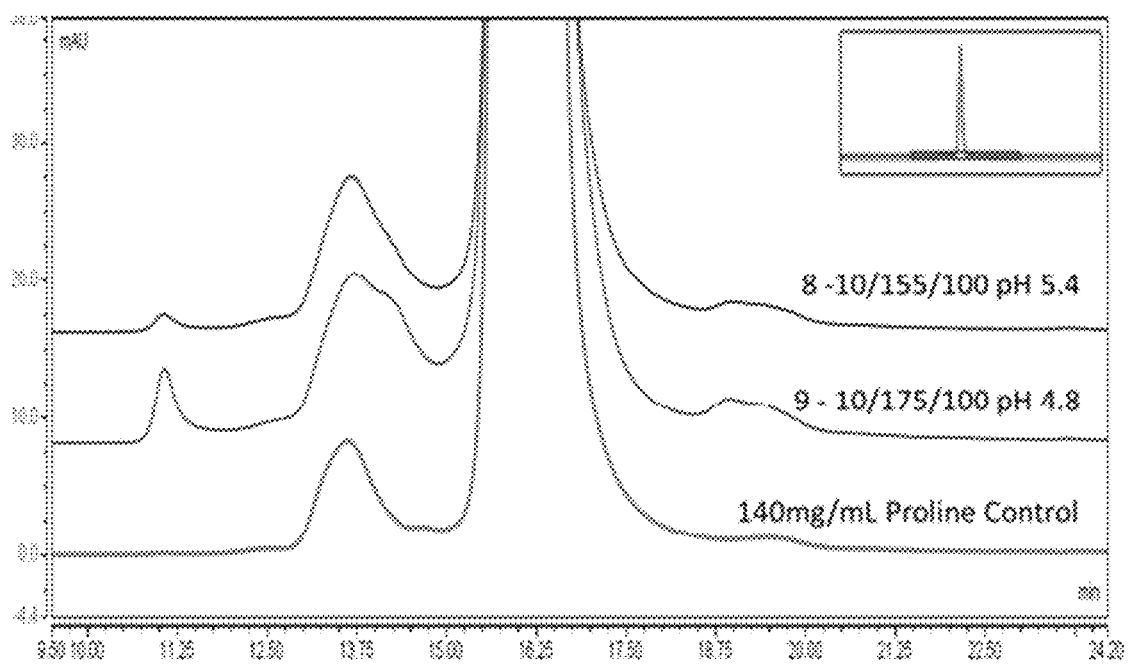
Figure 5C:
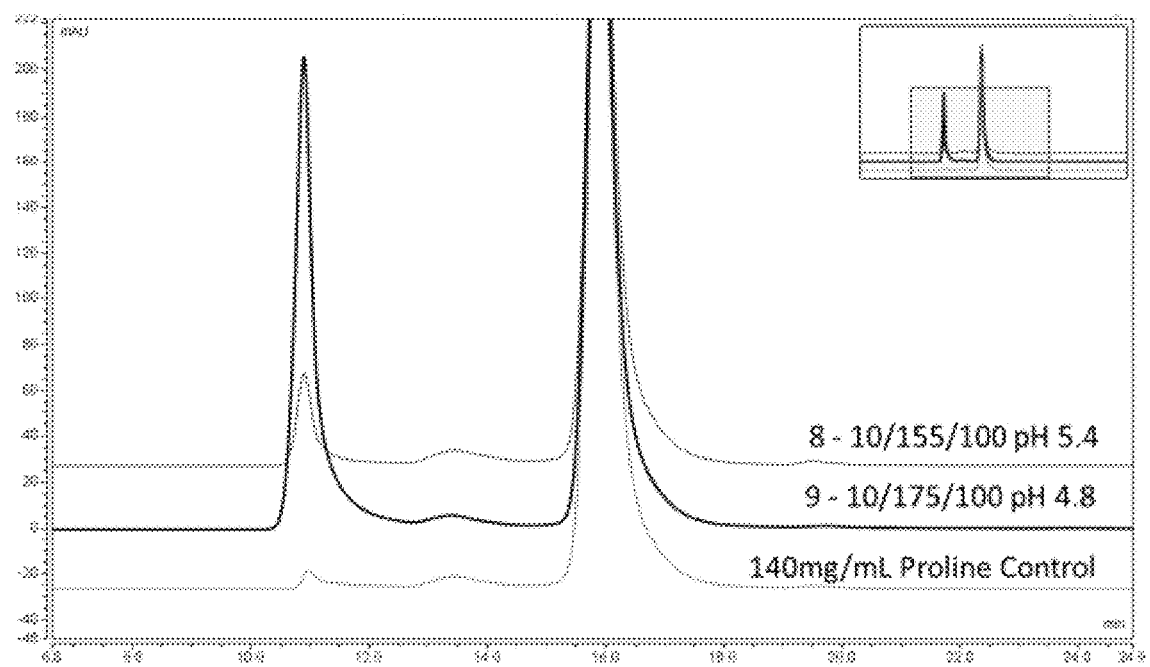

FIGS. 5A-5C show SE-HPLC chromatograms of selected pH 4.8 and pH 5.4 samples compared to 140 mg/mL proline control at 5° C. for 6 months, 25° C. for three months, and 40° C. for 1 month, respectively. The chromatograms show the trend of increasing levels of aggregate at pH 4.8 relative to pH 5.4. The chromatograms also indicate that the degradation profile was comparable for 210 mg/mL NAR/Arg HCl samples compared to the 140 mg/mL proline control despite faster rate of aggregation observed for 210 mg/mL NAR/Arg HCl samples.

Figure 6A:
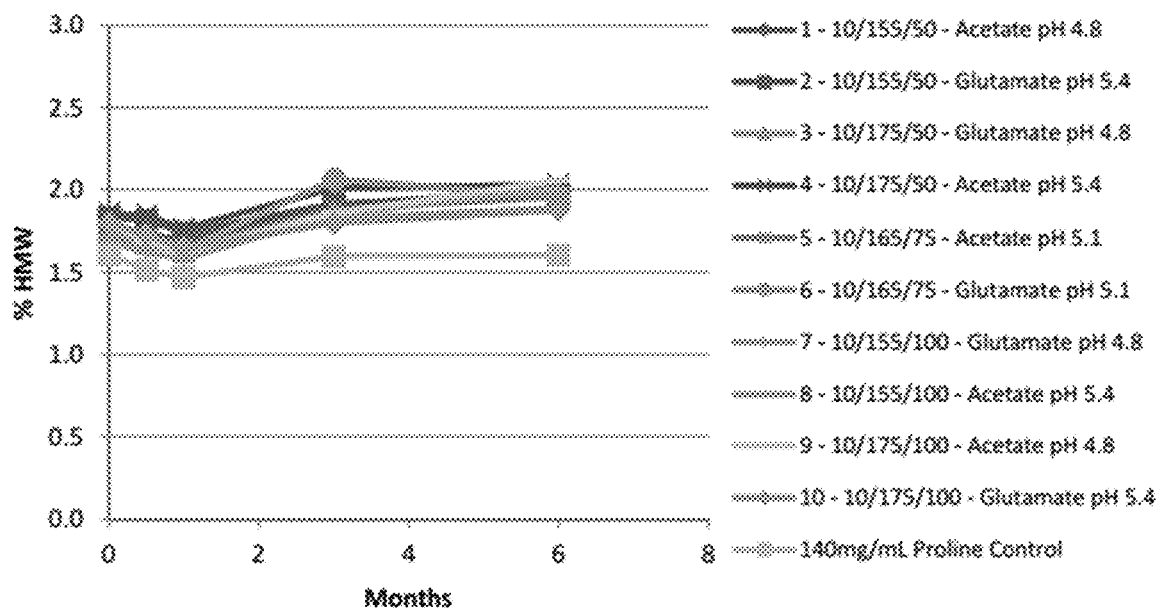
FIGS. 6A and 6B shows graphs of the percent of HMW species that develop over time for the indicated evolocumab formulations held at the indicated temperatures (5° C.
Figure 6B:
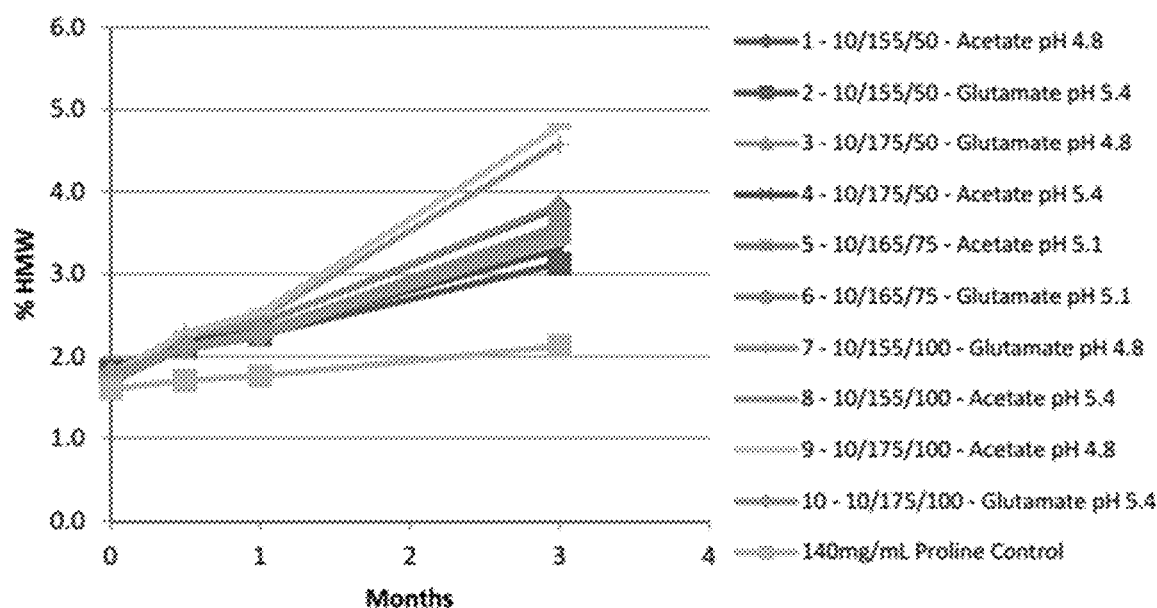
Figure 7A:
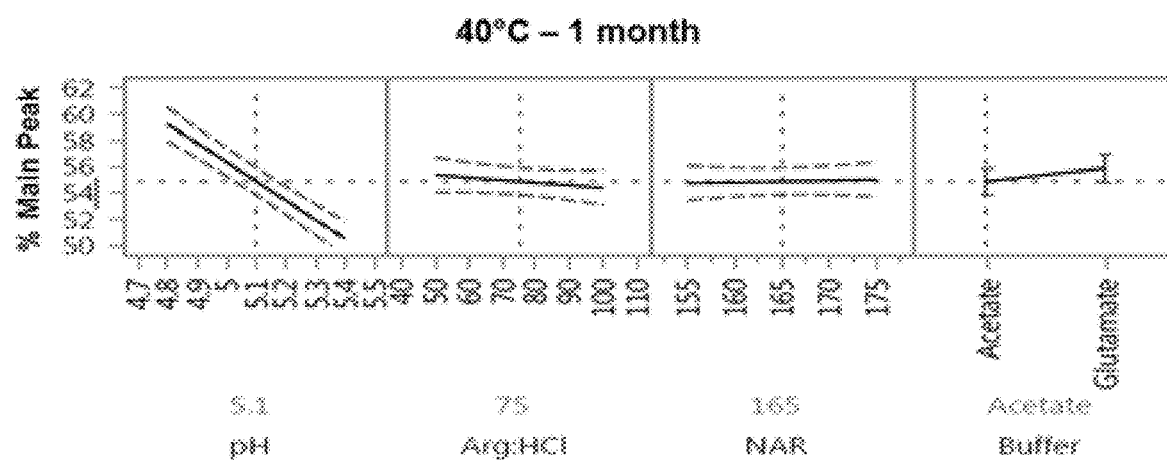
FIG. 7A shows graphs produced by JMP Prediction Profiler software of cation exchange chromatography-high pressure liquid chromatography (CEX-HPLC) data for evolocumab formulations held at 40° C. for one month.
Figure 7B:
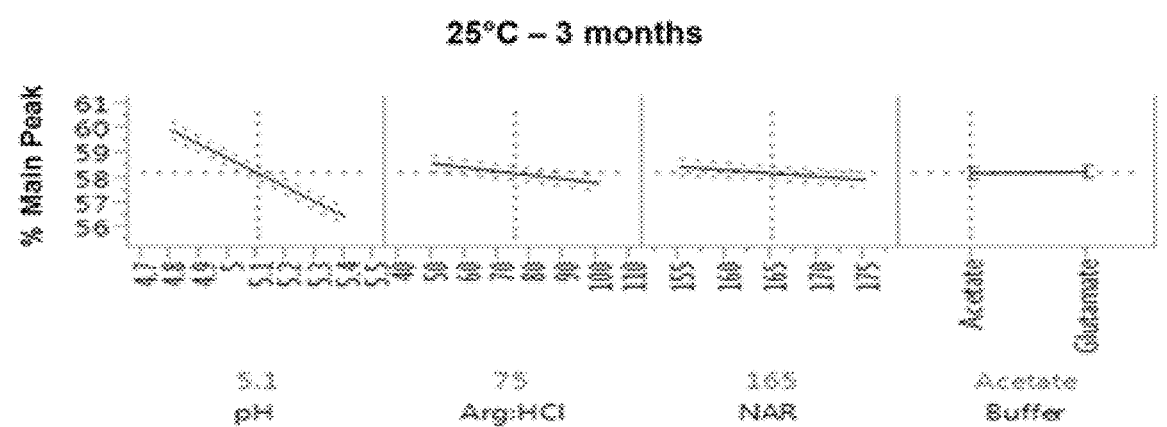
FIG. 7B shows similar data, except the samples were held at 25° C. for three months. See the Examples for further details.

Despite pH and Arg HCl concentration-dependent differences seen at 40° C., all formulations studied in this experiment showed comparable percent HMW species for up to 6 months at 5° C. and up to 1 month at 25° C. (FIG. 6A, 6B).

Figure 8:
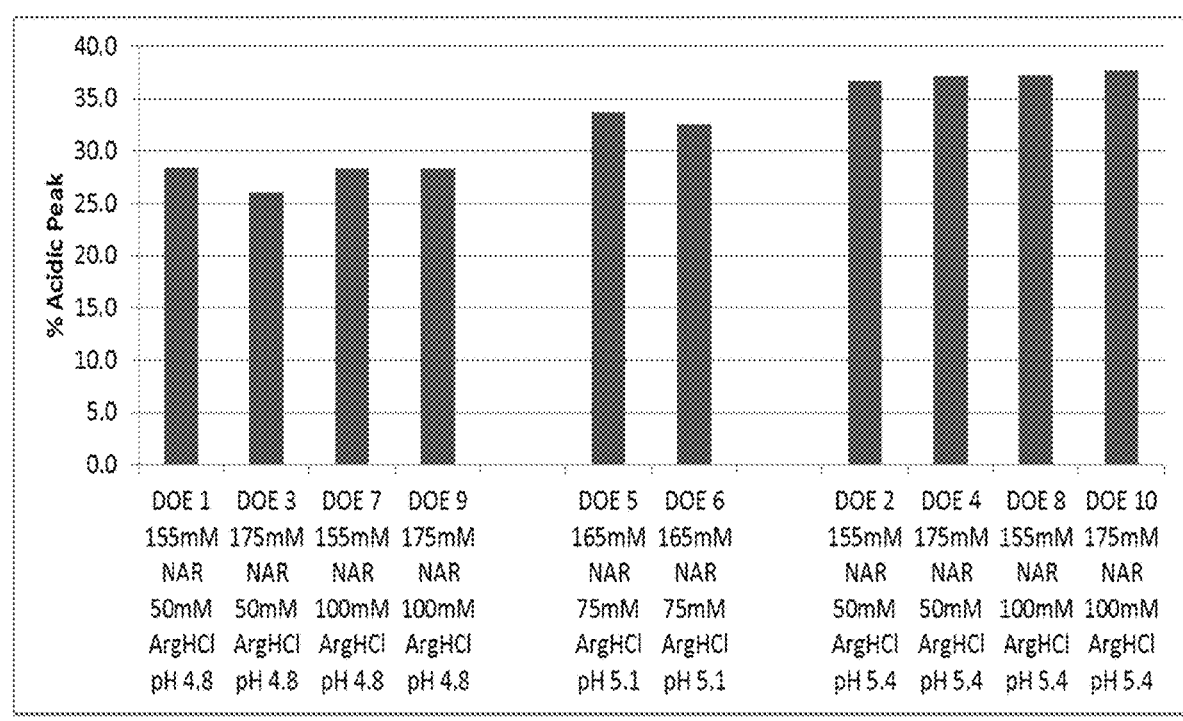
FIG. 8 shows a graph of the percent acidic peak by CEX-HPLC of 210 mg/mL evolocumab formulations held at 40° C. for one month.
Figure 9B:
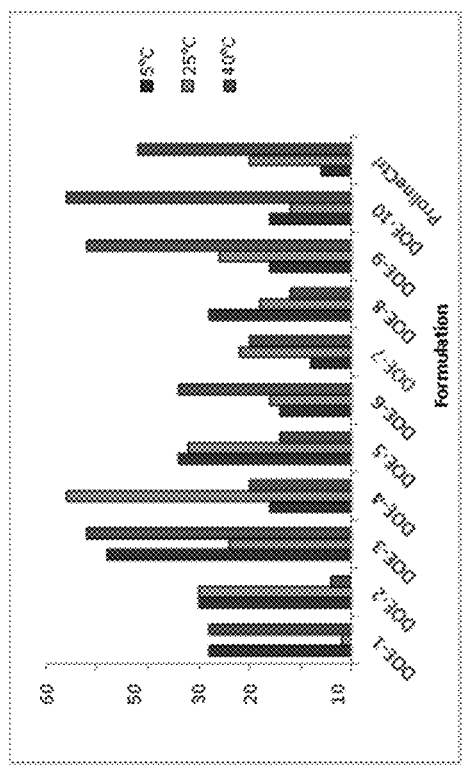
FIGS. 9A-9B show graphs of sub-visible particles as determined by light obscuration liquid borne particle counting (equal to or greater than 10 μM, FIG. 9A; or equal to or greater than 25 μM, FIG. 9B) per milliliter of various evolocumab formulations held at 5° C., 25° C., and 40° C. for three months.
Figure 9A:
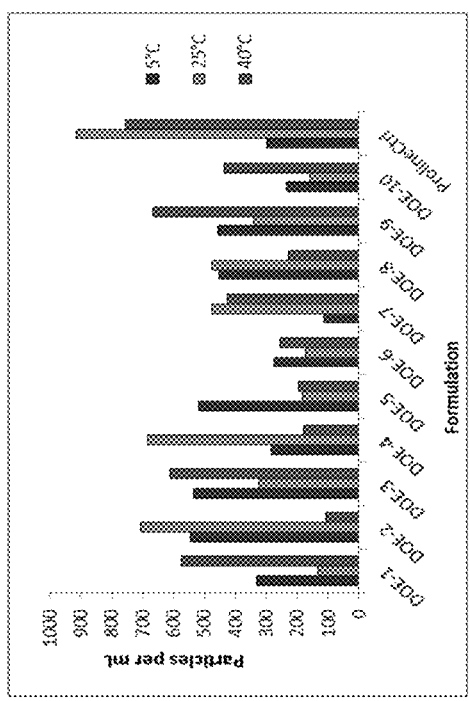
Figure 9C:
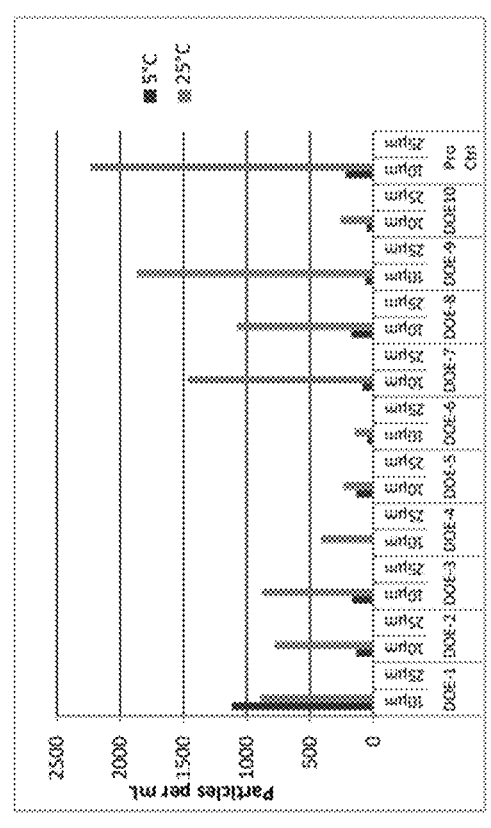
FIG. 9C shows a graph of sub-visible particles as determined by light obscuration liquid borne particle counting (greater than or equal to 10 μM or 25 μM) of various evolocumab formulations held at 5° C. or 25° C. for six months.
Figure 10:
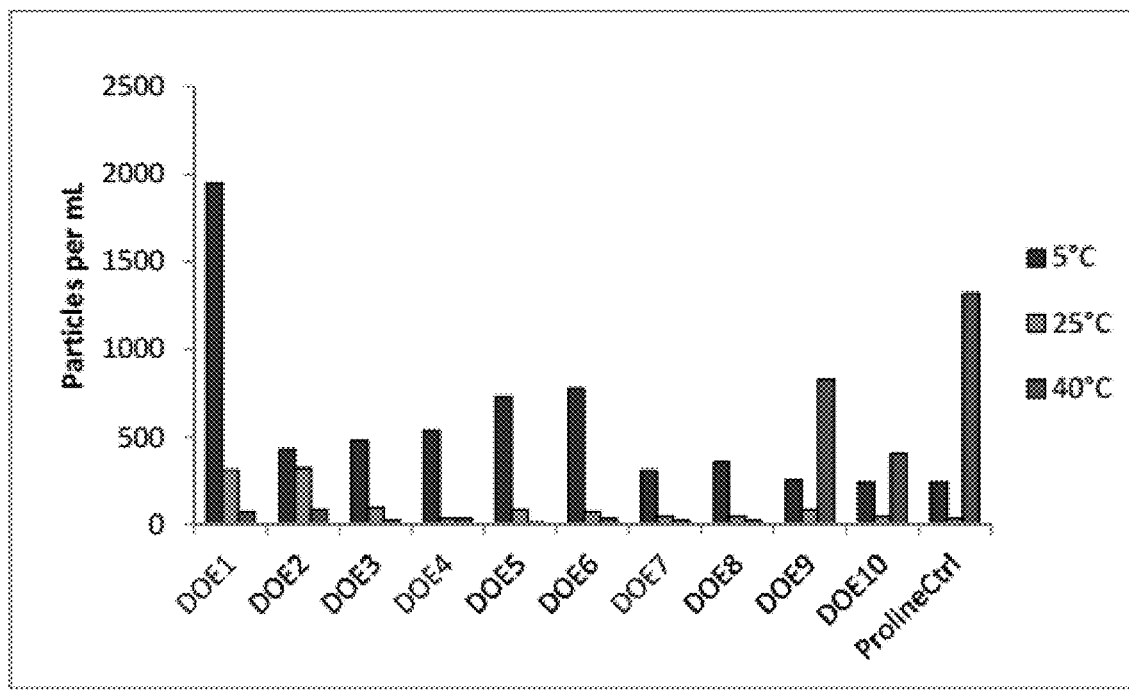
FIG. 10 shows a graph of sub-visible particles of various evolocumab formulations as determined by Micro Flow Imaging (MFI) analysis, filtered by aspect ratio (AR) of less than 0.70.

Tryptic peptide mapping with liquid chromatography-mass spectrometry (LC-MS) analysis was performed on selected samples Peptide map HPLC-ultraviolet (UV) chromatograms were visually compared to proline evolocumab formulation controls and evolocumab reference standard. No new peaks were observed in NAR/Arg HCl samples relative to controls (FIG. 8). In addition, analysis of chemical modifications detected by mass spectrometry showed no significant changes between NAR/Arg HCl samples and controls. Relative quantitation was performed and percentages of N55 and N33 deamidation as well as M246 and M422 oxidation are shown in Table 11. Slightly higher levels of N55 deamidation were seen in pH 5.4 NAR/Arg HCl samples relative to pH 5.1 NAR/Arg HCl and pH 5.0 proline samples, consistent with the increase in acidic peak seen by CEX. N33 (a potential deamidation site in the complementary determining region (CDR)) did not appear to show a significant increase in deamidation in the pH range and conditions assessed. Oxidation rates for both M246 and M422 were higher for 140 mg/mL proline control samples compared to 210 mg/mL NAR/Arg HCl samples following incubation at ASC.

TABLE 11

Deamidation and oxidation of evolocumab (selected samples)

| Sample | % N55 Deamidation | % N33 Deamidation | % M246 Oxidation | % M422 Oxidation |
|---|---|---|---|---|
| 10/165/75 Acetate pH 5.1 5° C. 3M | 11.6 | 0.8 | 5.4 | 3.7 |
| 10/165/75 Acetate pH 5.1 25° C. 3M | 11.8 | 0.7 | 6.0 | 3.8 |
| 10/165/75 Acetate pH 5.1 40°C 1M | 13.6 | 0.9 | 8.4 | 5.1 |
| 10/155/100 Acetate pH 5.4 5° C. 3M | 12.3 | 0.9 | 5.4 | 3.7 |
| 10/155/100 Acetate pH 5.4 25°C 3M | 12.1 | 0.6 | 6.1 | 3.9 |
| 10/155/100 Acetate pH 5.4 40°C 1M | 15.2 | 0.8 | 8.4 | 5.2 |
| 140 mg/mL Proline Control pH 5.0 5° C. 3M | 10.6 | 0.6 | 5.6 | 3.7 |
| 140 mg/mL Proline Control pH 5.0 25° C. 3M | 10.8 | 0.7 | 6.7 | 3.8 |
| 140 mg/mL Proline Control pH 5.0 40° C. 1M | 11.8 | 0.7 | 11.0 | 6.5 |

Sub-visible particles by light obscuration liquid borne particle counting and micro-flow imaging (MFI) showed no significant trends correlating with the formulation variables studied (FIGS. 9A-9C and FIG. 10). Sub-visible particle counts were comparable between 210 mg/mL NAR/Arg HCl samples and the 140 mg/mL proline control.

Figure 11:
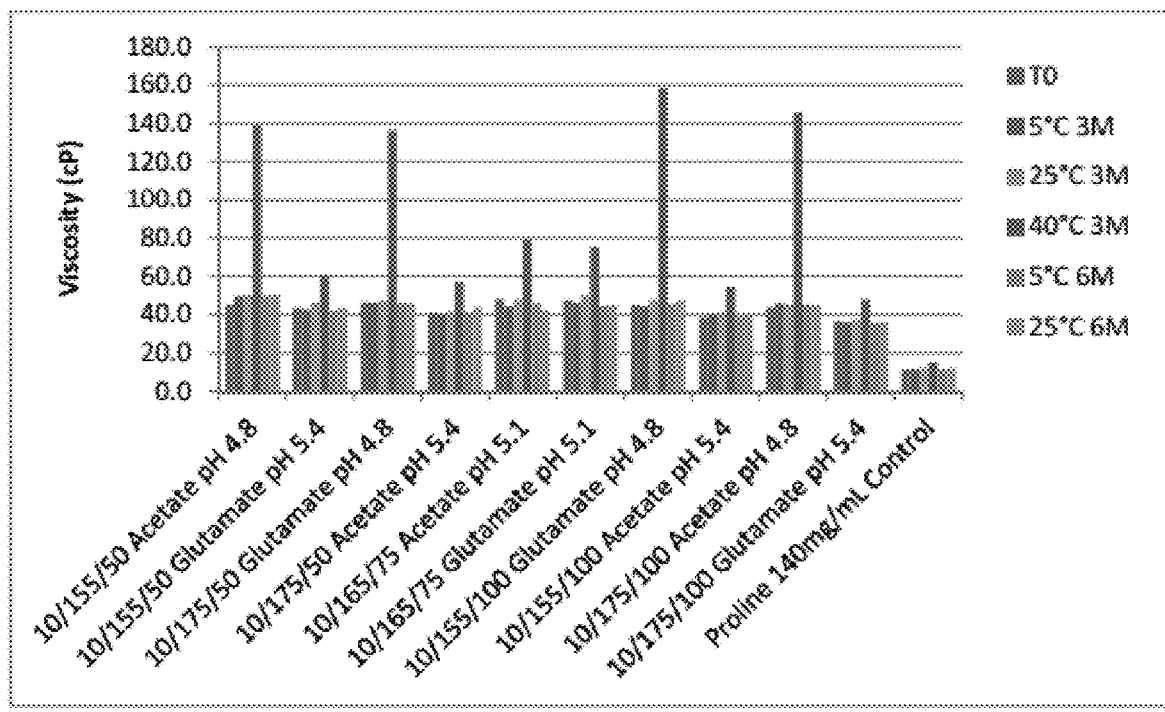
FIG. 11 shows a summary graph of the viscosities of various evolocumab formulations held for the specified times and temperatures as indicated where TO represents the initial viscosity values.

FIG. 11 compiles viscosity data from this study at time zero, three month, and six month time points. The data indicate that viscosity remained stable for up to six months at 5° C. and 25° C. for all formulations. 40° C. samples showed a pH-dependent increase in viscosity which was correlated to the increase in percent HMW species seen by SE-HPLC at 40° C. (FIG. 4).

Observations

An approximately isotonic formulation (~300 mOsm/kg) was achieved at the study midpoint formulation (10 mM buffer, 165 mM NAR, 75 mM arginine HCl)

Increasing pH lead to a decrease in percent aggregate following accelerated storage as observed using size exclusion chromatography (SEC) as well as an increase in deamidation with higher percent acidic species as detected by cation exchange.

Arginine HCl concentration had a greater impact on stability (lead to increased aggregation at 25° C. and 40° C.) at pH 4.8 and its effect was minimized at pH 5.4.

Acetate and glutamate are comparable in their effects on stability and viscosity.

No new peaks were observed for NAR/Arg HCl vs. proline controls by peptide mapping of selected samples for time points up to three months at 5° C. and 25° C. and one month at 40° C.

Viscosity remains stable up to six months at 5° C. and 25° C.

NAR remains soluble in formulations at 5° C. with DF buffer concentrations up to 175 mM with Arg HCl concentrations between 50-100 mM.

Example 3—pH Study

A pH study was designed to further investigate the effect of pH across a broader range. The study included formulations with a target pH range from 5.1-6.9. pH and buffer used for each sample is listed in Table 12. All samples formulated at 210 mg/mL with 10 mM buffer, 165 mM NAR, 75 mM Arginine HCl, 0.01% Polysorbate-80. Samples were sterile-filtered using 0.2 μm PVDF filters and hand-filled in glass PFS at a fill volume of 2.0 mL.

TABLE 12 pH and buffer variables for evolocumab (210 mg/mL) formulations having 165 mM NAR, 75 mM Arg HCl, and 0.01% (w/v) polysorbate-80

| Sample | pH | Buffer |
|---|---|---|
| 1 | 5.1 | Acetate |
| 2 | 5.4 | Acetate |
| 3 | 5.7 | Acetate |
| 4 | 6.0 | Histidine |
| 5 | 6.3 | Histidine |
| 6 | 6.6 | Phosphate |
| 7 | 6.9 | Phosphate |

Results

Figure 12:
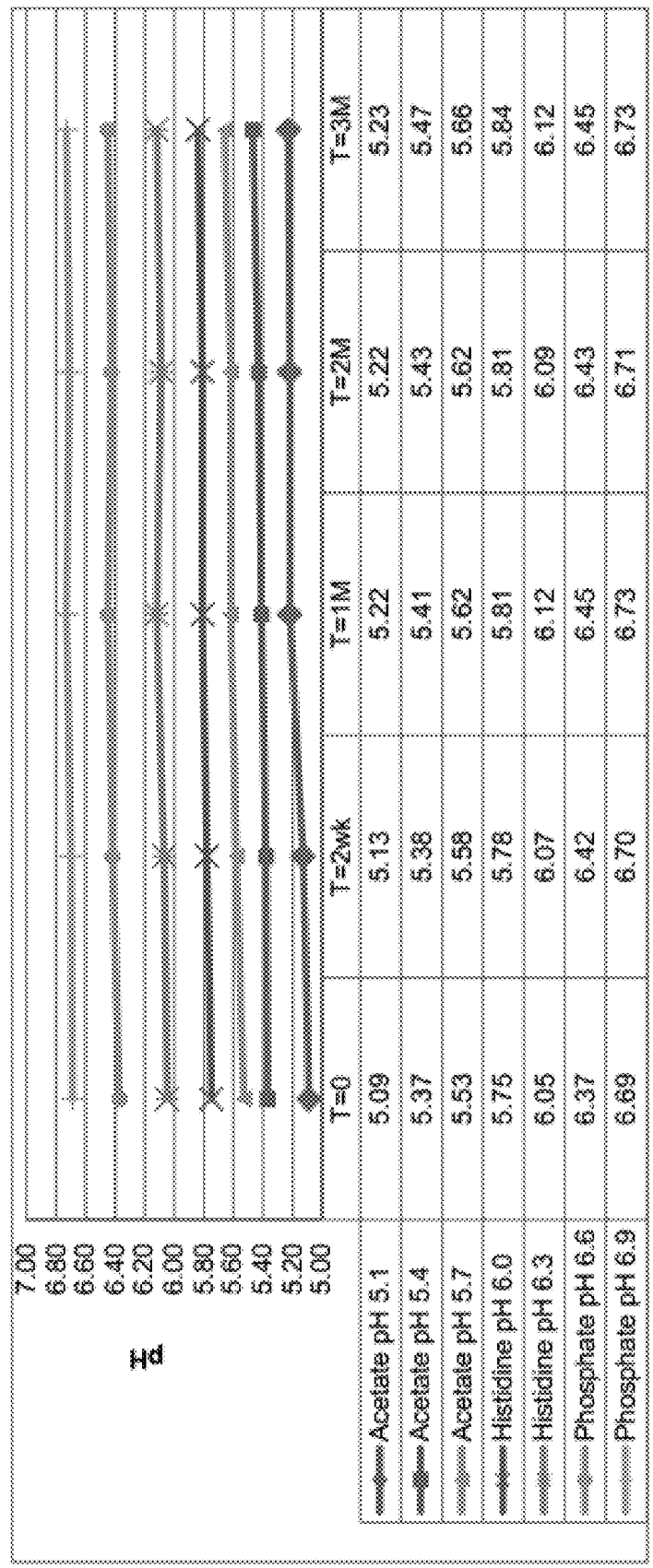
FIG. 12 shows a graph and a table showing the pH values of evolocumab formulations differing from each other by pH and buffer over time, up to three months. The samples were held at 40° C.

The pH values for each sample at time zero and over three months at 40° C. are shown in FIG. 12.

Figure 13A:
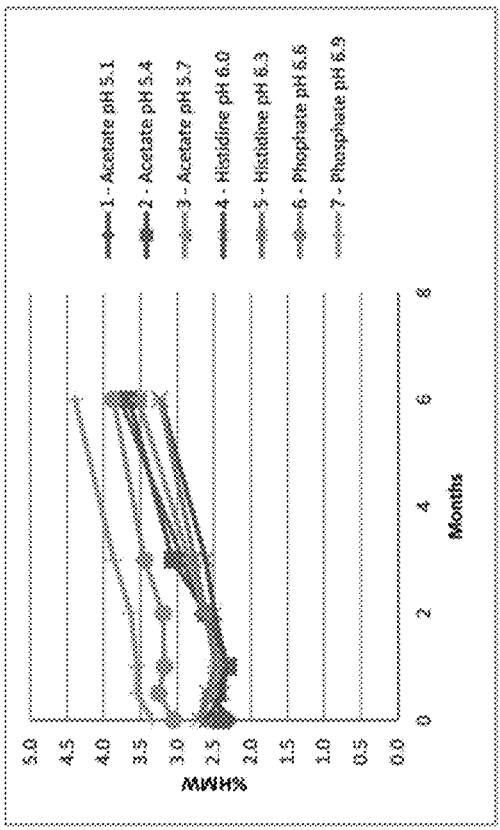
FIGS. 13A-13C show graphs of SE-HPLC data that demonstrate the effect of pH on percent HMW species of 210 mg/mL evolocumab formulations that differ by pH and buffer for up to three months at 4° C.
Figure 13B:
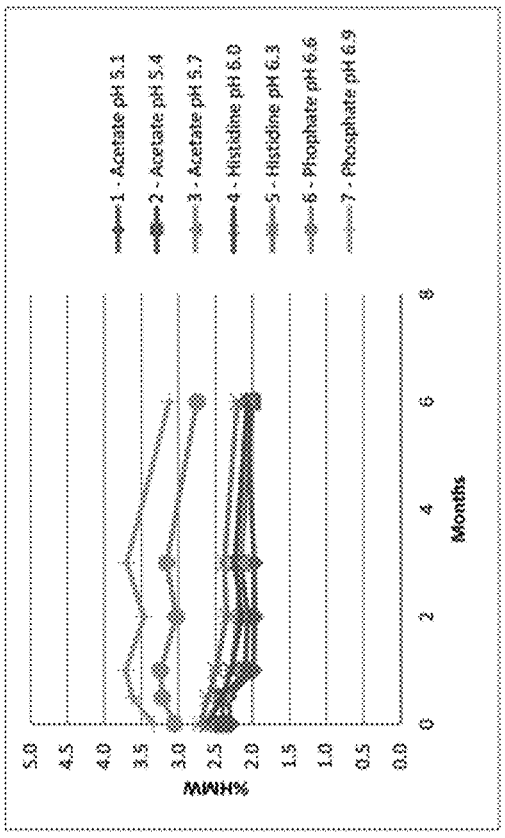
Figure 13C:
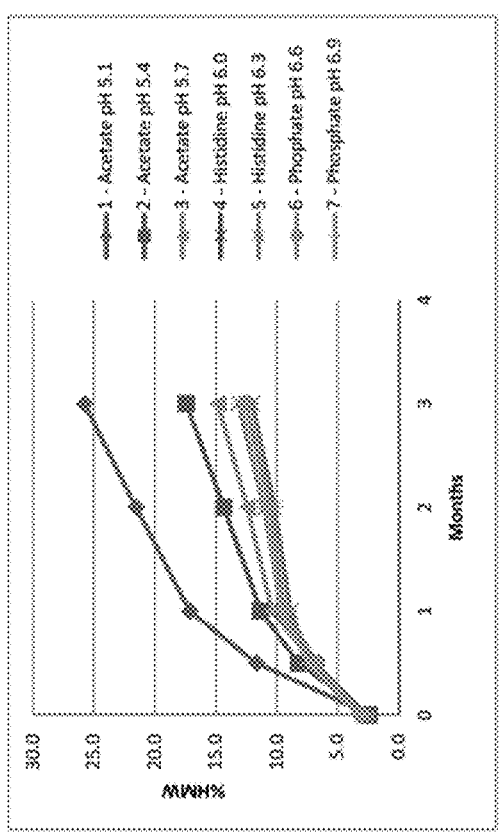
Figure 14:
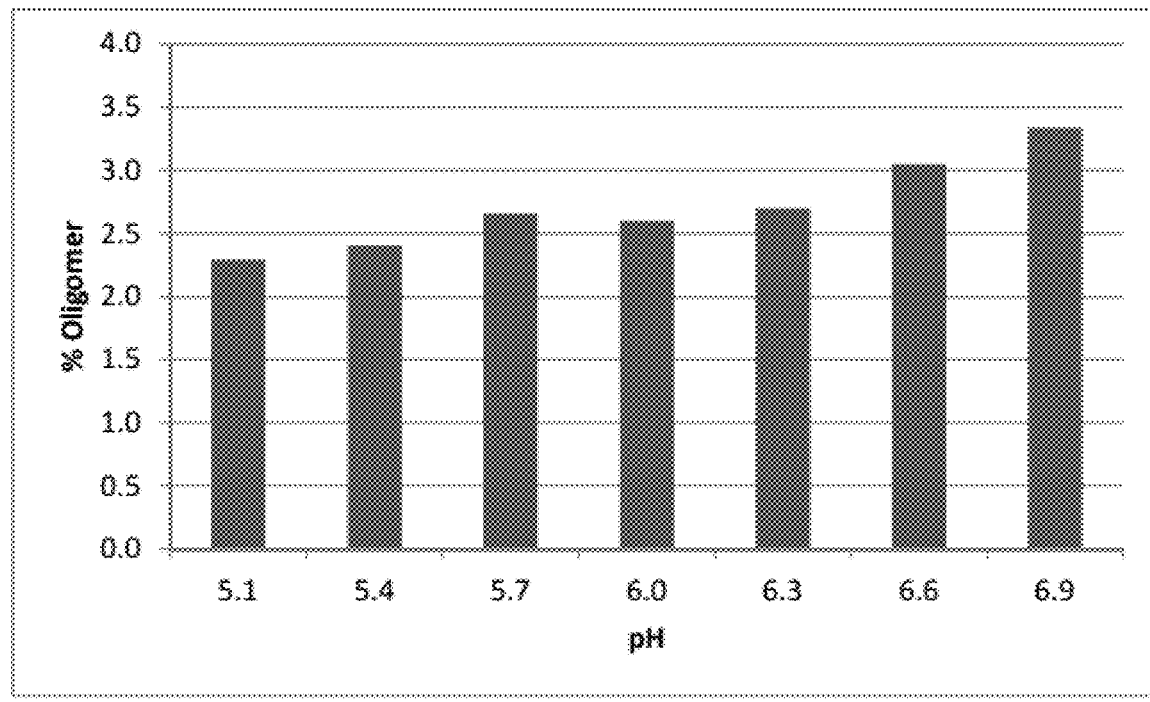
FIG. 14 shows a graph of oligomer levels of evolocumab formulations at varying pH immediately after formulation.

FIGS. 13A-13C show the effect of pH on percent HMW species (percent oligomer+percent aggregate) by SE-HPLC for up to three months at 4° C., 25° C., and 40° C., respectively. The 5° C. and 25° C. data showed minimal differentiation between formulations of varying pH. The most significant difference correlated with pH was higher levels of percent HMW species from time zero for pH 6.6 and pH 6.9 formulations. FIG. 14 shows a plot of time zero oligomer levels vs pH. A slight upward trend in oligomer was observed with increasing pH with a sharper increase observed above pH 6.3. Oligomer levels were minimized at lower pH.

As seen previously in the DOE study (Example 2), percent HMW species increased over time at 40° C. for each pH studied, with lower pH correlated with higher initial rates of increase.

Figure 15:
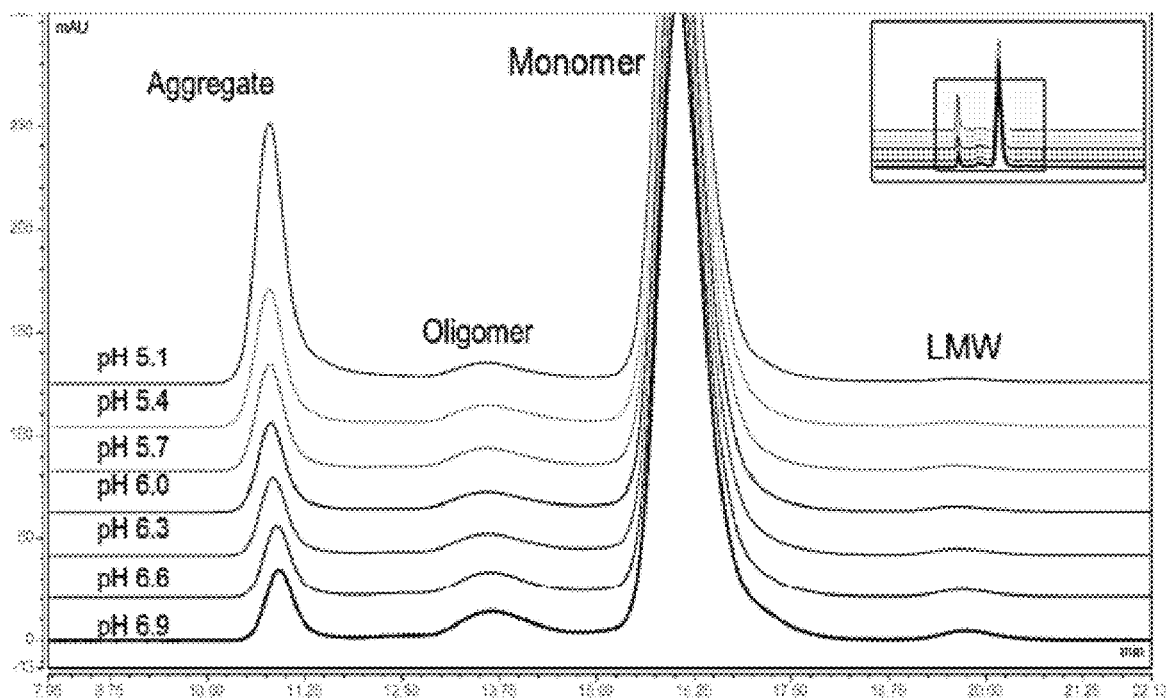
FIG. 15 shows chromatograms showing various sizes of protein molecules of evolocumab formulations that differ by pH and buffer after being held at 40° C. for three months. (LMW=low molecular weight species).

From a comparison of SE-HPLC chromatograms at the 40° C., three-month time point, increased levels of aggregate peak arose with decreasing pH (FIG. 15).

Figure 16A:
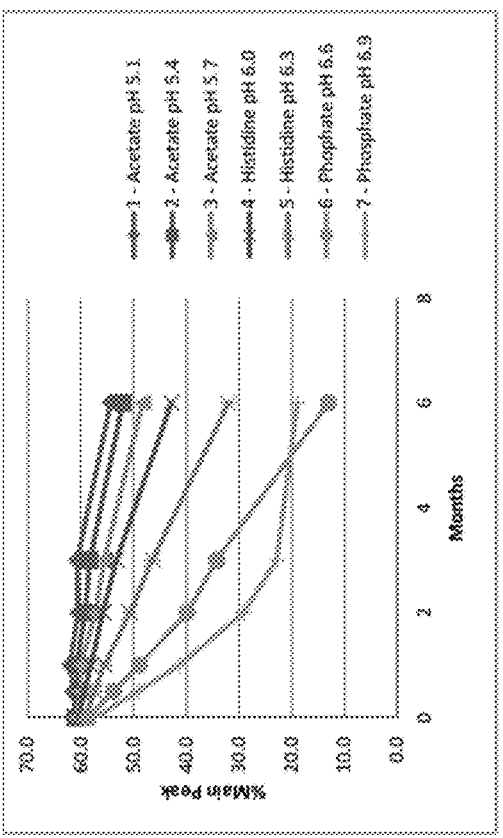
FIGS. 16A-16C show graphs of data from CEX-HPLC analyses (% main peak) of 210 mg/mL evolocumab formulations that differ by pH and buffer over time.
Figure 16B:
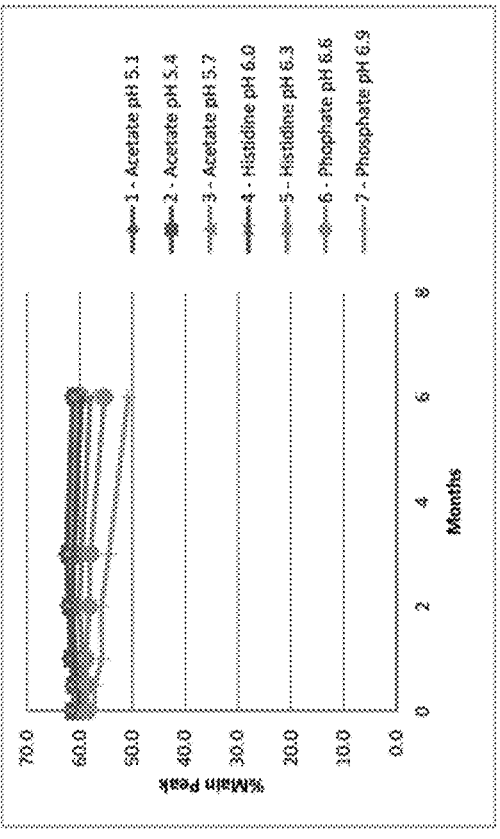
Figure 16C:
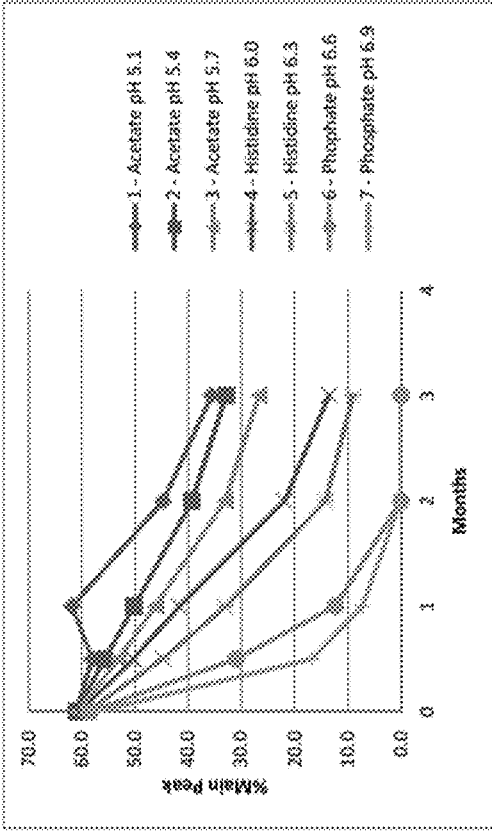

FIGS. 16A-16C show the effect of pH on percent main peak by CEX-HPLC for up to six months at 5° C. (FIG. 16A), 25° C. (FIG. 16B), and 40° C. (FIG. 16C). At 5° C., six month time point, there was no significant change in percent main peak for samples with pH 6.0, while there was an observed decrease in percent main peak for samples with pH>6.3 (FIG. 16A). CEX-HPLC data at ASC in FIG. 16B and FIG. 16C indicated that percent main peak decreased with increasing pH and that the rate of decrease significantly accelerated at pH>6.0.

Figure 17:
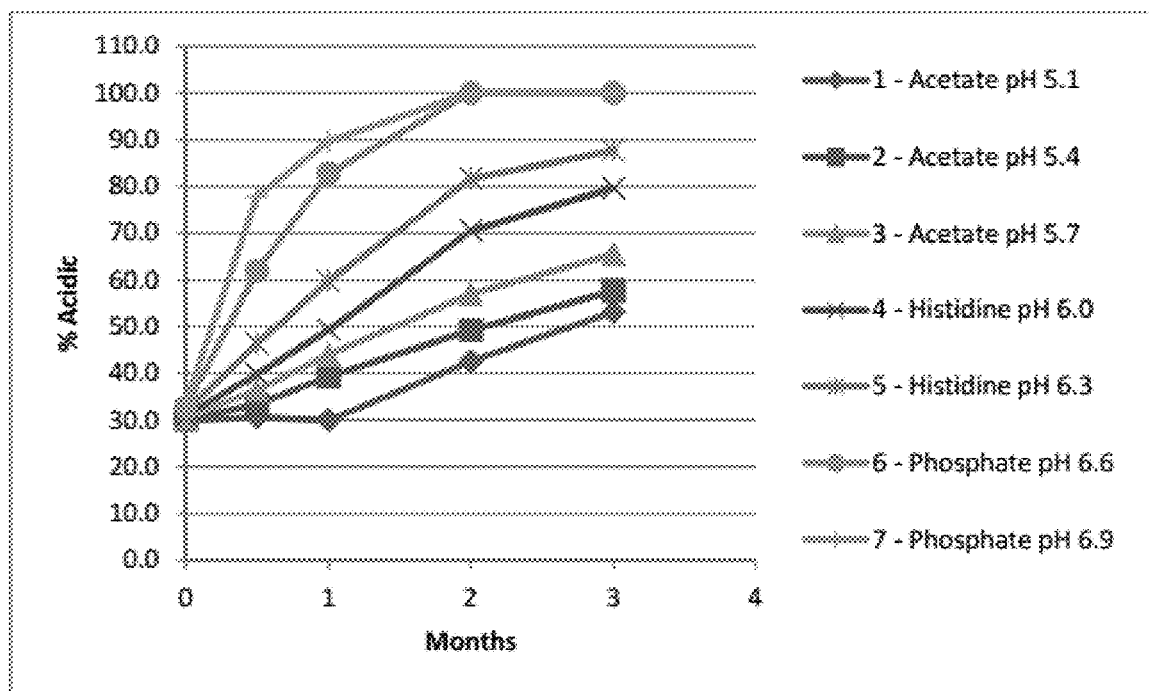
FIG. 17 shows a graph of data from CEX-HPLC analyses of 210 mg/mL evolocumab formulations that differ by pH and buffer held at 40° C. over time, measuring percent of acidic species in the formulations. In addition to 10 mM of each listed buffer, samples all contain 165 mM N-acetyl arginine, 75 mM arginine HCl, and 0.01% polysorbate-80.

FIG. 17 shows that the pH dependent decrease in CEX percent main peak at 40° C. was due to an increase in percent acidic species.

Figure 18:
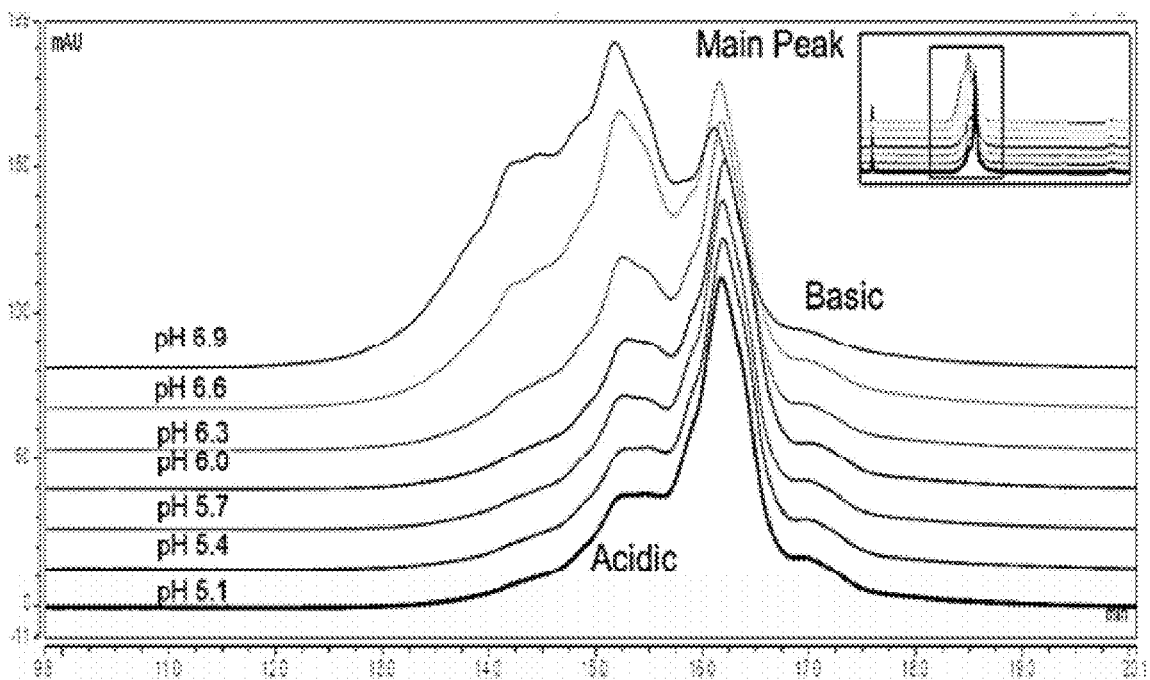
FIG. 18 shows chromatograms of CEX-HPLC data of 210 mg/mL evolocumab formulations that differ by pH and buffer held at 25° C. for three months, analyzing showing acidic, and basic, and main peak species. In addition to 10 mM of each listed buffer, samples all contain 165 mM N-acetyl arginine, 75 mM arginine HCl, and 0.01% polysorbate-80.

A comparison of CEX-HPLC chromatograms at the 25° C., three-month time point can be seen in FIG. 18. Percent acidic peak grew with increasing pH and there was a significant change in the chromatographic profile of samples having a pH greater than 6.3.

Figure 19:
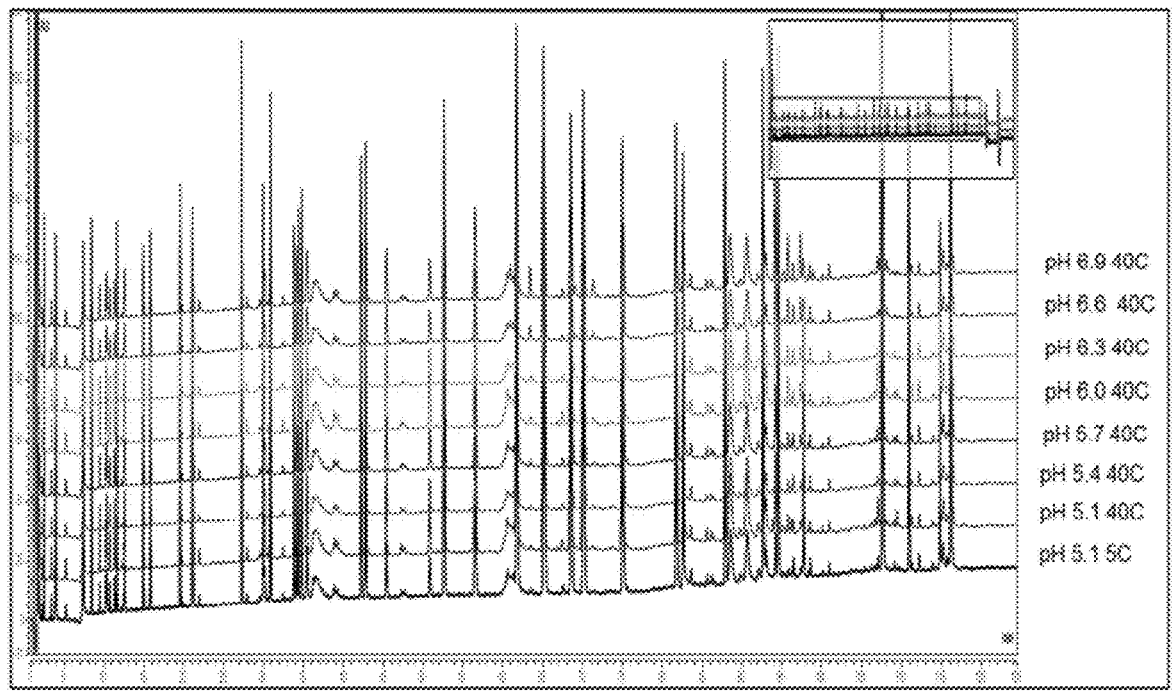
FIG. 19 shows chromatograms of peptide mapping data of various evolocumab formulations differing by pH and buffer, the samples having been held at 40° C. for one month. In addition to 10 mM of each listed buffer, samples all contain 165 mM N-acetyl arginine, 75 mM arginine HCl, and 0.01% polysorbate-80.

Tryptic peptide mapping with liquid chromatography-mass spectrometry (LC-MS) analysis was performed on samples after storage for 1 month at 40° C. Peptide map HPLC-UV chromatograms (FIG. 19) were visually compared to reference standard and across the pH range. In addition, chemical modification analysis by mass spectrometry showed no significant changes correlated with pH except for N55 and N33 deamidation. Relative quantitation levels of N55 and N33 deamidation as well as M246 and M422 oxidation are shown in Table 13. Increases in levels of percent N55 deamidation and percent N33 deamidation correlated with increased levels of percent acidic peak seen in CEX-HPLC data with increasing pH. There did not appear to be a significant effect of pH on oxidation levels for M246 or M422.

TABLE 13

Deamidation and oxidation of evolocumab

| Sample | % N55 Deamidation | % N33 Deamidation | % M246 Oxidation | % M422 Oxidation |
|---|---|---|---|---|
| pH 5.1—5° C. 4M | 10.7 | 0.7 | 5.8 | 1.5 |
| pH 5.1—40° C. 1M | 13.7 | 1.1 | 7.1 | 1.9 |
| pH 5.4—40° C. 1M | 15.5 | 0.9 | 6.5 | 1.5 |
| pH 5.7—40° C. 1M | 19.6 | 1.3 | 6.9 | 1.6 |
| pH 6.0—40° C. 1M | 24.8 | 2.0 | 6.3 | 1.5 |
| pH 6.3—40° C. 1M | 31.9 | 2.4 | 5.8 | 1.1 |
| pH 6.6—40° C. 1M | 53.3 | 4.9 | 6.7 | 1.3 |
| pH 6.9—40° C. 1M | 70.5 | 10.0 | 6.9 | 1.4 |

Figure 20:
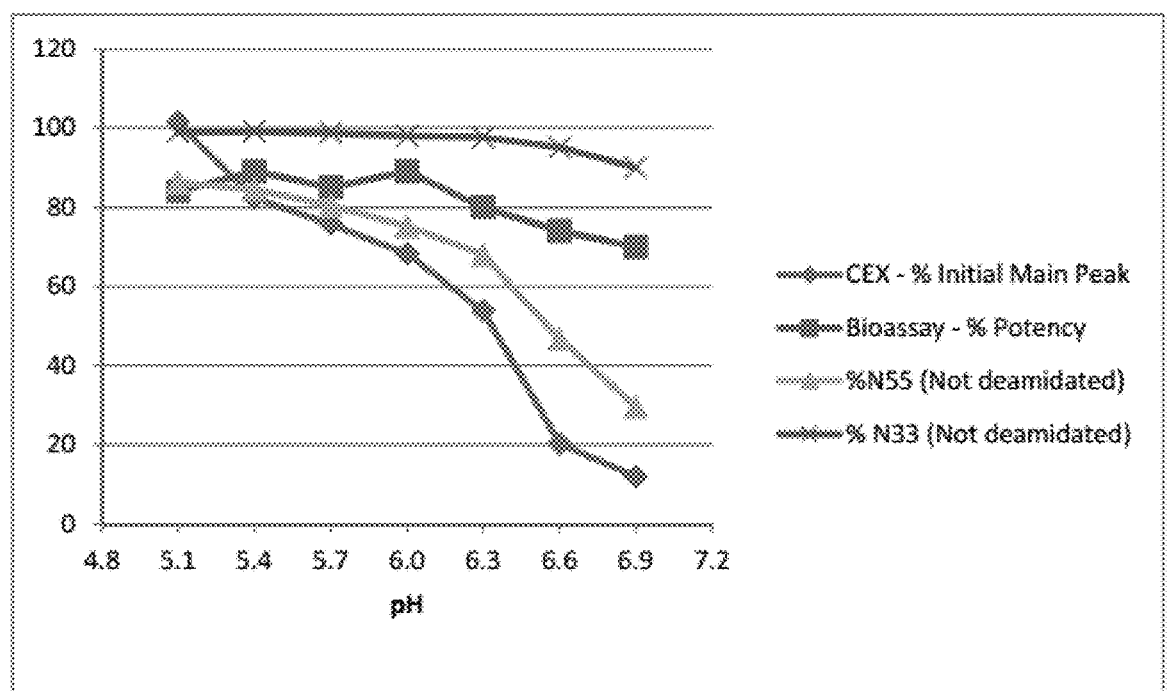
FIG. 20 shows a graph summarizing the results of several experiments that analyzed evolocumab in formulations that differ by pH and buffer after 1 month at 40° C. All samples contain 10 mM buffer 165 mM N-acetyl arginine, 75 mM arginine HCl, and 0.01% polysorbate-80. Refer to the figure and the Examples for further details.

Bioassay results for one month 40° C. samples is plotted in FIG. 20 alongside percent initial main peak (CEX-HPLC) and percent N55 and percent N33 (not deamidated).

Figure 22:
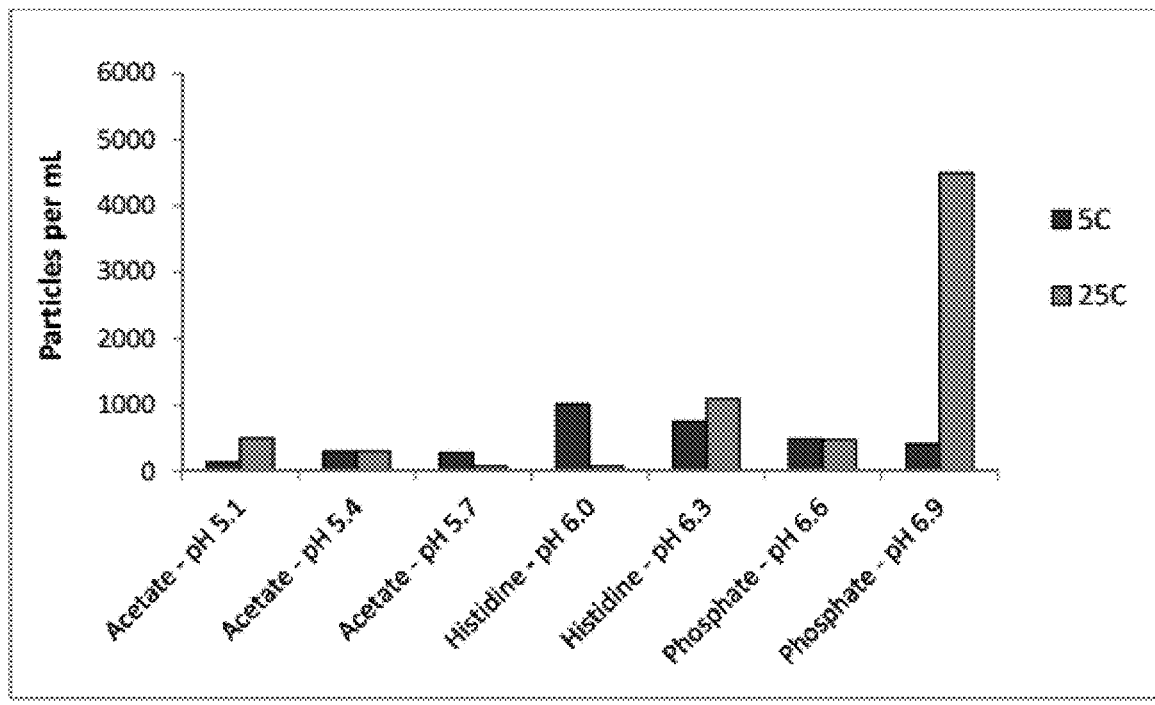
FIG. 22 shows a graph of sub-visible particles of evolocumab formulations that differ by pH and buffer as ascertained by Micro Flow Imaging (MFI). In addition to 10 mM of each listed buffer, samples all contain 165 mM N-acetyl arginine, 75 mM arginine HCl, and 0.01% polysorbate-80.

Sub-visible particles by light obscuration liquid borne particle counting (FIGS. 21A-21C) and MFI (FIG. 22) showed no significant trends that correlated with pH.

Figure 23:
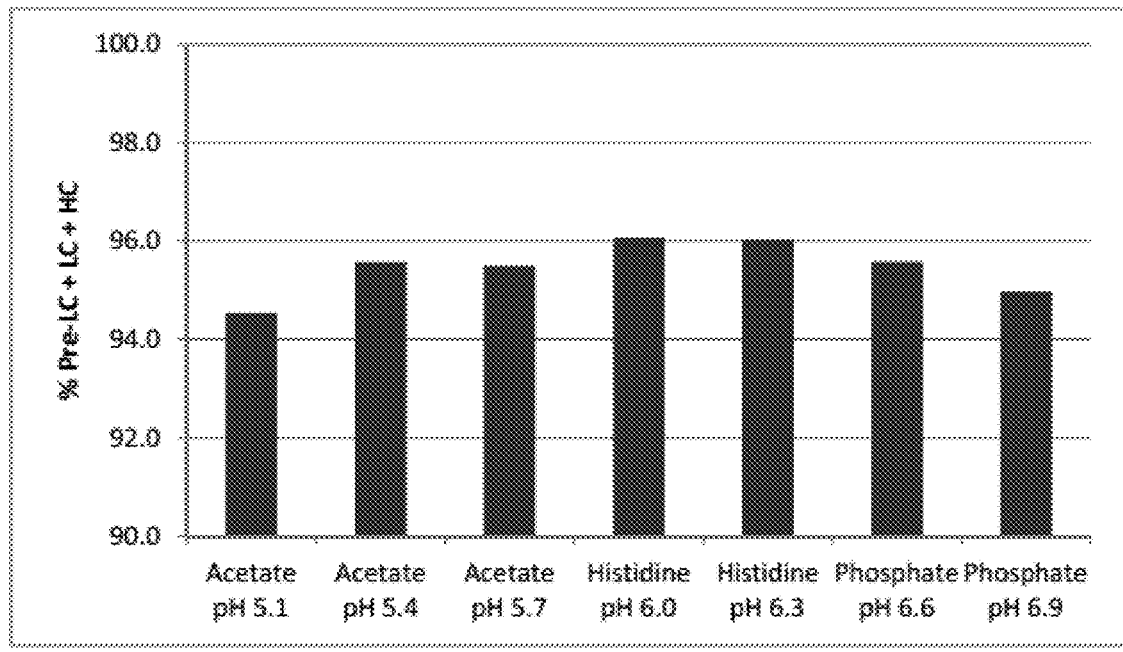
FIG. 23 shows a graph of the results of reduced capillary electrophoresis-sodium dodecyl sulfate (rCE-SDS) analyses on 210 mg/mL evolocumab formulations varying by pH and buffer held at 25° C. for 6 months. In addition to 10 mM of each listed buffer, samples all contain 165 mM N-acetyl arginine, 75 mM arginine HCl, and 0.01% polysorbate-80.

Data in FIG. 23 shows that pH had a minimal effect on fragmentation or other degradation as measured by reduced capillary electrophoresis-sodium dodecyl sulfate (rCE-SDS) analysis for up to six months at 25° C. Percent pre light chain plus light chain+heavy chain (pre LC+LC+HC) in FIG. 23 shows a slight decrease at the edges of the pH range. Lower pH samples contained slightly higher percent mid molecular weight (MMW) species while higher pH samples contained slightly higher percent HMW species. Percent low molecular weight (LMW) species is comparable across the pH range.

Figure 24:
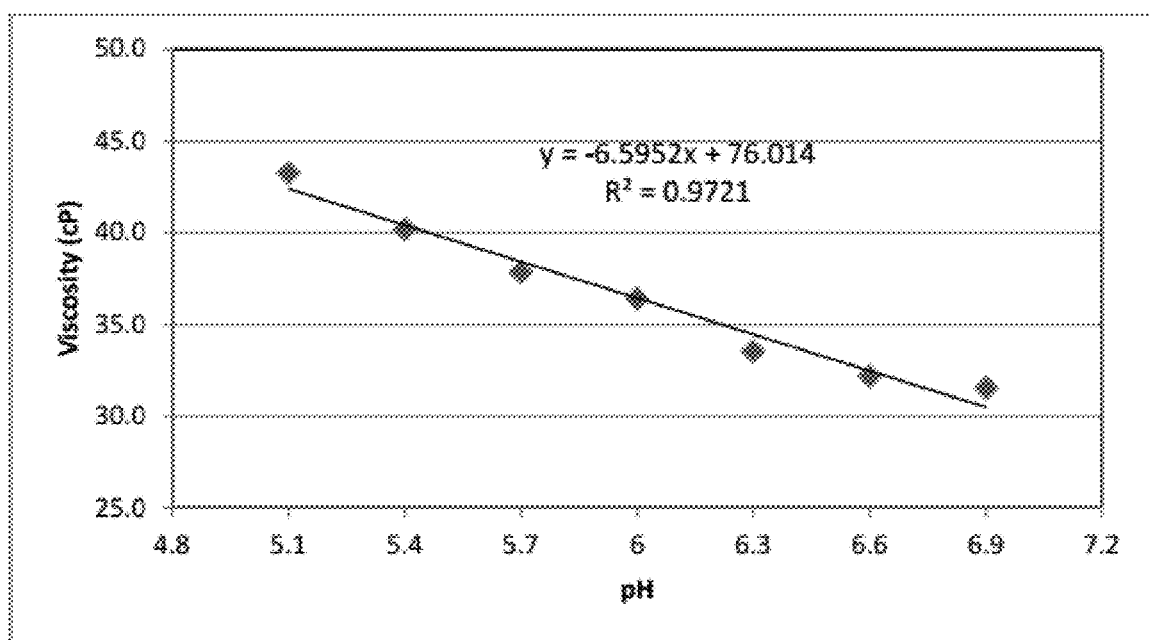
FIG. 24 shows a graph of the relationship between viscosity and pH of evolocumab formulations that differ in pH and buffer. All samples contain 10 mM buffer 165 mM N-acetyl arginine, 75 mM arginine HCl, and 0.01% polysorbate-80.

Finally, as shown in FIG. 24, there is a good linear relationship between viscosity and pH, with a decrease of 6.6 cP per pH unit.

Observations

Increasing pH led to (1) decreased aggregation rate at 40° C., (2) higher initial levels of oligomer, (3) increased rate of deamidation at 25° C. and 40° C., and (4) lower viscosity. pH did not appear to have a significant effect on visible or sub-visible particles, nor did pH appear to have a significant effect on fragmentation or other degradation as measured by rCE-SDS.

Example 4—Scale Down Study

Three formulations were subjected to commercial manufacturability and stability assessment. Formulation candidates were subjected to various unit operations, simulating commercial manufacturing prior to being placed on stability Results Physical properties were determined for each formulation drug substance.

pH was determined to be ~0.17 higher than the DF buffer pH for each formulation. DF buffer for formulation 3 was 0.14 above target which resulted in a DS pH which was 0.31 above target.

Figure 25A:
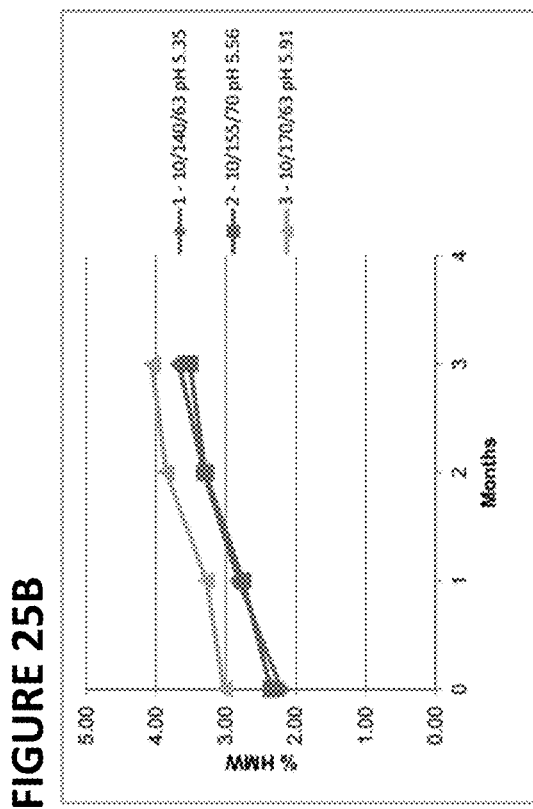
FIGS. 25A-25C show graphs of percent HMW species as measured by SE-HPLC of different evolocumab formulations held for the indicated time periods at 5° C.
Figure 25B:
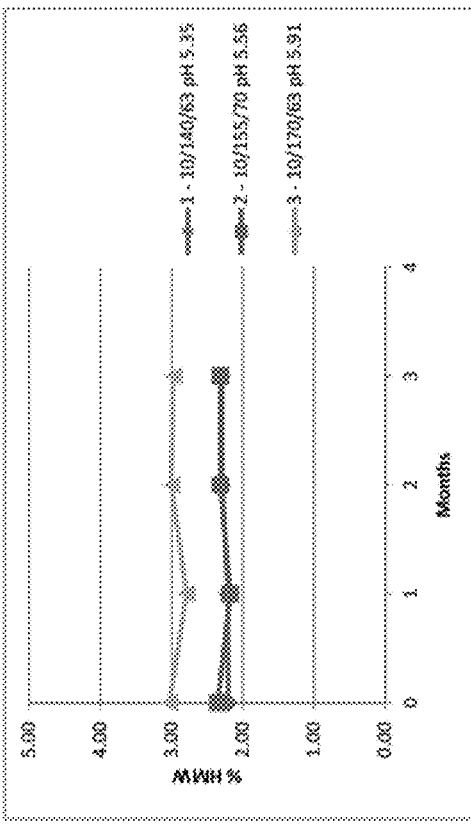
Figure 25C:
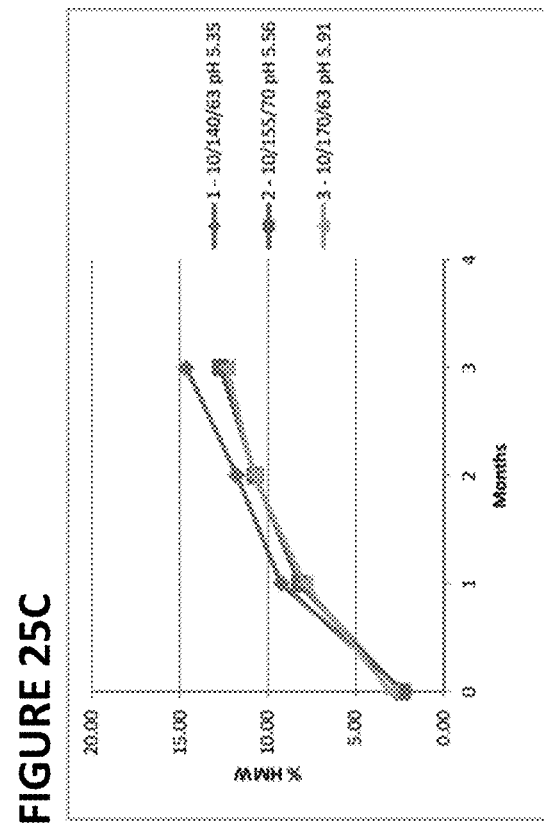

SE-HPLC (percent HMW species) results for drug product stability at 5° C., 25° C., and 40° C. are shown in FIGS. 25A-25C. Rates of increase in percent HMW species were comparable for all three samples at 5° C. and 25° C. while the rate of aggregation was slightly higher for sample 1 (having a lower pH) at 40° C.

Figure 26A:
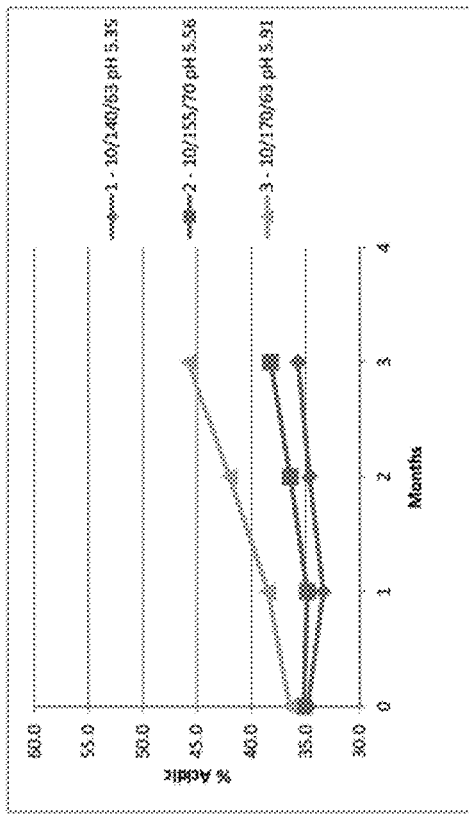
FIGS. 26A-26C show graphs of percent acidic peak as measured by CEX-HPLC of different evolocumab formulations held for the indicated time periods at 5° C.
Figure 26B:
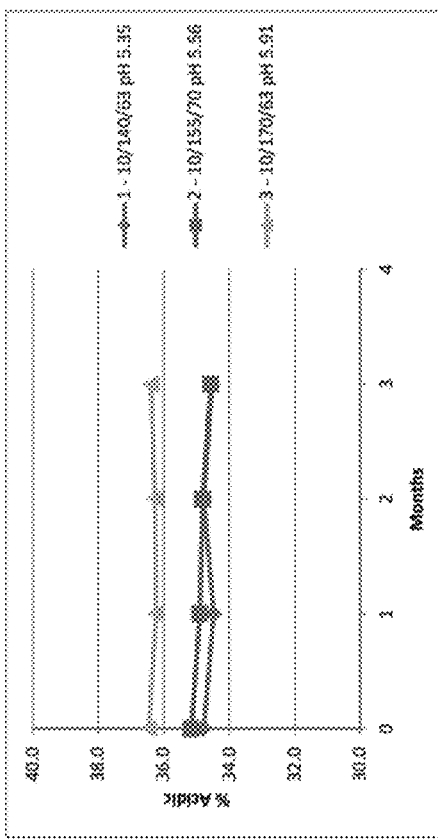
Figure 26C:
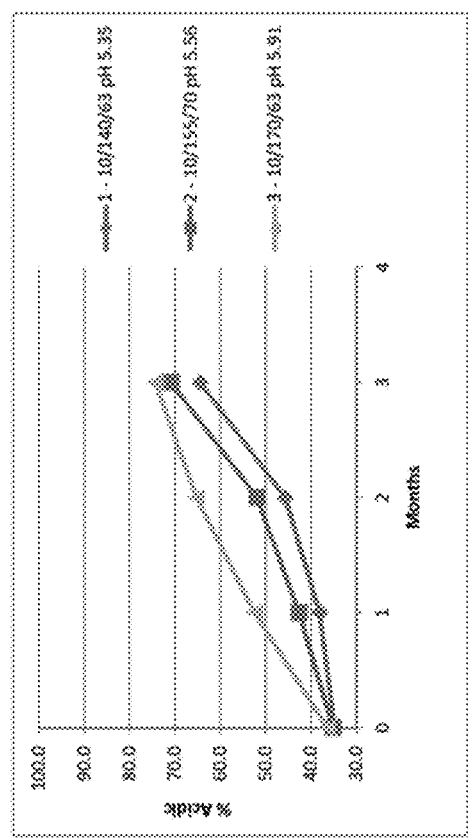
Figure 27:
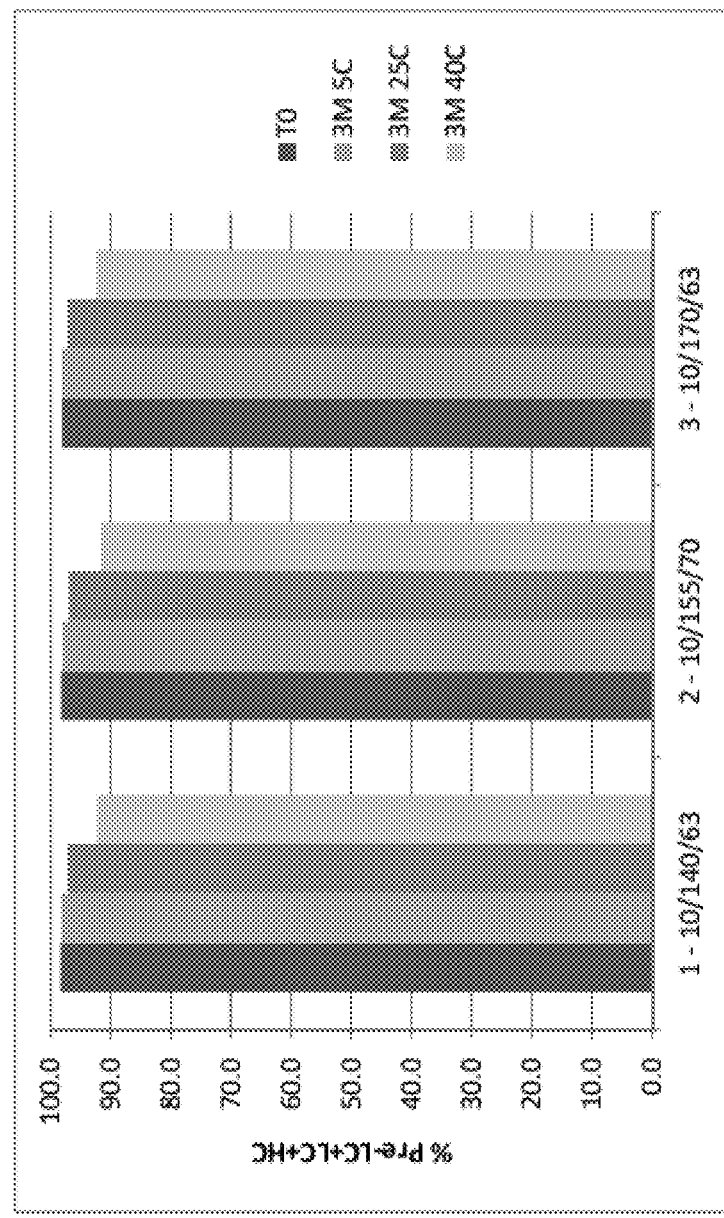
FIG. 27 shows a graph of percent Pre–LC+LC+HC (LC=Light chain, HC=Heavy Chain) by reduced capillary electrophoresis-sodium dodecyl sulfate (rCE-SDS) of different evolocumab formulations held for three months at 5° C., 25° C., and 40° C. compared to initial levels (TO). Key to formulations: [acetate (mM)]/[N-acetyl arginine (mM)]/[arginine HCl (mM)].

CEX-HPLC data are shown in FIGS. 26A-26C and show the expected pH and temperature dependent increases in percent acidic peak that were observed in previous studies (see previous Examples).

rCE-SDS data shown in FIG. 27 shows comparable levels of percent PreLC+HC+LC for each of the scale down formulations at all temperature and time points tested.

Turbidity levels did not significantly change for up to four months at 5° C. and 25° C. but did increase after 4 months at 40° C.

Figure 28:
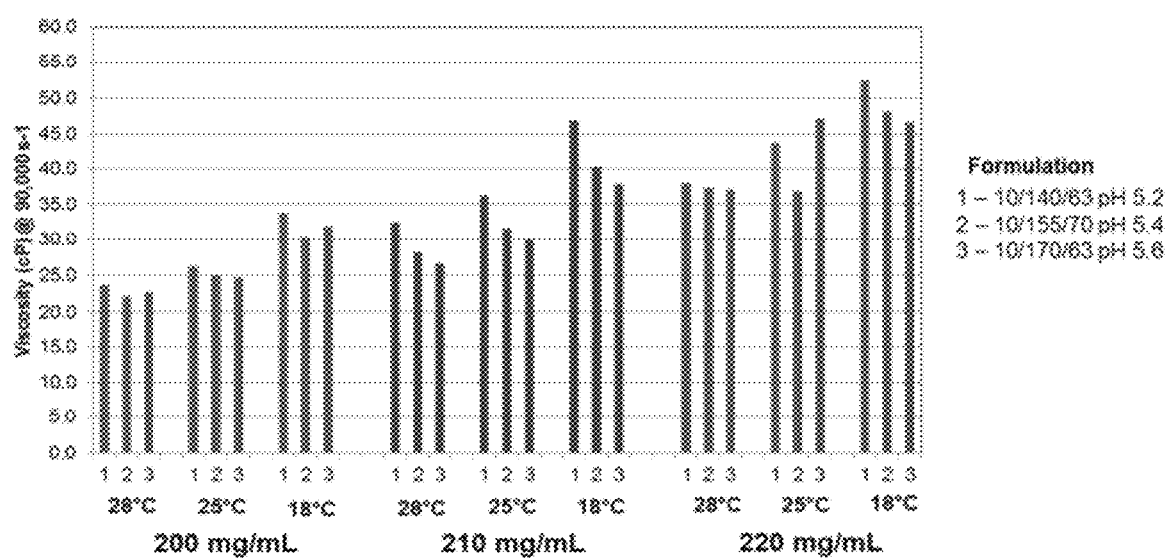
FIG. 28 shows a graph of the viscosities of different evolocumab formulations of three different concentrations of evolocumab; the viscosity data was determined using a rheometer at shear rates up to 90,000 $\sec^{-1}$ at the indicated temperatures. Key to formulations: [acetate (mM)]/[N-acetyl arginine (mM)]/[arginine HCl (mM)].

Scale down sample concentrations were adjusted to 200, 210, and 220 mg/mL for each formulation. Samples were tested by the m-VROC™ rheometer (RheoSense; San Ramon, CA) at shear rates up to 90,000 sec$^{-1}$ and at temperatures from 18° C. to 28° C. The data in FIG. 28 spanned a viscosity range from 22-52 cP and illustrated the impacts of protein concentration, temperature, and formulation variation on viscosity.

Observations

Levels of percent HMW species and aggregation rates by SE-HPLC were consistent with those observed in previous studies (e.g., see previous Examples).

Levels of percent main, acidic, and basic peaks and rates of change by CEX-HPLC were consistent with those observed in previous studies.

rCE-SDS data showed no significant fragmentation or other degradation up to three months at RSC and ASC Example 5—Ultrafiltration/Diafiltration of Evolocumab in Formulations Comprising N-Acetyl Arginine Materials and Methods The small-scale ultrafiltration/diafiltration (UF/DF) development experiments used Pellicon® 3 Cassette with Ultracel PLCTK Membrane, 30 kD molecular weight cut-off (D Screen, 0.11 m$^2$; EMD Millipore; Billerica, MA). The experiments were performed on a Tangential Flow Filtration (TFF) Process System (PendoTECH; Princeton, NJ). The experiments were performed at room temperature (22.2±2° C.).

The UF/DF development experiments were performed at small scale to evaluate three NAR formulation buffers with different pH values and compared their permeate flux data over concentration. Two DF steps were used in order to save cost on decreasing consumption of NAR. Additional experiments were performed in the UF1/DF1 step to evaluate two target concentrations (35 mg/mL and 70 mg/mL) on the high molecular weights formulation during the UF/DF process.

Other UF/DF operating parameters were not evaluated. General procedure of UF/DF experiments is described in Table 14.

TABLE 14

UF/DF general procedure and operating parameters

| Process Description | Condition | Evaluated |
|---|---|---|
| General | Membrane/Temperature/Membrane sizing | N |
| Equilibrium (EQ)/DF buffer | NAR formulation buffers | Y |
| | Concentrate to a target DF conc. | Y |
| Concentration 1 (UF1) | Transmembrane pressure (TMP) at 18 psi | N |
| | Feed cross-flow rate at 300 LMH (liters/m²/hr) | |
| | 3 diavolumes | Y |
| Diafiltration 1 (DF1) | TMP at 18 psi | N |
| | Feed cross-flow rate at 300 LMH | |
| | Concentrate to a target DF concentration | Y |
| Concentration 2 (UF2) | TMP at 18 psi | N |
| | Feed cross-flow rate at 300 LMH | |
| | 4 diavolumes | Y |
| Diafiltration 2 (DF2) | TMP at 18 psi | N |
| | Feed cross-flow rate at 300 LMH | |
| | Concentrate to a target concentration | Y |
| Concentration 3 (over-concentrated; OC) | TMP Initially at 18 psi; control value fully open | N |
| | Feed cross-flow rate at 60 LMH | |
| | Operating temp. 37° C. | |
| | 10 minute recirculation | N |
| Recirculation | Feed cross-flow rate at 60 LMH | |
| | Permeate path closed (no TMP) | |
| Recovery | Recover protein solution through low point or retentate port | N |
| | Chase with buffer through retentate port | |
| Cleaning | ≥20 L/m² single-pass | N |
| | 30 min recirculation, 20 L/m² | |
| Storage | ≥20 L/m² single-pass | N |

$A_{280}$ measurements were performed using a variable path length spectrophotometer (SoloVPE system; SoloVPE; Bridgewater, NJ) with an extinction coefficient of 1.5 $(cm)^{-1} (g/L)^{-1}$.

Analytical methods used to evaluate product pool quality included SE-HPLC, rCE-SDS, and CEX-HPLC.

NAR: Ac-Arg-OH, Biochem Catalog number—E-1025

NAR Formulation Buffer Study Results

This experiment evaluated three NAR formulation buffers in the UF/DF process. The UF/DF process followed the general guideline: (1) evolocumab was concentrated to 70 mg/mL through fed-batch concentration (UF1) and diafiltrated to NAR formulation buffer with 3 diavolumes (DF1); (2) the protein was further concentrated to 140 mg/mL (UF2) and diafiltrated to NAR formulation buffer with 4 diavolumes (DF2); (3) the protein was over-concentrated to target ~260 mg/mL and recovered from the system at 37° C. The protein loading/member area was 1468 g/m² for NAR pH 5.4 and 800 g/m² for NAR pH 5.2 and 5.6.

The flux data was plotted over concentration and compared across all NAR formulation buffers. In addition, the excipient levels were analyzed by sampling from each diafiltration step to study diafiltration performance and determine the minimal diavolumes.

Results and Observations

Figure 29:
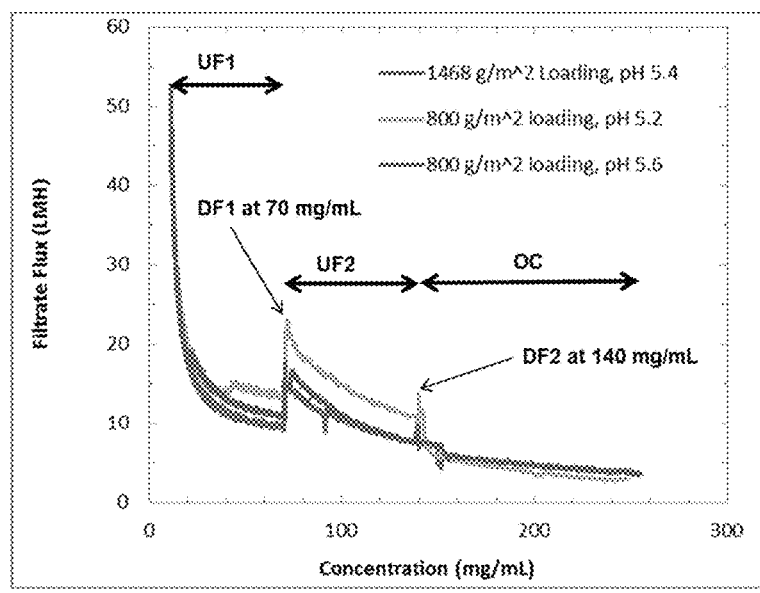
FIG. 29 shows a graph of evolocumab UF/DF flux data in three NAR formulation buffers.

The flux data from the UF/DF study was used to generate the filtrate flux vs. concentration plot shown in FIG. 29. The flux profiles were comparable across the three NAR formulation buffers. The flux increased with protein being buffer exchanged to NAR formulation buffer (DF1 and DF2), but decreased significantly with increase in protein concentration (UF1, UF2, and OC). The total process time for UF/DF was about 20 hours in NAR pH 5.4 and 10 hours in NAR pH 5.2 and 5.6 due to different membrane areas. The similar flux profile results showed that the NAR formulation buffer had no significant effect on the process flux. The summary of evolocumab drug substance (DS) small scale UF/DF studies are shown in Table 15.

Samples were taken at the diafiltration steps (DF1 and DF2) at each diavolume (1 to 7 DVs) to test diafiltration performance and determine minimal diavolumes. The representative sample analyses in Table 16 were from evolocumab NAR pH 5.4 UF/DF study. The results showed that after five diavolumes, the diafiltration to NAR pH 5.4 was essentially complete.

TABLE 15

Summary of evolocumab DS Small scale UF/DF studies

| Variable | pH 5.2 | pH 5.4 | pH 5.6 |
|---|---|---|---|
| Feed materials | evolocumab HMP VFP 11 mg/ml | | |
| Formulation buffer | 10 mM Acetate | 10 mM Acetate | 10 mM Acetate |
| | 140 mM NAR | 155 mM NAR | 170 mM NAR |
| | 63 mM Arg HCl | 70 mM Arg HCl | 63 mM Arg HCl |
| Membrane load (g/m²) | 800 | 1467.5 | 800 |
| OC (g/L) | 262 | 270 | 268 |
| DS concentration (g/L) | 226 | 217 | 222 |
| DS viscosity cP @1000 s−1 | 77.4 | 49.6 | 52.3 |

TABLE 16

Excipient levels at each DF step in evolocumab UF/DF NAR pH 5.4
NAR (mM) Na (mM) Cl (mM)

| Sample | Acetate (mM) | Arginine (mM) | NAR (mM) | Na (mM) | Cl (mM) | Tris (mM) |
|---|---|---|---|---|---|---|
| DF0 | 91.243 | NA | NA | 155.97 | 99.9 | 1.29 |
| DF1-1DV | 38.271 | 34.193 | 115.805 | 25.94 | 69.8 | 0.21 |
| DF1-2DV | 20.435 | 52.299 | 153.178 | 26.78 | 60.4 | 0.22 |
| DF1-3DV | 13.903 | 44.951 | 163.453 | 9.88 | 56.8 | 0.08 |
| DF2-4DV | 11.354 | 46.28 | 167.072 | 6.08 | 56.4 | 0.05 |

TABLE 16-continued

Excipient levels at each DF step in evolocumab UF/DF NAR pH 5.4
NAR (mM) Na (mM) Cl (mM)

| Sample | Acetate (mM) | Arginine (mM) | NAR (mM) | Na (mM) | Cl (mM) | Tris (mM) |
|---|---|---|---|---|---|---|
| DF2-5DV | 10.287 | 45.819 | 157.11 | 4.69 | 55.5 | 0.04 |
| DF2-6DV | 10.354 | 46.283 | 166.749 | 3.80 | 61.7 | 0.03 |
| DF2-7DV | 10.134 | 46.488 | 162.536 | 4.86 | 58.1 | 0.04 |

Example 6—Monitoring DS Concentration and HMW Formation During UF/DF of Evolocumab Formulations The purpose of the experiment was to evaluate the target concentration on Fed-Batch Concentration/Diafiltration (UF1/DF1), and to determine the target concentration to minimize the HMW formation during UF/DF operation. The UF/DF process followed the general guidelines listed in Table 17. Evolocumab (11-mg/mL) was concentrated to 35 mg/mL or 70 mg/mL through Fed-batch concentration (UF1). The protein loading/member area was 800 g/m² and the NAR formulation buffer included 10 mM Acetate, 155 mM N-Acetyl arginine, 70 mM arginine HCl, pH 5.3.

In addition, from each UF/DF step, protein samples were taken for product pool quality analysis in order to evaluate the UF/DF operation. The product pool quality data were used to study the effect of different UF1/DF1 product concentration on HMW formation.

Materials and Methods

Refer to Example 5.

Results and Observations

Figure 30:
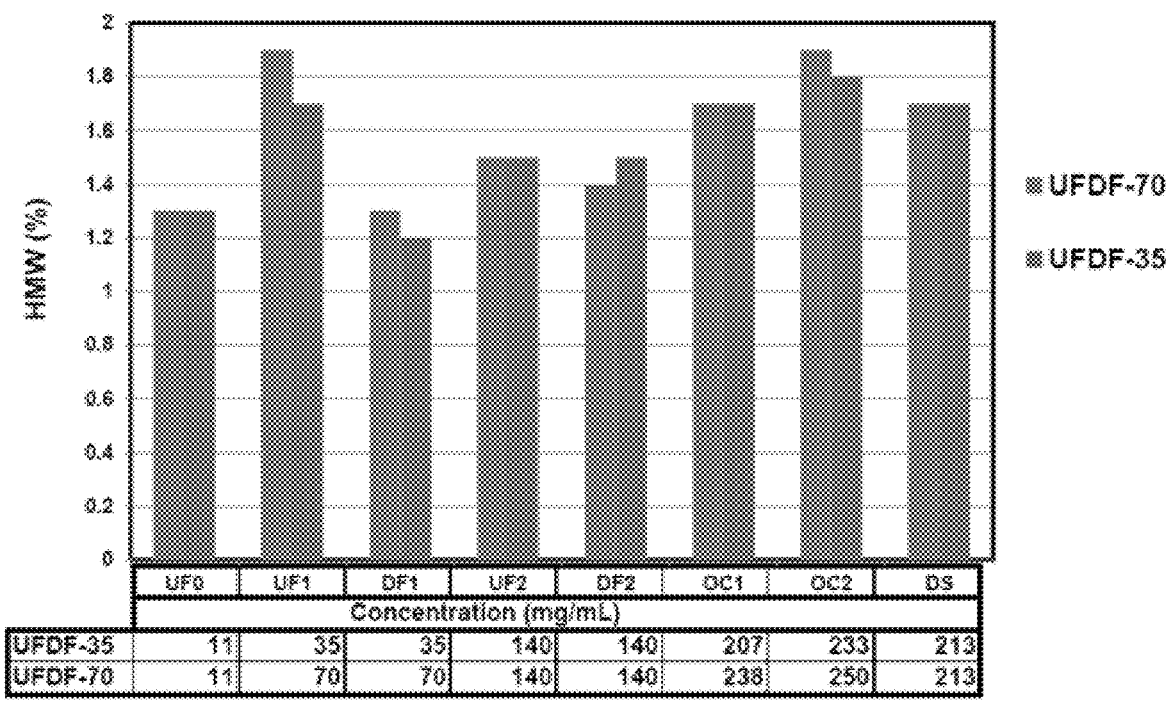
FIG. 30 shows a graph of the percentage of HMW species formation in the evolocumab UF/DF process with 35 mg/mL and 70 mg/mL evolocumab in UF1/DF1 (UF/DF-70 and UF/DF-35). The figure also shows the concentration of evolocumab in mg/mL at each step of the process for the two initial concentrations of evolocumab.
Figure 31A:
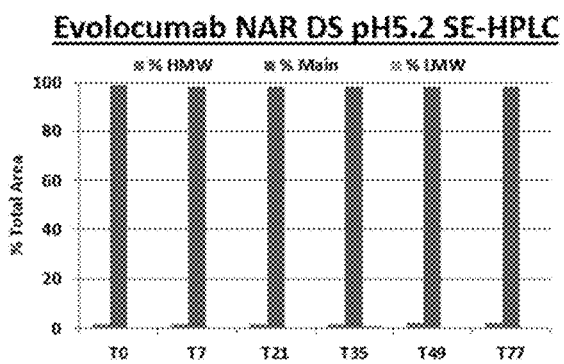
FIGS. 31A-31F show graphs of SE-HPLC (FIGS. 31A, 31C, and 31E) and CEX-HPLC (FIGS. 31B, 31D, and 31F) of evolocumab in NAR-containing formulations at pH 5.2 (FIGS. 31A and 31B), pH 5.4 (FIGS. 31C and 31D), and pH 5.6 (FIGS. 31E and 31F). The values of the bars for the percent HMW species, percent LMW species, and percent evolocumab shown in FIGS. 31A-31F are provided in Tables 17A-17F.
Figure 31B:
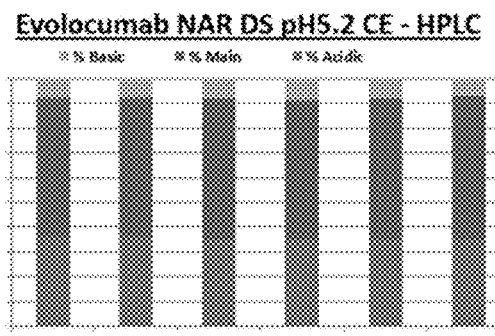
Figure 31C:
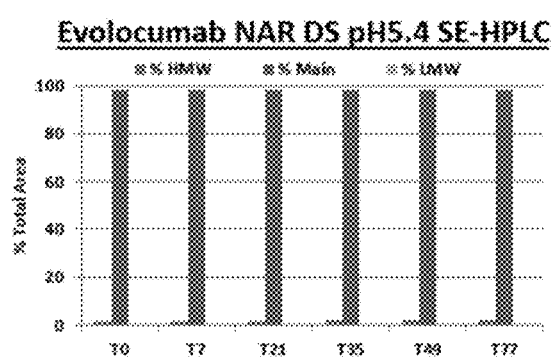
Figure 31D:
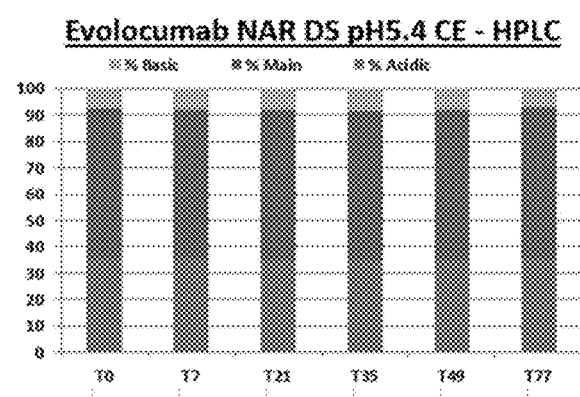
Figure 31E:
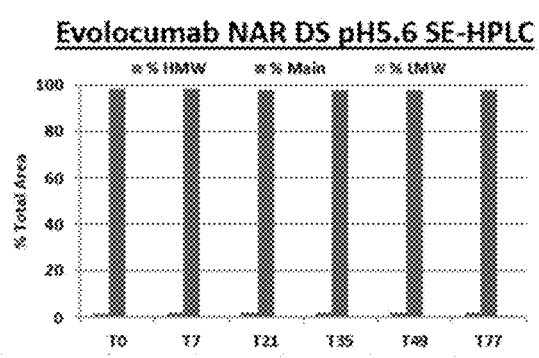
Figure 31F:
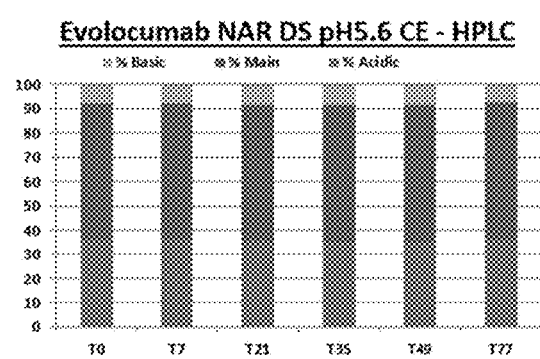

FIG. 30 shows a plot comparing HMW (%) formation in evolocumab UF/DF process with 35 mg/mL and 70 mg/mL in UF1/DF1 (UF/DF-70 and UF/DF-35). Initially, the HMW species (%) in UF/DF-70-UF1 was 0.2% higher than UF/DF-35-UF1, but the HMW (%) were comparable after UF1 and the same in the final DS. The result indicated that the HWM species was reversible and the target concentration on UF1 does not have significant effect on HWM species formation in final DS. It is recommended that 70 mg/mL be the target concentration to reduce pool volume.

Example 7—Pool Hold Studies on Three NAR DS from Small Scale UF/DF

In this example, the stability of three batches of evolocumab formulated to three NAR formulation buffers was monitored. Ten mL of each DS sample was held at 2-8° C. At each time point shown in FIGS. 31-A-31F, about 1 mL sample was taken out and shipped at 2-8° C. for analytical testing. The values of each bar shown in the graphs of FIGS. 31A-31F are provided in Tables 17A-17F, respectively.

TABLE 17A

| Evolocumab NAR DS pH 5.2-SE-HPLC | T0 | T7 | T21 | T35 | T49 | T77 |
|---|---|---|---|---|---|---|
| % HMW | 1.4 | 1.5 | 1.7 | 1.7 | 1.8 | 1.9 |
| % Main | 98.6 | 98.5 | 98.3 | 98.2 | 98.2 | 98.1 |
| % LMW | 0 | 0 | 0 | 0.1 | 0 | 0 |

TABLE 17B

| Evolocumab NAR DS pH 5.2-CE-HPLC | T0 | T7 | T21 | T35 | T49 | T77 |
|---|---|---|---|---|---|---|
| % HMW | 35.8 | 36 | 35.4 | 34.8 | 34.8 | 35.3 |
| % Main | 56.6 | 56.4 | 56.4 | 56.8 | 57.1 | 57.6 |
| % LMW | 7.6 | 7.6 | 8.2 | 8.5 | 8.1 | 7.1 |

TABLE 17C

| Evolocumab NAR DS pH 5.4-SE-HPLC | T0 | T7 | T21 | T35 | T49 | T77 |
|---|---|---|---|---|---|---|
| % HMW | 1.5 | 1.5 | 1.7 | 1.8 | 1.8 | 1.9 |
| % Main | 98.5 | 98.5 | 98.3 | 98.2 | 98.2 | 98.1 |
| % LMW | 0 | 0 | 0 | 0 | 0 | 0 |

TABLE 17D

| Evolocumab NAR DS pH 5.4-CE-HPLC | T0 | T7 | T21 | T35 | T49 | T77 |
|---|---|---|---|---|---|---|
| % HMW | 35.3 | 35.5 | 35.1 | 34.6 | 34.7 | 35.6 |
| % Main | 57.1 | 56.6 | 56.8 | 57 | 57.1 | 57.5 |
| % LMW | 7.6 | 8 | 8.1 | 8.3 | 8.1 | 7 |

TABLE 17E

| Evolocumab NAR DS pH 5.6-SE-HPLC | T0 | T7 | T21 | T35 | T49 | T77 |
|---|---|---|---|---|---|---|
| % HMW | 1.7 | 1.8 | 2 | 2.1 | 2.2 | 2.2 |
| % Main | 98.3 | 98.2 | 98 | 97.9 | 97.8 | 97.7 |
| % LMW | 0 | 0 | 0 | 0 | 0 | 0.1 |

TABLE 17F

| Evolocumab NAR DS pH 5.6-CE-HPLC | T0 | T7 | T21 | T35 | T49 | T77 |
|---|---|---|---|---|---|---|
| % HMW | 36.1 | 36 | 35.5 | 35.2 | 35.2 | 36.2 |
| % Main | 56.3 | 56.2 | 56.2 | 56.5 | 56.5 | 56.7 |
| % LMW | 7.7 | 7.8 | 8.3 | 8.3 | 8.3 | 7.1 |

Results and Observations

Figure 32:
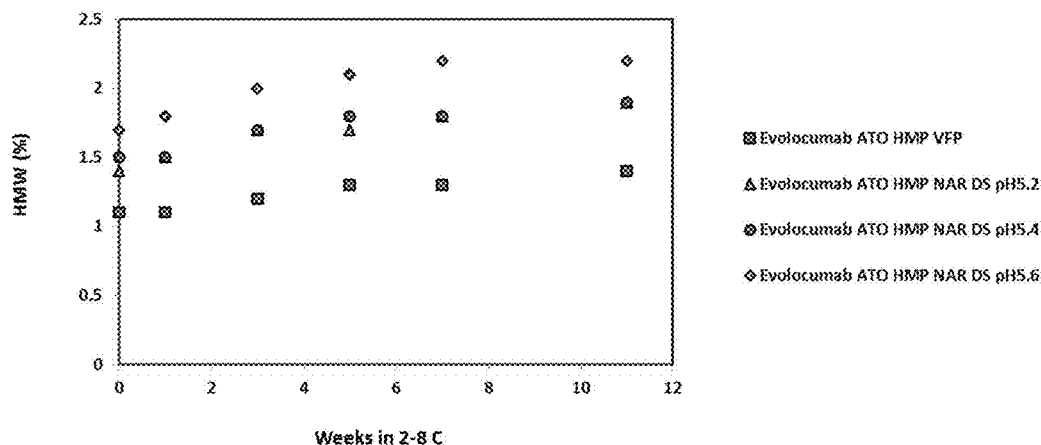
FIG. 32 shows percent HMW species formation of evolocumab NAR DS sample from pool hold studies at 2-8° C. and room temperature.

SE-HPLC and CEX results of evolocumab NAR evolocumab at 2-8° C. are shown in FIGS. 36 and 37. CEX and rCE-SDS results yielded comparable results. The DS batches generated from NAR pH 5.2, 5.4, and pH 5.6 possess 1.4%, 1.5%, and 1.7% HMW species respectively during UF/DF operation compared to 1.1% in the feed material. The % of HMW species was plotted to compare the evolocumab feed material and NAR DS for 11 weeks in FIG. 32. All three of the formulation batches had HMW (%) species increase by 0.4%-0.5%. These DS batches were stable at least for 7 days at 2-8° C.

Example 8—In-Process Pool Hold Studies on Evolocumab HMP CPD1 NAR Overconcentration (260 g/L) at 37° C. 39° C. 42° C. and 45° C.

The stability of the in-process evolocumab overconcentration (260 g/L) at 37° C., 39° C., 42° C., and 45° C. was evaluated. Thirty mL of OC samples was incubated in a water bath in a room with set controlled temperatures. At each time point shown in FIGS. 33 and 34, about 1 mL sample was taken, frozen, and shipped on dry ice for analysis. Viscosity values were measured on the OC samples at the higher temperatures and compared to those at held at 23° C. and 25° C.

Results and Observations

Figure 33:
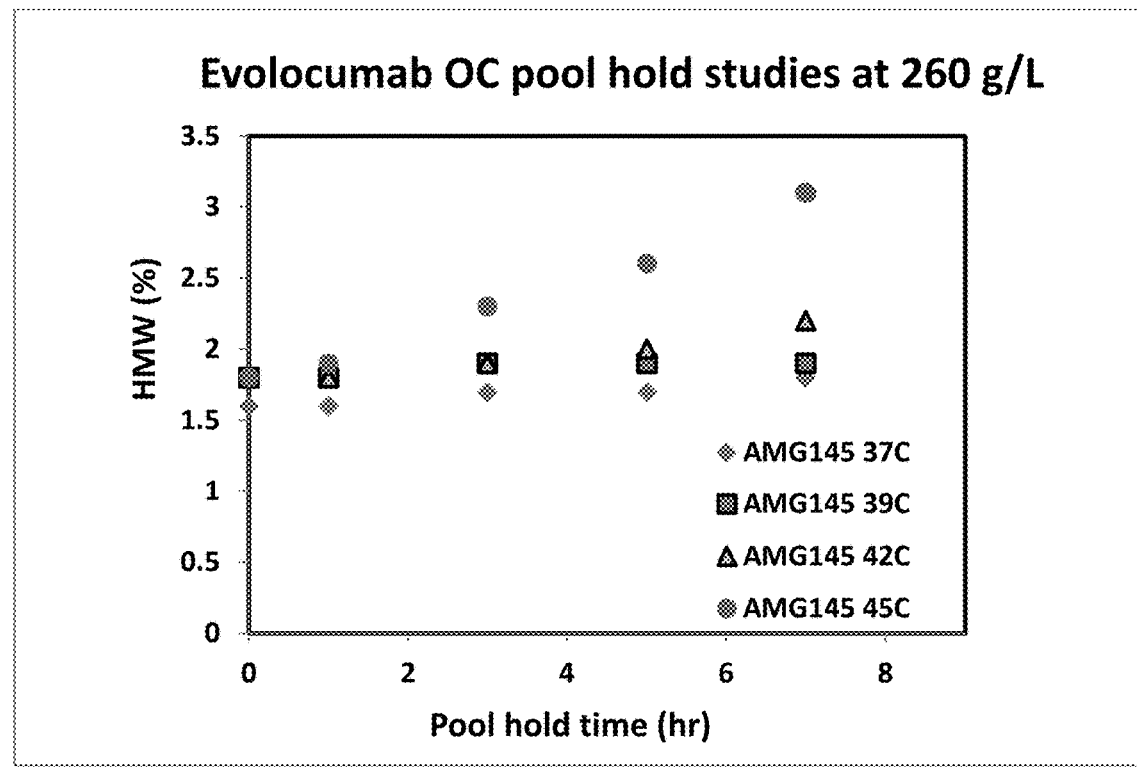
FIG. 33 shows a graph of percent HMW species formation of evolocumab NAR OC samples from pool hold studies at elevated temperature
Figure 34:
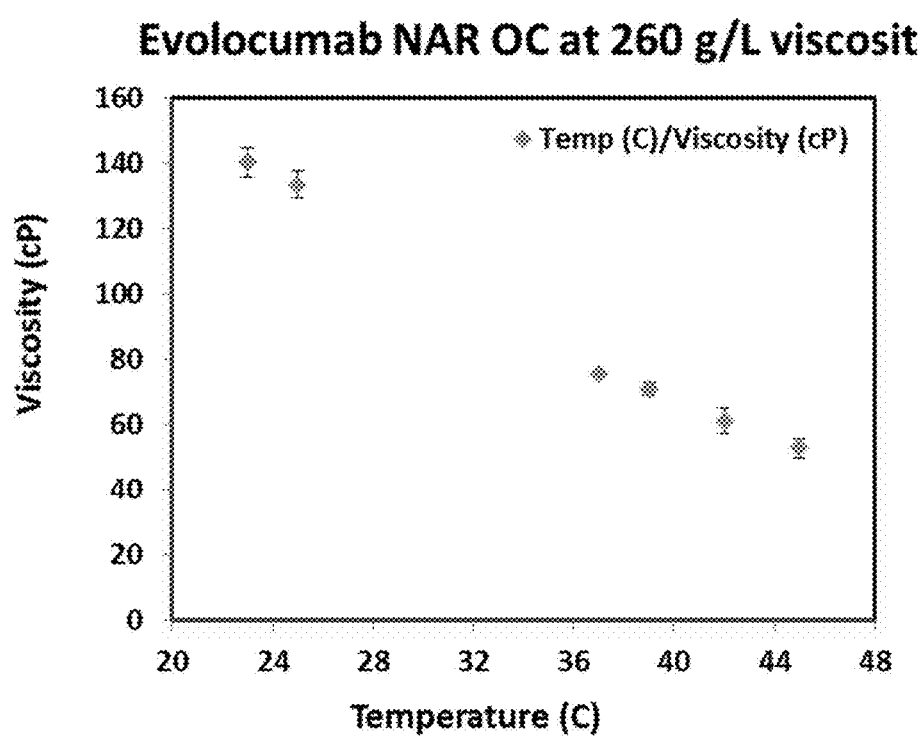
FIG. 34 shows a graph of viscosity measurements of evolocumab NAR formulations at different temperatures.

SE-HPLC results showed that evolocumab NAR OC was stable for three hours at 37° C., 39° C., and 42° C., but not at 45° C. as shown in FIG. 33. CEX and rCE-SDS results were comparable. FIG. 34 shows that the viscosity of OC decreased when the temperature increased and, when temperature increased from 37° C. to 42° C., the viscosity dropped by 19% (by 14.7 cP).

The section headings used herein are for organizational purposes only and are not to be construed as limiting the subject matter described. All documents, or portions of documents, cited in this application, including patents, patent applications, articles, books, and treatises, are hereby expressly incorporated by reference in their entirety for any purpose.

Example 9—Formulation Robustness DOE Study

A formulation robustness design of experiment (DOE) study was designed to investigate the effect of formulation variables within a specified design space on evolocumab stability. The study variables included evolocumab concentration, NAR concentration, Arg HCl concentration, and pH. Eighteen formulations listed in Table 18 were sterile-filtered using 0.2 μm PVDF filters and filled in 2.0 mL glass pre-filled syringes. Samples were tested by an array of stability indicating analytical methods following incubation at various temperatures. All formulations included 10 mM sodium acetate and 0.01% (w/v) polysorbate-80 in addition to the components listed in Table 18.

TABLE 18

Study design

| Sample | Sample code | [evolocumab] (mg/ml) | Excipients* | pH |
|---|---|---|---|---|
| 1 | 210A54NARRT80 | 210 | 140 mM NAR, 50 mM Arg HCl | 5.4 |
| 2 | 210A54NARRT80 | 210 | 140 mM NAR, 50 mM Arg HCl | 5.4 |
| 3 | 197A51NAR$_{154}$R$_{55}$T80 | 197 | 154 mM NAR, 55 mM Arg HCl | 5.1 |
| 4 | 197A51NAR$_{126}$R$_{45}$T80 | 197 | 126 mM NAR, 45 mM Arg HCl | 5.1 |
| 5 | 223A51NAR$_{154}$R$_{45}$T80 | 223 | 154 mM NAR, 45 mM Arg HCl | 5.1 |
| 6 | 223A51NAR$_{126}$R$_{45}$T80 | 223 | 126 mM NAR, 45 mM Arg HCl | 5.1 |
| 7 | 197A57NAR$_{126}$R$_{55}$T80 | 197 | 126 mM NAR, 55 mM Arg HCl | 5.7 |
| 8 | 197A51NAR$_{126}$R$_{55}$T80 | 197 | 126 mM NAR, 55 mM Arg HCl | 5.1 |
| 9 | 197A51NAR$_{154}$R$_{45}$T80 | 197 | 154 mM NAR, 45 mM Arg HCl | 5.1 |
| 10 | 223A51NAR$_{126}$R$_{55}$T80 | 223 | 126 mM NAR, 55 mM Arg HCl | 5.1 |
| 11 | 223A57NAR$_{126}$R$_{45}$T80 | 223 | 126 mM NAR, 45 mM Arg HCl | 5.7 |
| 12 | 223A57NAR$_{154}$R$_{55}$T80 | 223 | 154 mM NAR, 55 mM Arg HCl | 5.7 |
| 13 | 223A57NAR$_{154}$R$_{45}$T80 | 223 | 154 mM NAR, 45 mM Arg HCl | 5.7 |
| 14 | 197A57NAR$_{126}$R$_{45}$T80 | 197 | 126 mM NAR, 45 mM Arg HCl | 5.7 |
| 15 | 197A57NAR$_{154}$R$_{55}$T80 | 197 | 154 mM NAR, 55 mM Arg HCl | 5.7 |
| 16 | 223A57NAR$_{126}$R$_{55}$T80 | 223 | 126 mM NAR, 55 mM Arg HCl | 5.7 |
| 17 | 197A57NAR$_{154}$R$_{45}$T80 | 197 | 154 mM NAR, 45 mM Arg HCl | 5.7 |
| 18 | 223A51NAR$_{154}$R$_{55}$T80 | 223 | 154 mM NAR, 55 mM Arg HCl | 5.1 |

*formulations included 10 mM sodium acetate and 0.01% (w/v) polysorbate-80, as noted in text Table 19 shows the measured evolocumab concentrations, pH values, and excipient concentrations for each of the study formulations. All are close to the target levels listed in Table 18.

TABLE 19

Initial drug product formulation data

| Sample # | [evolocumab] (mg/ml) | pH | [NAR] (mM) | [Arginine] (mM) |
|---|---|---|---|---|
| 1 | 209 | 5.51 | 145.0 | 56.7 |
| 2 | 211 | 5.46 | 143.5 | 56.2 |
| 3 | 191 | 5.14 | 156.7 | 60.9 |
| 4 | 201 | 5.17 | 126.3 | 46.9 |
| 5 | 226 | 5.13 | 160.2 | 48.2 |
| 6 | 225 | 5.13 | 127.8 | 47.9 |
| 7 | 198 | 5.67 | 135.8 | 63.1 |
| 8 | 199 | 5.14 | 125.1 | 59.1 |
| 9 | 202 | 5.13 | 161.8 | 49.9 |
| 10 | 224 | 5.12 | 136.1 | 64.5 |
| 11 | 220 | 5.71 | 132.1 | 51.5 |
| 12 | 223 | 5.73 | 161.7 | 63.3 |
| 13 | 218 | 5.75 | 159.7 | 50.7 |
| 14 | 197 | 5.76 | 128.5 | 50.5 |
| 15 | 194 | 5.79 | 157.6 | 61.7 |
| 16 | 227 | 5.72 | 141.0 | 67.3 |
| 17 | 196 | 5.72 | 154.2 | 58.1 |
| 18 | 226 | 5.17 | 153.6 | 57.8 |

Results and Observations

Figure 35A:
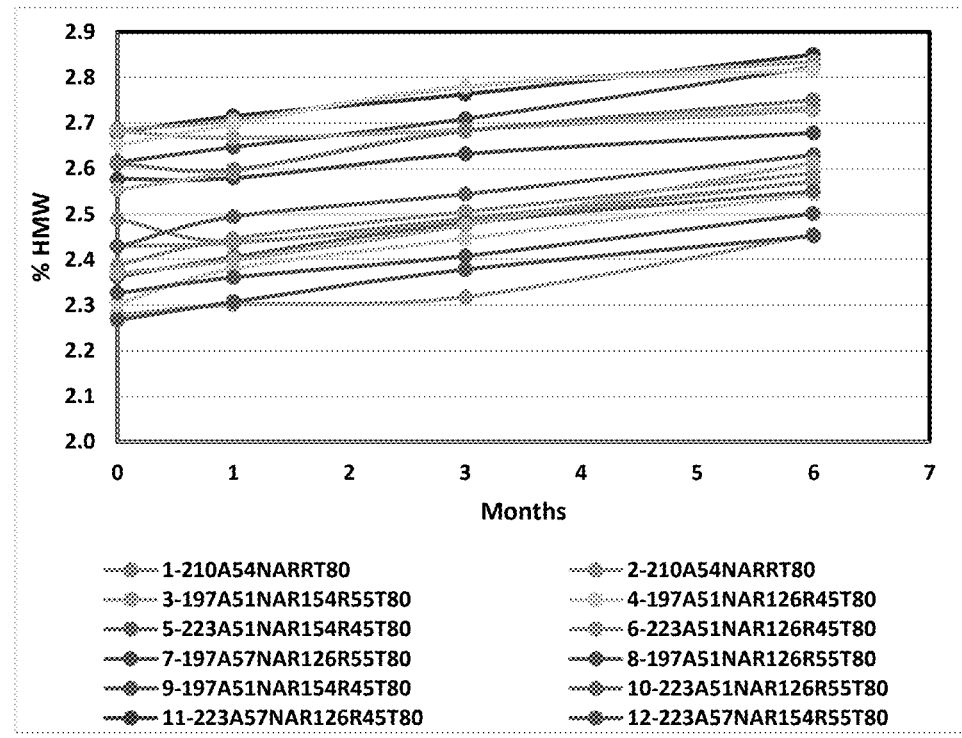
FIGS. 35A-35C show graphs of SE-HPLC data for all of the study formulations used in Example 9 following up to 6 months incubation at 4° C.
Figure 35B:
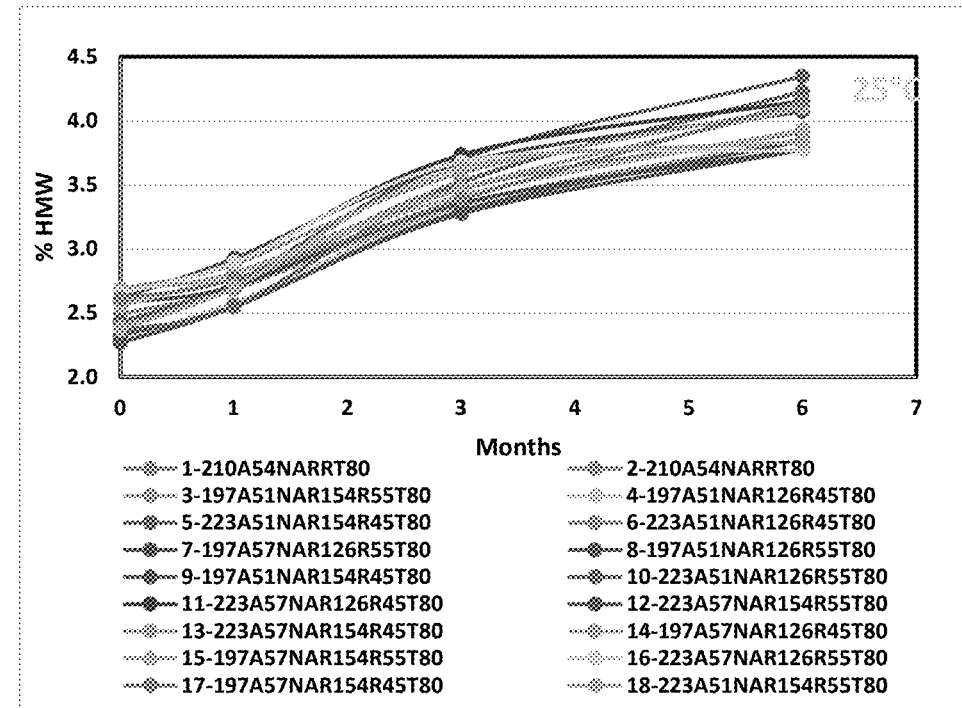
Figures 35C, 35D:
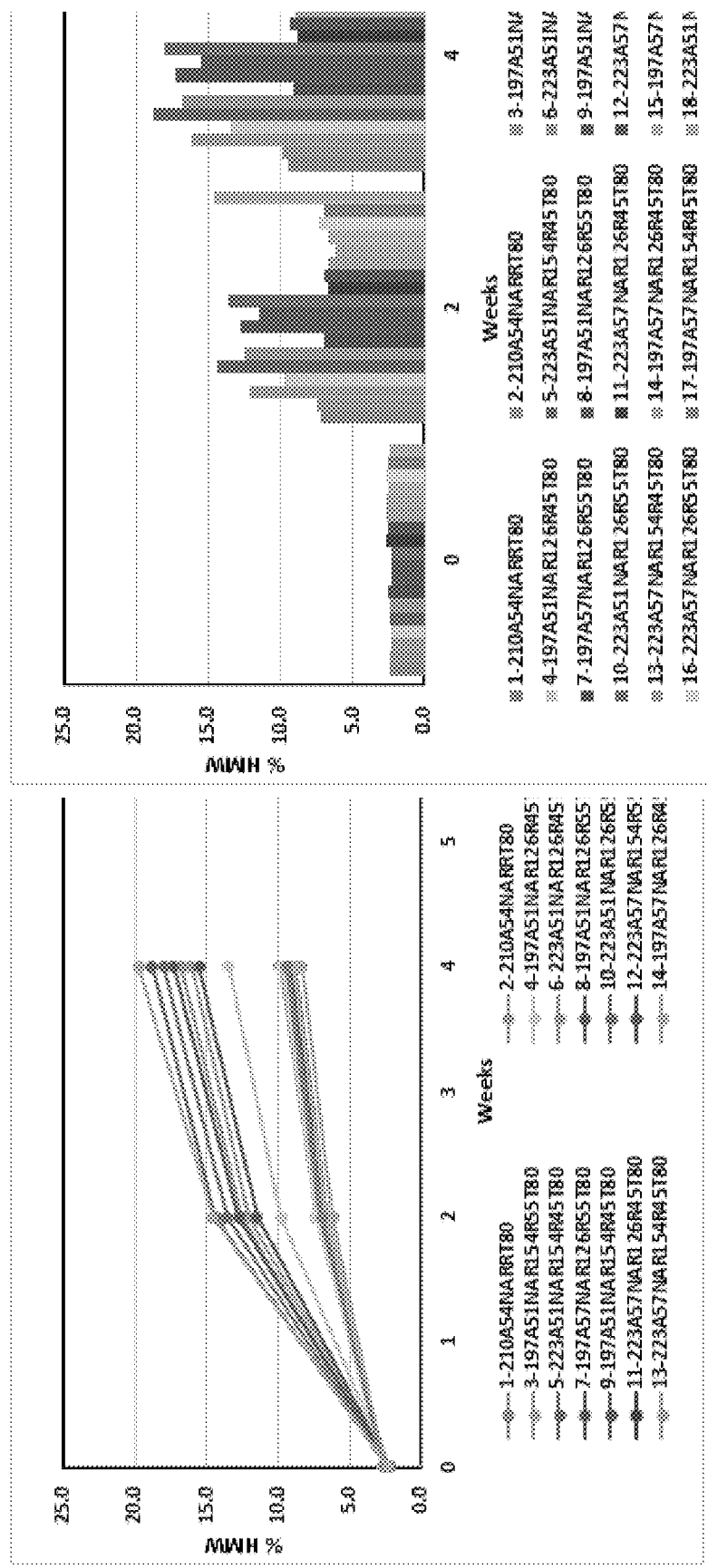
FIG. 35D displays the 40° C. SE-HPLC data (shown as a line graph in FIG. 35C) as a bar chart, making the comparison of aggregation levels between formulations more discernable.

To assess aggregation, SE-HPLC analysis was conducted on the formulations shown in Table 19 after 0-6 months incubation at 4° C. (FIG. 35A), 25° C. (FIG. 35B), and 40° C. (FIGS. 35C and 35D). The data indicated that rates of increase in % HMW species were similar for all formulations for 4° C. and 25° C. conditions, but a pH-dependent effect on aggregation was observed at the accelerated 40° C. stress condition. Lower pH samples at pH 5.1 were observed to have the fastest rate of aggregation at 40° C. while samples having a pH 5.7 were observed to have the slowest rate of aggregation (FIGS. 35C and 35D). Samples at pH 5.4 at 40° C. were observed to have intermediate aggregation rates between those of pH 5.1 and 5.7, but these rates were more similar to the lower aggregation rates observed for samples of pH 5.7 (FIGS. 35C and 35D).

Figure 36A:
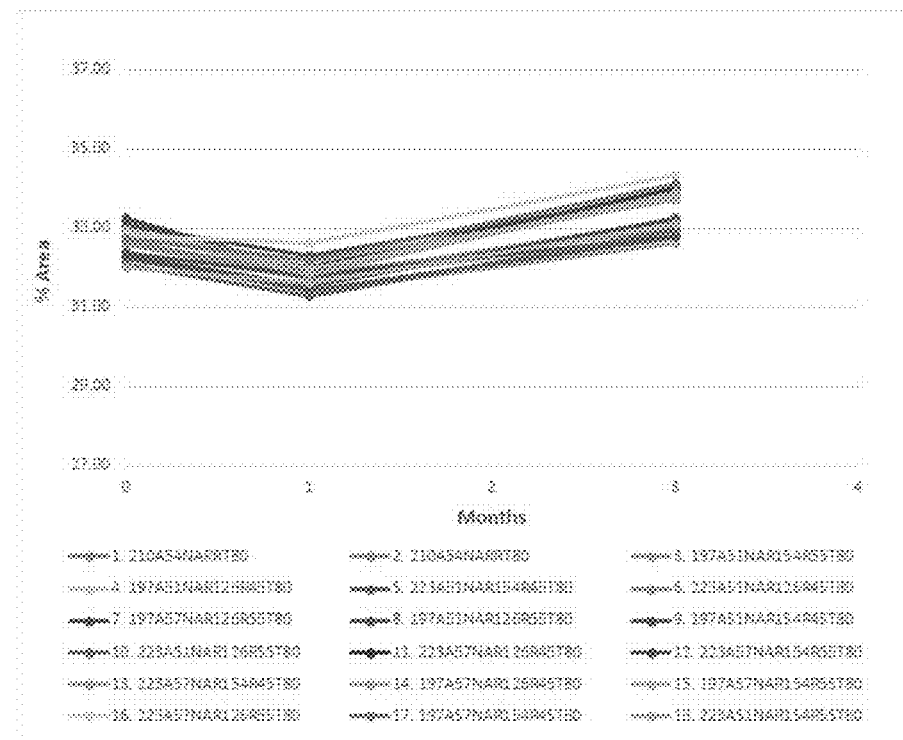
FIGS. 36A-36F show graphs of CEX-HPLC data for the study formulations used in Example 9 showing changes in % acidic and % basic peaks over time following up to three months incubation at 4° C.
Figure 36B:
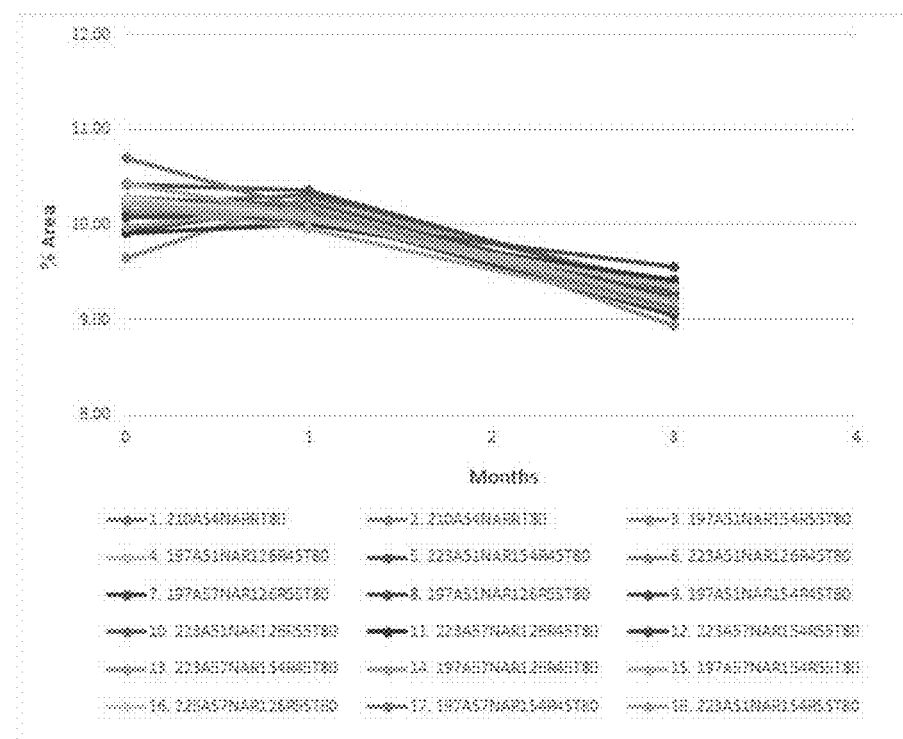
Figure 36C:
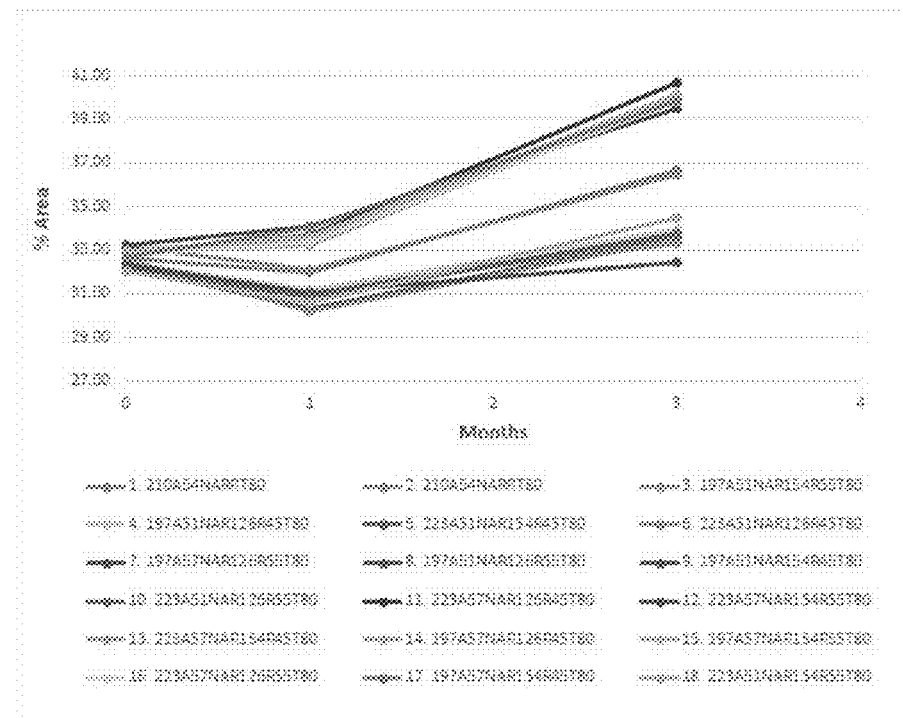
Figure 36D:
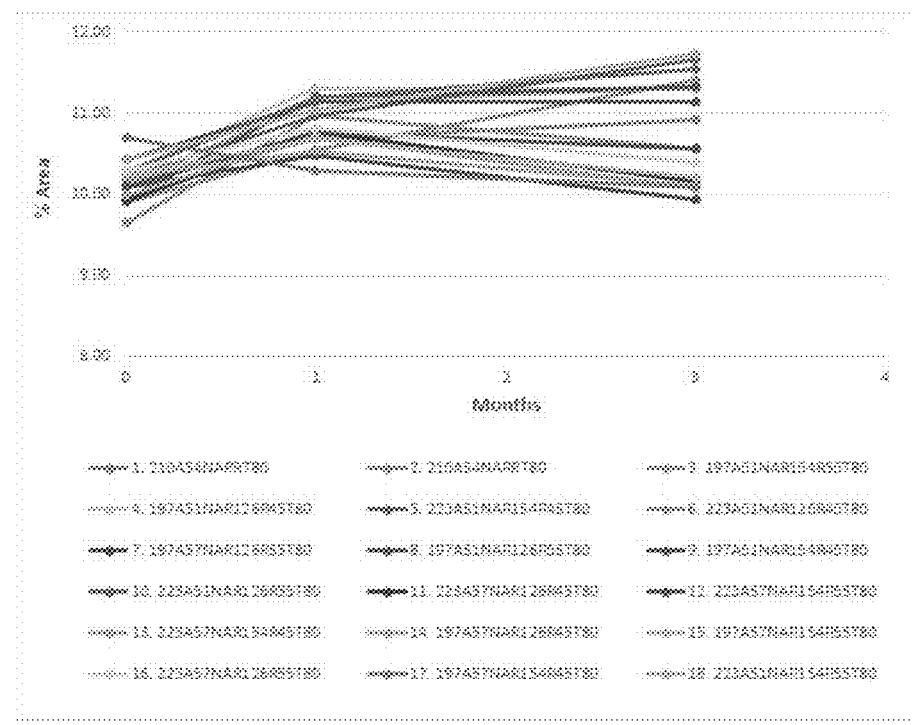
Figure 36E:
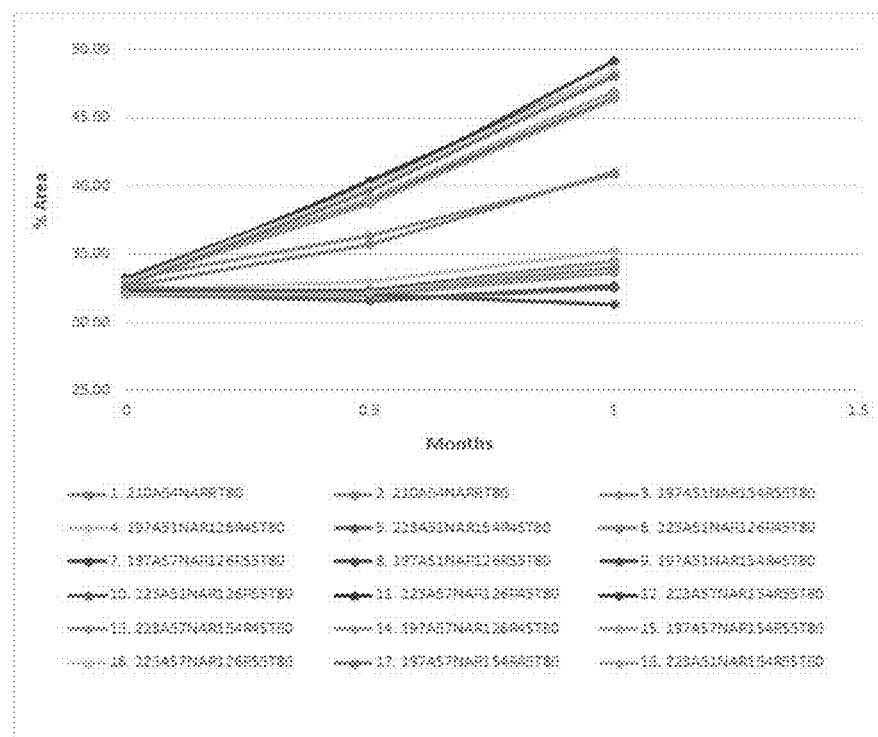
Figure 36F:
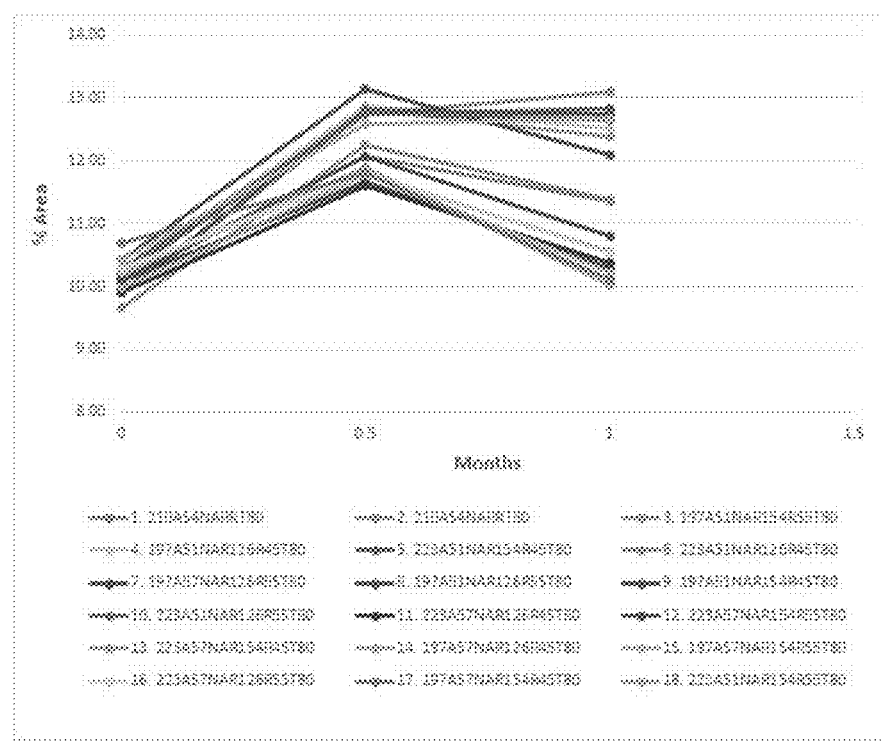

The effect of pH on increase in % acidic peak and % basic peak over time (up to three months) was examined using CEX-HPLC, which data are shown in FIGS. 36A (acidic peak) and 36B (basic peak) for 4° C.; FIGS. 36C (acidic peak) and 36D (basic peak) for 25° C.; and FIGS. 36E (acidic peak) and 36F (basic peak) for 40° C. As shown in the data for 25° C. and 40° C. samples (FIGS. 36C-36F), pH was observed to effect % acid and basic peaks in the formulations. Data for samples with pH 5.7 were tightly grouped with higher rates of increase in % acidic peak while data for samples with pH 5.1 showed the lowest rate of increase. The two samples of pH 5.4 were observed to have degradation rates directly between the observed rates of those samples of pH 5.1 and pH 5.7. Trends in % basic peak changes appeared to be less distinct, but a trend toward higher % basic peak levels at lower pH were observed from samples incubated at 40° C.

Figure 37A:
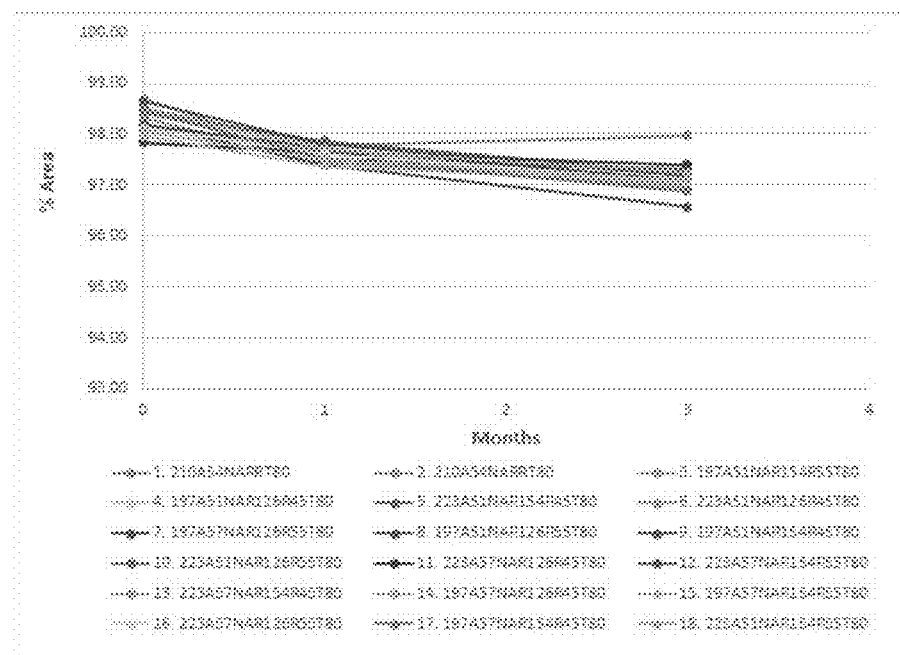
FIGS. 37A-37D show graphs of rCE-SDS data for % main peak and % LMW species for the study formulations used in Example 9 over time following up to three months incubation at 30° C.
Figure 37B:
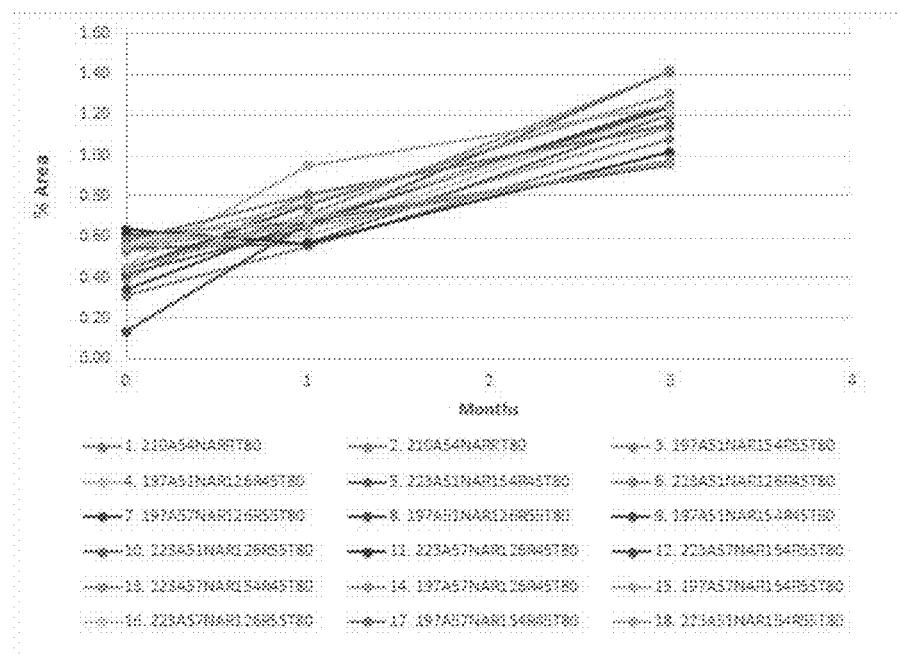
Figures 37C, 37D:
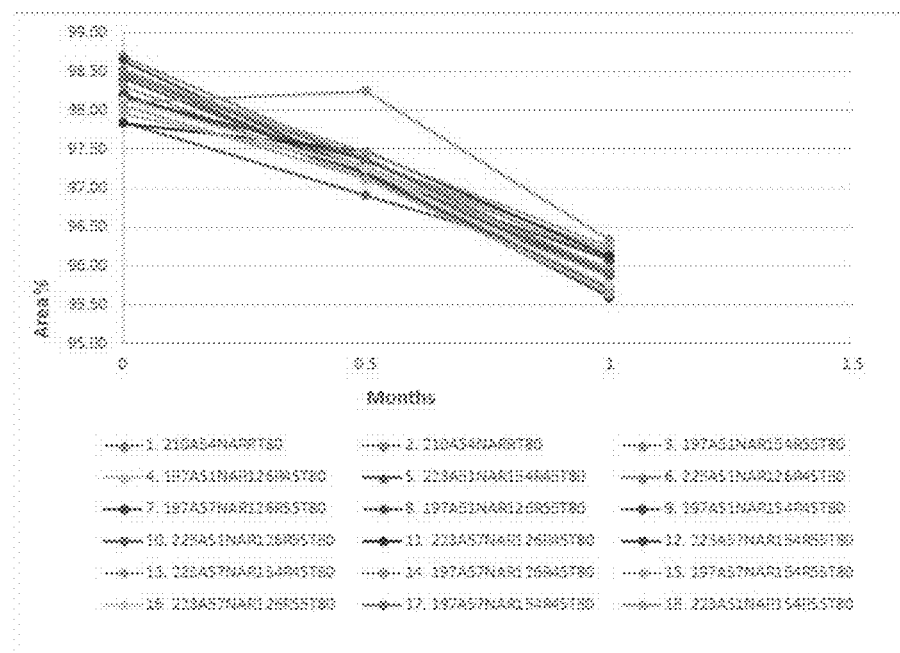

Fragmentation or other degradation of evolocumab in the formulations for up to three months at either 30° C. or 40° C. was assayed using rCE-SDS and SE-HPLC analyses; FIGS. 37A-37B present the data for samples incubated at 30° C., and FIGS. 37C-37D show the data for samples incubated at 40° C. No significant trend in the rCE-SDS data related to formulation composition within the design space of this study was observed.

Figure 38A:
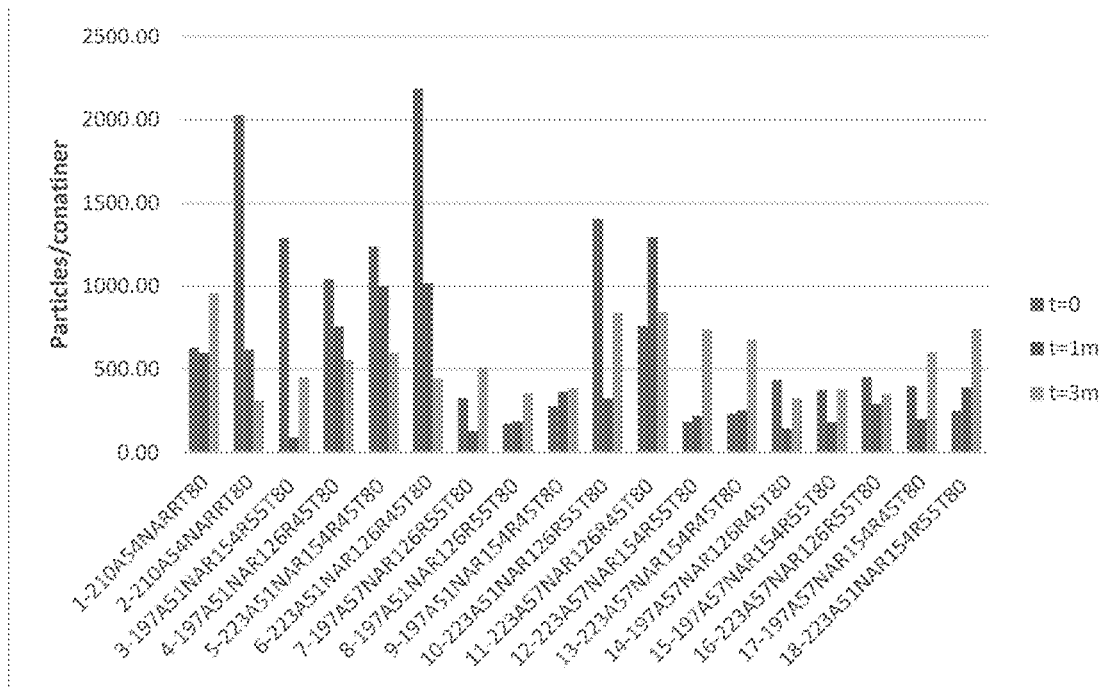
FIG. 38A-38D show graphs of subvisible particle data by light obscuration particle counting using HIAC for the study formulations used in Example 9 following incubation at 4° C. and 40° C. for up to three months.
Figure 38B:
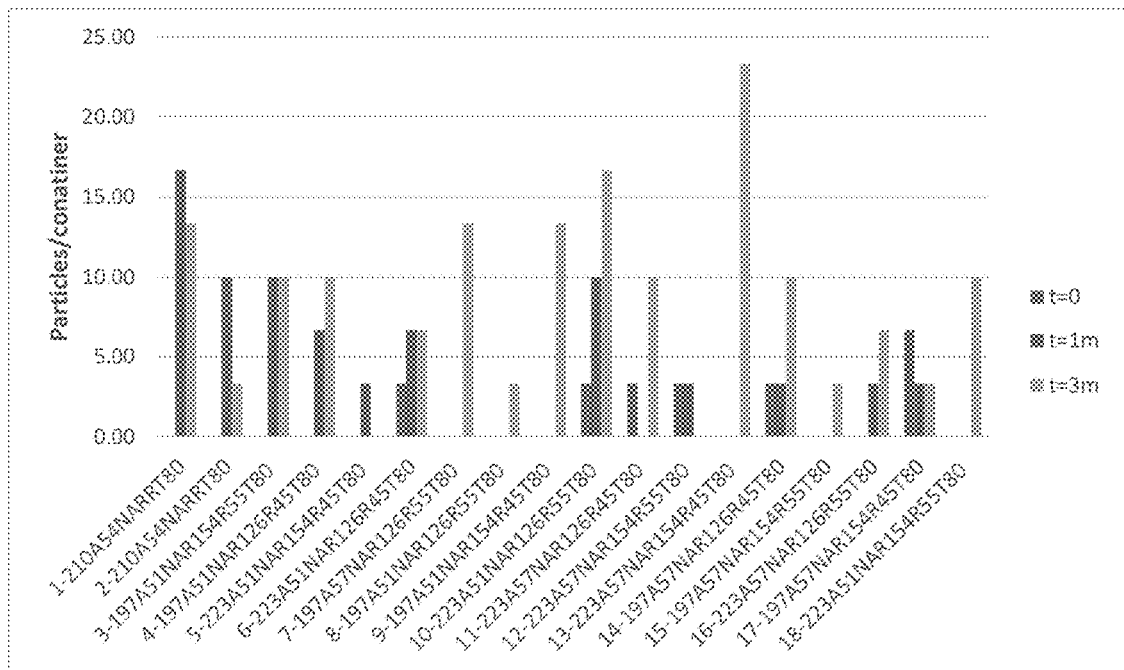
Figure 38C:
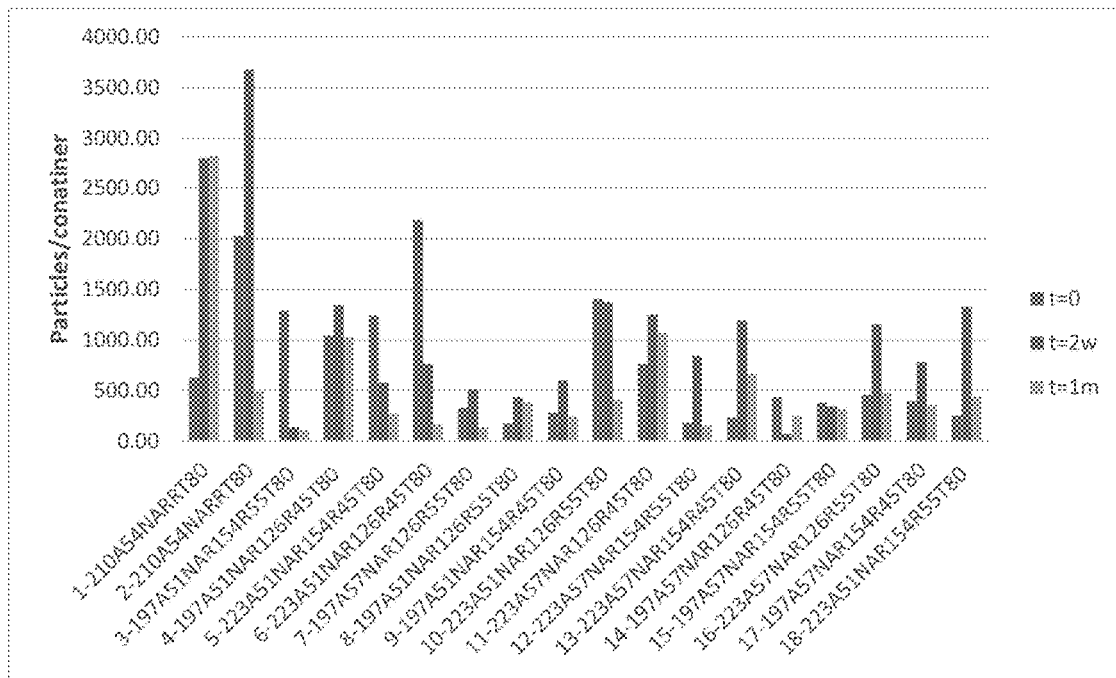
Figure 38D:
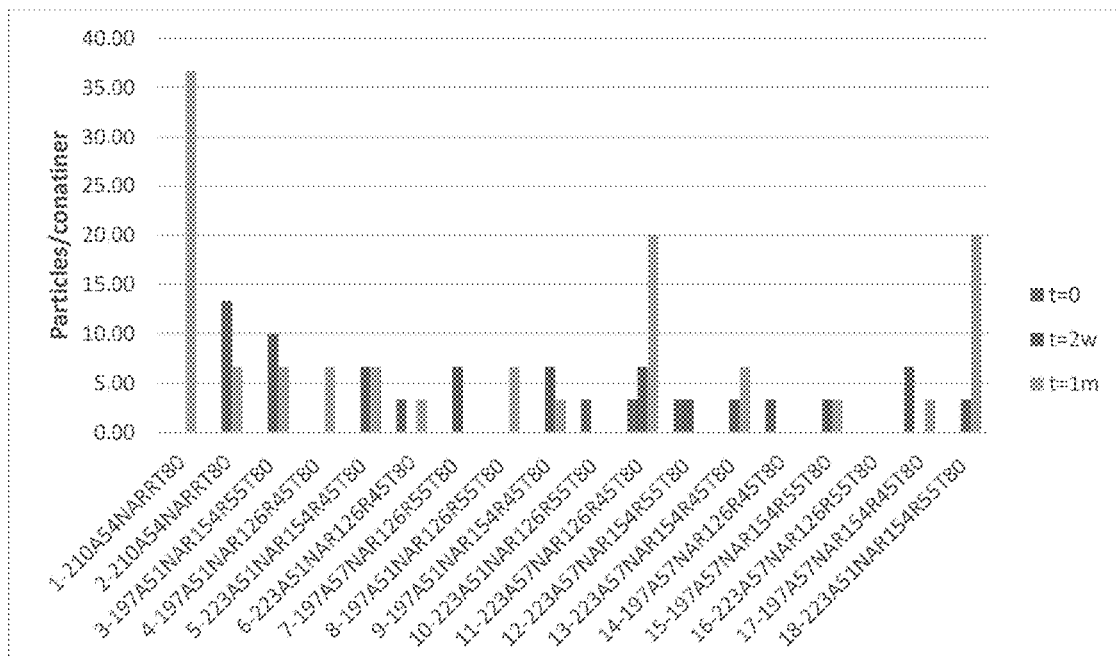

The presence and amounts of subvisible particles were determined for the formulations over time for up to three months as determined by light obscuration particle counting using HIAC following incubation at 4° C. and 40° C.; these data are shown in FIGS. 38A-38D. (FIGS. 38A (greater than or equal to 10 μm) and 38B (particles greater than or equal to 25 μm) shows the results for samples held at 4° C.; FIGS. 38C (greater than or equal to 10 μm) and 38D (particles greater than or equal to 25 μm) show the results for samples held at 40° C.). From these data, no significant trend in subvisible particle counts related to the studied formulation variables was observed.

From this example, the data demonstrated that within the studied narrow formulation design space, no significant impact to stability during storage at 4° C. or 25° C. was observed. The data related to pH at 40° C. suggested that pH effected aggregation rate as detected by SE-HPLC as well as percent acidic species and to a lesser extent percent basic species as detected by CEX-HPLC.

EXEMPLARY EMBODIMENTS

Disclosed herein, are exemplary embodiments of the pharmaceutical compositions comprising evolocumab, wherein such compositions comprise N-acetyl arginine and the pharmaceutical composition has a viscosity of at least less than about 80 cP (measured, for example, by a rheometer, such as TA Instruments (New Castle, DE) AESR-G2 cone and plate rheometer). Furthermore, disclosed herein are methods of formulating therapeutic polypeptides, such as evolocumab, wherein such compositions comprise NAR.

Embodiment 1: A pharmaceutical composition comprising
a. a PCSK9-binding polypeptide that selected from the group consisting of:
  i. a monoclonal antibody comprising a heavy chain polypeptide having an amino acid sequence of SEQ ID NO:1 and a light chain polypeptide having an amino acid sequence of SEQ ID NO:2 (evolocumab), or an antigen-binding fragment thereof;
  ii. a monoclonal antibody that competes with evolocumab for binding to PCSK9;
  iii. a monoclonal antibody, comprising:
    1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
    2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
  iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;
  v. a monoclonal antibody that binds to PCSK9 at an epitope on PCSK9 that overlaps with an epitope that is bound by an antibody that comprises:
    1. a heavy chain variable region of the amino acid sequence in SEQ ID NO:1; and
    2. a light chain variable region of the amino acid sequence in SEQ ID NO:2, and
    3. wherein the epitope of the monoclonal antibody further overlaps with a site to which an EGF-A domain of LDLR;

and
b. N-acetyl arginine,
wherein the pharmaceutical composition has a viscosity of at least less than about 80 cP.

Embodiment 2: The pharmaceutical composition of embodiment 1, wherein the PCSK9-binding polypeptide is a monoclonal antibody the comprises a heavy chain polypeptide comprising the following complementarity determining regions (CDRs):
a. heavy chain CDR1, CDR2, and CDR3 having an amino acid sequence of SEQ ID NOs:7, 8, and 9, respectively; and
b. light chain CDR1, CDR2, and CDR3 having an amino acid sequence of SEQ ID NOs:4, 5, and 6, respectively.

Embodiment 3: The pharmaceutical composition of embodiment 2 or 3, wherein the pharmaceutical composition has a viscosity of at least less than about 50 cP.

Embodiment 4: The pharmaceutical composition of embodiment 2 or 3, wherein the pharmaceutical composition has an osmolality of about 250 to about 400 mOsm/kg.

Embodiment 5: The pharmaceutical composition of embodiment 4, wherein the pharmaceutical composition has an osmolality of about 300 mOsm/kg.

Embodiment 6: The pharmaceutical composition of embodiment 5, wherein the pharmaceutical composition is isotonic to a human blood cell.

Embodiment 7: The pharmaceutical composition of embodiment 1, wherein the PCSK9-binding polypeptide is present at a concentration of about 140 mg/mL to about 260 mg/mL.

Embodiment 8: The pharmaceutical composition of embodiment 2, wherein the PCSK9-binding polypeptide concentration is about 210 mg/mL.

Embodiment 9: The pharmaceutical composition of any of embodiments 1-8, wherein the N-acetyl arginine is present at a concentration from about 25 mM to about 230 mM.

Embodiment 10: The pharmaceutical composition of embodiment 9, wherein the N-acetyl arginine is present at a concentration from about 140 mM to about 170 mM Embodiment 11: The pharmaceutical composition of embodiment 10, wherein the N-acetyl arginine is present at a concentration of about 140 mM.

Embodiment 12: The pharmaceutical composition of any of embodiments 1-11, further comprising a buffer.

Embodiment 13: The pharmaceutical composition of embodiment 13, wherein the buffer is selected from the group consisting of acetate, glutamate, histidine, and phosphate buffers, or a combination thereof.

Embodiment 14: The pharmaceutical composition of embodiment 13, wherein the buffer is present at a concentration of about 5 mM to about 30 mM.

Embodiment 15: The pharmaceutical composition of embodiment 14, wherein the buffer is sodium acetate and is present at a concentration of about 10 mM.

Embodiment 16: The pharmaceutical composition of any of embodiments 1-15, wherein the pH is about 4.8 to about 6.9.

Embodiment 17: The pharmaceutical composition of embodiment 11, wherein the pH is about 5.4.

Embodiment 18: The pharmaceutical composition of any of embodiments 1-17, further comprising a surfactant.

Embodiment 19: The pharmaceutical composition of embodiment 18, wherein the surfactant is selected from the group consisting of polyoxyethylenesorbitan monooleate (polysorbate 80 or polysorbate 20), polyoxyethylene-polyoxypropylene block copolymer (Poloxamers such as Pluronic® F-68 and other Pluronics®), Sorbitan alkyl esters (Spans®) Polyethylene glycol octylphenyl ethers (Triton X-100), Polyethylene glycol alkyl ethers (Brij), Polypropylene glycol alkyl ethers, Glucoside alkyl ethers, and D-α-tocopherol polyethylene glycol succinate (vitamin E TPGS).

Embodiment 20: The pharmaceutical composition of embodiment 19, wherein the surfactant is present at a concentration of about 0.0001% (w/v) to about 1% (w/v).

Embodiment 21: The pharmaceutical composition of embodiment 20, wherein the surfactant is polyoxyethylenesorbitan monooleate and is present at a concentration of about 0.01% (w/v).

Embodiment 22: The pharmaceutical composition of any of embodiments 1-21, further comprising proline.

Embodiment 23: The pharmaceutical composition of embodiment 22, wherein the proline is present at a concentration of about 50 mM to about 150 mM.

Embodiment 24: The pharmaceutical composition of embodiment 23, wherein the proline is present at a concentration of about 90 mM to about 120 mM.

Embodiment 25: The pharmaceutical composition of embodiment 22 or 23, where the proline is present at a concentration of about a concentration of about 120 mM.

Embodiment 26: The pharmaceutical composition of any of embodiments 1-25, further comprising an arginine salt.

Embodiment 27: The pharmaceutical composition of embodiment 26, wherein the arginine salt is present at a concentration of about 25 mM to about 150 mM.

Embodiment 28: The pharmaceutical composition of embodiment 27, wherein the arginine salt is present at a concentration of about 50 mM to about 100 mM Embodiment 29: The pharmaceutical composition of embodiment 26, wherein the arginine salt is arginine-HCl, arginine acetate, or arginine glutamate.

Embodiment 30: The pharmaceutical composition of embodiment 29, wherein the arginine HCl is present at a concentration of about 50 mM.

Embodiment 31: The pharmaceutical composition of any of embodiments 1-30, wherein the PCSK9-binding polypeptide is stable for at least about 2 years when stored at about −30° C. or colder.

Embodiment 32: The pharmaceutical composition of embodiment 31, wherein the PCSK9-binding polypeptide is stable for at least about 5 years.

Embodiment 33: The pharmaceutical composition of any of embodiments 1-30, wherein the PCSK9-binding polypeptide is stable for at least about 6 months when stored at about 5° C.

Embodiment 34: The pharmaceutical composition of embodiment 33, wherein the PCSK9-binding polypeptide is stable for at least about 24 months.

Embodiment 35: The pharmaceutical composition of any of embodiments 1-30, wherein the PCSK9-binding polypeptide is stable for at least about 1 month when stored at about 25° C.

Embodiment 36: The pharmaceutical composition of embodiment 35, wherein the PCSK9-binding polypeptide is stable for at least about three months.

Embodiment 37: The pharmaceutical composition of embodiment 35, wherein the PCSK9-binding polypeptide is stable for at least about 6 months.

Embodiment 38: The pharmaceutical composition of any of embodiments 1-30, wherein the PCSK9-binding polypeptide is stable for at least about 1 month when stored at about 40° C.

Embodiment 39: The pharmaceutical composition of any of embodiments 1-38, wherein the composition comprises high molecular weight aggregates or oligomers of the PCSK9-binding polypeptide at less than about 3% of the PCSK9-binding polypeptide concentration.

Embodiment 40: The pharmaceutical composition of embodiment 39, wherein the high molecular weight aggregates or oligomers of the PCSK9-binding polypeptide are present at less than about 2.5% of the PCSK9-binding polypeptide concentration.

Embodiment 41: A pharmaceutical composition comprising
  a. a PCSK9-binding polypeptide that selected from the group consisting of:
    i. a monoclonal antibody comprising a heavy chain polypeptide having an amino acid sequence of SEQ ID NO:1 and a light chain polypeptide having an amino acid sequence of SEQ ID NO:2 (evolocumab), or an antigen-binding fragment thereof;
    ii. a monoclonal antibody that competes with evolocumab for binding to PCSK9;
    iii. a monoclonal antibody, comprising:
      1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
      2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
    iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;
  v. a monoclonal antibody that binds to PCSK9 at an epitope on PCSK9 that overlaps with an epitope that is bound by an antibody that comprises:
   1. a heavy chain variable region of the amino acid sequence in SEQ ID NO:1; and
   2. a light chain variable region of the amino acid sequence in SEQ ID NO:2, and
   3. wherein the epitope of the monoclonal antibody further overlaps with a site to which an EGF-A domain of LDLR;
and
b. N-acetyl arginine;
c. an arginine salt;
d. a buffer; and
e. a surfactant
wherein the pharmaceutical composition has a viscosity of at least less than about 80 Cp (measured, for example, by a rheometer, such as TA Instruments (New Castle, DE) AESR-G2 cone and plate rheometer).

Embodiment 42: The pharmaceutical composition of embodiment 41, wherein the PCSK9-binding polypeptide is a monoclonal antibody the comprises a heavy chain polypeptide comprising the following complementarity determining regions (CDRs):
  a. heavy chain CDR1, CDR2, and CDR3 having an amino acid sequence of SEQ ID NOs:7, 8, and 9, respectively; and
  b. light chain CDR1, CDR2, and CDR3 having an amino acid sequence of SEQ ID NOs:4, 5, and 6, respectively.

Embodiment 43: The pharmaceutical composition of embodiment 41 or 42, wherein the pharmaceutical composition has a viscosity of at least less than about 50 cP.

Embodiment 44: The pharmaceutical composition of embodiment 41 or 42, wherein the pharmaceutical composition has an osmolality of about 250 to about 400 mOsm/kg.

Embodiment 45: The pharmaceutical composition of embodiment 44, wherein the pharmaceutical composition has an osmolality of about 300 mOsm/kg.

Embodiment 46: The pharmaceutical composition of embodiment 45, wherein the pharmaceutical composition is isotonic to a human blood cell.

Embodiment 47: The pharmaceutical composition of embodiment 41 or 42, wherein the PCSK9-binding polypeptide is present at a concentration of about 140 mg/mL to about 260 mg/mL.

Embodiment 48: The pharmaceutical composition of embodiment 47, wherein the PCSK9-binding polypeptide concentration is about 210 mg/mL.

Embodiment 49: The pharmaceutical composition of any of embodiments 41-48, wherein the N-acetyl arginine is present at a concentration from about 25 mM to about 230 mM.

Embodiment 50: The pharmaceutical composition of embodiment 49, wherein the N-acetyl arginine is present at a concentration from about 140 mM to about 170 mM.

Embodiment 51: The pharmaceutical composition of embodiment 50, wherein the N-acetyl arginine is present at a concentration of about 140 mM.

Embodiment 52: The pharmaceutical composition of embodiment 41 or 42, wherein the buffer is selected from the group consisting of acetate, glutamate, histidine, and phosphate buffers, or a combination thereof.

Embodiment 53: The pharmaceutical composition of embodiment 52, wherein the buffer is present at a concentration of about 5 mM to about 30 mM.

Embodiment 54: The pharmaceutical composition of embodiment 53, wherein the buffer is sodium acetate and is present at a concentration of about 10 mM.

Embodiment 55: The pharmaceutical composition of any of embodiments 41 or 42, wherein the pH is about 4.8 to about 6.9.

Embodiment 56: The pharmaceutical composition of embodiment 55, wherein the pH is about 5.4.

Embodiment 57: The pharmaceutical composition of embodiment 41 or 42, wherein the surfactant is selected from the group consisting of polyoxyethylenesorbitan monooleate (polysorbate 80 or polysorbate 20), polyoxyethylene-polyoxypropylene block copolymer (Poloxamers such as Pluronic® F-68 and other Pluronics®), Sorbitan alkyl esters (Spans®) Polyethylene glycol octylphenyl ethers (Triton X-100), Polyethylene glycol alkyl ethers (Brij), Polypropylene glycol alkyl ethers, Glucoside alkyl ethers, and D-α-tocopherol polyethylene glycol succinate (vitamin E TPGS).

Embodiment 58: The pharmaceutical composition of embodiment 57, wherein the surfactant is present at a concentration of about 0.0001% (w/v) to about 1% (w/v).

Embodiment 59: The pharmaceutical composition of embodiment 57, wherein the surfactant is polyoxyethylenesorbitan monooleate and is present at a concentration of about 0.01% (w/v).

Embodiment 60: The pharmaceutical composition of embodiment 41 or 42, further comprising proline.

Embodiment 61: The pharmaceutical composition of embodiment 60, wherein the proline is present at a concentration of about 50 mM to about 150 mM.

Embodiment 62: The pharmaceutical composition of embodiment 61, wherein the proline is present at a concentration of about 90 mM to about 120 mM.

Embodiment 63: The pharmaceutical composition of embodiment 62, where the proline is present at a concentration of about a concentration of about 120 mM.

Embodiment 64: The pharmaceutical composition of embodiment 41 or 42, wherein the arginine salt is present at a concentration of about 25 mM to about 150 mM.

Embodiment 65: The pharmaceutical composition of embodiment 64, wherein the arginine salt is present at a concentration of about 50 mM to about 100 mM.

Embodiment 66: The pharmaceutical composition of embodiment 64, wherein the arginine salt is arginine-HCl, arginine acetate, or arginine glutamate.

Embodiment 67: The pharmaceutical composition of embodiment 66, wherein the arginine HCl is present at a concentration of about 50 mM.

Embodiment 68: The pharmaceutical composition of any of embodiments 41-67, wherein the PCSK9-binding polypeptide is stable for at least about 2 years when stored at about −30° C. or colder.

Embodiment 69: The pharmaceutical composition of embodiment 68, wherein the PCSK9-binding polypeptide is stable for at least about 5 years.

Embodiment 70: The pharmaceutical composition of any of embodiments 41-67, wherein the PCSK9-binding polypeptide is stable for at least about 6 months when stored at about 5° C.

Embodiment 71: The pharmaceutical composition of embodiment 70, wherein the PCSK9-binding polypeptide is stable for at least about 24 months.

Embodiment 72: The pharmaceutical composition of any of embodiments 41-67, wherein the PCSK9-binding polypeptide is stable for at least about 1 month when stored at about 25° C.

Embodiment 73: The pharmaceutical composition of embodiment 72, wherein the PCSK9-binding polypeptide is stable for at least about three months.

Embodiment 74: The pharmaceutical composition of embodiment 73, wherein the PCSK9-binding polypeptide is stable for at least about 6 months.

Embodiment 75: The pharmaceutical composition of any of embodiments 41-67, wherein the PCSK9-binding polypeptide is stable for at least about 1 month when stored at about 40° C.

Embodiment 76: The pharmaceutical composition of any of embodiments 41-75, wherein the composition comprises high molecular weight aggregates or oligomers of the PCSK9-binding polypeptide at less than about 3% of the PCSK9-binding polypeptide concentration.

Embodiment 77: The pharmaceutical composition of embodiment 76, wherein the high molecular weight aggregates or oligomers of the PCSK9-binding polypeptide are present at less than about 2.5% of the PCSK9-binding polypeptide concentration.

Embodiment 78: A pharmaceutical composition comprising
  a. a PCSK9-binding polypeptide that at a concentration of about 195-225 mg/mL selected from the group consisting of:
    i. a monoclonal antibody comprising a heavy chain polypeptide having an amino acid sequence of SEQ ID NO:1 and a light chain polypeptide having an amino acid sequence of SEQ ID NO:2 (evolocumab), or an antigen-binding fragment thereof;
    ii. a monoclonal antibody that competes with evolocumab for binding to PCSK9;
    iii. a monoclonal antibody, comprising:
      1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
      2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
    iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;
    v. a monoclonal antibody that binds to PCSK9 at an epitope on PCSK9 that overlaps with an epitope that is bound by an antibody that comprises:
      1. a heavy chain variable region of the amino acid sequence in SEQ ID NO:1; and
      2. a light chain variable region of the amino acid sequence in SEQ ID NO:2, and
      3. wherein the epitope of the monoclonal antibody further overlaps with a site to which an EGF-A domain of LDLR;
  b. N-acetyl arginine present at a concentration of about 140 mM;
  c. arginine HCl present at a concentration of about 50 mM;
  d. polyoxyethylenesorbitan monooleate (polysorbate 80) at a concentration of from about 0.005% (w/v) to about 0.015% (w/v); and
  e. sodium acetate at a concentration of about 10 mM.

Embodiment 79: The pharmaceutical composition of embodiment 78, wherein the pharmaceutical composition has a pH of about 5.1 to about 5.7.

Embodiment 80: The pharmaceutical composition of embodiment 78 or 79, wherein the pharmaceutical composition has a viscosity of at least less than about 50 Cp (measured, for example, by a rheometer, such as TA Instruments (New Castle, DE) AESR-G2 cone and plate rheometer).

Embodiment 81: A pharmaceutical composition comprising
  a. a PCSK9-binding polypeptide that at a concentration of about 195-225 mg/mL selected from the group consisting of:
    i. a monoclonal antibody comprising a heavy chain polypeptide having an amino acid sequence of SEQ ID NO:1 and a light chain polypeptide having an amino acid sequence of SEQ ID NO:2 (evolocumab), or an antigen-binding fragment thereof;
    ii. a monoclonal antibody that competes with evolocumab for binding to PCSK9;
    iii. a monoclonal antibody, comprising:
      1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
      2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
    iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;
    v. a monoclonal antibody that binds to PCSK9 at an epitope on PCSK9 that overlaps with an epitope that is bound by an antibody that comprises:
      1. a heavy chain variable region of the amino acid sequence in SEQ ID NO:1; and
      2. a light chain variable region of the amino acid sequence in SEQ ID NO:2, and
  b. wherein the epitope of the monoclonal antibody further overlaps with a site to which an EGF-A domain of LDLR;

c. N-acetyl arginine present at a concentration of about 140 mM;
d. arginine HCl present at a concentration of about 63 mM;
e. polyoxyethylenesorbitan monooleate (polysorbate 80) at a concentration of about 0.005% (w/v) to about 0.015%; and
f. sodium acetate at a concentration of about 10 mM.

Embodiment 82: The pharmaceutical composition of embodiment 81, wherein the pharmaceutical composition has a pH of about 5.1 to about 5.7.

Embodiment 83: The pharmaceutical composition of embodiment 81 or 82, wherein the pharmaceutical composition has a viscosity of at least less than about 80 Cp (measured, for example, by a rheometer, such as TA Instruments (New Castle, DE) AESR-G2 cone and plate rheometer).

Embodiment 84: A pharmaceutical composition comprising
  a. a PCSK9-binding polypeptide that at a concentration of about 195-225 mg/mL selected from the group consisting of:
    i. a monoclonal antibody comprising a heavy chain polypeptide having an amino acid sequence of SEQ ID NO:1 and a light chain polypeptide having an amino acid sequence of SEQ ID NO:2 (evolocumab), or an antigen-binding fragment thereof;
    ii. a monoclonal antibody that competes with evolocumab for binding to PCSK9;
    iii. a monoclonal antibody, comprising:
      1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
      2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
    iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;
    v. a monoclonal antibody that binds to PCSK9 at an epitope on PCSK9 that overlaps with an epitope that is bound by an antibody that comprises:
      1. a heavy chain variable region of the amino acid sequence in SEQ ID NO:1; and
      2. a light chain variable region of the amino acid sequence in SEQ ID NO:2, and
      3. wherein the epitope of the monoclonal antibody further overlaps with a site to which an EGF-A domain of LDLR;
  b. N-acetyl arginine present at a concentration of about 155 mM;
  c. arginine HCl present at a concentration of about 70 mM;
  d. polyoxyethylenesorbitan monooleate (polysorbate 80) at a concentration of about 0.005% (w/v) to about 0.015% (w/v); and
  e. sodium acetate at a concentration of about 10 mM.

Embodiment 85: The pharmaceutical composition of embodiment 84, wherein the pharmaceutical composition has a pH of about 5.1 to about 5.7.

Embodiment 86: The pharmaceutical composition of embodiment 84 or 85, wherein the pharmaceutical composition has a viscosity of at least less than about 45 Cp (measured, for example, by a rheometer, such as TA Instruments (New Castle, DE) AESR-G2 cone and plate rheometer).

Embodiment 87: A pharmaceutical composition comprising
  a. a PCSK9-binding polypeptide that at a concentration of about 195-225 mg/mL selected from the group consisting of:
    i. a monoclonal antibody comprising a heavy chain polypeptide having an amino acid sequence of SEQ ID NO:1 and a light chain polypeptide having an amino acid sequence of SEQ ID NO:2 (evolocumab), or an antigen-binding fragment thereof;
    ii. a monoclonal antibody that competes with evolocumab for binding to PCSK9;
    iii. a monoclonal antibody, comprising:
      1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
      2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
    iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;
    v. a monoclonal antibody that binds to PCSK9 at an epitope on PCSK9 that overlaps with an epitope that is bound by an antibody that comprises:
      1. a heavy chain variable region of the amino acid sequence in SEQ ID NO:1; and
      2. a light chain variable region of the amino acid sequence in SEQ ID NO:2, and
      3. wherein the epitope of the monoclonal antibody further overlaps with a site to which an EGF-A domain of LDLR;
  b. N-acetyl arginine present at a concentration of about 170 mM;
  c. arginine HCl present at a concentration of about 63 mM;
  d. polyoxyethylenesorbitan monooleate (polysorbate 80) at a concentration of about 0.005% (w/v) to about 0.015%; and
  e. sodium acetate at a concentration of about 10 mM.

Embodiment 88: The pharmaceutical composition of embodiment 87, wherein the pharmaceutical composition has a pH of about 5.1 to about 5.7.

Embodiment 89: The pharmaceutical composition of embodiment 87 or 88, wherein the pharmaceutical composition has a viscosity of at least less than about 60 Cp (measured, for example, by a rheometer, such as TA Instruments (New Castle, DE) AESR-G2 cone and plate rheometer).

Embodiment 90: A pharmaceutical composition comprising
a. a PCSK9-binding polypeptide that at a concentration of about 195-225 mg/mL selected from the group consisting of:
  i. a monoclonal antibody comprising a heavy chain polypeptide having an amino acid sequence of SEQ ID NO:1 and a light chain polypeptide having an amino acid sequence of SEQ ID NO:2 (evolocumab), or an antigen-binding fragment thereof;
  ii. a monoclonal antibody that competes with evolocumab for binding to PCSK9;
  iii. a monoclonal antibody, comprising:
    1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
    2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
  iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238;
  v. a monoclonal antibody that binds to PCSK9 at an epitope on PCSK9 that overlaps with an epitope that is bound by an antibody that comprises:
    1. a heavy chain variable region of the amino acid sequence in SEQ ID NO:1; and
    2. a light chain variable region of the amino acid sequence in SEQ ID NO:2, and
    3. wherein the epitope of the monoclonal antibody further overlaps with a site to which an EGF-A domain of LDLR;
b. N-acetyl arginine present at a concentration of about 155 mM;
c. proline present at a concentration of about 120 mM;
d. polyoxyethylenesorbitan monooleate (polysorbate 80) at a concentration of about 0.005% (w/v) to about 0.015% (w/v); and
e. sodium acetate at a concentration of about 10 mM.

Embodiment 91: The pharmaceutical composition of embodiment 90, wherein the pharmaceutical composition has a pH of about 5.1 to about 5.7.

Embodiment 92: The pharmaceutical composition of embodiment 90 or 91, wherein the pharmaceutical composition has a viscosity of at least less than about 60 Cp (measured, for example, by a rheometer, such as TA Instruments (New Castle, DE) AESR-G2 cone and plate rheometer).

Embodiment 93: The pharmaceutical composition of any of embodiments 78-92, wherein the PCSK9-binding polypeptide is stable for at least about 2 years when stored at about −30° C. or colder.

Embodiment 94: The pharmaceutical composition of embodiment 93, wherein the PCSK9-binding polypeptide is stable for at least about 5 years.

Embodiment 95: The pharmaceutical composition of any of embodiments 78-92, wherein the PCSK9-binding polypeptide is stable for at least about 6 months when stored at about 5° C.

Embodiment 96: The pharmaceutical composition of embodiment 95, wherein the PCSK9-binding polypeptide is stable for at least about 24 months.

Embodiment 97: The pharmaceutical composition of any of embodiments 78-92, wherein the PCSK9-binding polypeptide is stable for at least about 1 month when stored at about 25° C.

Embodiment 98: The pharmaceutical composition of embodiment 97, wherein the PCSK9-binding polypeptide is stable for at least about three months.

Embodiment 99: The pharmaceutical composition of embodiment 98, wherein the PCSK9-binding polypeptide is stable for at least about 6 months.

Embodiment 100: The pharmaceutical composition of any of embodiments 78-92, wherein the PCSK9-binding polypeptide is stable for at least about 1 month when stored at about 40° C.

Embodiment 101: The pharmaceutical composition of any of embodiments 78-92, wherein the composition comprises high molecular weight aggregates or oligomers of the PCSK9-binding polypeptide at less than about 3% of the PCSK9-binding polypeptide concentration.

Embodiment 102: The pharmaceutical composition of embodiment 101, wherein the high molecular weight aggregates or oligomers of the PCSK9-binding polypeptide are present at less than about 2.5% of the PCSK9-binding polypeptide concentration.

Embodiment 103: The pharmaceutical composition of any of embodiments 1-102, wherein the pharmaceutical composition is liquid.

Embodiment 104: A method of treating a subject in need thereof, comprising administering the pharmaceutical composition of any of embodiments 1-103.

Embodiment 105: A kit, comprising the pharmaceutical composition of any of embodiments 1-103 and a delivery device selected from the group consisting of a syringe, an injector pen, a body injector, and an autoinjector.

Embodiment 106: The kit of embodiment 105, further comprising instructions for administration of the pharmaceutical composition using the delivery device.

Embodiment 107: A method of preparing a PCSK9-binding polypeptide in a pharmaceutical composition comprising at least 140 mg/mL of PCSK9-binding polypeptide, comprising adding to a pharmaceutical composition comprising the PCSK9-binding polypeptide an effective amount of N-acetyl arginine, such that the viscosity of the pharmaceutical composition is reduced when compared to the pharmaceutical composition lacking the N-acetyl arginine, and wherein the PCSK9-binding polypeptide is selected from the group consisting of:
  a. a monoclonal antibody comprising a heavy chain polypeptide having an amino acid sequence of SEQ ID NO:1 and a light chain polypeptide having an amino acid sequence of SEQ ID NO:2 (evolocumab), or an antigen-binding fragment thereof;

b. a monoclonal antibody that competes with evolocumab for binding to PCSK9;
c. a monoclonal antibody, comprising:
  i. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
  ii. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
    d. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, and D238, K243, S373, D374, S376, T377, F379, I154, T1897, H193, E195, I196, M201, V202, C223, T228, S235, G236, A239, G244, M247, I369, S372, C375, C378, R237, and D238; and
    e. a monoclonal antibody that binds to PCSK9 at an epitope on PCSK9 that overlaps with an epitope that is bound by an antibody that comprises:
  iii. a heavy chain variable region of the amino acid sequence in SEQ ID NO:1; and
  iv. a light chain variable region of the amino acid sequence in SEQ ID NO:2, and
  v. wherein the epitope of the monoclonal antibody further overlaps with a site to which an EGF-A domain of LDLR.

Embodiment 108: The method of embodiment 107, wherein the viscosity of the pharmaceutical composition is less than 80 Cp (measured, for example, by a rheometer, such as TA Instruments (New Castle, DE) AESR-G2 cone and plate rheometer).

Embodiment 109: The method of embodiment 108, wherein the viscosity of the pharmaceutical composition is less than 50 cP.

Embodiment 110: The method of any of embodiments 107-109, wherein the pharmaceutical composition has an osmolality of about 250 to about 400 mOsm/kg.

Embodiment 111: The method of embodiment 110, wherein the pharmaceutical composition has an osmolality of about 300 mOsm/kg.

Embodiment 112: The method of embodiment 111, wherein the pharmaceutical composition is isotonic to a human blood cell.

Embodiment 113: The method of embodiment 107, wherein the PCSK9-binding polypeptide is present at a concentration of about 180 mg/mL to about 260 mg/mL.

Embodiment 114: The method of embodiment 113, wherein the PCSK9-binding polypeptide concentration is about 210 mg/mL.

Embodiment 115: The method of any of embodiments 107-114, wherein the N-acetyl arginine is present at a concentration of about 25 mM to about 230 mM.

Embodiment 116: The method of embodiment 115, wherein the N-acetyl arginine is present at a concentration of about 140 mM to about 170 mM.

Embodiment 117: The method of embodiment 115, wherein the N-acetyl arginine is present at a concentration of about 140 mM.

Embodiment 118: The method of any of embodiments 107-117, further comprising a buffer.

Embodiment 119: The method of embodiment 118, wherein the buffer is selected from the group consisting of acetate, glutamate, histidine, and phosphate buffers, or a combination thereof.

Embodiment 120: The method of embodiment 119, wherein the buffer is present at a concentration of about 5 mM to about 30 mM.

Embodiment 121: The method of embodiment 120, wherein the buffer is sodium acetate and is present at a concentration of about 10 mM.

Embodiment 122: The method of any of embodiments 107-121, wherein the pH is about 4.8 to about 6.9.

Embodiment 123: The method of embodiment 122, wherein the pH is about 5.4.

Embodiment 124: The method of any of embodiment 107-123, further comprising a surfactant.

Embodiment 125: The method of embodiment 124, wherein the surfactant is selected from the group consisting of polyoxyethylenesorbitan monooleate (polysorbate 80 or polysorbate 20), polyoxyethylene-polyoxypropylene block copolymer (Poloxamers such as Pluronic® F-68 and other Pluronics®), Sorbitan alkyl esters (Spans®) Polyethylene glycol octylphenyl ethers (Triton X-100), Polyethylene glycol alkyl ethers (Brij), Polypropylene glycol alkyl ethers, Glucoside alkyl ethers, and D-α-tocopherol polyethylene glycol succinate (vitamin E TPGS).

Embodiment 126: The method of embodiment 125, wherein the surfactant is present at a concentration of about 0.0001% (w/v) to about 1.0% (w/v).

Embodiment 127: The method of embodiment 126, wherein the surfactant is polyoxyethylenesorbitan monooleate and is present at a concentration of about 0.01% (w/v).

Embodiment 128: The method of any of embodiments 107-127, further comprising proline.

Embodiment 129: The method of embodiment 128, wherein the proline is present at a concentration of about 50 mM to about 150 mM.

Embodiment 130: The method of embodiment 129, wherein the proline is present at a concentration of about 90 mM to about 120 mM.

Embodiment 131: The method of embodiment 130, where the proline is present at a concentration of about a concentration of about 120 mM.

Embodiment 132: The method of any of embodiments 107-131, further comprising an arginine salt.

Embodiment 133: The method of embodiment 132, wherein the arginine salt is present at a concentration of about 25 mM to about 150 mM.

Embodiment 134: The method of embodiment 133, wherein the arginine salt is present at a concentration of about 50 mM to about 100 mM Embodiment 135: The method of embodiment 133, wherein the arginine salt is arginine-HCl, arginine acetate, or arginine glutamate.

Embodiment 136: The method of embodiment 135, wherein the arginine HCl is present at a concentration of about 50 mM.

Embodiment 137: The method of any of embodiments 107-136, wherein the PCSK9-binding polypeptide is stable for at least about 2 years when stored at about −30° C. or colder.

Embodiment 138: The method of embodiment 137, wherein the PCSK9-binding polypeptide is stable for at least about 5 years.

Embodiment 139: The method of any of embodiments 107-136, wherein the PCSK9-binding polypeptide is stable for at least about 6 months when stored at about 5° C.

Embodiment 140: The method of embodiment 139, wherein the PCSK9-binding polypeptide is stable for at least about 24 months.

Embodiment 141: The method of any of embodiments 107-136, wherein the PCSK9-binding polypeptide is stable for at least about 1 month when stored at about 25° C.

Embodiment 142: The method of embodiment 141, wherein the PCSK9-binding polypeptide is stable for at least about three months.

Embodiment 143: The method of embodiment 142, wherein the PCSK9-binding polypeptide is stable for at least about 6 months.

Embodiment 144: The method of any of embodiments 107-136, wherein the PCSK9-binding polypeptide is stable for at least about 1 month when stored at about 40° C.

Embodiment 145: The method of any of embodiments 107-136, wherein the composition comprises high molecular weight aggregates or oligomers of the PCSK9-binding polypeptide at less than about 3% of the PCSK9-binding polypeptide concentration.

Embodiment 146: The method of embodiment 145, wherein the high molecular weight aggregates or oligomers of the PCSK9-binding polypeptide are present at less than about 2.5% of the PCSK9-binding polypeptide concentration.

Embodiment 147: A method of formulating a therapeutic polypeptide, comprising
  a. a first concentration step, wherein the polypeptide in a first solution is concentrated;
  b. a first solution exchange step, wherein the concentrated polypeptide in the first solution is exchanged into a second solution comprising N-acetyl arginine using diafiltration;
  c. a second concentration step, wherein the polypeptide in the second solution is concentrated;
  d. a second solution exchange step, wherein the polypeptide in the concentrated second solution is exchanged into a third solution comprising N-acetyl arginine using diafiltration; and
  e. a third concentration step, wherein the polypeptide in the third solution is concentrated;
  wherein the therapeutic polypeptide comprises a PCSK9-binding polypeptide that blocks binding of PCSK9 to LDLR and is selected from the group consisting of:
    i. a monoclonal antibody comprising a heavy chain having an amino acid sequence of SEQ ID NO:1 and a light chain having an amino acid sequence of SEQ ID NO:2 (evolocumab), or an antigen-binding fragment thereof;
    ii. a monoclonal antibody that competes with evolocumab for binding to PCSK9;
    iii. a monoclonal antibody, comprising:
      1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
      2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
      i. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, D238, K243, S373, D374, S376, T377, F379, I154, T1897, H193, E195, I196, M201, V202, C223, T228, S235, G236, A239, G244, M247, I369, S372, C375, C378, R237, D238;
    ii. a monoclonal antibody that binds to PCSK9 at an epitope on PCSK9 that overlaps with an epitope that is bound by an antibody that comprises:
      3. a heavy chain variable region of the amino acid sequence in SEQ ID NO:1; and
      4. a light chain variable region of the amino acid sequence in SEQ ID NO:2, and
      5. wherein the epitope of the monoclonal antibody further overlaps with a site to which an EGFa domain of LDLR.

Embodiment 148: The method of embodiment 147, wherein the PCSK9-binding polypeptide that blocks binding of PCSK9 to LDLR is a monoclonal antibody the comprises a heavy chain polypeptide comprising the following complementarity determining regions (CDRs):
  a. heavy chain CDR1, CDR2, and CDR3 having an amino acid sequence of SEQ ID NOs: 7, 8, and 9, respectively; and
  b. light chain CDR1, CDR2, and CDR3 having an amino acid sequence of SEQ ID NOs: 4, 5, and 6, respectively.

Embodiment 149: The method of embodiment 147, wherein before the third concentration step, the temperature of the solution comprising the polypeptide is increased from about 25° C. to about 37° C.

Embodiment 150: The method of embodiment 147, wherein the first solution exchange step is accomplished using at least three diavolumes of the second solution.

Embodiment 151: The method of embodiment 147, wherein the second solution exchange step is accomplished using at least four diavolumes of the third solution.

Embodiment 152: The method of embodiment 147, wherein the initial concentration of the therapeutic protein is about 11 mg/mL or less.

Embodiment 153: The method of embodiment 147, wherein in the first concentration step, the therapeutic polypeptide concentration is increased from about 3- to about 7-fold.

Embodiment 154: The method of embodiment 153, wherein the increased concentration of the polypeptide is from about 35 mg/mL to about 70 mg/mL.

Embodiment 155: The method of embodiment 147, wherein in the second concentration step, the therapeutic polypeptide concentration is increased from about 2- to 4-fold from the first concentration step.

Embodiment 156: The method of embodiment 155, wherein the increased polypeptide concentration is about 140 mg/mL.

Embodiment 157: The method of embodiment 147, wherein in the third concentration step, the therapeutic polypeptide concentration is increased from about 1.5- to about 2-fold from the second concentration step.

Embodiment 158: The method of embodiment 157, wherein the increased polypeptide concentration is about 260 mg/mL.

Embodiment 159: The method of embodiment 147, wherein the therapeutic polypeptide has a final concentration that is at least about 19-20-fold more concentrated than the initial concentration of the therapeutic polypeptide.

Embodiment 160: The method of embodiment 159, wherein the final concentration of the therapeutic polypeptide is about 210 mg/mL.

Embodiment 161: The method of embodiment 147, wherein the concentration steps comprise fed-batch ultrafiltration.

Embodiment 162: The method of embodiment 147, wherein the second solution and the third solution are identical.

Embodiment 163: The method of embodiment 147, wherein the second or third solution comprising N-acetyl arginine comprises an arginine salt and a buffer.

Embodiment 164: The method of embodiment 163, wherein the N-acetyl arginine is present at a concentration of about 25 mM to about 230 mM; the arginine salt is Arg HCl, Arg acetate, or Arg glutamate and is present at a concentration of about 25 mM to about 150 mM; and the buffer is a sodium acetate buffer at a concentration of about 5 mM to about 30 mM.

Embodiment 165: The method of embodiment 164, wherein the N-acetyl arginine is present at a concentration of about 140 to about 170 mM; the Arg HCl, Arg acetate, or Arg glutamate is present at a concentration of about 63 to about 70 mM and the sodium acetate buffer is present at a concentration of about 10 mM.

Embodiment 166: The method of embodiment 164, wherein the N-acetyl arginine is present at a concentration of about 140 mM, the Arg HCl, Arg acetate, or Arg glutamate is present at a concentration of about 63 mM, the sodium acetate buffer is present at a concentration of about 10 mM.

Embodiment 167: The method of embodiment 164, wherein the N-acetyl arginine is present at a concentration of about 155 mM, the Arg HCl, Arg acetate, or Arg glutamate is present at a concentration of about 70 mM, the sodium acetate buffer is present at a concentration of about 10 mM.

Embodiment 168: The method of embodiment 164, wherein the N-acetyl arginine is present at a concentration of about 170 mM, the Arg HCl, Arg acetate, or Arg glutamate is present at a concentration of about 63 mM, the sodium acetate buffer is present at a concentration of about 10 mM.

Embodiment 169: The method of embodiment 165 or 166, further comprising proline, wherein the proline is present at a concentration of about 50 mM to about 150 mM.

Embodiment 170: The method of any of embodiments 163-169, wherein the second or third solution has a pH from about 4.8 to about 6.9.

Embodiment 171: The method of embodiment 170, wherein the pH is about 5.4.

Embodiment 172: The method of embodiment 147, wherein in the first and second solution exchange steps, a diafiltration membrane is used having at least one characteristic selected from the group consisting of:
  a. mesh openings that are greater than about 350 μm but less than or equal to about 500 μm;
  b. an open area that is greater than about 32% but less than or equal to about 36% of the membrane area;
  c. a mesh count of less than about 16.2 n/cm but greater than or equal to about 12.2 n/cm;
  d. a wire diameter that is greater than about 270 μm but less than or equal to about 340 μm;
  e. a basis weight that is greater than about 160 g/m$^2$ but less than or equal to 180 g/m$^2$;
  f. a thickness greater than about 515 μm but less than or equal to about 610 μm;
  g. a membrane load of greater than about 1138.1 g/m$^2$ but less than or equal to about 1919.3 g/m$^2$; and
  h. a maximum feed pressure of about 60 psi.

Embodiment 173: The method of any of embodiments 147-172, wherein surfactant is added to the third solution after being concentrated.

Embodiment 174: The method of embodiment 173, wherein the surfactant is selected from the group consisting of polyoxyethylenesorbitan monooleate (polysorbate 80 or polysorbate 20), polyoxyethylene-polyoxypropylene block copolymer (Poloxamers such as Pluronic® F-68 and other Pluronics®), Sorbitan alkyl esters (Spans®) Polyethylene glycol octylphenyl ethers (Triton X-100), Polyethylene glycol alkyl ethers (Brij), Polypropylene glycol alkyl ethers, Glucoside alkyl ethers, and D-α-tocopherol polyethylene glycol succinate (vitamin E TPGS) and is present at a concentration of about 0.0001% to about 1%.

Embodiment 175: The method of embodiment 175, wherein the surfactant is polyoxyethylenesorbitan monooleate (polysorbate 80) and is present at a concentration of about 0.01% (w/v).

Embodiment 176: A method of formulating a therapeutic polypeptide, comprising
  a. a first concentration step, wherein the polypeptide in a first solution is concentrated using fed-batch ultrafiltration;
  b. a first solution exchange step, wherein the concentrated polypeptide in the first solution is exchanged into a second solution comprising N-acetyl arginine, arginine salt, and a buffer, using diafiltration and three diavolumes of the second solution;
  c. a second concentration step, wherein the polypeptide in the second solution is concentrated using fed-batch ultrafiltration;
  d. a second solution exchange step, wherein the polypeptide in the concentrated second solution is exchanged into third solution comprising N-acetyl arginine, arginine salt, and a buffer using diafiltration and four diavolumes of the third solution;
  e. the temperature of the solution comprising the polypeptide is increased from about 25° C. to about 37° C. after the second solution exchange step; and
  f. a third concentration step, wherein the polypeptide is further concentrated using fed-batch ultrafiltration concentration;
wherein in the first and second solution exchange steps, a diafiltration membrane is used having at least one characteristic selected from the group consisting of:
  g. mesh openings that are greater than about 350 μm but less than or equal to about 500 μm;
  h. an open area that is greater than about 32% but less than or equal to about 36% of the membrane area;
    i. a mesh count of less than about 16.2 n/cm but greater than or equal to about 12.2 n/cm;
  j. a wire diameter that is greater than about 270 μm but less than or equal to about 340 μm;
  k. a basis weight that is greater than about 160 g/m$^2$ but less than or equal to 180 g/m$^2$;
  l. a thickness greater than about 515 μm but less than or equal to about 610 μm;
  m. a membrane load of greater than about 1138.1 g/m$^2$ but less than or equal to about 1919.3 g/m$^2$; and
  n. a maximum feed pressure of about 60 psi;
and
wherein the therapeutic polypeptide comprises a PCSK9-binding polypeptide that blocks binding of PCSK9 to LDLR and is selected from the group consisting of:
    i. a monoclonal antibody comprising a heavy chain having an amino acid sequence of SEQ ID NO:1 and a light chain having an amino acid sequence of SEQ ID NO:2 (evolocumab), or an antigen-binding fragment thereof;

ii. a monoclonal antibody that competes with evolocumab for binding to PCSK9;

iii. a monoclonal antibody, comprising:
1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;

iv. monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, D238, K243, S373, D374, S376, T377, F379, I154, T1897, H193, E195, I196, M201, V202, C223, T228, S235, G236, A239, G244, M247, I369, S372, C375, C378, R237, D238;

v. a monoclonal antibody that binds to PCSK9 at an epitope on PCSK9 that overlaps with an epitope that is bound by an antibody that comprises:
1. a heavy chain variable region of the amino acid sequence in SEQ ID NO:1; and
2. a light chain variable region of the amino acid sequence in SEQ ID NO:2, and
3. wherein the epitope of the monoclonal antibody further overlaps with a site to which an EGFa domain of LDLR.

Embodiment 177: The method of embodiment 176, wherein before the third concentration step, the temperature of the solution comprising the polypeptide is increased from about 25° C. to about 37° C.

Embodiment 178: The method of embodiment 176, wherein the initial concentration of the therapeutic protein is 11 mg/mL or less.

Embodiment 179: The method of embodiment 176, wherein in the first concentration step, the therapeutic polypeptide concentration is increased from about 3- to about 7-fold.

Embodiment 180: The method of embodiment 179, wherein the increased concentration of the polypeptide is from about 35 mg/mL to about 70 mg/mL.

Embodiment 181: The method of embodiment 176, wherein in the second concentration step, the therapeutic polypeptide concentration is increased about 2- to 4-fold from the first concentration step.

Embodiment 182: The method of embodiment 181, wherein the increased polypeptide concentration is about 140 mg/mL.

Embodiment 183: The method of embodiment 176, wherein in the third concentration step, the therapeutic polypeptide concentration is increased from about 1.5- to about 2-fold from the second concentration step.

Embodiment 184: The method of embodiment 183, wherein the increased polypeptide concentration is about 260 mg/mL.

Embodiment 185: The method of embodiment 176, wherein the therapeutic polypeptide has a final concentration that is at least about 19-20-fold more concentrated than the initial concentration of the therapeutic polypeptide.

Embodiment 186: The method of embodiment 185, wherein the final concentration of the therapeutic polypeptide is about 210 mg/mL.

Embodiment 187: The method of embodiment 176, wherein the N-acetyl arginine is present at a concentration of about 25 mM to about 230 mM; the arginine salt is Arg HCl, Arg acetate, or Arg glutamate and is present at a concentration of about 25 mM to about 150 mM, and the buffer is a sodium acetate buffer at a concentration of about 5 mM to about 30 mM.

Embodiment 188: The method of embodiment 188, wherein the N-acetyl arginine is present at a concentration of about 140 to about 170 mM; the Arg HCl, Arg acetate, or Arg glutamate is present at a concentration of about 63 to about 70 mM and the sodium acetate buffer is present at a concentration of about 10 mM.

Embodiment 189: The method of embodiment 188, wherein the N-acetyl arginine is present at a concentration of about 140 mM, the Arg HCl, Arg acetate, or Arg glutamate is present at a concentration of about 63 mM, the sodium acetate buffer is present at a concentration of about 10 mM.

Embodiment 190: The method of embodiment 188, wherein the N-acetyl arginine is present at a concentration of about 155 mM, the Arg HCl, Arg acetate, or Arg glutamate is present at a concentration of about 70 mM, the sodium acetate buffer is present at a concentration of about 10 mM.

Embodiment 191: The method of embodiment 188, wherein the N-acetyl arginine is present at a concentration of about 170 mM, the Arg HCl, Arg acetate, or Arg glutamate is present at a concentration of about 63 mM, the sodium acetate buffer is present at a concentration of about 10 mM.

Embodiment 192: The method of embodiment 176, further comprising proline, wherein the proline is present at a concentration of about 50 mM to about 150 mM.

Embodiment 193: The method of any of embodiments 176-192, wherein the second or third solution has a pH from about 4.8 to about 6.9.

Embodiment 194: The method of embodiment 193, wherein the pH is about 5.4.

Embodiment 195: The method of any of embodiments 176-194, wherein surfactant is added to the third solution after being concentrated.

Embodiment 196: The method of embodiment 195, wherein the surfactant is wherein the surfactant is selected from the group consisting of polyoxyethylenesorbitan monooleate (polysorbate 80 or polysorbate 20), polyoxyethylene-polyoxypropylene block copolymer (Poloxamers such as Pluronic® F-68 and other Pluronics®), Sorbitan alkyl esters (Spans®) Polyethylene glycol octylphenyl ethers (Triton X-100), Polyethylene glycol alkyl ethers (Brij), Polypropylene glycol alkyl ethers, Glucoside alkyl ethers, and D-α-tocopherol polyethylene glycol succinate (vitamin E TPGS) and is present at a concentration of about 0.0001% to about 1%.

Embodiment 197: The method of embodiment 196, wherein the surfactant is polyoxyethylenesorbitan monooleate (polysorbate 80) and is present at a concentration of about 0.01% (w/v).

Embodiment 198: A method of formulating a therapeutic polypeptide, comprising
a. a first concentration step, wherein the polypeptide in a first solution is concentrated using fed-batch ultrafiltration;

b. a first solution exchange step, wherein the concentrated polypeptide in the first solution is exchanged into a second using diafiltration and three diavolumes of the second solution;
c. a second concentration step, wherein the polypeptide in the second solution is concentrated using fed-batch ultrafiltration;
d. a second solution exchange step, wherein the polypeptide in the concentrated second solution is exchanged into third solution using diafiltration and four diavolumes of the third solution;
e. the temperature of the solution comprising the polypeptide is increased from about 25° C. to about 37° C. after the second solution exchange step; and
f. a third concentration step, wherein the polypeptide is further concentrated using fed-batch ultrafiltration concentration;
g. alternatively, a step adding polyoxyethylenesorbitan monooleate at a concentration of about 0.01% (w/v) to the resulting solution of the third concentration step,
wherein the second and third solutions comprise a solution selected from the group consisting of a solution comprising about 140 mM N-acetyl arginine, about 50 mM Arg HCl, and about 10 mM sodium acetate, the solution having a pH of about 5.2; a solution comprising about 155 mM N-acetyl arginine, about 70 mM Arg HCl, and about 10 mM sodium acetate, the solution having a pH of about 5.4; and a solution comprising about 170 mM N-acetyl arginine, about 10 mM sodium acetate, the solution having a pH of about 5.6;
wherein in the first and second solution exchange steps, a diafiltration membrane is used having at least one characteristic selected from the group consisting of:
h. mesh openings that are greater than about 350 µm but less than or equal to about 500 µm;
i. an open area that is greater than about 32% but less than or equal to about 36% of the membrane area;
j. a mesh count of less than about 16.2 n/cm but greater than or equal to about 12.2 n/cm;
k. a wire diameter that is greater than about 270 µm but less than or equal to about 340 µm;
l. a basis weight that is greater than about 160 g/m$^2$ but less than or equal to 180 g/m$^2$;
m. a thickness greater than about 515 µm but less than or equal to about 610 µm;
n. a membrane load of greater than about 1138.1 g/m$^2$ but less than or equal to about 1919.3 g/m$^2$; and
o. a maximum feed pressure of about 60 psi;
and
wherein the therapeutic polypeptide comprises a PCSK9-binding polypeptide that blocks binding of PCSK9 to LDLR and is selected from the group consisting of:
i. a monoclonal antibody comprising a heavy chain having an amino acid sequence of SEQ ID NO:1 and a light chain having an amino acid sequence of SEQ ID NO:2 (evolocumab), or an antigen-binding fragment thereof;
ii. a monoclonal antibody that competes with evolocumab for binding to PCSK9;
iii. a monoclonal antibody, comprising:
1. a heavy chain polypeptide comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and 2. a light chain polypeptide comprising the following CDRs: a light chain CDR1 that is a CDR1 in SEQ ID NOs:15 or 17; a light chain CDR2 that a CDR2 in SEQ ID NOs:15 or 17; and a light chain CDR3 that is a CDR3 in SEQ ID NOs:15 or 17;
iv. a monoclonal antibody that binds to at least one of the following residues of PCSK9, the PCSK9 comprising an amino acid sequence of SEQ ID NO:3: S153, D188, I189, Q190, S191, D192, R194, E197, G198, R199, V200, D224, R237, D238, K243, S373, D374, S376, T377, F379, I154, T1897, H193, E195, I196, M201, V202, C223, T228, S235, G236, A239, G244, M247, I369, S372, C375, C378, R237, D238;
v. a monoclonal antibody that binds to PCSK9 at an epitope on PCSK9 that overlaps with an epitope that is bound by an antibody that comprises:
1. a heavy chain variable region of the amino acid sequence in SEQ ID NO:1; and
2. a light chain variable region of the amino acid sequence in SEQ ID NO:2, and
wherein the epitope of the monoclonal antibody further overlaps with a site to which an EGFa domain of LDLR.

Embodiment 199: The method of embodiment 104, wherein the subject has a disease or disorder selected from the group consisting of
a cholesterol related disease or disorder selected from the group consisting of familial hypercholesterolemia (including heterozygous hypercholesterolemia, homozygous hypercholesterolemia, familial defective apop lipoprotein B-100; polygenic hypercholesterolemia), non-familial hypercholesterolemia, hyperlipidemia, heart disease, metabolic syndrome, diabetes, coronary heart disease, stroke, cardiovascular diseases, Alzheimer's disease and dyslipidemias (including primary and secondary dyslipidemias, such as metabolic syndrome, diabetes mellitus, familial combined hyperlipidemia, familial hypertriglyceridemia; remnant removal disease, hepatic lipase deficiency; dyslipidemia secondary to dietary indiscretion, hypothyroidism, drugs including estrogen and progestin therapy, beta-blockers, and thiazide diuretics; nephrotic syndrome, chronic renal failure, Cushing's syndrome, primary biliary cirrhosis, glycogen storage diseases, hepatoma, cholestasis, acromegaly, insulinoma, isolated growth hormone deficiency, or alcohol-induced hypertriglyceridemia.
atherosclerotic disease selected from the group consisting of cardiovascular death, non-cardiovascular or all-cause death, coronary heart disease, coronary artery disease, peripheral arterial disease, stroke (ischaemic and hemorrhagic), angina pectoris, cerebrovascular disease and acute coronary syndrome, myocardial infarction and unstable angina; and
a disease or disorder that can be addressed using statins.

Embodiment 200: The method of embodiment 104, wherein the treating the subject comprises reducing the risk of a condition selected from the group consisting of fatal and nonfatal heart attack, fatal and non-fatal stroke, heart surgery, hospitalization for heart failure, chest pain in a subject having heart disease, and/or cardiovascular events because of established heart disease, cardiovascular condition due to elevated CRP or hsCRP, and a recurrent cardiovascular event.

Embodiment 201: The pharmaceutical composition of any of embodiments 1-103 for use as a medicament.

Embodiment 202: The pharmaceutical composition of embodiment 201, wherein the medicament is for use in the treatment of a disease or disorder selected from the group consisting of a cholesterol related disease or disorder selected from the group consisting of familial hypercholesterolemia (including heterozygous hypercholesterolemia, homozygous hypercholesterolemia, familial defective apop lipoprotein B-100; polygenic hypercholesterolemia), non-familial hypercholesterolemia, hyperlipidemia, heart disease, metabolic syndrome, diabetes, coronary heart disease, stroke, cardiovascular diseases, Alzheimer's disease and dyslipidemias (including primary and secondary dyslipidemias, such as metabolic syndrome, diabetes mellitus, familial combined hyperlipidemia, familial hypertriglyceridemia; remnant removal disease, hepatic lipase deficiency; dyslipidemia secondary to dietary indiscretion, hypothyroidism, drugs including estrogen and progestin therapy, beta-blockers, and thiazide diuretics; nephrotic syndrome, chronic renal failure, Cushing's syndrome, primary biliary cirrhosis, glycogen storage diseases, hepatoma, cholestasis, acromegaly, insulinoma, isolated growth hormone deficiency, or alcohol-induced hypertriglyceridemia.

atherosclerotic disease selected from the group consisting of cardiovascular death, non-cardiovascular or all-cause death, coronary heart disease, coronary artery disease, peripheral arterial disease, stroke (ischaemic and hemorrhagic), angina pectoris, cerebrovascular disease and acute coronary syndrome, myocardial infarction and unstable angina; and a disease or disorder that can be addressed using statins.

Embodiment 203: The method of embodiment 202, wherein the medicament is for to reduce the risk of a condition selected from the group consisting of fatal and nonfatal heart attack, fatal and non-fatal stroke, heart surgery, hospitalization for heart failure, chest pain in a subject having heart disease, and/or cardiovascular events because of established heart disease, cardiovascular condition due to elevated CRP or hsCRP, and a recurrent cardiovascular event.

ABBREVIATIONS

Abbreviation Definition
  Arg HCl arginine HCl
  ASC Ambient storage conditions
  CDR Complementary determining region
  CEX Cation exchange
  DF Diafiltration
  DIW Deionized water
  DOE Design of Experiment
  DS Drug substance
  DV Diavolume
  EGF-A Epidermal growth factor-like repeat A
  EQ Equilibrium
  FR Framework region
  HC Heavy chain (antibody)
  HCVR Heavy chain variable region (antibody)
  HDLC High-density lipoprotein cholesterol
  HIAC Subvisible particle detection by light obscuration
  HMW High molecular weight
  HPLC High-pressure liquid chromatography
  HPLC-UV High pressure liquid chromatography ultraviolet
  LC Light chain (antibody)
  LCVR Light chain variable region (antibody)
  LDL Low-density lipoprotein
  LDLR Low-density lipoprotein receptors
  LMH Liters/m$^2$/hr
  LMW Low molecular weight
  mAb Monoclonal antibody
  MFI Micro-flow imaging
  NaOAC Sodium acetate
  NAR N-acetyl arginine
  NTU Nephelometric Turbidity Unit
  OC Over-concentrated, Over-concentration
  PEG Polyethylene glycol
  PFS Pre-filled syringe
  PVDF Polyvinylidene fluoride
  PW Purified water
  rCE-SDS Reduced capillary electrophoresis—sodium dodecyl sulfate
  RT Room temperature
  SEC Size-exclusion chromatography
  SE-HPLC Size-exclusion high pressure liquid chromatography
  TFF Tangential flow filtration
  TMP Transmembrane pressure
  UF Ultrafiltration
  UFDF Ultrafiltration/diafiltration
  UV Ultraviolet
  VF Viral filtration
  VLDL-C Very-low-density lipoprotein cholesterol
  WFI Water for injection

REFERENCES

Chan, J., Gibbs, J., Dias, C., Wasserman, S., Scott, R., Clogston, C., . . . Stein, E. (2012). WO Patent No. WO2012154999.

Chothia, C., & Lesk, A. M. (1987). Canonical structures for the hypervariable regions of immunoglobulins. *J Mol Biol,* 196(4), 901-917.

Chothia, C., Lesk, A. M., Tramontano, A., Levitt, M., Smith-Gill, S. J., Air, G., . . . et al. (1989). Conformations of immunoglobulin hypervariable regions. Nature, 342 (6252), 877-883. doi: 10.1038/342877a0 Cunningham, D., Danley, D. E., Geoghegan, K. F., Griffor, M. C., Hawkins, J. L., Subashi, T. A., . . . Qiu, X. (2007). Structural and biophysical studies of PCSK9 and its mutants linked to familial hypercholesterolemia. *Nat Struct Mol Biol,* 14(5), 413-419. doi: 10.1038/nsmb1235

Horton, J. D., Cohen, J. C., & Hobbs, H. H. (2007). Molecular biology of PCSK9: its role in LDL metabolism. *Trends Biochem Sci,* 32(2), 71-77. doi: 10.1016/j.tibs.2006.12.008

Jackson, S. M., Walker, N. P., Piper, D. E., Shan, B., Shen, W., Chan, J., . . . Carabeo, T. (2009). WO Patent No. WO 2009/026558.

Kabat, E., Wu, T., Perry, H., Gottesman, K., & Foeller, C. (1991). *Sequences of proteins of immunological interest* (Vol. Publication No. 91-3242). Bethesda, MD: National Institutes of Health.

Kabat, E., Wu, T., Reid-Miller, M., Perry, H., & Gottesman, K. (1987). *Sequences of proteins of immunological interest* (4th ed. Vol. No. 165-492). Bethesda, MD: US Government Printing Office.

Morichika, T., & Kameoka, D. (2007). WO Patent No. WO2007074880.

Piper, D. E., Jackson, S., Liu, Q., Romanow, W. G., Shetterly, S., Thibault, S. T., . . . Walker, N. P. (2007). The crystal structure of PCSK9: a regulator of plasma LDL-cholesterol. Structure, 15(5), 545-552. doi: 10.1016/j.str.2007.04.004

Seidah, N. G., Benjannet, S., Wickham, L., Marcinkiewicz, J., Jasmin, S. B., Stifani, S., . . . Chretien, M. (2003). The secretory proprotein convertase neural apoptosis-regulated convertase 1 (NARC-1): liver regeneration and neuronal differentiation. *Proc Natl Acad Sci USA*, 100(3), 928-933. doi: 10.1073/pnas.0335507100

Seidah, N. G., & Prat, A. (2007). The proprotein convertases are potential targets in the treatment of dyslipidemia. *J Mol Med (Berl)*, 85(7), 685-696. doi: 10.1007/s00109-007-0172-7

The invention claimed is:

1. A method of formulating a therapeutic polypeptide, comprising
   a. a first concentration step, wherein the polypeptide in a first solution is concentrated;
   b. a first solution exchange step, wherein the concentrated polypeptide in the first solution is exchanged into a second solution comprising N-acetyl arginine using diafiltration;
   c. a second concentration step, wherein the polypeptide in the second solution is concentrated;
   d. a second solution exchange step, wherein the polypeptide in the concentrated second solution is exchanged into a third solution comprising N-acetyl arginine using diafiltration; and
   e. a third concentration step, wherein the polypeptide in the third solution is concentrated;

wherein the therapeutic polypeptide comprises (A) an antibody:
      heavy chain having an amino acid sequence of SEQ ID NO:1 and an antibody light chain having an amino acid sequence of SEQ ID NO:2; or
      (B) an antibody heavy chain comprising the following complementarity determining regions (CDRs): a heavy chain CDR1 that is a CDR1 in SEQ ID NOs:14 or 16; a heavy chain CDR2 that is a CDR2 in SEQ ID NOs:14 or 16; a heavy chain CDR3 that is a CDR3 in SEQ ID NOs:14 or 16, and
      an antibody light chain comprising the following CDRs: a light chain CDR1 that is a CDR1 in SEQ ID NOs:15 or 17; a light chain CDR2 that a CDR2 in SEQ ID NOs:15 or 17; and a light chain CDR3 that a CDR3 in SEQ ID NOs:15 or 17.

2. The method of claim 1, wherein the therapeutic polypeptide comprises the antibody heavy chain having the amino acid sequence of SEQ ID NO:1 and the antibody light chain having the amino acid sequence of SEQ ID NO:2.

3. The method of claim 1, wherein the:
   a. antibody heavy chain comprises a complementarity determining region (CDR) 1 CDR2, and CDR3 having the amino acid sequence of SEQ ID NOs: 7, 8, and 9, respectively; and
   b. the antibody light chain comprises a CDR1, CDR2, and CDR3 having the amino acid sequence of SEQ ID NOs: 4, 5, and 6, respectively.

4. The method of claim 1, wherein before the third concentration step, the temperature of the solution comprising the polypeptide is increased from 25° C. to 37° C.

5. The method of claim 1, wherein in the first concentration step, the therapeutic polypeptide concentration is increased from 3-fold to 7-fold.

6. The method of claim 1, wherein in the second concentration step, the therapeutic polypeptide concentration is increased from 2-fold to 4-fold from the first concentration step.

7. The method of claim 1, wherein in the third concentration step, the therapeutic polypeptide concentration is increased from 1.5-fold to 2-fold from the second concentration step.

8. The method of claim 1, wherein the therapeutic polypeptide has a final concentration that is at least 19-fold to 20-fold more concentrated than the initial concentration of the therapeutic polypeptide.

9. The method of claim 1, wherein the concentration steps comprise fed-batch ultrafiltration.

10. The method of claim 1, wherein the second or third solution has a pH from 4.8 to 6.9.

11. The method of claim 1, wherein in the first and second solution exchange steps, a diafiltration membrane is used having at least one characteristic selected from the group consisting of:
   a. mesh openings that are greater than 350 µm but less than or equal to 500 µm;
   b. an open area that is greater than 32% but less than or equal to 36% of the membrane area;
   c. a mesh count of less than 16.2 n/cm but greater than or equal to 12.2 n/cm;
   d. a wire diameter that is greater than 270 µm but less than or equal to 340 µm;
   e. a basis weight that is greater than 160 $g/m^2$ but less than or equal to 180 $\mu g/m^2$;
   f. a thickness greater than 515 µm but less than or equal to 610 µm;
   g. a membrane load of greater than 1138.1 $g/m^2$ but less than or equal to 1919.3 $g/m^2$; and
   h. a maximum feed pressure of 60 psi.

12. The method of claim 1, wherein surfactant is added to the third solution after being concentrated.

* * * * *